(12) United States Patent
Hickey et al.

(10) Patent No.: US 6,417,192 B1
(45) Date of Patent: Jul. 9, 2002

(54) PYRIMIDINONE COMPOUNDS AND PHARMACEUTICAL COMPOSITIONS CONTAINING THEM

(75) Inventors: Deirdre Mary Bernadette Hickey, Saffron Walden; Robert John Ife; Colin Andrew Leach, both of Stevenage; Ivan Leo Pinto, Sutton; Roderick Alan Porter; Stephen Allan Smith, both of Bishops Stortford, all of (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/530,713

(22) PCT Filed: Oct. 23, 1998

(86) PCT No.: PCT/EP98/06988
§ 371 (c)(1),
(2), (4) Date: Jun. 28, 2000

(87) PCT Pub. No.: WO99/24420
PCT Pub. Date: May 20, 1999

(30) Foreign Application Priority Data

Nov. 6, 1997 (GB) .............................................. 9723352
Nov. 6, 1997 (GB) .............................................. 9723358

(51) Int. Cl.[7] ................... C07D 239/54; C07D 239/56; C07D 403/12; A61K 31/505; A61P 9/10
(52) U.S. Cl. ..................... 514/274; 544/296; 544/309; 544/310; 544/311; 544/313; 544/314
(58) Field of Search ..................... 514/274; 544/296, 544/309, 310, 311, 313, 314

(56) References Cited

U.S. PATENT DOCUMENTS 4,154,834 A * 5/1979 Brown et al. ................ 424/251
5,037,830 A * 8/1991 Zolyomi et al. ............ 514/269

FOREIGN PATENT DOCUMENTS

| DE | 3803063 A1 | * | 8/1989 |
| EP | 0 141 973 A | | 5/1985 |
| EP | 141973 | * | 5/1985 |
| EP | 0 391 254 | | 10/1990 |
| GB | 1 582 527 A | | 1/1981 |
| JP | 54/46760 | * | 4/1979 |
| JP | 54/132586 | * | 10/1979 |

OTHER PUBLICATIONS

Kopple, H.C. et al, J. Org. Chem., 26, 1961, 1884–1890.*
Kaneko, Masakatsu; Tanaka, Hiroyuki; Kimura, Misako; Shimizu, Bunji, Chem. Pharm. Bull., 25(9), 2458–60 (English) 1977.*

* cited by examiner

Primary Examiner—Richard L. Raymond
Assistant Examiner—Thomas C McKenzie
(74) Attorney, Agent, or Firm—James M. Kanagy; Charles M. Kinzig

(57) ABSTRACT

A group of novel pyrimidone compounds are inhibitors of the enzyme LDL $PLA_2$ and therefore of use in treating atherosclerosis.

17 Claims, No Drawings

PYRIMIDINONE COMPOUNDS AND PHARMACEUTICAL COMPOSITIONS CONTAINING THEM

The present invention relates to certain novel pyrimidinone compounds, processes for their preparation, intermediates useful in their preparation, pharmaceutical compositions containing them and their use in therapy, in particular in the treatment of atherosclerosis.

WO 95/00649 (SmithKline Beecham plc) describe the phospholipase A2 enzyme Lipoprotein Associated Phospholipase $A_2$ (Lp-$PLA_2$), the sequence. isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscler Thromb Vas Biol 1996:16:591–9) wherein it is referred to as LDL-$PLA_2$. A later patent application (WO 95/09921, Icos Corporation) and a related publication in Nature (Tjoelker et al, vol 374, Apr. 6, 1995, 549) describe the enzyme PAF-AH which has essentially the same sequence as Lp-$PLA_2$ and suggest that it may have potential as a therapeutic protein for regulating pathological inflammatory events.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, a component of oxidised LDL, known to be a potent chemoattractant for circulating monocytes. As such, lysophosphatidylcholine is thought play a significant role in atherosclerosis by being responsible for the accumulation of cells loaded with cholesterol ester in the arteries. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. An Lp-$PLA_2$ inhibitor could also find utility in other disease states that exhibit endothelial dysfunction including diabetes, hypertension, angina pectoris and after ischaemia and reperfusion.

In addition, Lp-$PLA_2$ inhibitors may also have a general application in any disorder that involves activated monocytes, macrophages or lymphocytes, as all of these cell types express Lp-$PLA_2$. Examples of such disorders include psoriasis.

Furthermore, Lp-$PLA_2$ inhibitors may also have a general application in any disorder that involves lipid peroxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, reperfusion injury and acute and chronic inflammation. Further such conditions include various neuropsychiatric disorders such as schizophrenia (see Psychopharmacology Bulletin, 31, 159–165, 1995).

Patent applications WO 96/12963, WO 96/13484, WO 96119451, WO 97/02242, WO 97/217675, WO 97/217676, WO 96/41098, and WO 97/41099 (SmithKline Beecham plc) disclose inter alia various series of 4-thionyl/sulfinyl/sulfonyl azetidinone compounds which are inhibitors of the enzyme Lp-$PLA_2$. These are irreversible, acylating inhibitors (Tew et al, Biochemistry, 37, 10087, 1998). GB 1 582 527 describes, as compounds of formula (7), a group of pyrimidone compounds of the formula (A):

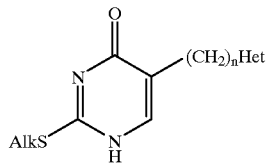

in which Alk is lower alkyl, Het is selected from 2- or 4-imidazolyl, 2-pyridyl, 2-thiazolyl, 3-isothiazolyl, 1,2,5-thiadiazolyl and n is from 1 to 4. These compounds are said to be useful as intermediates in the preparation of further compounds which are H2 antagonists.

A new class of pyrimidone compounds has now been identified which are inhibitors of the enzyme Lp-$PLA_2$.

Accordingly, the present invention provides compounds of formula (I):

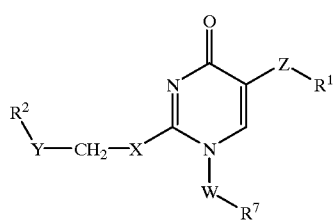

in which:

Z is a bond and $R^1$ is halogen; or

Z is $CR^3R^4$, where $R^3$ and $R^4$ are each hydrogen or $C_{(1-4)}$ alkyl, or $R^3$ and $R^4$ together with the intervening carbon atom form a $C_{(3-6)}$cycloalkyl ring; and $R^1$ is an aryl or heteroaryl group, optionally substituted by 1, 2, 3 or 4 substituents selected from $C_{(1-18)}$alkyl, $C_{(1-18)}$alkoxy, $C_{(1-18)}$alkylthio, aryl$C_{(1-18)}$alkoxy, oxo, hydroxy, halogen, CN, $COR^5$, $COOR^5$, $CONR_5R^6$, $NR^5COR^6$, $SO_2NR^5R^6$, $NR^5SO_2R^6$, $NR^5R^6$, mono to perfluoro-$C_{(1-4)}$alkyl and mono to perfluoro-$C_{(1-4)}$alkoxy;

X is O or S;

Y is a group of formula —$A^1$—$A^2$-$A^3$— in which $A^1$ and $A^3$ each represent a bond or a straight chain or branched $C_{(1-10)}$alkylene group and $A^2$ represents a bond or O, S, SO, $SO_2$, CO, C=$CH_2$, CH=CH , C≡C, CONH, NHCO, or $CR^5R^6$, providing that when $A^2$ is O, S, SO, $SO_2$ or CONH, $A^3$ contains at least two carbon atoms linking the $A^2$ group and the $CH_2$ group in formula (I);

$R^2$ is an aryl or heteroaryl group, optionally substituted by 1, 2, 3 or 4 substituents selected from the substituents hereinbefore defined for $R^1$, as well as aryl and aryl$C_{(1-4)}$alkyl, W is a bond and $R^7$ is hydrogen; or W is $SO_2$ or a bond; and $R^7$ is $R^1$ or a hydrocarbyl group which hydrocarbyl group may be optionally interupted within the carbon chain by a group selected from O, COO, OCO, CO, CONR$^8$, NR$^8$CO, NR$^8$CONR$^9$, NR$^8$COO, OCONR$^8$, and NR$^8$, and which hydrocarbyl group may also be optionally substituted by 1 or 2 substituents selected from mono to perfluoro-C$_{(1-4)}$alkyl, OR$^8$, COOR$^8$, CONR$^8$R$^9$, NR$^8$COR$^9$, NR$^8$CONR$^9$R$^{10}$, NR$^8$COOR$^9$, OCONR$^8$R$^9$, NR$_{11}$R$^{12}$ and R$^1$;

R$^5$ and R$^6$ are independently hydrogen or C$_{(1-20)}$alkyl, for instance C$_{(1-4)}$alkyl (e.g. methyl or ethyl);

R$^8$, R$^9$ and R$^{10}$ are independently selected from hydrogen, C$_{(1-20)}$alkyl (for instance C$_{(1-15)}$alkyl), (which may optionally be fluorinated, including up to perfluorinated on the terminal 1 to 3 carbon atoms), C$_{(1-20)}$alkenyl (preferably C$_{(12-18)}$alkenyl), aryl, arylC$_{(1-10)}$alkyl, C$_{(1-10)}$alkoxyC$_{(1-10)}$alkyl, or aryloxyC$_{(1-10)}$alkyl and in which an aryl group may have one or two substituents selected from halogen, C$_{(1-20)}$alkyl, C$_{(1-20)}$alkoxy, aryloxy and COOC$_{(1-20)}$alkyl; and R$^{11}$ and R$^{12}$ are independently selected from one of the values hereinbefore defined for R$^8$ and R$^9$ or R$^{11}$ and R$^{12}$ together with the nitrogen atom to which they are attached form a 5- to 7 membered ring optionally containing one or two further heteroatoms selected from oxygen, nitrogen and sulphur, and optionally substituted by one or two substituents selected from hydroxy, oxo, C$_{(1-4)}$alkyl, phenyl, or benzyl.

Preferably, Z is CH$_2$.

Representative examples of R$^1$ when an aryl group include phenyl and naphthyl. Representative examples of R$^1$ when a heteroaryl group include pyridyl, pyrimidyl, pyrazolyl, furyl, thienyl, thiazolyl, quinolyl, benzothiazolyl, pyridazolyl and pyrazinyl.

Preferably R$^1$ is a 5- or 6-membered, monocyclic heteroaryl group containing 1 or 2 nitrogen heteroatoms, preferably pyridyl, pyrimidyl or pyrazolyl, more preferably, pyrid-4-yl or pyrimid-5-yl and optionally substituted by 1 or 2 substituents preferably selected from arylC$_{(1-4)}$alkyl (e.g. benzyl), C$_{(1-8)}$alkyl (e.g. methyl or ethyl), halogen (e.g. chlorine), oxo, hydroxy, C$_{(1-4)}$alkoxy (e.g. methoxy) and arylC$_{(1-4)}$alkoxy (e.g. benzyloxy). More preferably, R$^1$ is pyrimid-5-yl or a 2-oxo-pyrimid-5-yl group, optionally substituted at N-1 by C$_{(1-8)}$alkyl (e.g. undecyl, methyl or ethyl), or a 2-C$_{(1-4)}$alkoxy- or arylC$_{(1-4)}$alkoxy-pyrimid-5-yl group.

Preferably, ZR$^1$ is 2-oxo-pyrid-4-ylmethyl, pyrimid-5-ylmethyl or 2-oxo-pyrimid-5-ylmethyl in which the 2-oxo-pyrimid-5-yl moiety is as hereinbefore defined.

Preferably X is S.

Preferred compounds of formula (I) include those in which Y is a bond, i.e. A$^1$, A$^2$ and A$^3$ each represent a bond. Other preferred examples of the groups A$^1$ and A$^3$ are straight chain C$_{(1-10)}$alkylene groups. When A$^2$ is other than a bond, A$^1$ is preferably a bond. Preferred examples of A$^2$ when other than a bond include CO, C=CH$_2$ and O, the CO group being especially preferred. Other preferred examples of Y are (CH$_2$)$_7$ and CO(CH$_2$)$_6$.

Representative examples of R$^2$ when an aryl group include phenyl and naphthyl. Representative examples of R$^2$ when a heteroaryl group include pyridyl, pyrimidinyl, pyrazolyl, furanyl, thienyl, thiazolyl, quinolyl, benzothiazolyl, pyridazolyl and pyrazinyl Preferably, R$^2$ is phenyl optionally substituted by 1, 2 or 3 substituents selected from halogen (e.g. chlorine or fluorine), C$_{(1-4)}$alkyl (e.g. methyl or ethyl) or C$_{(1-4)}$alkoxy (e.g. methoxy). Further optional substituents include phenyl and benzyl.

Representative examples of R$^2$YCH$_2$X include 4-fluorobenzylthiogroup, 4-chlorophenylheptylthio and 4-chlorophenyl-1-oxaheptylthio. Preferably, R$^2$YCH$_2$X is 4-fluorobenzylthio group.

Preferably W is a bond.

Representative examples of R$^7$ when a hydrocarbyl group include C$_{(1-20)}$alkyl, C$_{(2-20)}$alkenyl, C$_{(2-20)}$alkynyl, C$_{(3-6)}$cycloalkyl, C$_{(3-6)}$cycloalkylC$_{(1-5)}$alkyl, or C$_{(1-15)}$alkoxyC$_{(1-10)}$alkyl each of which may be optionally substituted by 1 or 2 substituents as hereinbefore defined.

Preferably, W is a bond and R$^7$ is C$_{(1-20)}$alkyl, especially C$_{(10-20)}$alkyl. Preferably, R$^7$ is also C$_{(1-10)}$alkyl, more preferably a C$_{(1-6)}$alkyl which is substituted by one or two substituents selected from hydroxy, C$_{(1-10)}$alkoxy (e.g. methoxy), COOC$_{(1-10)}$alkyl (e.g. COOCH$_3$, COOC$_2$H$_5$), CONR$^8$R$^9$, NR$^8$CONR$^9$R$^{10}$, NHCOR$^8$ (in which R$^8$, R$^9$ and R$^{10}$ is each independently C$_{(1-20)}$alkyl e.g. methyl). Further optional substituents include aryl, preferably phenyl which may be optionally substituted by COOC$_{(1-6)}$alkyl (e.g methyl) and heteroaryl (for instance pyridyl, imidazolyl, furanyl, thienyl and 2-oxo pyrrolidinyl). Preferred examples of the substituent NR$^{11}$R$^{12}$ include morpholino, piperidino or 2-oxo-pyrrolidino group.

A preferred sub-group of compounds of formula (I) are those in which W is a bond and R$^7$ is a phenyl or a phenylC$_{(1-8)}$alkyl group, for instance benzyl or phenethyl, substituted in the phenyl ring by 1 or 2 substituents selected from C$_{(6-12)}$alkyl (for instance hexyl and decyl), C$_{(6-12)}$alkoxy, COOH, COOC$_{(6-12)}$alkyl and CONHC$_{(6-12)}$alkyl. Alternatively, R$^7$ maybe heteroarylC$_{(1-8)}$alkyl, preferably heteroarylC$_{(1-3)}$alkyl in which the heteroaryl ring is monocyclic with 5 to 6 members and one or two heteroatoms selected from nitrogen, oxygen and sulphur, such as pyridyl, furanyl, thienyl and imidazolyl. A further preferred subgroup of compounds of formula (I) are those in which W is a bond and R$^7$ is a group of the formula (CH$_2$)$_n$BR$^{13}$ where n is an integer from 1 to 6, preferably 1 to 4, B is selected from NR$^{14}$CO, CONR$^{14}$, NR$^{14}$CONR$^{15}$, NR$^{15}$COO (in which R$^{14}$ and R$^{15}$ are independently selected from hydrogen or C$_{(1-6)}$alkyl, preferably hydrogen) and R$^{13}$ is C$_{(8-18)}$alkyl (which may optionally be fluorinated, including up to perfluorinated on the terminal 1 to 3 carbon atoms), C$_{(8-18)}$alkenyl, phenyl C$_{(1-6)}$alkyl and phenylC$_{(1-8)}$alkoxyC$_{(1-6)}$alkyl in which phenyl may be optionally substituted by halogen or C$_{(1-6)}$alkyl. Prefered examples of C$_{(8-18)}$alkyl are straight chains and include octyl, dodecyl and fatty alkyl groups such as lauryl and stearyl. Preferred values of C$_{(8-18)}$alkenyl include octadec-9-(Z)-en-1yl. Preferred examples of optionally substituted phenylC$_{(1-6)}$alkyl and phenylC$_{(1-8)}$alkoxyC$_{(1-6)}$alkyl include 4-fluorophenylhexyl, 4-pentylphenylethyl and 4-fluorophenylhexoxyethyl. Particularly preferred compounds of formula (I) are those in which R$^{12}$ is C$_{(12-18)}$alkyl or C$_{(12-18)}$alkenyl. Such a long, lipophilic substituent is found to be especially beneficial for enzyme inhibition When used herein, the term 'alkyl' and similar terms such as 'alkoxy' includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the term "hydrocarbyl" refers to a group having from 1 to 20 carbon atoms which may be in a straight chain or a branched chain and include a saturated carbocyclic ring having from 3 to 6 carbon atoms and which chain may contain unsaturation (double and/or triple carbon-carbon bonds).

When used herein, the term 'aryl' refers to, unless otherwise defined, a mono- or bicyclic aromatic ring system containing up to 10 carbon atoms in the ring system, for instance phenyl or naphthyl.

When used herein, the term 'heteroaryl' refers to a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring. Representative examples include pyridyl, pyridyl N-oxide, pyrimidyl, pyrazolyl, furyl, thienyl, thiazolyl, pyridazolyl and pyrazinyl, quinolyl and benzothiazolyl.

When used herein, the terms 'halogen' and 'halo' include fluorine, chlorine, bromine and iodine and fluoro, chloro, bromo and iodo, respectively. Compounds of formula (I) are inhibitors of Lp-PLA$_2$ and as such are expected to be of use in treating atherosclerosis and the other disease conditions noted elsewhere. Such compounds are found to act as inhibitors of Lp-PLA$_2$ in in vitro assays Particularly preferred compounds of formula (I) are
2-(4-Fluorobenzylthio)-5-((pyrimid-5-yl)methyl)pyrimidin-4-one;
1-Methyl-2-(4-fluorobenzyl)thio-5-(pyrimid-5-ylmethyl)pyrimidin-4-one;
1-(Tetradec-1-ylaminocarbonylmethyl)-2-(4-fluorobenzyl)thio-5-(pyrimid-5-ylmethyl)pyrimidin-4-one;
1-(N-(Dodec-1-yl)-N-methylaminocarbonylmethyl)-2-(4-fluorobenzyl)thio-5-(pyrimid-5-ylmethyl)pyrimidin-4-one; and
1-(N-Methyl-N-(dodec-1-yl)aminocarbonylmethyl)-2-(4-fluorobenzyl)thio-5-(2-methoxypyrimid-5-ylmethyl)pyrimidin-4-one.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase A$_2$ (Lp-PLA$_2$) and as such are expected to be of use in therapy, in particular in the treatment of atherosclerosis. In a further aspect therefore the present invention provides a compound of formula (I) for use in therapy. The compounds of formula (I) are inhibitors of lysophosphatidylcholine production by Lp-PLA$_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid peroxidation in conjunction with enzyme activity, for example in addition to conditions such as atherosclerosis and diabetes, other conditions such as rheumatoid arthritis, stroke, inflammatory conditions of the brain such as Alzheimer's Disease, myocardial infarction, reperfusion injury, sepsis, and acute and chronic inflammation. Further such conditions include various neuropsychiatric disorders such as schizophrenia (see Psychopharmacology Bulletin, 31, 159–165, 1995).

Further applications include any disorder that involves activated monocytes, macrophages or lymphocytes, as all of these cell types express Lp-PLA$_2$. Examples of such disorders include psoriasis.

Accordingly, in a further aspect, the present invention provides for a method of treating a disease state associated with activity of the enzyme Lp-PLA$_2$ which method involves treating a patient in need thereof with a therapeutically effective amount of an inhibitor of the enzyme. The disease state may be associated with the increased involvement of monocytes, macrophages or lymphocytes: with the formation of lysophosphatidylcholine and oxidised free fatty acids: with lipid peroxidation in conjunction with Lp PLA2 activity; or with endothelial dysfunction.

Compounds of the present invention may also be of use in treating the above mentioned disease states in combination with anti-hyperlipidaemic or anti-atherosclerotic or anti-diabetic or anti-anginal or anti-inflammatory or anti-hypertension agents. Examples of the above include cholesterol synthesis inhibitors such as statins, anti-oxidants such as probucol, insulin sensitisers, calcium channel antagonists, and anti-inflammatory drugs such as NSAIDs.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier. Suitable pharmaceutical compositions include those which are adapted for oral or parenteral administration or as a suppository.

Suitable pharmaceutical compositions include those which are adapted for oral or parenteral administration or as a suppository. Compounds of formula (I) which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 500 mg (and for parenteral administration contains preferably from 0.1 to 25 mg) of a compound of the formula (I). The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

Compounds of formula (I) may be conveniently prepared from readily available starting materials by adapting synthetic methodology well known in the art for the preparation and derivatisation of pyrimidones by a process.

Accordingly, in a first aspect, the present invention provides a process for preparing a compound of formula (I) which process comprises:

(a) treating a compound of formula (IIA):

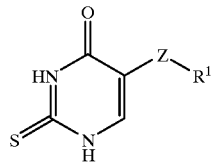

(IIA)

which $R^1$ and Z are as hereinbefore defined; with a compound of formula (III):

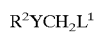 (III)

in which Y and $R^2$ are as hereinbefore defined and $L^1$ is a leaving group e.g. bromine or iodine; to give a compound of formula (IA):

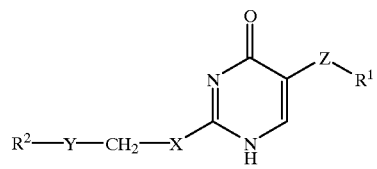

(IA)

in which Z, Y, $R^1$ and $R^2$ are as hereinbefore defined and X is S; or (b) treating a compound of formula (IV):

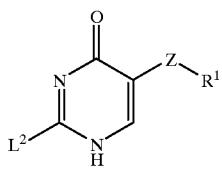

(IV)

in which Z and $R_1$ are as hereinbefore defined and $L^2$ is a leaving, group, e.g. halogen such as chlorine or bromine, alkylthio such as methylthio, or —NHNO$_2$, with a compound of formula (V):

 (V)

in which X, Y and $R^2$ are as hereinbefore defined; advantageously at an elevated temperature, in a solvent such as pyridine, to give a compound of formula (IA); and thereafter, and if so desired;

treating, a compound of formula (IA) form (a) or (b) above with a compound of formula (VI):

 (VI)

in which $L^1$, W and $R^7$ are as hereinbefore defined; to give a compound of formula (IB):

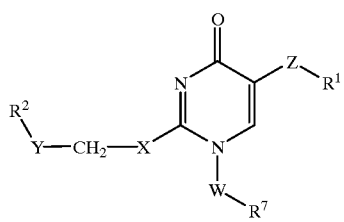

(IB)

in which X, Y, Z, $R_1$ and $R^2$ are as hereinbefore defined and $WR^7$ is as hereinbefore defined, other than —H; or (c) treating a compound of formula (IIB):

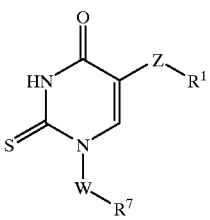

(IIB)

in which W is a bond, Z and $R^1$ are as hereinbefore defined and $R^7$ are as hereinbefore defined, other then H, with a compound of formula (III) as hereinbefore defined, to obtain a compound of formula (IB); and, thereafter and if so desired;

treating a compound of formula (IA) or (IB) in which X is S with a compound of formula (V):

 (VII)

in which Y and $R^2$ are as hereinbefore defined;

to give a corresponding compound of formula (I) in which X is O.

In the above process, the reaction of the compounds of formulae (IIA/B) and (III) is advantageously effected in the presence of a base such as sodium ethoxide, potassium carbonate, preferably in a solvent such as ethanol or dimethylformamide, or a base such as di-isopropyl ethylamine, preferably in a solvent such as dichloromethane.

In the above process, the reaction of the compounds of formulae (IA) and (VI) is advantageously effected at a temperature of 20–100 degrees C., in the presence of sodium hydride in a solvent such as dimethylformamide; or by the compound of formula (IA) being pre-treated with tributyl tin chloride in the presence of di-isopropylethylamine, for example in a dichloromethane solvent at reflux temperature, followed by addition of (VI) Alternatively, the compound of formula (IA) may be treated directly with a compound of formula (VI) and di-isopropylethylamine in a dichloromethane solvent at room temperature.

In the above processes, the reaction of the compounds of formulae (IA/IB) and (VII) is conveniently effected in the presence of pyridine at an elevated temperature, containing a catalytic amount of 4-dimethylaminopyridine.

A compound of formula (I) in which Z is a bond and $R^1$ represents halogen may be obtained by treating a compound of formula (VIII):

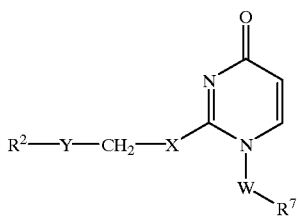

(VIII)

in which W, Y, $R^2$, and $R^7$ are as hereinbefore defined; with a halogenating agent, preferably with bromine to form a compound of formula (I) in which Z is a bond and $R^1$ is bromine, the reaction being advantageously effected in a solvent such as dichloromethane.

A compound of formula (IIA) may be obtained from a compound of formula (IX):

$$L^3OCOCH_2ZR^1 \quad (IX)$$

in which $L^3$ is $C_{(1-6)}$alkyl, for instance methyl, and Z and $R^1$ are as hereinbefore defined;
by the initial treatment thereof with a formylating agent such ethyl formate in the presence of a strong base such as potassium t-butoxide or sodium hydride, to give an enolate metal salt compound of formula (X):

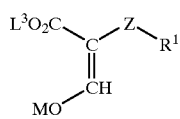

(X)

in which $L^3$, Z and $R^1$ are as hereinbefore defined and M is a metal cation, for instance sodium or potassium. Further treatment of a compound of formula (X) or a salt thereof with thiourea leads to a compound of formula (IIA). The two steps, starting form the compound of formula (IX) may conveniently be carried out as a "one-pot" process.

A compound of formula (IIB) may be obtained from a compound of formula (X), in a series of steps. In a first step, a compound of formula (X) is converted into the corresponding methyl enol ether by treatment with a methylating agent such as dimethyl sulphate in the presence of a base such as potassium carbonate. The corresponding carboxylic acid may then be obtained by conventional hydrolysis, for instance basic hydrolysis, using, for instance aqueous sodium hydroxide. The acid may then be converted into the corresponding acyl chloride, by treatment with oxalyl chloride, and the acyl chloride treated with potassium thiocyanate in a solvent such as acetonitrile, to give an intermediate of the formula (XI):

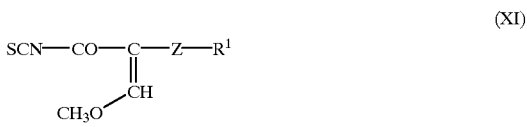

(XI)

in which $R^1$ and Z are as hereinbefore defined. Treatment of a compound of formula (XI) with a compound of formula (XII):

$$R^7WNH_2 \quad (XII)$$

in which $R^7$ is as hereinbefore defined and W is a bond, followed by the addition of an organic base such as sodium ethoxide, leads to a compound of formula (IIB).

A compound of formula (IV) in which $L^2$ is $N(H)NO_2$ can be conveniently prepared by reacting a compound of formula (X) above with a compound of formula (XIII):

(XIII)

in which the reaction is carried out in a conventional manner.

A compound of formula (VIII) may be obtained by treating a 3,3-dialkoxypropionic ester of the formula (XIV):

$$(L^3)O_2CCH_2CH(OL^3)_2 \quad (XIV)$$

in which $L^3$ is as hereinbefore defined;
with a thiourea of the formula (XV):

$$R^7NHCSNH_2 \quad (XV)$$

in which $R^7$ is as hereinbefore defined;
in the presence of sodium hydride followed by aqueous acetic acid.

Compounds of formula (I) in which $R^7$ comprises an amide moiety can be prepared from a precursor comprising an ester, for instance a methyl or ethyl ester, by first converting the ester to an acid, by hydrolysis and then treating the acid with an appropriate amine, under amide bond forming conditions. The acid may preferably be converted into an activated derivative, prior to amide bond formation.

Compounds of formula (I) in which $R^7$ comprises a urea moiety can be prepared from a precursor comprising an amine moiety, by treating the amine with an isocyanate, under urea forming conditions, well known in the art.

The present invention will now be illustrated by the following examples.

Intermediate A1

8-Bromo-1-(4-chlorophenyl)octan-1-one

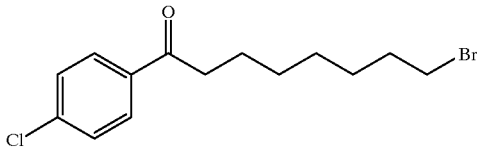

To a stirring suspension of aluminium chloride (33.6 g) in dry dichloromethane (474 ml) was added 8-bromo-n-octanoyl chloride (67.8 g) over 10 min. Chlorobenzene (123 ml) was then added over 10 min and the mixture allowed to stir at 25° C. for 74 h and stood for 64 h. The mixture was poured into ice/water (540 ml) and diethyl ether (1.3 L). The organic layer was removed and was washed with water (540 ml), saturated sodium hydrogen carbonate (540 ml), water (400 ml) and brine (400 ml) and dried over magnesium sulfate. Removal of the organic layer under reduced pressure and chromatography of the residue on silica gel using 5% ethyl acetate in hexane gave 8-bromo-1-(4-chlorophenyl) octan-1-one (35.5 g). $^1$H-NMR (CDCl$_3$) δ 1.2–1.6 (6H, m), 1.6–1.95 (4H, m), 2.95 (2H, t), 3,42 (2H, t), 7.43 (2H, m) and 7.90 (2H, m).

Intermediate A2

8-Hydroxy-1-(4-chlorophenyl)octan-1-one

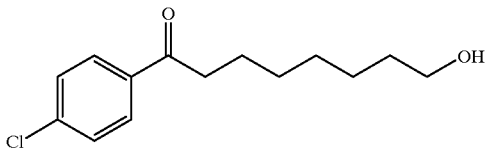

To 8-bromo-1-(4-chlorophenyl)octan-1-one (4.0 g) in ethanol (170 ml) was added 3% aqueous sodium hydroxide (70 ml). The mixture was heated at reflux for 3 h, cooled and evaporated to one third volume. Water (50 ml) and dichloromethane (100 ml) were added. The organic layer was separated and the aqueous layer was re-extracted with dichloromethane (2×50 ml). The combined extracts were washed with water (30 ml) and dried over magnesium sulphate. The solvent was removed under reduced pressure and the residue was crystallised from 40–60° C. petroleum ether to give 8-hydroxy-1-(4-chlorophenyl)octan-1-one (1.0 g). $^1$H-NMR (CDCl$_3$) δ 1.25–1.9 (10H, m), 2.94 (2H, t), 3.64 (2H, t), 7.43 (2H, m) and 7.89 (2H, m). (EI) Found M$^+$=254. C$_{14}$H$_{19}$ClO$_2$ requires 254.

Intermediate A3

8-Bromo-1-(4-methoxyphenyl)octan-1-one

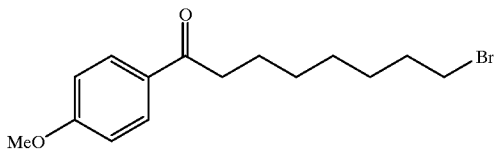

Prepared analogously to intermediate A1. $^1$H-NMR (CDCl$_3$) δ 1.3–1.95 (10H, m), 2.91 (2H, t), 3.41 (2H, t), 3.87 (3H, s), 6.93 (2H, m) and 7.94 (2H, m).

Intermediate A4

8-Bromo-1-(4-bromophenyl)octan-1-one

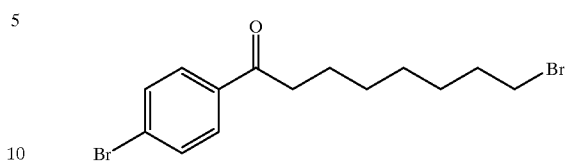

Prepared analogously to intermediate A1. $^1$H-NMR (CDCl$_3$) δ 1.25–1,.55 (6H, m), 1.65–1.95 (4H, m), 2.93 (2H, t), 3.41 (2H, t), 7.60 (2H, m) and 7.83 (2H, t).

Intermediate A5

8-Bromo-1-(2-thienyl)octan-1-one

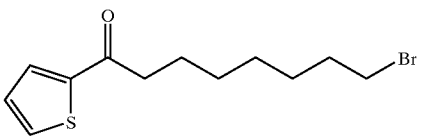

Prepared analogously to intermediate A1, except using SnCl$_4$ as catalyst in place of AlCl$_3$. $^1$H-NMR (CDCl$_3$) δ 1.3–1.55 (6H, m), 1.65–1.95 (4H, m), 2.90 (2H, t), 3.41 (2H, t), 3.41 (2H, t), 7.13 (1H, dd), 7.63 (1H, dd) and 7.70 (1H, dd).

Intermediate A6

8-Bromo-1-(2-furyl)octan-1-one

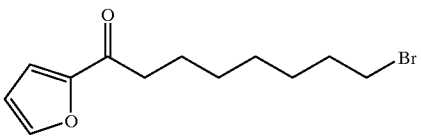

Prepared analogously to intermediate A1, except using SnCl$_4$ as catalyst in place of AlCl$_3$. $^1$H-NMR (CDCl$_3$) δ 1.3–1.55 (6H, m), 1.6–1.95 (4H, m), 2.82 (2H, t), 3.41 (2H, t), 6.53 (1H, m), 7.18 (1H, m) and 7.58 (1H, m).

Intermediate A7

8-Bromo-1-(4-methylphenyl)octan-1-one

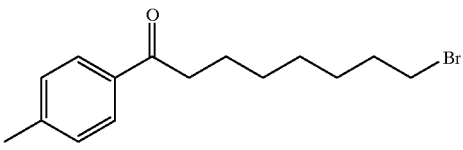

Prepared analogously to intermediate A1. $^1$H-NMR (CDCl$_3$) δ 1.3–1.55 (6H, m), 1.65–1.95 (4H, m), 2.41 (3H, s), 2.94 (2H, t), 3.41 (2H, t), 7.25 (2H, m) and 7.86 (2H, m).

Intermediate A8

8-Bromo-1-(4-fluorophenyl)octan-1-one

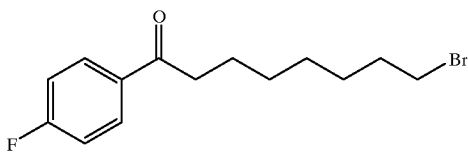

Prepared analogously to intermediate A1. ¹H-NMR (CDCl₃) δ 1.3–1.6 (6H, m), 1.6–1.95 (4H, m), 2.94 (2H, t), 3.41 (2H, t), 7.13 (2H, m) and 7.98 (2H, m).

Intermediate A9

8-Bromo-1-(4-methyl-1-naphthyl)octan-1-one

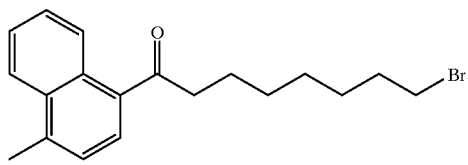

Prepared analogously to intermediate A1. ¹H-NMR (CDCl₃) δ 1.3–1.55 (6H, m), 1.7–1.95 (4H, m), 2.74 (3H, s), 3.03 (2H, t), 3.41 (2H, t), 7.32 (1H, m), 7.5–7.65 (2H, m), 7.76 (1H, d), 8.0–8.1 (1H, m) and 8.55–8.7 (1H, m).

Intermediate A10

1-Bromo-8-(2-thiazolinyl)octane

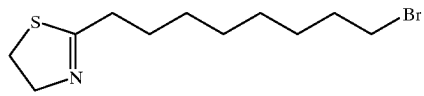

To a solution of 2-methyl-2-thiazoline (1.01 g) in dry tetrahydrofuran at −70° C. was added a solution of n-butyl lithium in hexanes (2.5M, 4.0 ml) dropwise over 10 min. After stirring at −70° C. for 2 h, 1,7-dibromoheptane (12.9 g) was added in one portion (temperature increased to −45° C.). The mixture was cooled again to −70° C. for 1 h and then allowed to warm to room temperature over 1 h. The mixture was cooled to 0° C. and water (10 ml) added, followed by dilute hydrochloric acid (to pH 2). The organic layer was separated and the aqueous layer extracted with diethyl ethyl (2×20 ml). The organic layers were combined and washed with water and brine and dried over magnesium sulfate. Evaporation under reduced pressure gave an oil that was chromatographed on silica gel using 40–60° C. petroleum ether:ethyl acetate 5:1 to give 1-bromo-8-(2-thiazolinyl)octane (1.06 g). ¹H-NMR (CDCl₃) δ 1.2–1.5 (6H, m), 1.5–1.75 (4H, m), 1.75–1.95 (2H, m), 2.50 (2H, t), 3.28 (2H, t), 3.40 (2H, t) and 4.21 (2H, dt).

Intermediate A11

1-Bromo-8-(2-pyridyl)octane

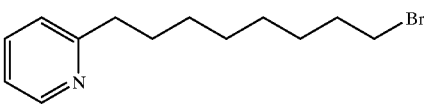

Prepared analogously to intermediate A10. ¹H-NMR (CDCl₃) δ 1.2–1.55 (8H, m), 1.6–1.95 (4H, m), 2.76 (2H, t), 3.41 (2H, t), 7.05–7.2 (2H, m), 7.5–7.65 (1H, m) and 8.52 (1H, m).

Intermediate A12

8-(3,4-Dichlorophenyl)oct-7-yn-1-ol

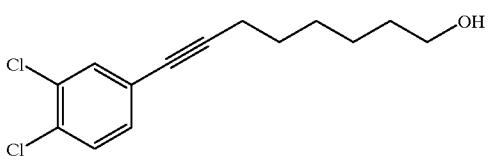

A mixture of 3,4-dichloroiodobenzene (2.16 g), oct-7-yn-1-ol (1.20 g), tetrakis (triphenylphosphine)palladium (0) (0.185 g), copper (I) iodide (0.046 g) and triethylamine (15 ml) was stirred at room temperature for 16 h. The solid was filtered off and the filtrate evaporated under reduced pressure. The residual oil was dissolved in ethyl acetate (15 ml) and washed with water (10 ml), 2M hydrochloric acid (2×10 ml) and brine (10 ml). Drying over magnesium sulfate and removal of the solvent under reduced pressure gave an oil that was purified by flash chromatography on silica gel using dichloromethane as eluent. This gave 8-(3,4-dichlorophenyl)oct-7-yn-1-ol (1.89 g). ¹H-NMR (CDCl₃) δ 1.2–1.75 (8H, m), 2.40 (2H, t), 3.66 (2H, t), 7.19 (1H, dd), 7.35 (1H, d) and 7.47 (1H, dd).

Intermediate A13

8-(3,4-Dichlorophenyl)octan-1-ol

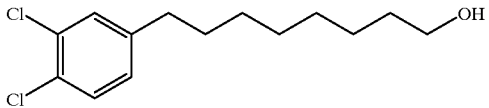

To a solution of 8-(3,4-dichlorophenyl)-oct-7-yn-1-ol (0.70 g) in methanol (20 ml) was added platinum dioxide (0.05 g) and the mixture reacted under an atmosphere of hydrogen (initial pressure 50 psi). After 1 h. the catalyst was filtered through Hyflo and washed with methanol. The combined methanol layers were evaporated under reduced pressure to give 8-(3,4-dichlorophenyl)octan-1-ol (0.69 g). ¹H-NMR (CDCl₃) δ 1.1–1.8 (12H, m), 2.55 (2H, t), 3.64 (2H, m), 6.99 (1H, dd) and 7.2–7.4 (2H, m).

Intermediate A14

8-Bromo-1-(3,4-dichlorophenyl)-1-octyne

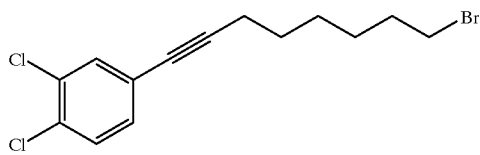

A solution of 8-(3,4-dichlorophenyl)-oct-7-yn-1-ol (0.52 g) in diethyl ether (2.5 ml) was treated with phosphorous tribromide (0.23 g) at 0° C. (ice/salt bath). The solution was stirred at 0–5° C. for 2 h and allowed to warm to room temperature. Aqueous sodium hydrogen carbonate solution was added. The aqueous layer was extracted with further diethyl ether (2×5 ml) and the combined organic layers were washed with brine (5 ml) and dried over magnesium sulfate. Removal of the solvent under reduced pressure gave an oil that was chromatographed on silica gel using dichloromethane as eluent. This gave 8-bromo-1-(3,4-dichlorophenyl)-1-octyne (0.25 g). $^1$H-NMR (CDCl$_3$) δ 1.35–1.7 (6H, m), 1.75–1.95 (2H, m), 2.33 (2H, t), 3.35 (2H, t), 7.13 (1H, dd), 7.27 (1H, d) and 7.40 (1H, d).

Intermediate A15

1-Bromo-8-(3,4-dichlorophenyl)octane

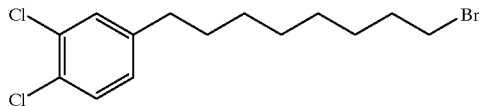

A solution of 8-(3,4-dichlorophenyl)octan-1-ol (0.66 g) in 48% hydrobromic acid (7 ml) was stirred under reflux for 2 h. Water (20 ml) and diethyl ether (20 ml) were added. The organic layer was separated and the aqueous layer reextracted with diethyl ether (10 ml). The combined organic extracts were washed with water (10 ml), sodium hydrogen carbonate solution (10 ml) and brine (10 ml) and dried over magnesium sulfate. The solution was treated with charcoal, filtered and evaporated under reduced pressure to give 1-bromo-8-(3,4-dichlorophenyl)octane (0.74 g). $^1$H-NMR (CDCl$_3$) δ 1.2–1.8 (12H, m), 2.55 (2H, t), 3.41 (2H, t), 7.00 (1H, dd), 7.25 (1H, dd) and 7.33 (1H, d).

Intermediate A16

8-(3-Chlorophenyl)oct-7-yn-1-ol

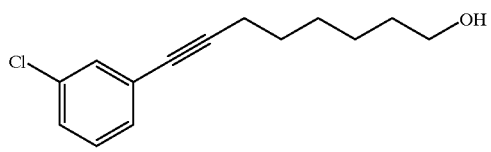

Prepared analogously to intermediate A12. $^1$H-NMR (CDCl$_3$) δ 1.25 (8H, m), 2.41 (2H, t), 3.66 (2H, t), 7.13–7.33 (3H, m) and 7.37 (1H, m)

Intermediate A17

8-(3-Chlorophenyl)octan-1-ol

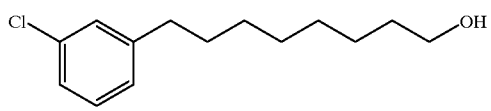

Prepared analogously to intermediate A13. $^1$H-NMR (CDCl$_3$) δ 1.1–1.8 (12H, m), 2.57 (2H, t), 3.64 (2H, t), 7.0–7.4 (4H, m)

Intermediate A18

1-Bromo-8-(3-chlorophenyl)octane

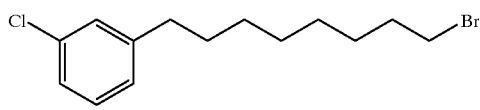

Prepared analogously to intermediate A15. $^1$H-NMR (CDCl$_3$) δ 1.05–1.9 (12H, m), 2.50 (2H, t), 3.33 (2H, t) and 6.9–7.25 (4H, m).

Intermediate A19

8-(4-Acetylphenyl)octan-1-ol

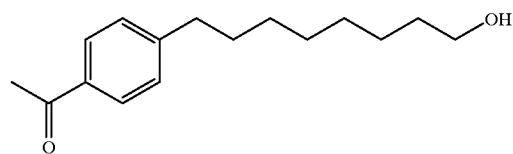

Prepared analogously to intermediate A13. $^1$H-NMR (CDCl$_3$) δ 1.2–1.8 (12H, m), 2.59 (3H, s), 2.68 (2H, t), 3.63 (2H, t) 7.25 (2H, m) and 7.88 (2H, m)

Intermediate A20

1-Bromo-8-(4-acetylphenyl)octane

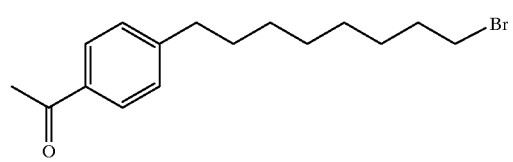

Prepared analogously to intermediate A15. $^1$H-NMR (CDCl$_3$) δ 1.2–1.75 (10H, m), 1.85 (2H, m), 2.59 (3H, s), 2.67 (2H, m), 3.40 (2H, t), 7.2–7.3 (2H, m) and 7.88 (2H, m).

Intermediate A21

1-Bromo-8-(4-fluorophenyl)octane

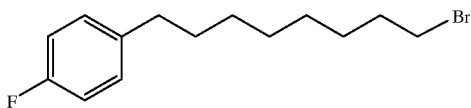

Triethylsilane (30.5 g, 260 mmol) was added dropwise to 8-bromo-1-(4-fluorophenyl)octan-1-one (230 ml, 105 mmol) over 20 min, with cooling to keep the temperature at ca 30° C. After 2 hours stirring, a further 3.1 g (27 mmol) triethylsilane was added, and reaction continued for an additional 2 hours. The mixture was poured into ice-water (200 ml) and ether (300 ml), then the organic layer was washed with aqueous sodium hydroxide. dried and evaporated, finally at 65° C./0.01 mm. The residue was filtered through silica gel, eluting with petroleum ether, then distilled, collecting the fraction at 122–140° C./0.5 mm (24.2 g). $^1$H-NMR (CDCl$_3$) δ 1.2–1.7 (10H, m), 1.85 (2H, m), 2.57 (2H, t), 3.40 (2H, t), 6.9–7.05 (2H, m) and 7.05–7.2 (2H, m).

Intermediate A22

1-Bromo-8-(4-methoxyphenyl)octane

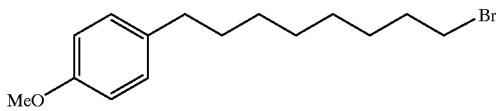

Intermediate A23

1-Bromo-8-(4-pyridyl)octane

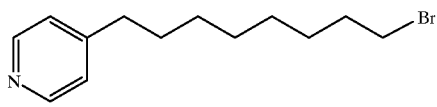

Prepared analogously to intermediate A10. $^1$H-NMR (CDCl$_3$) δ 1.2–1.95 (12H, m), 2.48 (2H, t), 3.42 (2H, t), 7.11 (2H, d) and 8.47 (2H, m).

Intermediate A24

1-Bromo-8-(4-chlorophenyl)octane

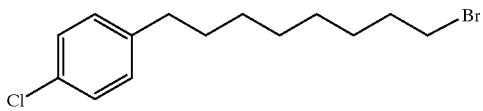

Prepared analogously to intermediate A21. $^1$H-NMR (CDCl$_3$) δ 1.2–1.5 (8H, m), 1.5–1.7 (2H, m), 1.75–1.95 (2H, m), 2.56 (2H, t), 3.40 (2H, t), 7.08 (2H, m) and 7.23 (2H, m).

Intermediate A25

1-Bromo-6-(4-chlorobenzyloxy)hexane

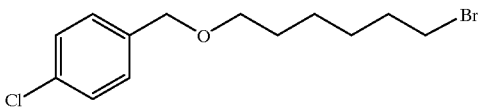

Sodium hydride (60%, 0.39 g) was added to a mixture of 6-bromohexanol (1.78 g) and 4-chlorobenzyl bromide (2.02 g) in dry tetrahydrofuran (150 ml). The mixture was stirred at 25° C. for 5 h and poured into 1M hydrochloric acid. Extraction with diethyl ether (3×), and washing the combined extracts with water and brine gave a solution that was dried over magnesium sulfate and evaporated under reduced pressure. The residue so obtained was chromatographed on silica gel using 40–60° C. petroleum ether to 10% diethyl ether in 40–60° C. petroleum ether as eluents. This gave 1-bromo-6-(4-chlorobenzyloxy)hexane (1.7 g). $^1$H-NMR (CDCl$_3$) δ 1.3–1.55 (4H, m), 1.55–1.7 (2H, m), 1.75–1.95 (2H, m), 3.35–3.55 (4H, m), 4.46 (2H, s) and 7.2–7.4 (4H, m).

Intermediate A26

1-Bromo-6-(4-fluorobenzyloxy)hexane

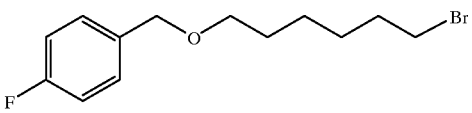

Prepared analogously to intermediate A25. $^1$H-NMR (CDCl$_3$) δ 1.3–1.5 (4H, m), 1.6 (2H, m), 1.9 (2H, m), 3.39 (2H, t), 3.45 (2H, t), 4.44 (2H, s), 7.0–7.1 (2H, m), 7.2–7.4 (2H, m).

Intermediate A27

1-Bromo-6-benzyloxyhexane

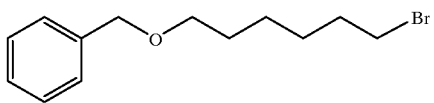

Intermediate A28

1-Bromo-7-phenoxyheptane

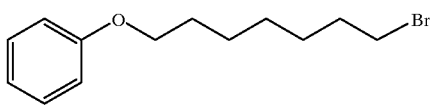

To a mixture of phenol (0.58 g) and 1,7-dibromoheptane (4.76 g) in dimethylformamide (5 ml) was added potassium carbonate (4.3 g) and the mixture was heated at 80° C. for 6 h. The mixture was cooled and the solvent was removed under reduced pressure. Toluene (10 ml) was added and removed under reduced pressure. The residue was chromatographed on silica gel using hexane as eluent. This gave 1-bromo-7-phenoxyheptane (1.15 g). $^1$H-NMR (CDCl$_3$) δ 1.3–1.7 (6H, m), 1.7–2.1 (4H, m), 3.41 (2H, t), 3.95 (2H, t), 6.8–7.0 (3H, m) and 7.2–7.4 (2H, m).

Intermediate A29

1-Bromo-7-(4-chlorophenoxy)heptane

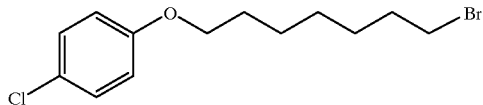

Prepared analogously to intermediate A28. $^1$H-NMR (CDCl$_3$) δ 1.3–1.6 (6H, m), 1.7–2.0 (4H, m), 3.41 (2H, t), 3.91 (2H, t), 6.75–6.9 (2H, m) and 7.15–7.3 (2H, m).

Intermediate A30

1-Bromo-7-(4-chlorophenylthio)heptane

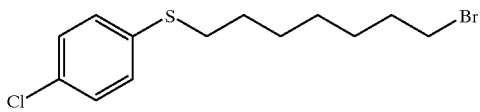

To 1,7-dibromoheptane (23 g) and potassium carbonate (10 g) in dry dimethylformamide (100 ml) was added 4-chlorothiophenol (4.3 g) dropwise with stirring at 25° C. After 6 h, the mixture was filtered and the solvent removed under reduced pressure. Chromatography of the residue on silica gel using hexane as eluent gave 1-bromo-7-(4-chlorophenylthio)heptane (9.6 g). $^1$H-NMR (CDCl$_3$) δ 1.2–1.55 (6H, m), 1.55–1.75 (2H, m), 1.8–2.0 (2H, m), 2.89 (2H, t), 3.40 (2H, t) and 7.2–7.4 (4H, m).

Intermediate A31

1-Bromo-7-(4-chlorophenylsulfinyl)heptane

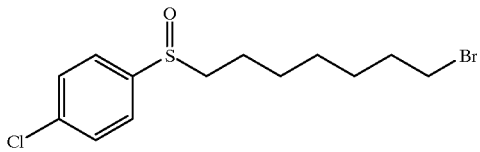

A solution of 1-bromo-7-(4-chlorophenylthio)heptane (0.80 g) in dichloromethane (10 ml) was cooled to −78° C. (cardice/acetone) and a slurry of metachloroperbenzoic acid (60%, 0.72 g) in dichloromethane (5 ml) was added over 20min. After 40 min, the reaction was allowed to warm to room temperature and shaken with aqueous sodium sulfite/sodium hydrogen carbonate solution. The organic layer was dried over magnesium sulfate and evaporated under reduced pressure. The residue was chromatographed on silica gel using dichloromethane to 4% methanol in dichloromethane as eluents to give 1-bromo-7-(4-chlorophenylsulfinyl)heptane (0.43 g). $^1$H-NMR (CDCl$_3$) δ 1.2–2.0 (10H, m), 2.77 (2H, t), 3.39 (2H, t) and 7.4–7.7 (4H, m).

Intermediate A32

1-Bromo-7-(4-chlorophenylsulfonyl)heptane

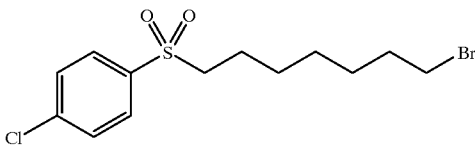

To a solution of 1-bromo-7-(4-chlorophenylthio)heptane (1.19 g) in dichloromethane (20 ml) at −20° C. was added metachloroperbenzoic acid (60%, 2.23 g) portionwise over 15 min. The mixture was allowed to warm to room temperature over 1 h and was shaken with aqueous sodium sulfite/sodium hydrogen carbonate solution. The organic layer was dried over magnesium sulfate and evaporated under reduced pressure. The residue was chromatographed on silica gel using 50:50 hexane:dichloromethane as eluent to give 1-bromo-7-(4-chlorophenylsulfonyl)heptane (1.17 g). $^1$H-NMR (CDCl$_3$) δ 1.2–2.0 (10H, m), 3.07 (2H, m), 3.38 (2H, t), 7.5–7.6 (2H, m) and 7.8–7.9 (2H, m).

Intermediate A33

1-Bromo-7-phenylthioheptane

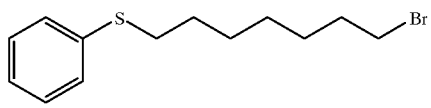

Prepared analogously to intermediate A30. $^1$H-NMR (CDCl$_3$) δ 1.2–1.55 (6H, m), 1.6–1.75 (2H, m), 1.75–1.95 (2H, m), 2.91 (2H, t), 3.40 (2H, t) and 7.1–7.4 (5H, m).

Intermediate A34

1-Bromo-7-phenylsulfinylheptane

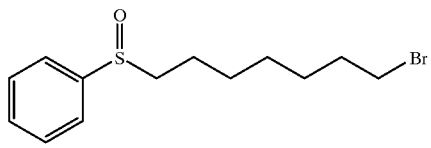

Prepared analogously to intermediate A31. $^1$H-NMR (CDCl$_3$) δ 1.2–1.95 (10H, m), 2.91 (2H, t), 3.40 (2H, m) and 7.1–7.4 (5H, m).

Intermediate A35

1-Bromo-7-phenylsulfonylheptane

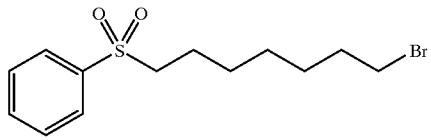

Prepared analogously to intermediate A32. $^1$H-NMR (CDCl$_3$) δ 1.2–2.0 (1H, m), 3.09 (2H, m), 3.38 (2H, t), 7.5–7.8 (3H, m) and 7.85–8.0 (2H, m).

Intermediate A36

8-Bromo-1-(4-chlorophenyl)-1-hydroxyoctane

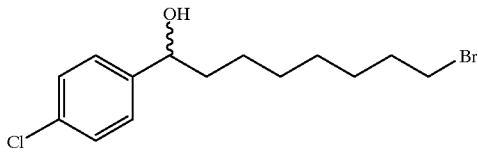

To a solution of 8-bromo-1-(4-chlorophenyl)octan-1-one (0.95 g) in industrial methylated spirit (10 ml) was added sodium borohydride (0.115 g) at −10° C. After stirring for 1 h, glacial acetic acid (0.2 g) was added and the mixture was poured into water (60 ml) and extracted with diethyl ether. The diethyl ether layer was washed with brine and dried over magnesium sulfate. Removal of the solvent under reduced pressure gave an oil that was chromatographed on silica gel using dichloromethane as eluent. This gave 8-bromo-1-(4-chlorophenyl)-1-hydroxyoctane (0.70 g). $^1$H-NMR (CDCl$_3$) δ 1.15–1.95 (12H, m), 3.40 (2H, t), 4.65 (1H, t) and 7.2–7.4 (4H, m).

Intermediate A37

9-Bromo-2-(4-fluorophenyl)-1-nonene

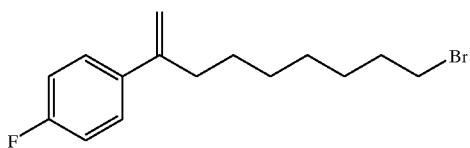

To a solution of butyl lithium (2.5M. 3.2 ml) in anhydrous tetrahydrofuran (75 ml) was added triphenylmethylphosphonium bromide (2.86 g) in portions over 10 min. The mixture was stirred at 25° C. for 3 h and a solution of 8-bromo-1-(4-fluorophenyl)octan-1-one (1.20 g) in dry tetrahydrofuran (15 ml) added dropwise over 5 min. After stirring at 25° C. for 1 h, the mixture was heated at reflux for 24 h. The mixture was evaporated under reduced pressure and partitioned between diethyl ether (70 ml) and water (4×30 ml). The organic layer was washed with brine and dried over magnesium sulfate. Removal of the solvent under reduced pressure gave an oil that was chromatographed on silica gel using 5% diethyl ether in hexane. This gave 9-bromo-2-(4-fluorophenyl)-1-nonene (0.75 g). $^1$H-NMR (CDCl$_3$) δ 1.2–1.55 (8H, m), 1.80 (2H, m), 2.46 (2H, t), 3.39 (2H, t), 5.03 (1H, bs), 5.20 (1H, bs), 7.03 (2H, m) and 7.3–7.45 (2H, m).

Intermediate A38

1-(3-Chlorophenyl)hex-1-yn-6-ol

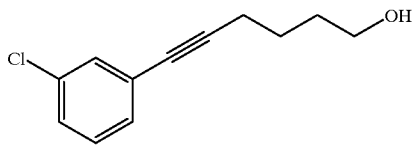

Prepared analogously to intermediate A12. $^1$H-NMR (CDCl$_3$) δ 1.6–1.85 (4H, m), 2.45 (2H, bt), 3.71 (2H, t), 7.15–7.33 (3H, m) and 7.37 (1H, m).

Intermediate A39

6-(3-Chlorophenyl)hexan-1-ol

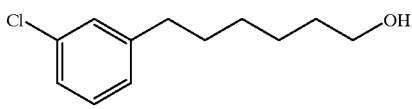

Prepared analogously to intermediate A13. $^1$H-NMR (CDCl$_3$) δ 1.2–1.8 (8H, m), 2.58 (2H, t), 3.64 (2H, t) and 7.0–7.3 (4H, m).

Intermediate A40

1-Bromo-6-(3-chlorophenyl)hexane

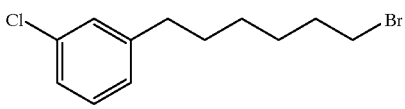

Prepared analogously to intermediate A15. $^1$H-NMR (CDCl$_3$) δ 1.2–1.95 (8H, m), 2.59 (2H, t), 3.40 (2H, t) and 7.0–7.3 (4H, m)

Intermediate A41

9-Bromo-1-(4-chlorophenyl)nonan-1-one

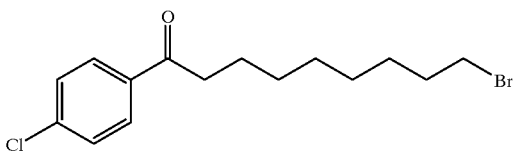

9-Bromononanoyl chloride was obtained from the carboxylic acid (reference 12) by treatment with thionyl chloride. 9-Bromo-1-(4-chlorophenyl)nonan-1-one was prepared analogously to intermediate A1. $^1$H-NMR (CDCl$_3$) δ 1.2–2.0 (12H, m), 2.95 (2H, t), 3.41 (2H, t), 7.44 (2H, m) and 7.90 (2H, m).

Intermediate A42

N-(6-(4-Fluorophenyl)hexyl)-2-bromoacetamide

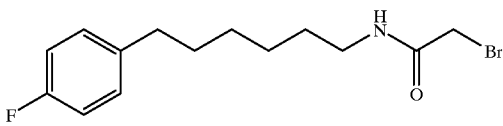

To a solution of 6-(4-fluorophenyl)-1-hexylamine (21.8 g) in dry dichloromethane (200 ml) at 0° C. under an argon atmosphere was added diisopropylethylamine (14.4 g) followed by broimoacetyl bromide (22.5 g) over 30min whilst maintaining the temperature between 0–5° C. The resulting orange solution was stirred at 0–5° C. for 45 min and evaporated to dryness. The residue was mixed with diethyl ether and the hydrobromide salt filtered off. The filtrate was evaporated under reduced pressure and the residue was chromatographed on silica gel using 5:1 to 3:2 40–60° C.

petroleum ether:ethyl acetate as eluents. This gave a yellow oil that was triturated with 40–60° C. petroleum ether, filtered and dried to give N-(1-(4-fluorophenyl)-hexyl) bromoacetamide (24.8 g). $^1$H-NMR (CDCl$_3$) δ 1.25–1.45 (4H, m), 1.45–1.75 (4H, m), 2.57 (2H, t), 3.28 (2H, q), 3.88 (2H ,s), 6.5 (1H, bs), 6.85–7.05 (2H, m) and 7.05–7.2 (2H, m).

Intermediate A43

1-Bromo-4-(3-phenylpropyloxy)butane

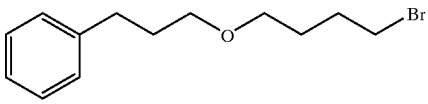

Prepared as in reference 13.

Intermediate A44

6-(4-Chlorobenzoylamino)hexan-1-ol

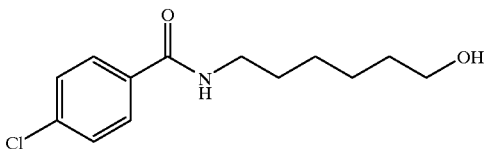

To a solution of 6-amino-1-hexanol (12.9 g) and diisopropylethylamine (11.9 g) in dry dichloromethane (100 ml) at 5° C. was added 4-chlorobenzoyl chloride (16.1 g) in dry dichloromethane at such a rate to maintain the temperature below 10° C. After stirring for 16 h, the mixture was poured into water and filtered. The solid was washed with water, 2M hydrochloric acid (150 ml), water, dichloromethane and was dried under reduced pressure to give 6-(4-chlorobenzoylamino)hexan-1-ol (19.2 g). $^1$H-NMR (d$_6$-DMSO) δ 1.25–1.65 (8H, m), 3.24 (2H, q), 3.38 (2H, t), 7.52 (2H, m), 7.84 (2H, m) and 8.54 (1H, bt)

Intermediate A45

1-Bromo-6-(4-chlorobenzoylamino)hexane

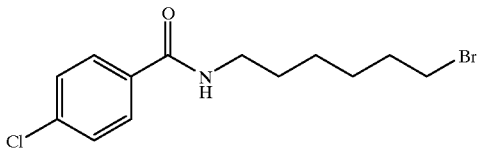

6-(4-Chlorobenzoylamino)hexan-1-ol (17.0 g) was refluxed in 48% hydrobromic acid (260 ml) for 2.5 h. The mixture was cooled and added to water (450 ml) and diethyl ether (450 ml). The organic layer was washed with saturated sodium bicarbonate (450 ml) and brine (450 ml) and was dried over magnesium sulfate. Evaporation followed by recrystallisation from diethyl ether gave 1-bromo-6-(4-chlorobenzoylamino)hexane (8.6 g). $^1$H-NMR (CDCl$_3$) δ 1.3–2.0 (8H, m), 3.35–3.55 (4H, m), 6.15 (1H, bs), 7.40 (2H, m) and 7.70 (2H, m).

Intermediate B1

Ethyl 3-(5-pyrimidinyl)acrylate

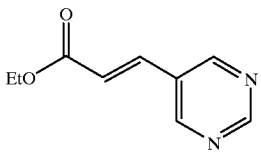

A mixture of 5-bromopyrimidine (5.93 g), ethyl acrylate (5.08 g), palladium acetate (0.112 g), triphenyl phosphine (0.23 g) and triethylamine (4.5 g) was stirred at 150° C. in a pressure vessel for 6 hours. After cooling overnight, water (50 ml) was added to the dark residue, and the product was extracted into toluene. Drying, charcoaling and evaporation gave a pale oil, which was triturated with pet. ether to obtain ethyl 3-(5-pyrimidyl)acrylate (4.78 g). $^1$H-NMR (CDCl$_3$) δ 1.36 (3H, t), 4.27 (2H, q), 6.59 (1H, d), 7.62 (1H, d), 8.88 (2H, s), 9.20 (1H, s).

Intermediate B2

Ethyl 3-(5-pyrimidyl)propionate

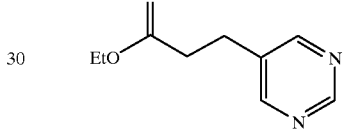

To a solution of ethyl 3-(5-pyrimidyl)acrylate (4.75 g) in ethanol (90 ml) was added 5% palladium on charcoal (0.2 g). The mixture was hydrogenated at an initial pressure of 50 psi, then filtered to remove catalyst and the solvent evaporated. Water was added, and the product extracted into ether. Drying, charcoaling and evaporation gave ethyl 3-(5-pyrimidyl)propionate (2.3 g) as a yellow oil. $^1$H-NMR (CDCl$_3$) δ 1.23 (3H, t), 2.69 (2H, t), 2.96 (2H, t), 4.14 (2H, q), 8.635 (2H, s) and 9.09 (1H, s).

Intermediate B3

Ethyl 2-formyl-3-(5-pyrimidyl)propionate

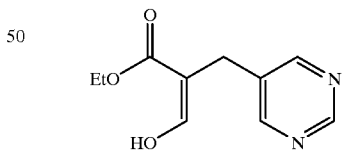

A mixture of ethyl 3-(5-pyrimidyl)propionate (2.28 g) and ethyl formate (1.41 ml) dissolved in dry dimethoxyethane (5 ml) was added dropwise over 30 min to a suspension of sodium hydride (60%, 4.0 g) in DME (5 ml) under nitrogen, keeping the temperature below 0° C. Stirring was continued for a further 24 h, then the mixture was poured onto ice and washed with ether. The aqueous layer was adjusted to pH 7, then evaporated and the residue extracted with acetone. Filtration and evaporation gave crude product, which was taken up in ethyl acetate, charcoaled, dried and evaporated to give ethyl 2-formyl-3-(5-pyrimidyl)propionate. Like other compounds of this type, this proved difficult to characterise and was used without further purification.

Intermediate B4

3-(5-Pyrimidyl)acrylic acid

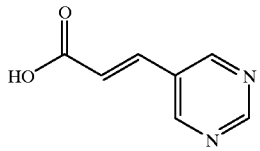

A mixture of 5-bromopyrimidine (100 g), acrylic acid (48 g), triphenylphosphine (2.5 g) and palladium II acetate (0.1 g) was refluxed in tri-n-butylamine (260 ml) with overhead stirring for 4.5 h at 145–160° C. The mixture was cooled and a 10% solution of potassium carbonate (2 L) added followed by dichloromethane (500 mL). The organic layer was separated and the aqueous phase extracted with diethyl ether (3×300 ml). The aqueous layer was brought to pH 3 with concentrated hydrochloric acid (ice-cooling) and the solid so formed was filtered and dried in vacuo to give 3-(5-pyrimidyl)acrylic acid (35 g). $^1$H-NMR (d$_6$-DMSO) δ 6.82 (1H, d), 7.60(1H, d) and 9.15(3H, 2xs)

Intermediate B5

Methyl 3-(5-pyrimidinyl)acrylate

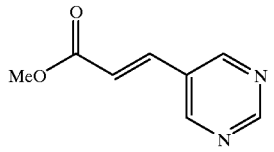

3-(5-Pyrimidyl)acrylic acid (100 g) was added to a mixture of dry methanol (2 L) and 4M hydrogen chloride in dioxan (445 ml) and allowed to stir at 60° C. under argon for 18 h. The mixture was cooled, and the solvent removed under reduced pressure. The residue was partitioned between dichloromethane (500 ml) and was washed with saturated sodium bicarbonate (300 ml). The aqueous layer was extracted with dichloromrethane and the combined dichloromethane layers were dried over magnesium sulfate and evaporated in vacuo to give methyl 3-(5-pyrimidinyl)acrylate (85 g). $^1$H-NMR (d$_6$-DMSO) δ 3.82(3H, s), 7.03 (1H, d), 7.75(1H, d) and 9.28(3H, s).

Intermediate B6

Methyl 3-(5-pyrimidyl)propionate

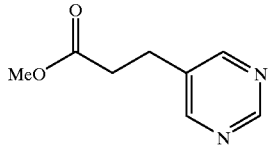

To a solution of methyl 3-(5-pyrimidyl)acrylate (85 g) in glacial acetic acid was added 10% palladium on charcoal (11.3 g) and ammonium formate (74.2 g) under argon. The mixture was heated at 110° C. for 20 min, cooled and the solvent removed in vacuo. The resulting oil was dissolved in dichloromethane (1.5 L) and washed with saturated sodium bicarbonate (750 ml). The aqueous layer was extracted with further dichloromethane (200 ml), the organic layers were combined and dried over magnesium sulfate. Removal of the solvent under reduced pressure gave an oil. This was distilled under reduced pressure to give methyl 3-(5-pyrimidyl)propionate (26 g). $^1$H-NMR (CDCl$_3$) δ 2.69(2H, t), 2.97(2H, t), 3.70(3H, s), 8.65(2H, s) and 9.12(1H, s).

Intermediate B7

Methyl 2-(5-pyrimidyl)methyl)-3-methoxyacrylate

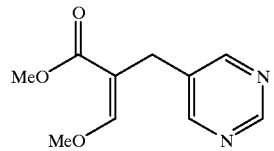

A mixture of methyl 3-(5-pyrimidyl)propionate (13.1 g) and methyl formate (7.1 ml) dissolved in dry dimethoxyethane (20 ml) was added portionwise to a suspension of sodium hydride (60%, 4.0 g) in DME (10 ml) under argon. Reaction initiated rapidly and was stirred for a further 2 h, diluted with dry diethyl ether (50 ml) and filtered. The solid so separated was washed with further diethyl ether (50 ml) and was dried in vacuo to give a solid that was dissolved in dry dimethyl formamide (50 ml) and potassium carbonate (11.3 g) added under argon. A solution of dimethyl sulfate (7.0 ml) was, then added over 1 hour. The mixture was stirred for 18 h and the solvent removed in vacuo. The residue was partitioned between ethyl acetate (200 ml) and water (100 ml). The aqueous layer was re-extracted with ethyl acetate (2×100 ml) and the combined ethyl acetate layers washed with brine (50 ml) and dried over sodium sulfate. The solvent was removed in vacuo to give methyl 2((5-pyrimidyl)methyl)-3-methoxyacrylate (9.1 g).

Intermediate B8

2-(5-Pyrimidyl)methyl)-3-methoxyacrylic acid

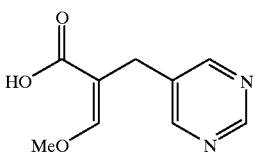

To methyl 2-((5-pyrimidyl)methyl)-3-methoxyacrylate (9.0 g) was added, with stirring, a solution of sodium hydroxide (3.5 g) in water (43 ml) at RT under argon. After 20 h, the pH of the solution was brought to 3.5 with concentrated hydrochloric acid. Sonication of the oil so formed gave 2-((5-pyrimidyl)methyl)-3-methoxyacrylic acid (5.4 g) as a pale yellow solid.

Intermediate B9

5-(Pyrimid-5-ylmethyl)-2-thiouracil

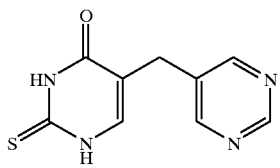

Sodium (0.25 g) was dissolved in ethanol (5 ml), thiourea (0.77 g) added, and the mixture stirred under reflux for 1 hour. A solution of ethyl 2-formyl-3-(5-pyrimidyl)propionate (1.99 g) in ethanol (5 ml) was added slowly, and reflux continued for 18 hours. The solvent was evaporated, and the residue taken up in water and washed with dichloromethane. The aqueous solution was acidified to pH 5, and the precipitate filtered off, washed with water and dried to obtain 5-(pyrimid-5-ylmethyl)-2-thiouracil (0.71 g). $^1$H-NMR (d6-DMSO) δ 3.58 (2H, s), 7.54 (1H, s), 8.70 (2H, s) and 9.02 (1H, s). MPt 265–6° C.

Intermediate B10

5-((1-Benzyl-2-oxo-pyrid-4-yl)methyl)-2-thiouracil

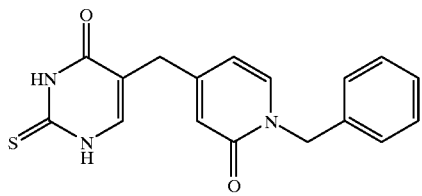

Prepared from methyl 2-(1-benzyl-2-oxo-pyrid-4-yl)methyl)-3-hydroxyacrylate (reference 7) analogously to intermediate B9. $^1$H-NMR (d6-DMSO) δ 5.04 (2H, s), 6.15 (1H, dd), 6.21 (1H, bs), 7.2–7.4 (5H, m), 7.45 (1H, s) and 7.67 (1H, d); (EI) M=325. $C_{17}H_{15}N_3O_2S$ requires 325.

Intermediate B11

5-((1-Methyl-2-oxo-pyrid-4-yl)methyl)-2-thiouracil

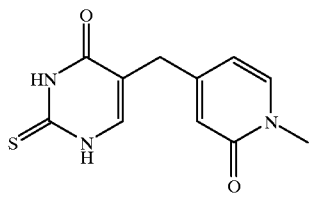

Prepared from methyl 2-(1-methyl-2-oxo-pyrid-4-yl)methyl)-3-hydroxyacrylate (reference 7) analogously to intermediate B9. $^1$H-NMR (CD$_3$OD) δ 3.50,3.51 (5H, 2xs), 6.32 (1H, dd), 6.40 (1H, bs), 7.35 (1H, s) and 7.54 (1H, d).

Intermediate B12

5-((2,3-Dimethylpyrid-5-yl)methyl)-2-thiouracil

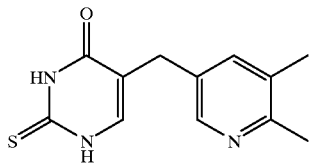

Prepared analogously to intermediate B9. $^1$H-NMR (d6-DMSO) δ 2.19 (3H, s), 2.35 (3H, s), 7.36 (2H, m) and 8.13 (1H, bs).

Intermediate B13

5-(Fur-2-ylmethyl)-2-thiouracil

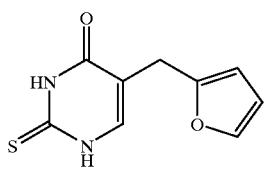

Prepared analogously to intermediate B9. $^1$H-NMR (d$_6$-DMSO) δ 3.58 (2H, s), 6.11 (1H, m), 6.35 (1H, m), 7.27 (1H, s), 7.52 (1H, m), 12 41 (2H, br, m). Mpt 205–7° C. (dec)

Intermediate B14

5-(Pyrazin-2-ylmethyl)-2-thiouracil

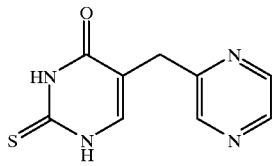

Prepared from methyl 3-(2-pyrazinyl)propionate (reference 10) analogously to intermediate B9. $^1$H-NMR (d$_6$-DMSO) δ 3.77 (2H, s), 7.48 (1H, s), 8.46 (1H, d), 8.51 (1H, t) and 8.59 (1H, d). Mpt 265–7° C. (dec)

Intermediate B15

5-(Fur-3-ylmethyl)-2-thiouracil

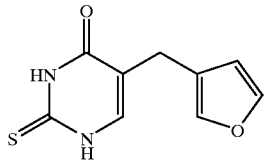

Prepared from methyl 3-(3-furyl)propionate (reference 9) analogously to intermediate B9. $^1$H-NMR (d6-DMSO) δ 3.33 (2H, s), 6.38 (1H, m), 7.19 (1H, s) 7.47 (1H, m), 7.56 (1H, m). Mpt 197–9° C. (dec)

Intermediate B16

5-(Quinolin-3-ylmethyl)-2-thiouracil

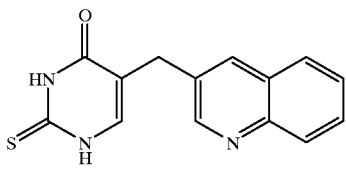

Prepared analogously to intermediate B9. $^1$H-NMR (d6-DMSO) δ 3.77 (2H, s), 7.54 (2H, m), 7.71 (1H, m), 7.94 (2H, m), 8.14 (1H, m), 8.84 (1H, m) Mpt 274–9° C.

Intermediate B17

5-(2-(Pyrid-4-yl)ethyl)-2-thiouracil

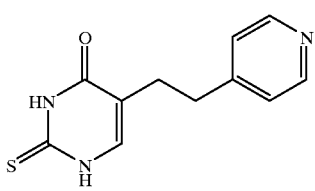

Prepared analogously to intermediate B9. $^1$H-NMR (d6-DMSO) δ 2.53 (2H, t), 2.77 (2H, t), 7.20 (3H, m) and 8.45 (2H, m). MPt 265–7° C. (dec)

Intermediate B18

5-(Pyrid-2-ylmethyl)-2-thiouracil

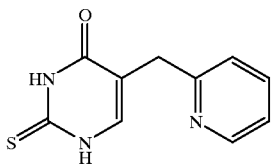

Prepared as in reference 2.

Intermediate B19

5-(Pyrid-3-ylmethyl)-2-thiouracil

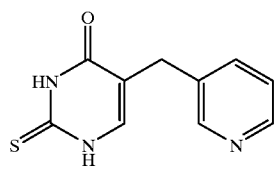

Prepared as in reference 11.

Intermediate B20

5-(Pyrid-4-ylmethyl)-2-thiouracil

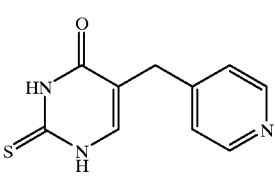

Prepared analogously to intermediate B9. $^1$H-NMR (d6-DMSO) δ 3.57 (2H, s), 7.25 (2H, m), 7.47 (1H, s), 8.44 (2H, m), 12.43 (2H, br, m) Mpt >250° C.

Intermediate B21

5-((2-Methylpyrid-5-yl)methyl)-2-thiouracil

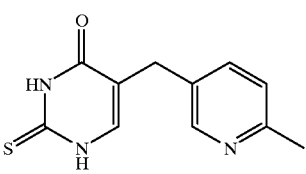

Prepared as in reference 5.

Intermediate B22

5-(Thiazol-2-ylmethyl)-2-thiouracil

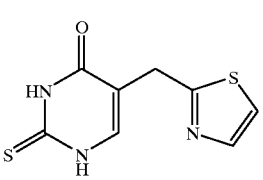

Prepared as in reference 2.

Intermediate B23

5-Benzyl-2-thiouracil

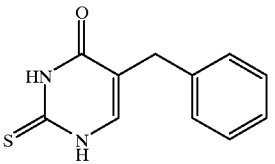

Prepared as in reference 6.

Intermediate B24

5-(Pyrid-3-ylmethyl)-2-(nitroamino)pyrimidin-4-one

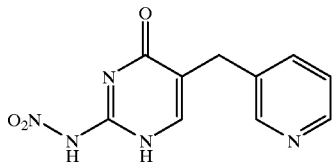

Prepared as in reference 4.

Intermediate B25

5-(2-Methoxypyrid-4-ylmethyl)-2-(nitroamino)pyrimidin-4-one

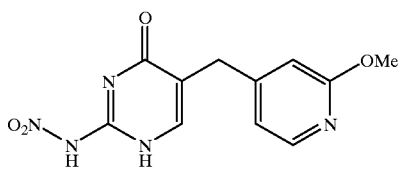

Prepared as in reference 3.

Intermediate B26

5-(4-Methoxypyrid-2-ylmethyl)-2-(nitroamino)pyrimidin-4-one

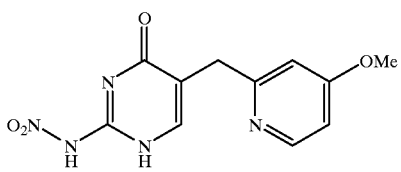

Prepared as in reference 4.

Intermediate B27

5-((1-Butyl-2-oxo-pyrid-4-yl)methyl)-2-(nitroamino)pyrimidin-4-one

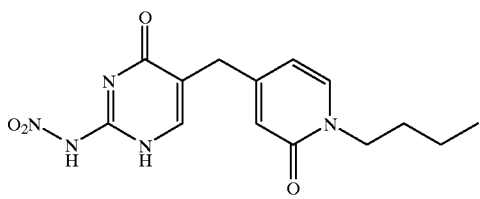

Prepared as in reference 7.

Intermediate B28

5-((1-Oxo-2-methylpyrid-5-yl)methyl)-2-(nitroamino)pyrimidin-4-one

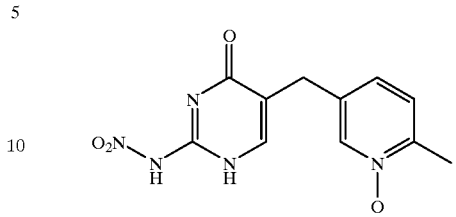

Prepared as in reference 3.

Intermediate B29

5-((2,4-Dimethylpyrid-5-yl)methyl)-2-(nitroamino)pyrimidin-4-one

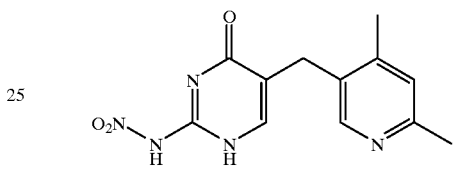

Prepared as in reference 8.

Intermediate B30

3-(1-Methylpyrazol-4-yl)acrylic acid

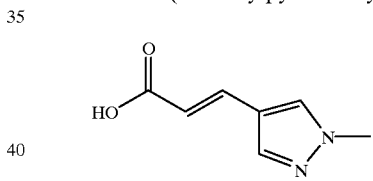

A mixture of 1-methylpyrazole-4-carboxaldehyde (made as in reference 15) (18.1 g), malonic acid (17.1 g), pyridine (15 ml) and piperidine (0.2 ml) was heated to 100° C. for 1 hour. After cooling, water was added, followed by aqueous ammonia to obtain a clear solution, which was acidified to pH5 with hydrochloric acid. The resulting solid was filtered off, washed with water and dried to obtain 3-(1-methylpyrazol-4-yl)acrylic acid (18.9 g). $^1$H-NMR ($d_6$-DMSO) δ 3.83 (3H, s), 6.18 (1H, d), 7.44 (1H, d), 7.83 (1H, s), 8.07 (1H, s). (APCI) M+H=153. $C_7H_8N_2O_2$ requires 152.

Intermediate B31

Methyl 3-(1-methylpyrazol-4-yl)acrylate

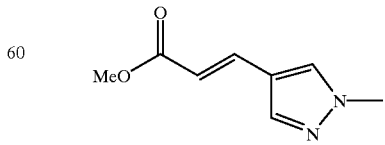

3-(1-Methylpyrazol-4-yl)acrylic acid (18.86 g) was added to a solution of sulphuric acid (15 ml) in methanol (150 ml), and the mixture refluxed for 2 hours, cooled, and poured onto ice. The acid was neutralised with solid sodium carbonate and the product extracted into dichloromethane, which was dried and evaporated. Crystallisation from ether/petrol gave methyl 3-(1-methylpyrazol-4-yl)acrylate (16.0 g). $^1$H-NMR (d$_6$-DMSO) δ 3.77 (3H, s), 3.91 (3H, s), 6.16 (1H, d), 7.54 (1H, s), 7.56 (1H, d), 7.69 (1H, s). (APCI) M+H=167. C$_8$H$_{10}$N$_2$O$_2$ requires 166.

Intermediate B32

Methyl 3-(1-methylpyrazol-4-yl)propionate

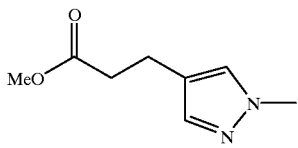

Prepared analogously to intermediate B6. $^1$H-NMR (d$_6$-DMSO) δ 2.56 (2H, t), 2.79 (2H, t), 3.67 (3H, s), 3.85 (3H, s), 7.17 (1H, s), 7.31 (3H, s). (APCI) M+H=169. C$_8$H$_{12}$N$_2$O$_2$ requires 168.

Intermediate B33

Methyl 2-formyl-3-(1-methylpyrazol4-yl)propionate, sodium salt

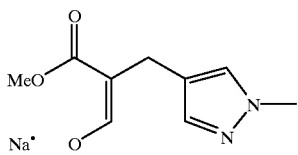

Sodium hydride (2.62 g, 60% in oil) was washed with petrol and suspended in dry dimethoxyethane (20 ml). Methyl 3-(1-methylpyrazol-4-yl)propionate (8.8 g) and methyl formate (4.87 ml) were dissolved in DME (20 ml), and a few drops of the mixture added to the sodium hydride suspension, which was warmed briefly to initiate the reaction before continuing dropwise addition at a rate which sustained controlled evolution of hydrogen. The mixture was stirred for a further 16 hours at room temperature, then diluted with ether. The solid was filtered off, washed with ether and immediately dried, and was used promptly without further purification.

Intermediate B34

5-((1-Methylpyrazol-4-yl)methyl)-2-thiouracil

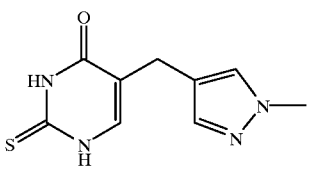

Prepared analogously to intermediate B9, except using the preformed sodium salt instead of adding sodium ethoxide. $^1$H-NMR (d$_6$-DMSO) δ 3.33 (3H, s), 3.75 (3H, s), 7.15 (1H, s), 7.23 (1H, s), 7.46 (1H, s), 12.2 (1H, br s), 12.4 (1H, br s). (APCI) M+H=223. C$_9$H$_{10}$N$_4$OS requires 222.

Intermediate B35

Ethyl 3-(2-methoxypyrimidin-5-yl)acrylate

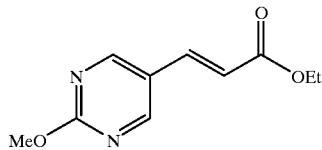

A mixture of 2-methoxy-5-bromopyrimidine (75.43 g, 0.399 mol), ethyl acrylate (47.5 ml, 0.439 mol), palladium (II) acetate (1.07 g, 0.0048 mol), tri-o-tolylphosphine (2.92 g, 0.0096 mol) and triethylamine (84 ml) were heated at 135° C. with stirring under argon for 12 h. After allowing to cool the solid mass was dissolved in water and ethyl acetate, filtered, and the aqueous phase separated and further extracted with ethyl acetate. The combined extracts were washed with saturated aqueous ammonium chloride, dried (MgSO$_4$) and evaporated. The solid thus obtained was triturated with ether/light petrol (1:3, 350 ml), filtered, washed and dried, yield 52.41 g (63%). $^1$H-NMR (CDCl$_3$) δ 1.33 (3H, t), 4.06 (3H, s), 4.28 (2H, q), 6.45 (1H, d), 7.58 (1H, d), 8.67 (2H, s); MS (APCI+) found (M+H)=209; C$_{10}$H$_{12}$N$_2$O$_3$ requires 208.

Intermediate B36

Ethyl 3-(2-methoxypyrimidin-5-yl)propionate

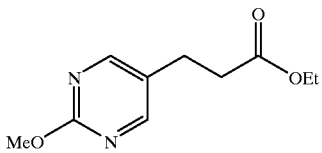

A suspension of ethyl 3-(2-methoxypyrimidin-5-yl)acrylate (52.4 g, 0.252 mol) in ethanol (400 ml) and triethylamine (50 ml) was treated with 10% palladium on carbon (3 g) and hydrogenated at 50 psi for 1.75 h. The catalyst was filtered off through hyflo and the filtrate evaporated. The residue was dissolved in dichloromethane, washed twice with saturated aqueous ammonium chloride, dried (MgSO$_4$) and evaporated to an oil, yield 41.2 g (78%). $^1$H-NMR (CDCl$_3$) δ 1.23 (3H, t), 2.61 (2H, t), 2.87 (2H, t), 3.99 (3H, s), 4.13 (2H, q), 8.39 (2H, s); MS (APCI+) found (M+H)= 211; C$_{10}$H$_{14}$N$_2$O$_3$ requires 210.

Intermediate B37

2-(Methoxymethylene)-3-(2-methoxypyrimidin-5-yl)propionic acid, mixed methyl/ethyl esters

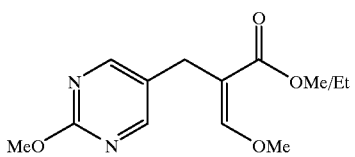

To a stirring suspension of sodium hydride (0.83 g of a 60% dispersion in oil) in anhydrous 1,2-dimethoxyethane (6 ml) was added dropwise a solution of methyl formate (1.54 ml) and ethyl 3-(2-methoxypyrimid-5-yl)propionate (3.5 g) in anhydrous 1,2-dimethoxyethane (6 ml) at such a rate as to maintain the reaction temperature at 25–30° C. After 1 h, ether was added and the precipitated oil allowed to settle. The solution was decanted off and replaced with fresh ether, and the oil slowly solidified. The solid 2-(hydroxymethylene) derivative was filtered, washed and dried, yield 3.8 g. A 1.33 g portion was suspended in dimethyl formamide (10 ml) together with anhydrous potassium carbonate (1.15 g), and a solution of dimethyl sulphate (0.48 ml) in dimethylformamide (10 ml) was added dropwise with stirring over 30 min. After 16 h the solvent was evaporated and the residue treated with water and extracted with ethyl acetate. The extracts were washed with water, dried (MgSO$_4$) and evaporated to give the product as an oil, yield 0.91 g. $^1$H-NMR (CDCl$_3$) δ 1.23 (3H, t), 3.46 (2H, s), 3.69 (3H, s, methyl ester), 3.88 (3H, s), 3.97 (3H, s), 4.16 (2H, q), 7.39 (1H, s), 8.40 (2H, s), 3:2 ratio of methyl:ethyl esters. MS (APCI+) found (M+1)=253, 239 (ethyl and methyl esters); C$_{12}$H$_{16}$N$_2$O$_4$ requires 252. C$_{11}$H$_{14}$N$_2$O$_4$ requires 238.

Intermediate B38

2-(Methoxymethylene)-3-(2-methoxypyrimidin-5-yl)propionic acid

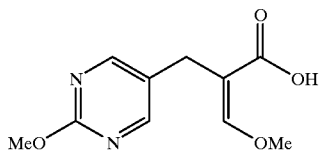

A suspension of the mixed esters of intermediate 5 (0.9 g) in 2M aqueous sodium hydroxide (3.6 ml) was stirred at ambient temperature for 16 h to give a clear solution. This was diluted with water, extracted with dichloromethane and evaporated to about half volume, then acidified to pH 3–4 (2M hydrochloric acid) when the product crystallised out. The white solid was filtered, washed with ice-cold water and dried, yield 0.46 g. $^1$H-NMR (CDCl$_3$) δ 3.43 (2H, s), 3.91 (3H, s), 3.99 (3H, s,), 7.49 (1H, s), 8.42 (2H, s); MS (APCI+) found (M+1)=225, C$_{10}$H$_{12}$N$_2$O$_4$ requires 224.

Intermediate B39

5-(2-Methoxypyrimidin-5-ylmethyl)-2-thiouracil

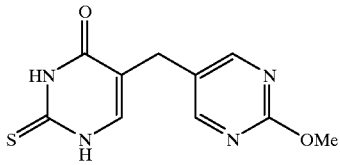

To an ice cooled solution of potassium t-butoxide (7.83 g, 0.07 mol) in anhydrous THF (60 ml) was added dropwise with stirring under argon over 1 hour to a solution of ethyl 3-(2-methoxypyrimidin-5-yl) propionate (5.87 g, 0.028 mol) and methyl formate (3.6 ml, 0.059 mol) in anhydrous ether (70 ml). After stirring for 16 h, the solvents were evaporated, thiourea (4.25 g, 0.056 mol) and propan-2-ol (80 ml) added and the mixture refluxed for 5 h. The solvent was evaporated and the residue dissolved in water, extracted twice with ether and acidified to pH 4.5 with acetic acid. The solid which precipitated was filtered, washed well with water and dried, yield 5.57 g (80%). $^1$H-NMR (d$_6$-DMSO) δ 3.47 (2H, s), 3.85 (3H, s), 7.43 (1H, s), 8.48 (2H, s), 12.25 (1H, br s), 12.46 (1H, br s); MS (APCI+) found (M+H)=251; C$_{10}$H$_{10}$N$_4$O$_2$S requires 250.

Intermediate B40

5-(2-Benzyloxypyrimid-5-ylmethyl)-2-thiouracil

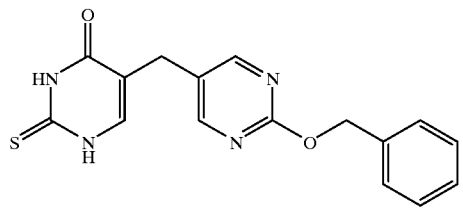

To a solution of benzyl alcohol (20 ml) in dry dimethylformamide (20 ml) was added sodium hydride ((60% in oil) 2.3 g) over 0.5 h under argon. A slurry of 2-methoxypyrimidyl thiouracil (3.6 g) in dry dimethylformamide (10 ml) was added in one portion and the solution heated to 80° C. for 2.5 h. After cooling, the solvent was removed under reduced pressure and the residue partitioned between diethyl ether and water. The aqueous layer was washed with further diethyl ether and then acidified to pH4 with glacial acetic acid. The solid so formed was filtered, washed with water and diethyl ether and dried in vacuo to give the desired material. $^1$H-NMR (d$_6$-DMSO) δ 3.49 (2H, s), 5.36 (2H, s), 7.2–7.5 (6H, m), 8.50 (2H, s); MS (APCI+) found (M+1)=327; C$_{16}$H$_{14}$N$_4$O$_2$S requires 326.

Intermediate B41

Methyl 2-benzyl-3-methoxyacrylate

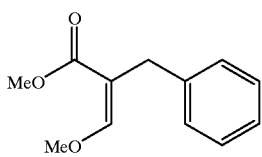

Prepared analogously to intermediate B7.

Intermediate B42

2-Benzyl-3-methoxyacrylic acid

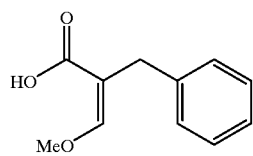

Prepared analogously to intermediate B8.

Intermediate B43

Methyl 2-(1-methyl-2-oxo-pyrid-4-yl)methyl)-3-methoxyacrylate

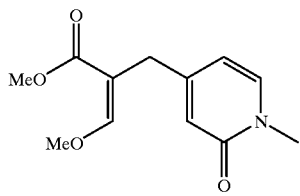

Prepared from methyl 3-(1-methyl-2-oxo-pyrid-4-yl) propionate (reference 7) analogously to intermediate B7.

Intermediate B44

2-((1-Methyl-2-oxo-pyrid-4-yl)methyl)-3-methoxyacrylic acid

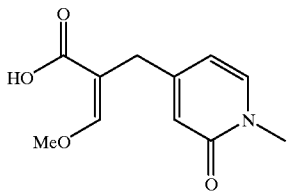

Prepared analogously to intermediate B8.

Intermediate B45

1-(Pyrid-2-ylmethyl)-5-(pyrimid-5-ylmethyl)-2-thiouracil

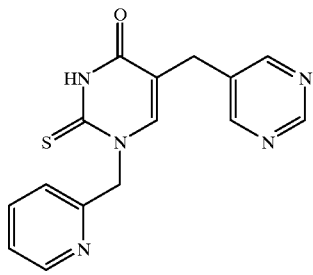

2-((5-pyrimidyl)methyl)-3-methoxyacrylic arid (5.5 g) was slurried in dry dichloromethane (100 ml) and oxalyl chloride (4.3 ml) added over 5 min. After stirring at RT for 3 h, the solvent was removed in vacuo and the residue triturated with toluene. The solvent was removed in vacuo to give a solid that was slurried in dry acetonitrile (100 ml) under Ar. Dried powdered potassium thiocyanate (3.25 g) was added in one portion at RT and the mixture was stirred for 15 h. Removal of the solvent in vacuo gave a solid that was slurried with dry dimethylformamide (90 ml). One ninth of the slurry was added to triethylamine (0.42 ml) and 2-pyridylmethylamine (0.49 g). The mixture was stirred for 19 h under argon and a solution of sodium ethoxide (3M) in ethanol (1.5 ml) was added in one portion. The mixture was heated on an oil bath (bath temp 101° C.) for 2 h, cooled and the solvent removed under reduced pressure. The residue was dissolved in water (12 ml) and brought to pH 4 with glacial acetic acid. The solid so formed was filtered and dried in vacuo to give 1-(pyrid-2-ylmethyl)-5-(pyrimid-5-ylmethyl)-2-thiouracil (0.69 g). $^1$H-NMR (d$_6$-DMSO) δ 3.63(2H, s), 5.47(2H, s), 7.2–7.4(2H, m), 7.7–7.85(1H, m), 8.04(1H, s), 8.5(1H, m), 8.7(2H, s) and 9.04(1H, s), (APCI) M+H=312. $C_{15}H_{13}N_5OS$ requires 311.

Intermediate B46

1-(4-Hydroxycyclohexyl)-5-(pyrimid-5-ylmethyl)2-thiouracil

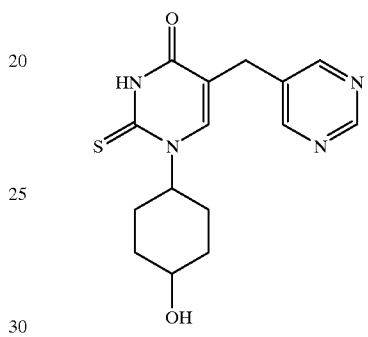

Prepared analogously to intermediate B45. $^1$H-NMR (d$_6$-DMSO) δ 1.0–2.0(8H, m), 3.63(2H, s), 8.10(1H, s), 8.72 (2H, s) and 9.02(1H, s); (ES−) Found (M−1)=317. $C_{15}H_{18}N_4O_2S$ requires 318.

Intermediate B47

1-(3-(1-Imidazolyl)prop-1-yl)-5-(pyrimid-5-ylmethyl)-2-thiouracil

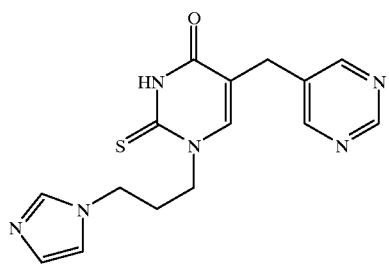

Prepared analogously to intermediate B45. $^1$H-NMR (d$_6$-DMSO) δ 2.22 (2H, m), 3.58 (2H, s), 4.13 (4H, m), 7.12 (1H, m), 7.36 (1H, m), 7.88 (1H, s), 8.08 (1H, s), 8.73 (2H, s), 9.05 (1H, s), 12.68 (1H, br s); (APCI+) Found (M+1)= 329. $C_{15}H_{16}N_6OS$ requires 328

Intermediate B48

1-(3-(1-Morpholino)prop-1-yl)-5-(pyrimid-5-ylmethyl)-2-thiouracil

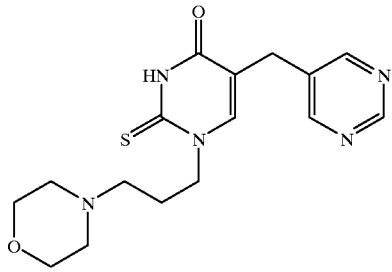

Prepared analogously to intermediate B45. ¹H-NMR (d₆-DMSO) δ 2.35–2.6(6H+d5-DMSO, m), 3.4–3.8(6H+HOD, m), 4.19(2H, t), 7.96(1H, s), 8.74(2H, s) and 9.04); (APCI+) Found (M+1)=348. $C_{16}H_{21}N_5O_2S$ requires 347.

Intermediate B49

1-(3-(2-Oxo-1-pyrrolidino)prop-1-yl)-5-(pyrimid-5-ylmethyl)-2-thiouracil

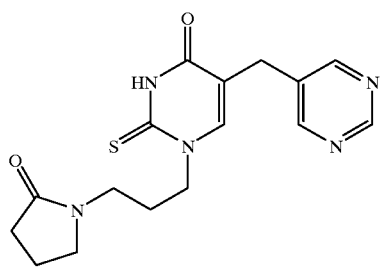

Prepared analogously to intermediate B45. ¹H-NMR (d₆-DMSO) δ 1.91 (4H, m), 2.20 (2H, t), 3.24 (2H, t), 3.37 (2H, t), 3.58 (2H, s), 4.09 (2H, t), 7.97 (1H, s), 8.74 (2H, s), 9.04 (1H, s); (APCI+) Found (M+1)=346. $C_{16}H_{19}N_5O_2S$ requires 345

Intermediate B50

1-(3-Ethoxycarbonylprop-1-yl)-5-(pyrimid-5-ylmethyl)-2-thiouracil

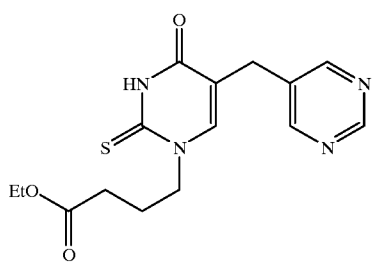

Prepared analogously to intermediate B45. ¹H-NMR (d₆-DMSO) δ 1.17(1H, t), 1.98(2H, m), 2.34(2H, t), 3.59(2H, s), 4.04(2H, q), 4.16(2H, t), 7.90(1H, s), 9.03(1H, s); (ES+) Found (M+1)=335. $C_{15}H_{18}N_4O_3S$ requires 334.

Intermediate B51

1-(3-Dimethylaminoprop-1-yl)-5-(pyrimid-5-ylmethyl)-2-thiouracil

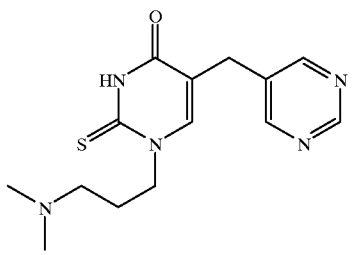

Prepared analogously to intermediate B45. ¹H-NMR (d₆-DMSO) δ 2.21(6H, s), 3.60(2H, s), 4.15(2H, t), 7.91(1H, s), 8.72(2H, s), 9.03(1H, s); (APCI+) Found (M+1)=306. $C_{14}H_{19}N_5O_2S$ requires 305.

Intermediate B52

1-(3-Hydroxyprop-1-yl)-5-(pyrimid-5-ylmethyl)-2-thiouracil

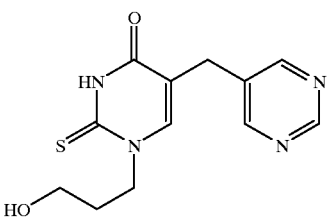

Prepared analogously to intermediate B45. ¹H-NMR (d₆-DMSO) δ 1.85(2H, m), 3.45(2H, b), 3.61(2H, s), 4.19(2H, t), 4.65(1H, bs), 7.85–8.0(2H, m), 8.71(2H, s) and 9.04(1H, s); (APCI) M+H=279. $C_{12}H_{14}N_4O_2S$ requires 278.

Intermediate B53

1-(3-Hydroxyprop-1-yl)-5-benzyl-2-thiouracil

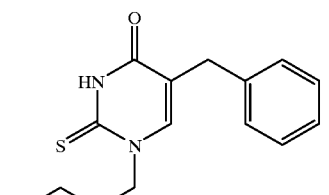

Prepared analogously to intermediate B45. ¹H-NMR (d₆-DMSO) δ 1.85(2H, m), 3.46(2H, m), 3.56(2H, s), 4.19(2H, t), 4.65(1H, t), 7.1–7.4(5H, m) and 7.81(1H, s); (FAB) M+H=277. $C_{14}H_{16}N_2O_2S$ requires 276.

Intermediate B54

1-(3-Methoxyprop-1-yl)-5-(pyrimid-5-ylmethyl)-2-thiouracil

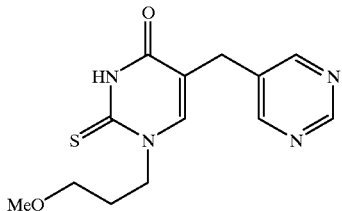

Prepared analogously to intermediate B45. $^1$H-NMR (d$_6$-DMSO) δ 1.94(2H, m), 3.21(3H, s), 8.55(2H, s), 4.20(2H, t), 7.88(1H, s), 8.72(2H, s) and 9.03(1H, s); (ES−) Found (M−1)=291. C$_{19}$H$_{22}$BrClN$_2$O$_2$S requires 292.

Intermediate B55

1-(3-Phenylprop-1-yl)-5-(pyrimid-5-ylmethyl)-2-thiouracil

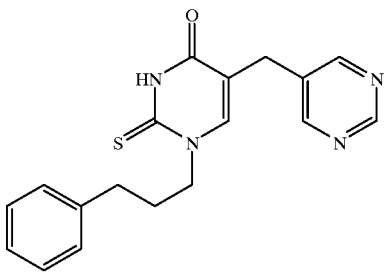

Prepared analogously to intermediate B45. $^1$H-NMR (d$_6$-DMSO) δ 2.04(2H, m), 2.63(2H, t), 3.58(2H, s), 4.18(2H, t), 7.1–7.35(5H, m), 7.92(1H, s), 8.72(2H, s) and 9.03(1H, s); (APCI+) Found (M+1)=339. C$_{18}$H$_{18}$N$_4$OS requires 338.

Intermediate B56

1-(5-Hydroxypent-1-yl)-5-(pyrimid-5-ylmethyl)-2-thiouracil

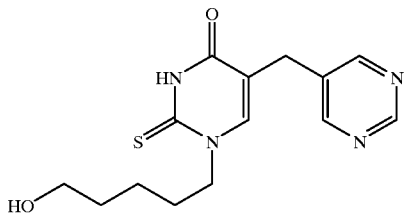

Prepared analogously to intermediate B45. $^1$H-NMR (d$_6$-DMSO) δ (HOAc salt) 1.79(3H, s), 3.59(2H, s), 4.13(2H, t), 7.96(1H, s), 8.72(2H, s) and 9.02(1H, s); (APCI+) Found (M+1)=307. C$_{14}$H$_{18}$N$_4$O$_2$S requires 306.

Intermediate B57

1-(Pyrid-2-ylmethyl)-5-benzyl-2-thiouracil

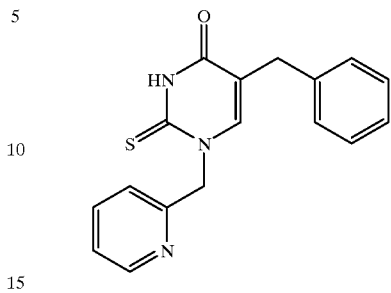

Prepared analogously to intermediate B45. $^1$H-NMR (d$_6$-DMSO) δ 3.59(2H, s), 5.49(2H, s), 7.1–7.45(7H, m), 7.79 (1H, m), 7.95(1H, s) and 8.51(1H, m); MPt 171–4° C.; (EI) M=309. C$_{17}$H$_{15}$N$_3$OS requires 309.

Intermediate B58

1-(Pyrid-3-ylmethyl)-5-((1-methyl-2-oxo-pyrid-4-yl)methyl)-2-thiouracil

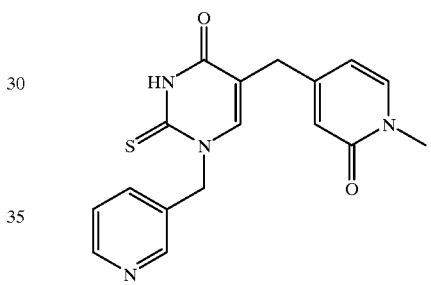

Prepared analogously to intermediate B45. $^1$H-NMR (d$_6$-DMSO) δ 3.11 (3H, s), 3.15 (2H, s), 5.21 (2H, s), 5.86 (1H, m), 5.95 (1H, m), 7.15 (1H, m), 7.34 (1H, m), 7.52 (1H, m), 7.80 (1H, s), 8.26 (1H, m), 8.34 (1H, m), 12.55 (1H, br, s); (APCI+) Found (M+1)=341. C$_{17}$H$_{16}$N$_4$OS requires 340

Intermediate B59

1-(Pyrid-3-ylmethyl)-5-(pyrimid-5-ylmethyl)-2-thiouracil

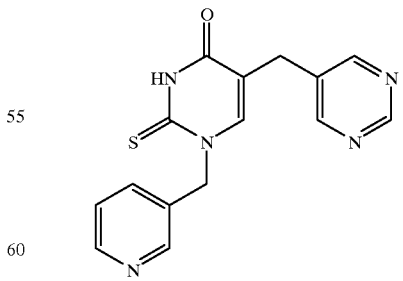

Prepared analogously to intermediate B45. $^1$H-NMR (d$_6$-DMSO) δ 3.49 (2H, s), 5.33 (2H, s), 7.28 (1H, m), 7.64 (1H, m), 7.97 (1H, s), 8.42 (2H, s), 8.59 (2H, s), 8.88 (1H, m), 12.70 (1H, br. s) Mpt>250° C.

Intermediate B60

1-(Pyrid-3-ylmethyl)-5-benzyl-2-thiouracil

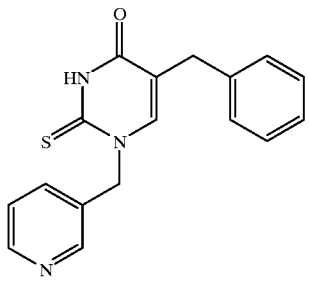

Prepared analogously to intermediate B45. $^1$H-NMR (d$_6$-DMSO) δ 3.57(2H, s), 5.46(2H, s), 7.1–7.35(5H, m), 7.40 (1H, m), 7.75(1H, s), 8.02(1H, s), 8.51(1H, m) and 8.59(1H, m). MPt 236–8° C.; (EI) M=309. C$_{17}$H$_{15}$N$_3$OS requires 309.

Intermediate B61

1-(Pyrid-4-ylmethyl)-5-((1-methyl-2-oxo-pyrid-4-yl)methyl)-2-thiouracil

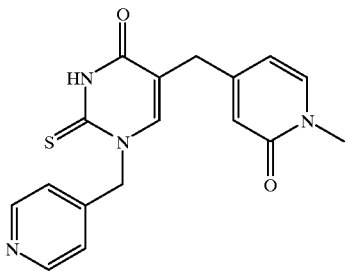

Prepared analogously to intermediate B45. $^1$H-NMR (d$_6$-DMSO) δ 3.39(3H, s), 5.45(2H, s), 6.11(1H, dd), 6.21(1H, m), 7.25(2H, m), 7.58(1H, d), 7.96(1H, s) and 8.54(2H, m). MPt 181–3° C.; (EI) M=340. C$_{17}$H$_{16}$N$_4$O$_2$S requires 340.

Intermediate B62

1-(Pyrid-4-ylmethyl)-5-(pyrimid-5-ylmethyl)-2-thiouracil

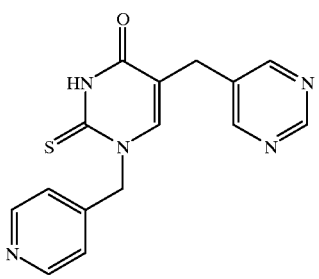

Prepared analogously to intermediate B45. $^1$H-NMR (d$_6$-DMSO) δ 3.64 (2H, s), 5.45 (2H, s), 7.28 (2H, m), 8.00 (1H, s), 8.55 (2H, m), 8.73 (2H, m), 9.05 (1H, m), 12.85 (1H, br s) Mpt>250° C.

Intermediate B63

1-(Pyrid-4-ylmethyl)-5-benzyl-2-thiouracil

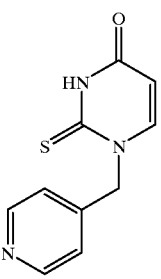

Prepared analogously to intermediate B45. $^1$H-NMR (d$_6$-DMSO) δ 3.58(2H, s), 5.46(2H, s), 7.1–7.4(7H, m), 7.93 (1H, s) and 8.54(2H, m); MPt 174–6° C.; (EI) M=309. C$_{17}$H$_{15}$N$_3$OS requires 309.

Intermediate B64

1-(Pyrid-4-ylmethyl)-2-thiouracil

Prepared from 3-methoxyacrylic acid, analogously to intermediate B45. $^1$H-NMR (d$_6$-DMSO) δ 5.45(2H, s), 6.03(2H, d), 7.23(2H, m), 7.94(2H, d) and 8.54(2H, m); MPt 267–70° C.; (EI) M=219. C$_{10}$H$_9$N$_3$OS requires 219.

Intermediate B65

1-(2-(Pyrid-2-yl)ethyl)-5-(pyrimid-5-ylmethyl)-2-thiouracil

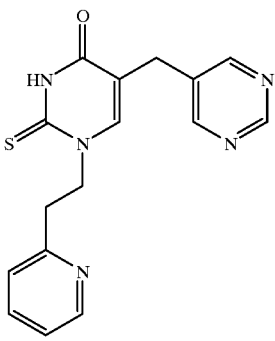

Prepared analogously to intermediate B45. $^1$H-NMR (d$_6$-DMSO) δ 3.22(2H, t), 3.51(2H, s), 4.51(2H, t), 7.25(2H, m), 7.7(2H, m), 8.47(1H, m), 8.61(2H, s) and 9.03(1H, s); (APCI+) Found (M+1)=326. C$_{16}$H$_{15}$N$_5$OS requires 325.

Intermediate B66

1-(2-(Pyrid-3-yl)ethyl)-5-((1-methyl-2-oxo-pyrid-4-yl)methyl)-2-thiouracil

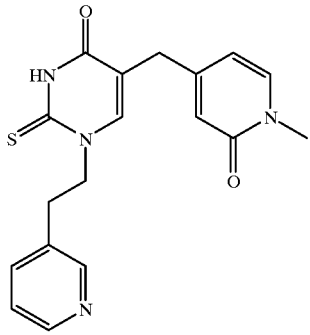

Prepared analogously to intermediate B45. $^1$H-NMR (d$_6$-DMSO) δ 3.08 (2H, t), 3.29 (2H, s), 3.37 (3H, s), 4.38 (2H, t), 5.96 (1H, m), 6.13 (1H, m), 7.34 (1H, m), 7.60 (1H, m), 7.67 (1H, m), 7.71 (1H, s), 8.46 (2H, m), 12.73 (1H, br. s); (APCI+) Found (M+1)=355. C$_{18}$H$_{18}$N$_4$O$_2$S requires 354

Intermediate B67

1-(2-(Pyrid-3-yl)ethyl)-5-(pyrimid-5-ylmethyl)-2-thiouracil

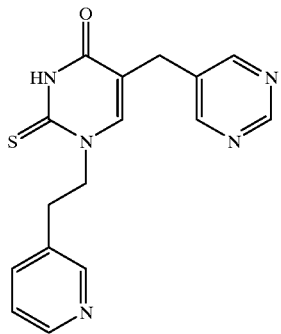

Prepared analogously to intermediate B45. $^1$H-NMR (d$_6$-DMSO) δ 3.08(2H, t), 3.53(2H, s), 4.36(2H, t), 7.3(1H, m), 7.65(1H, m), 7.78(1H, s), 8.45(2H, bs), 8.65(2H, s) and 9.05(1H, s); (APCI+) Found (M+1)=326. C$_{16}$H$_{15}$N$_5$OS requires 325.

Intermediate B68

1-(2-(Pyrid-4-yl)ethyl)-5-((1-methyl-2-oxo-pyrid-4-yl)methyl)-2-thiouracil

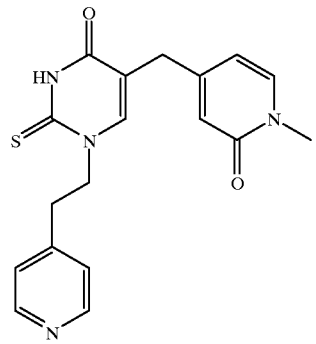

Prepared analogously to intermediate B45. $^1$H-NMR (d$_6$-DMSO) δ 3.07 (2H, t), 3.30 (2H, s), 3.37 (3H, s), 4.39 (2H, t), 5.94 (1H, m), 6.15 (1H, m), 7.27 (2H, m), 7.56 (1H, m), 7.72 (1H, s), 8.48 (2H, m), 12.72 (1H, br. s); (APCI+) Found (M+1)=355. C$_{18}$H$_{18}$N$_4$O$_2$S requires 354

Intermediate B69

1-(2-(Pyrid-4-yl)ethyl)-5-(pyrimid-5-ylmethyl)-2-thiouracil

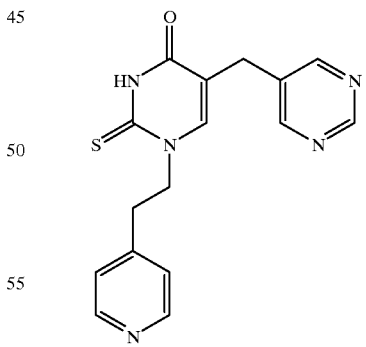

Prepared analogously to intermediate B45. $^1$H-NMR (d$_6$-DMSO) δ 3.16(2H, t), 3.54(2H, s), 4.45(2H, t), 7.48(2H, d), 7.82(1H, s), 8.60(2H, d), 8.67(2H, s) and 9.05(1H, s); (ES+) Found (M+1)=326. C$_{16}$H$_{15}$N$_5$OS requires 325.

Intermediate B70

1-(2-Phenylethyl)-5-((1-methyl-2-oxo-pyrid-4-yl)methyl)-2-thiouracil

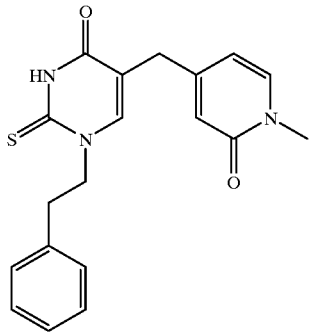

Prepared analogously to intermediate B45. $^1$H-NMR (d$_6$-DMSO) δ 3.04(2H, t), 3.27(3H, s), 4.35(2H, t), 5.93(1H, m), 6.12(1H, bs), 7.1–7.45(5H, m), 7.56(1H, d) and 7.67(1H, s); MPt 230–3° C.; (APCI) M+H=354. $C_{19}H_{19}N_3O_2S$ requires 353.

Intermediate B71

Benzyl-5-((1-methyl-2-oxo-pyrid-4-yl)methyl)-2thiouracil

Prepared analogously to intermediate B45. $^1$H-NMR (d$_6$-DMSO) δ 3.38(s), 5.44(2H, s), 6.07(1H, m), 6.18(1H, m), 7.1–7.5(5H, m), 7.57(1H, d) and 7.96(1H, s). (EI) M=339. $C_{18}H_{17}N_3O_2S$ requires 339.

Intermediate B72

1,5-Dibenzyl-2-thiouracil

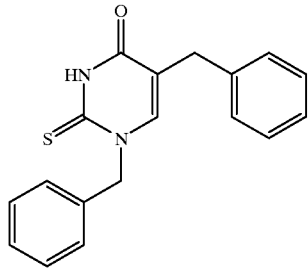

Prepared analogously to intermediate B45. $^1$H-NMR (CDCl$_3$) δ 3.63(2H, s), 5.35(2H, s), 6.84(1H, s) and 7.05–7.45(10H, m). MPt 151–2° C.; (EI) M=308. $C_{18}H_{16}N_2OS$ requires 308.

Intermediate B73

1-(2-Thienylmethyl)-5-(pyrimid-5-ylmethyl)-2-thiouracil

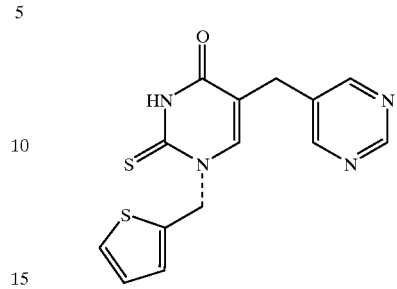

Prepared analogously to intermediate B45. $^1$H-NMR (d$_6$-DMSO) δ 3.60 (2H, s), 5.58 (2H, s), 7.03 (1H, m), 7.26 (1H, m), 7.50 (1H, m), 8.08 (1H, s), 8.69 (2H, s), 9.04 (1H, s), 12.18 (1H, br s) (APCI+) Found (M+1)=317. $C_{14}H_{12}N_4OS_2$ requires 316

Intermediate B74

1-(2,2-Dimethylprop-1-yl)-5-(pyrimid-5-ylmethyl)-2-thiouracil

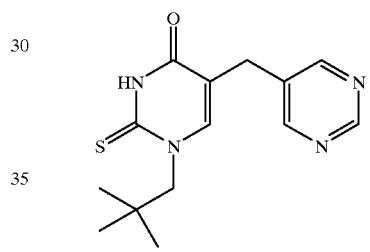

Prepared analogously to intermediate B45. $^1$H-NMR (d$_6$-DMSO) δ 0.96(9H, s), 3.62(2H, s), 4.17(2H, s), 7.77(1H, s), 8.73(2H, s) and 9.04(1H, s); (APCI+) Found (M+1)=291. $C_{14}H_{18}N_4OS$ requires 290.

Intermediate B75

1-(2-(1-Piperidino)ethyl)-5-(pyrimid-5-ylmethyl)-2thiouracil

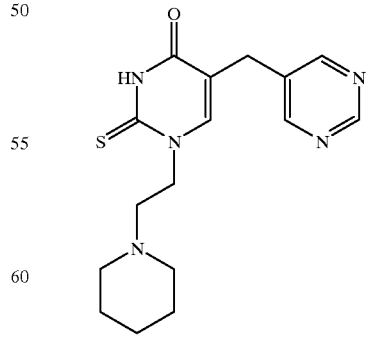

Prepared analogously to intermediate B45. $^1$H-NMR (d$_6$-DMSO) δ 1.28–1.72 (6H, m), 2.50 (4H, m), 2.73 (2H, t), 3.61 (2H, s), 4.29(2H, t), 7.80 (1H, s), 8.73 (2H, s), 9.05 (1H, s), 12.71 (1H, br s); (APCI+) Found (M+1)=332. $C_{16}H_{21}N_5OS$ requires 331

Intermediate B76

1-(2-Acetylaminoethyl)-5-(pyrimid-5-ylmethyl)-2-thiouracil

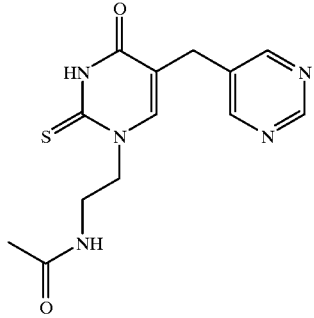

Prepared analogously to intermediate B45. $^1$H-NMR ($d_6$-DMSO) δ 1.75(3H, s), 3.43(2H, m), 3.61(2H, s), 4.18(2H, t), 7.78(1H, s), 8.03(1H, bt), 8.73(2H, s) and 9.03 (1H, s); (ES+) Found (M+1)=306. $C_{13}H_{15}N_5O_2S$ requires 305.

Intermediate B77

1-(2-Hydroxyethyl)-5-(pyrimid-5-ylmethyl)-2-thiouracil

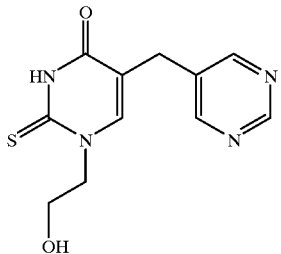

Prepared analogously to intermediate B45. $^1$H-NMR ($d_6$-DMSO) δ 3.60(2H, s), 3.72(2H, bq), 4.21(2H, t), 4.99(1H, t), 7.83(1H, s), 8.73(2H, s) and 9.03(1H, s); (ES+) Found (M+1)=265. $C_{11}H_{12}N_4O_2S$ requires 264.

Intermediate B78

1-(2-Hydroxyethyl)-5-benzyl-2-thiouracil

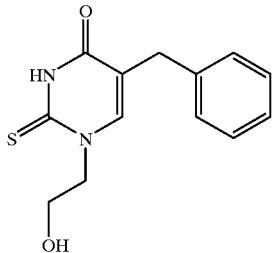

Prepared analogously to intermediate B45. $^1$H-NMR ($d_6$-DMSO) δ 3.55(2H, s), 3.71(2H, bm), 4.20(2H, t), 4.99(1H, bs), 7.1–7.45(5H, m) and 7.70(1H, s); MPt 171.3–3° C.; (FAB) M+H=263. $C_{13}H_{14}N_2O_2S$ requires 262.

Intermediate B79

1-Dimethylaminocarbonylmethyl-5-(pyrimid-5-ylmethyl)-2-thiouracil

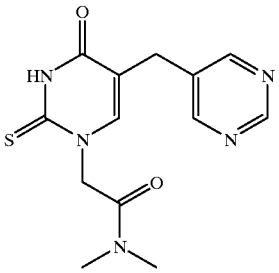

Prepared analogously to intermediate B45. $^1$H-NMR ($d_6$-DMSO) δ 2.86 (3H, s), 3.02 (3H, s), 3.61 (2H, s), 5.09 (2H, s), 7.76 (1H, s), 8.71 (2H, s), 9.05 (1H, s); (APCI+) Found (M+1)=306. $C_{13}H_{15}N_5O_2S$ requires 305

Intermediate B80

1-Ethoxycarbonylmethyl-5-(pyrimid-5-ylmethyl)-2-thiouracil

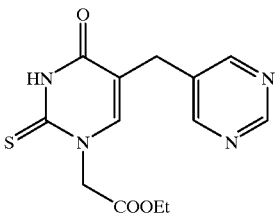

Prepared analogously to intermediate B45. $^1$H-NMR ($d_6$-DMSO) δ 1.19 (3H, t), 3.62 (2H, s), 4.16 (2H, q), 4.94 (2H, s), 7.88 (1H, s), 8.73 (2H, s), 9.06 (1H, s); (APCI+) Found (M+1)=307. $C_{13}H_{14}N_4O_3S$ requires 306

Intermediate B81

1-(Fur-2-ylmethyl)-5-(pyrimid-5-ylmethyl)-2-thiouracil

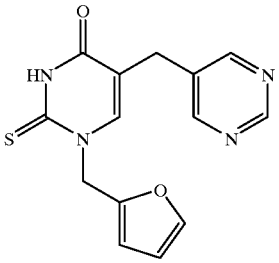

Prepared analogously to intermediate B45. $^1$H-NMR ($d_6$-DMSO) δ 3.62 (2H, s), 5.43 (2H, s), 6.47 (2H, m), 7.66 (1H, m), 7.98 (1H, s), 8.70 (2H, s), 9.04 (1H, s), 12.75 (1H, br s); (APCI+) Found (M+1)=301. $C_{14}H_{12}N_4O_2S$ requires 300

Intermediate B82

1-(Fur-2-ylmethyl)-5-benzyl-2-thiouracil

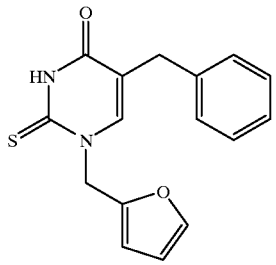

Prepared analogously to intermediate B45. $^1$H-NMR (d$_6$-DMSO) δ 3.57(2H, s), 5.43(2H, s), 6.45(2H, s), 7.1–7.4(5H, m), 7.66(1H, m) and 7.85(1H, s); MPt 153–5° C.; (FAB) M+H=299. C$_{16}$H$_{14}$N$_2$O$_2$S requires 298.

Intermediate B83

1-Methyl-5-((1-methyl-2-oxo-pyrid-4-yl)methyl)-2-thiouracil

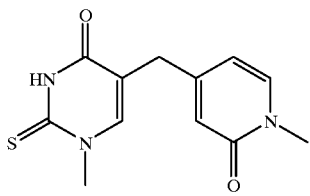

Prepared analogously to intermediate B45. $^1$H-NMR (d$_6$-DMSO) δ 3.57(3H, s), 6.12(1H, m), 6.20(1H, bs), 7.57(1H, d) and 7.87(1H, s); (EI) M=263. C$_{12}$H$_{13}$N$_3$O$_2$S requires 263.

Intermediate B84

1-Methyl-5-(pyrimid-5-ylmethyl)-2-thiouracil

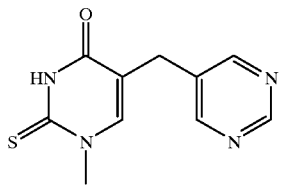

Prepared analogously to intermediate B45. $^1$H-NMR (d$_6$-DMSO) δ 3.33(3H, s), 7.93(1H, s) 8.73(2H, s) and 9.02(1H, s); (APCI) M+H=235. C$_{10}$H$_{10}$N$_4$OS requires 234.

Intermediate B85

1-Methyl-5-benzyl-2-thiouracil

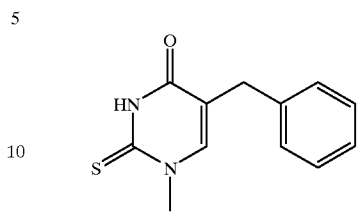

Prepared analogously to intermediate B45. $^1$H-NMR (CDCl$_3$) δ 3.55(2H, s), 3.57(3H, s), 7.1–7.4(5H, m) and 7.84(1H, s); MPt 143–6° C.; (EI) M=232. C$_{12}$H$_{12}$N$_2$OS requires 232.

Intermediate B86

1-Phenyl-5-((1-methyl-2-oxo-pyrid-4-yl)methyl)-2-thiouracil

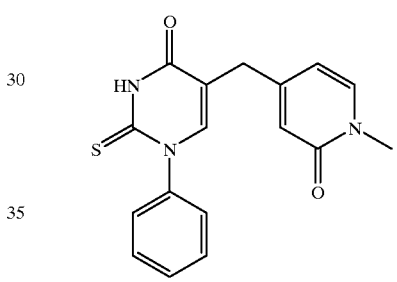

Prepared analogously to intermediate B45. $^1$H-NMR (CDCl$_3$) δ 3.51(3H+MeOH, s), 6.16(1H, m), 6.48(1H, m), 7.1–7.45(4H, m) and 7.45–7.65(3H, m); (EI) M=325; C$_{17}$H$_{15}$N$_3$O$_2$S requires 325.

Intermediate B87

1-(2-Methoxyethyl)-5-(pyrimid-5-ylmethyl)-2-thiouracil

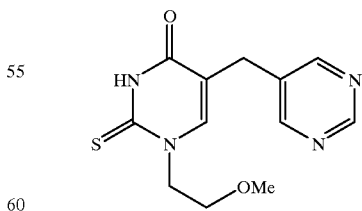

Prepared analogously to intermediate B45. $^1$H-NMR (CDCl$_3$) δ 3.26 (3H, s), 3.60 (2H, s), 3.65 (2H, t), 4.33 (2H, t), 7.83 (1H, s), 8.70 (2H, s), 9.04 (1H, s); (ES+) M+H=279; C$_{12}$H$_{14}$N$_4$O$_2$S requires 278.

Intermediate B88

1-(2-Methylprop-1-yl)-5-(pyrimid-5-ylmethyl)-2-thiouracil

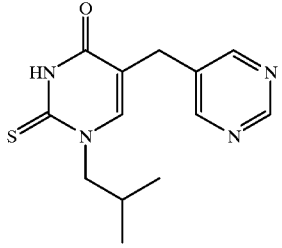

Prepared analogously to intermediate B45. (APCI) M−H= 275. $C_{13}H_{16}N_4OS$ requires 276.

Intermediate B89

1-Ethyl-5-(pyrimid-5-ylmethyl)-2-thiouracil

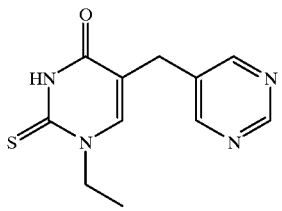

Prepared analogously to intermediate B45. $^1$H-NMR (d$_6$-DMSO) δ 1.23 (3H, t), 3.60 (2H, s), 4.19 (2H, q), 7.95(1H, s) 8.73(2H, s) and 9.04(1H, s); (APCI) M−H=247. $C_{11}H_{12}N_4OS$ requires 248.

Intermediate B90

1-(8-Phenyloctyl)-5-(pyrimid-5-ylmethyl)-2-thiouracil

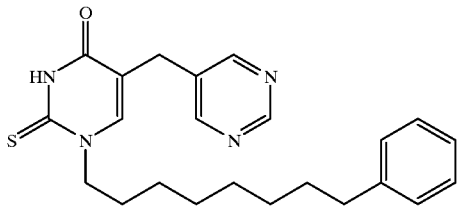

Prepared analogously to intermediate B45. $^1$H-NMR (d$_6$-DMSO) δ 1.15–1.4(8H, m), 1.45–1.8(4H, m), 2.56(2H, t), 3.6 (2H, s), 4.11(2H, t), 7.1–7.35(5H, m), 7.94(1H, s), 8.73(2H, s) and 9.02(1H, s). (APCI) M+H=409. $C_{23}H_{28}N_4OS$ requires 408.

Intermediate B91

1-(9-Phenylnonyl)-5-(pyrimid-5-ylmethyl)-2-thiouracil

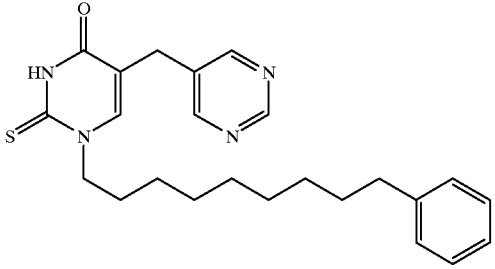

Prepared analogously to intermediate B45. $^1$H-NMR (d$_6$-DMSO) δ 1.15–1.4(8H, m), 1.45–1.8(4H, m), 2.55(2H, t), 3.58 (2H, s), 4.12(2H, t), 7.1–7.35(5H, m), 7.95(1H, s), 8.72(2H, s) and 9.02(1H, s), (APCI) M+H=421. $C_{24}H_{30}N_4OS$ requires 422.

Intermediate B92

1-Undecyl-5-(2-ethoxypyrimid-5-ylmethyl)-2-thiouracil

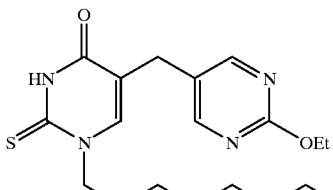

Prepared analogously to intermediate B45. $^1$H-NMR (d$_6$ DMSO) δ 0.8–0.95 (3H, m), 1.05–1.5 (19H, m), 1.6–1.8 (2H, m), 3.49 (2H, s), 4.11 (2H, t), 4.31 (2H, q), 8.48 (2H, s); MS (APCI+) found (M+1)=418; $C_{22}H_{34}N_4O_2S$ requires 417.

Intermediate B93

1-(2-Phenylethyl)-5-(pyrimid-5-ylmethyl)-2-thiouracil

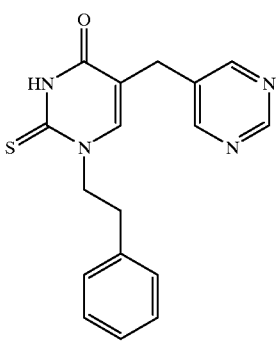

Prepared analogously to intermediate B45. Solid. $^1$H-NMR (DMSO) δ 3.00–3.10 (2H, t), 3.50 (2H, s), 4.29–4.40 (2H, t), 7.10–7.33 (5H, m), 7.71 (1H, s), 8.68 (2H, s), 9.00 (1H, s), 12.62–12.75 (1H, br.s); MS (APCI–) found (M–1)=323; C17H16N4OS requires 324.

Intermediate B94

1-Benzyl-5-(pyrimid-5-ylmethyl)-2-thiouracil

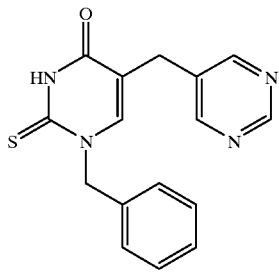

Prepared analogously to intermediate B45. Solid. $^1$H-NMR (DMSO) δ 3.57 (2H, s), 4.46 (2H, s), 7.10–7.44 (6H, m), 7.91 (1H, s), 8.69 (2H, s), 9.01 (1H, s); MS (APCI+) found (M+1)=311; $C_{16}H_{14}N_4OS$ requires 310.

Intermediate B95

1-Undecyl-5-(pyrimid-5-ylmethyl)-2-thiouracil

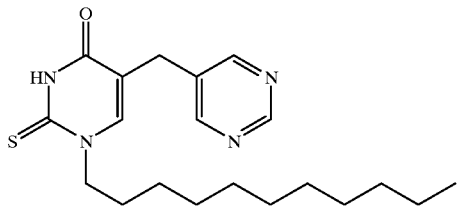

Prepared analogously to intermediate B45. Solid. $^1$H-NMR (DMSO) δ 0.79–0.93 (3H, t), 1.12–1.44 (16H, m), 1.60–1.79 (2H, t), 3.59 (2H, s), 4.05–4.20 (2H, t), 7.96 (1H, s), 8.70 (2H, s), 9.01 (1H, s), 12.61 (1H, s), MS (APCI–) found (M–1)=373; $C_{20}H_{30}N_4OS$ requires 374.

Intermediate B96

1-Dodecyl-5-(pyrimid-5-ylmethyl)-2-thiouracil

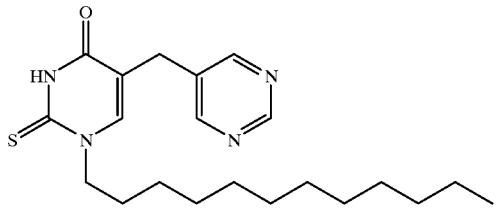

Prepared analogously to intermediate B45. Solid. $^1$H-NMR (DMSO) δ 0.79–0.94 (3H, t), 1.13–1.47 (18H, s), 1.60–1.80 (2H, br.t), 3.59 (2H, s), 4.06–4.20 (2H, t), 7.96 (1H, s), 8.71 (2H, s), 9.03 (1H, s); MS (ES–) found (M–1)=387; $C_{21}H_{32}N_4OS$ requires 388.

Intermediate B97

1-(2-(Thien-2-yl)ethyl)-5-(pyrimid-5-ylmethyl)-2-thiouracil

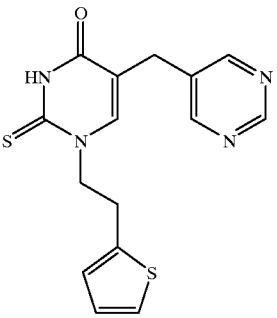

Prepared analogously to intermediate B45. Solid. $^1$H-NMR (DMSO) δ 3.17–3.47 (2H, t), 3.52 (2H, s), 4.30–4.43 (2H, t), 6.80–7.04 (2H, m), 7.27–7.40 (1H, m), 7.73 (1H, s), 8.62 (2H, s), 9.03 (1H, s) 11.97–12.5 (1H, br.s); MS (APCI–) found (M–1)=329; $C_{15}H_{14}N_4OS_2$ requires 330.

Intermediate B98

1-(5-Methylfuran-2-ylmethyl)-5-(pyrimid-5-ylmethyl)-2-thiouracil

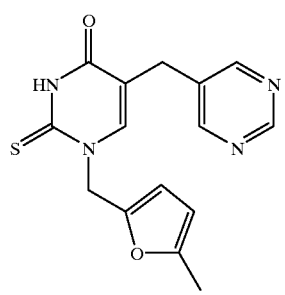

Prepared analogously to intermediate B45. Solid. $^1$H-NMR (DMSO) δ 2.24 (3H, s), 3.63 (2H, s), 5.37 (2H, s), 6.01–6.08 (1H, d), 6.30–6.38 (1H, d), 7.92 (1H, s), 8.72 (2H, s), 9.04 (1H, s) 12.73 (1H, s), MS (ES–) found (M–1)=313; $C_{15}H_{14}N_4O_2S$ requires 314.

Intermediate B99

1-(4-Fluorobenzyl)-5-(pyrimid-5-ylmethyl)-2-thiouracil

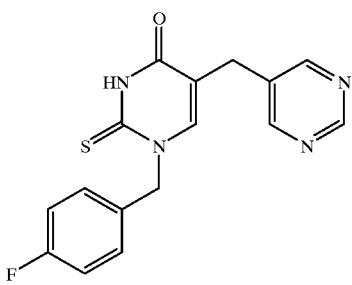

Prepared analogously to intermediate B45. Solid. $^1$H-NMR (DMSO) δ 3.60 (2H, s), 5.41 (2H, s), 7.13–7.25 (2H, m), 7.35–7.47 (2H, m), 8.02 (1H, s), 8.70 (2H, s), 9.03 (1H, s), 12.78 (1H, s); MS found (M−1)=327; $C_{16}H_{13}FN_4OS$ requires 328.

Intermediate B100

1-(2-(2-Chlorophenyl)ethyl)-5-(Pyrimid-5-ylmethyl)-2-thiouracil

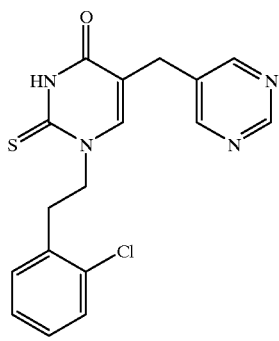

Prepared analogously to intermediate B45. Solid. $^1$H-NMR (DMSO) δ 3.12–3.22 (2H, t), 3.49 (2H, s), 4.34–4.46 (2H, t), 7.14–7.43 (4H, m), 7.52 (1H, s), 8.57 (2H, s), 9.04 (1H, s), 11.40–11.85 (1H, br.s); MS (APCI−) found (M−1)=357; $C_{17}H_{15}ClN_4OS$ requires 358.

Intermediate B101

1-(2-Phenoxyethyl)-5-(Pyrimid-5-ylmethyl)-2-thiouracil

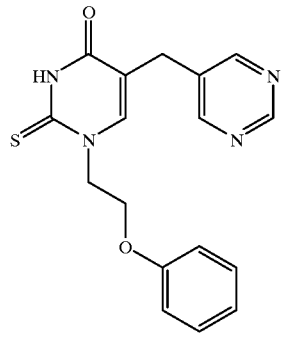

Prepared analogously to intermediate B45. Solid. $^1$H-NMR (DMSO) δ 3.63 (2H, s), 4.25–4.37 (2H, t), 4.50–4.60 (2H, t), 6.84–7.00 (3H, m), 7.20–7.33 (2H, t), 7.94 (1H, s), 8.71 (2H, s), 9.06 (1H, s), 12.78 (1H, s); MS (ES+) found (M+1)=341; $C_{17}H_{16}N_4O_2S$ requires 340.

Intermediate B102

1-(5-Ethoxycarbonylpent-1-yl)-5-(Pyrimid-5-ylmethyl)-2-thiouracil

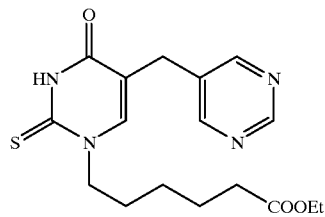

Prepared analogously to intermediate B45. Solid. $^1$H-NMR (DMSO) δ 1.10–1.20 (3H, t), 1.21–1.39 (2H, m), 1.45–1.80 (4H, m), 2.22–2.38 (2H, m), 3.59 (2H, s), 3.96–4.19 (4H, m), 7.94 (1H, s), 8.70 (2H, s), 9.03 (1H, s), 12.12–12.35 (1H, br.s); MS (ES−) found (M−1) 361; $C_{17}H_{22}N_4O_3S$ requires 362.

Intermediate B103

1-(1-Ethoxycarbonylethyl)-5-(pyrimid-5-ylmethyl)-2-thiouracil

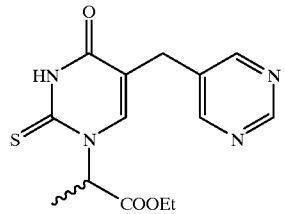

Prepared analogously to intermediate B45. Solid. ¹H-NMR (DMSO) δ 1.06–1.30 (3H, t), 1.58–1.70 (3H, d), 3.67 (2H, d), 4.02–4.27 (2H, m), 6.02–6.19 (1H, q), 8.05 (1H, s), 8.70 (2H, s), 9.03 (1H, s), 12.80 (1H, s); MS (APCI+) found (M+1)=321; $C_{14}H_{16}N_4O_3S$ requires 320.

Intermediate B104

1-(1-Methylethyl)-5-(pyrimid-5-ylmethyl)-2-thiouracil

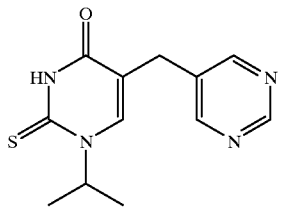

Prepared analogously to intermediate B45. Solid. ¹H-NMR (DMSO) δ 1.26–1.45 (6H, d), 3.65 (2H, s), 5.53–5.74 (1H, m), 8.10 (1 h, s), 8.72 (2H, s), 9.02 (1H, s), 12.60 (1H, s); MS (APCI–) found (M+1)=261; $C_{12}H_{14}N_4OS$ requires 262.

Intermediate B105

1-Cyclopropyl-5-(pyrimid-5-ylmethyl)-2-thiouracil

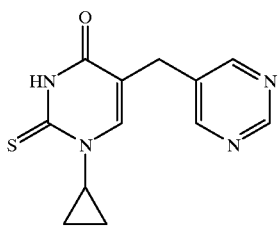

Prepared analogously to intermediate B45. Solid. ¹H-NMR (DMSO) δ 0.92–1.10 (4H, m), 3.37–3.43 (1H, m), 3.60 (2H, s), 7.89 (1H, s), 8.71 (2H, s), 9.02 (1H, s), 12.60 (1H, s); MS (APCI–) found (M–1)=259; $C_{12}H_{12}N_4OS$ requires 260.

Intermediate B106

1-(1-Ethoxycarbonylcycloprop-1-yl)-5-(pyrimid-5-ylmethyl)-2-thiouracil

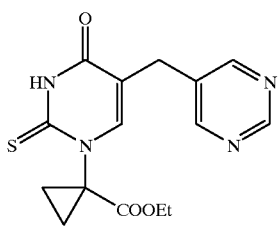

Prepared analogously to intermediate B45. Solid. ¹H-NMR (DMSO) δ 1.05–1.20 (3H, t), 1.40–1.95 (4H, m), 3.61 (2H, s), 4.02–4.18 (2H, q), 7.98 (1H, s), 8.72 (2H, s), 9.04 (1H, s), 12.04 (1H, s); MS (APCI+) found (M+1)=333; $C_{15}H_{16}N_4OS$ requires 332.

Intermediate B107

1-(4-Ethoxycarbonylbenzyl)-5-(pyrimid-5-ylmethyl)-2-thiouracil

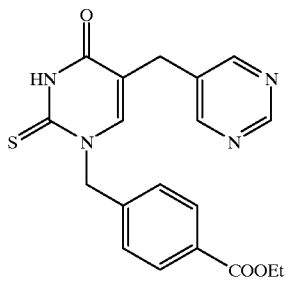

Prepared analogously to intermediate B45. Solid. ¹H-NMR (DMSO) δ 1.23–1.38 (3H, t), 3.60 (2H, s), 4.24–4.40 (2H, q), 5.50 (2H, s), 7.35–7.47 (2H, m), 7.86–8.00 (2H, m), 8.04 (1H, s), 8.70 (2H, s), 9.03 (1H, s), 12.07–12.40 (1H, br.s); MS (APCI–) found (M–1)=381; $C_{19}H_{18}N_4O_3S$ requires 382.

Intermediate B108

1-(4-Methoxycarbonylcyclohex-1-yl)-5-(pyrimid-5-ylmethyl)-2-thiouracil

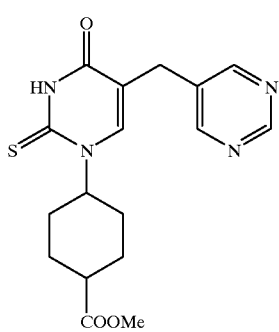

Prepared analogously to intermediate B45. Solid. ¹H-NMR (DMSO) δ 1.32–1.92 (6H, m), 2.10–2.30 (2H, m), 2.67–2.80 (1H, m), 3.64 (3H, s), 3.69 (2H, s), 5.17–5.34 (1H, br.s), 7.87 (1H, s), 8.70 (2H, s), 9.01 (1H, s), 12.63 (1H, s); MS (APCI–) found (M–1)=359; $C_{17}H_{20}N_4O_3S$ requires 360.

Intermediate B109

1-(2-(6-(4-Fluorophenyl)hex-1-yloxy)ethyl)-5-(pyrimid-5-ylmethyl)-2-thiouracil

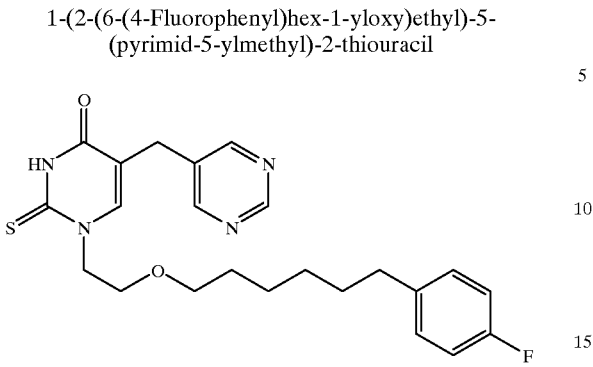

Prepared analogously to intermediate B45. Solid. $^1$H-NMR (DMSO) δ 1.14–1.60 (12H, m), 3.60 (2H, s), 3.62–3.70 (2H, t), 4.26–4.35 (2H, t), 7.00–7.12 (2H, t), 7.14–7.24 (2H, m), 7.80 (1H, s), 8.70 (2H, s), 9.00 (1H, s), 12.64–12.77 (1H, br.s); MS (APCI−) found (M−1)=441; $C_{23}H_{27}FN_4O_2S$ requires 442.

Intermediate B110

1-Undecyl-5-(1-methyl-2-oxopyrid-4-ylmethyl)-2-thiouracil

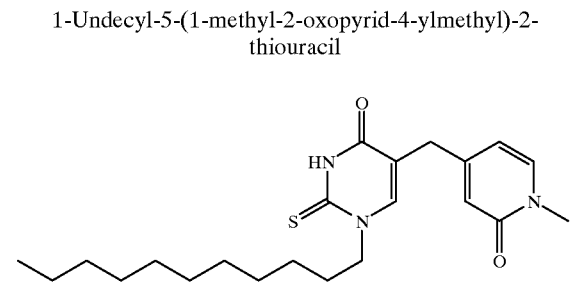

Prepared analogously to intermediate B45. $^1$H-NMR (CDCl$_3$) δ 0.88 (3H, t), 1.26 (14H, m), 1.32 (2H, t), 1.75 (2H, m), 3.48 (2H, s), 3.52 (3H, s), 4.11 (2H, t), 6.10 (1H, m), 6.40 (1H, s), 7.08 (1H, s), 7.22 (1H, d), 9.56 (1H, bs); MS (APCI+) M+1=404, $C_{22}H_{33}N_3O_2S$ requires 403. MPt 137–140° C. (cream solid)

Intermediate B111

1-(3-Ethoxycarbonylpropyl)-5-(1-methyl-2-oxopyrid-4-ylmethyl)-2-thiouracil

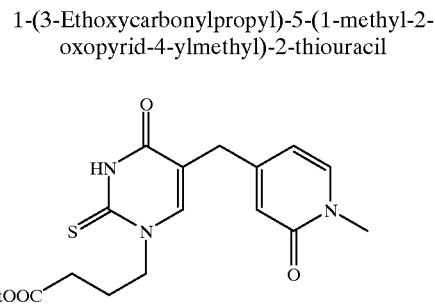

Prepared analogously to intermediate B45. $^1$H-NMR (d$_6$-DMSO) δ 1.17 (3H, t), 1.95 (2H, m), 2.35 (2H, m), 3.34 (5H, m), 4.03 (2H, q), 4.17 (2H, m), 6.11 (1H, m), 6.20 (1H, s), 7.57 (1H, d), 7.83 (1H, s), 12.63 (1H, bs); MS (APCI+) M+1=3642, $C_{17}H_{21}N_3O_4S$ requires 363. MPt 168–170° C. (cream solid).

Intermediate B112

1-(2-(4-Pent-1-ylphenyl)ethyl)-5-(pyrimid-5-ylmethyl)-2-thiouracil

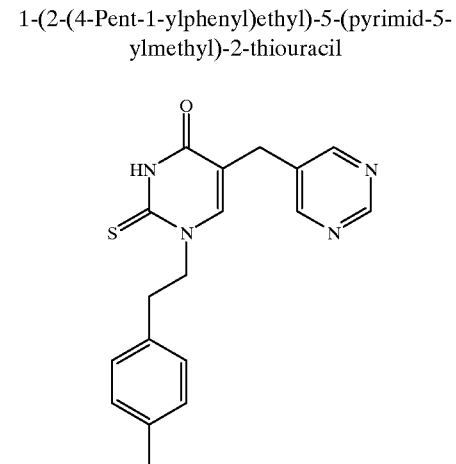

Prepared analogously to intermediate B45. $^1$H-NMR (d$_6$-DMSO) δ 0.85 (3H, m), 1.25 (4H, m), 1.53 (2H, m), 2.52 (2H, m), 2.99 (2H, m), 3.49 (2H, s), 4.33 (2H, m), 7.03–7.24 (4H, m), 7.71 (1H, s), 8.59 (2H, s), 9.03 (1H, s), 12.70 (1H, bs); MS (APCI+) M+1=395, $C_{22}H_{26}N_4OS$ requires 394. (light brown solid)

Intermediate B113

1-(2-(4-Pent-2-en-1-ylphenyl)ethyl)-5-(pyrimid-5-ylmethyl)-2-thiouracil

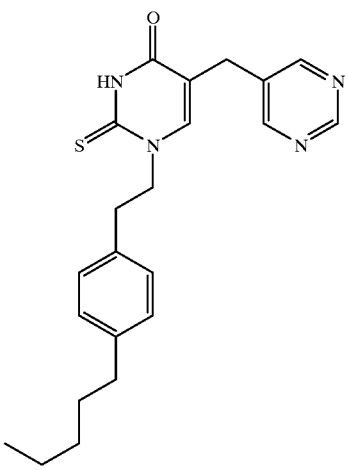

Prepared analogously to intermediate B45. $^1$H-NMR (d$_6$-DMSO) δ 0.89 (3H, m), 1.30–1.60 (2H, m), 2.24 (2H, m), 3.03 (2H, m), 3.51 (2H, s), 4.35 (2H, m), 5.63 (1H, m), 6.33 (1H, s), 7.10–7.33 (4H, m),7.76 (1H, s), 8.61 (2H, s), 9.03 (1H, s), 12.70 (1H, bs); MS (APCI+) M+1=393, $C_{22}H_{24}N_4OS$ requires 392. (light brown solid)

Intermediate B114

1-(2-(4-Bromophenyl)ethyl)-5-(pyrimid-5-ylmethyl)-2-thiouracil

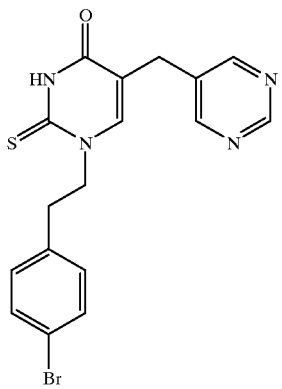

Prepared analogously to intermediate B45. $^1$H-NMR (d$_6$-DMSO) δ 3.02 (2H, t), 3.53 (2H, s), 4.33 (2H, t), 7.22 (2H, m), 7.49 (2H, m), 7.77 (1H, s), 8.60 (2H, s), 9.02 (1H, s), 12.7 (1H, bs), MS (APCI+) M+1=403, C$_{17}$H$_{15}$BrN$_4$OS requires 402

Intermediate B115

1-(4-Bromobenzyl)-5-(pyrimid-5-ylmethyl)-2-thiouracil

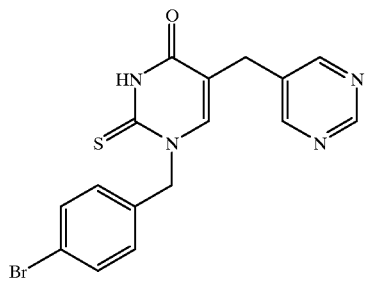

Prepared analogously to intermediate B45. $^1$H-NMR (d$_6$-DMSO) δ 3.60 (2H, s), 5.39 (2H, s), 7.29 (2H, d), 7.57 (2H, d), 8.01 (1H, s), 8.70 (2H, s), 9.03 (1H, s), 12.75 (1H, bs), MS (APCI+) M+1=389, C$_{16}$H$_{13}$BrN$_4$OS requires 388

Intermediate B116

1-(2-(3-Pent-1-ylphenyl)ethyl)-5-(pyrimid-5-ylmethyl)-2-thiouracil

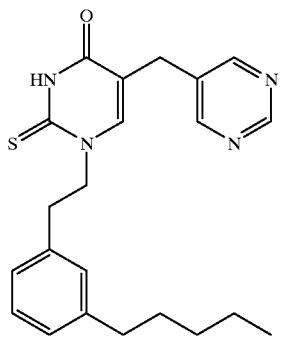

Prepared analogously to intermediate B45. $^1$H-NMR (CDCl$_3$) δ 0.89 (3H, m), 1.30 (4H, m), 1.55 (2H, m), 2.53 (2H, t), 3.10 (2H, t), 3.42 (2H, s), 4.35 (2H, t), 6.49 (1H, s), 6.91–7.22 (4H, m), 8.44 (2H, s), 9.11 (1H, s), 9.60 (1H, bs) MS(APCI+) M+1=395, C$_{22}$H$_{26}$N$_4$OS requires 394. MPt 137.5° C. (colourless solid)

Intermediate B117

1-(2-(2-Pent-1-ylphenyl)ethyl)-5-(pyrimid-5-ylmethyl)-2-thiouracil

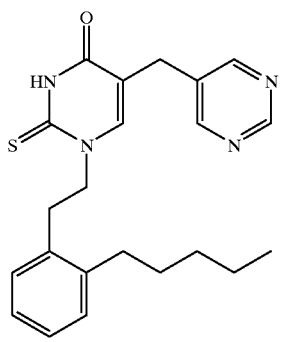

Prepared analogously to intermediate B45. $^1$H-NMR (CDCl$_3$) δ 0.88 (3H, t), 1.28 (4H, m), 1.49 (2H, m), 2.50 (2H, t), 3.15 (2H, t), 3.42 (2H, s), 4.34 (2H, t), 6.41 (1H, s), 7.03–7.21 (4H, m), 8.50 (2H, s), 9.12 (1H, s), 9.70 (1H, bs); MS(APCI+) M+1=395, C$_{22}$H$_{26}$N$_4$OS requires 394. MPt 181.6° C. (pale orange solid)

Intermediate B118

1-(3-Ethoxycarbonylphenyl)-5-(pyrimid-5-ylmethyl)-2-thiouracil

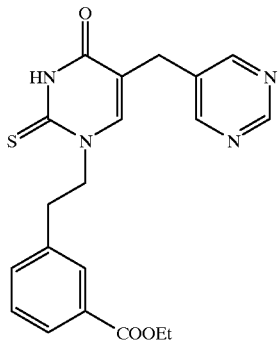

Prepared analogously to intermediate B45. ¹H NMR (CDCl₃) δ: 1.41 (t, 3H), 3.70 (s, 2H), 4.41 (q, 2H), 7.30 (s, 1H), 7.35 (m, 1H), 7.60 (m, 2H), 7.98 (m, 1H), 8.15 (d, 1H), 8.71 (s, 2H), 9.10 (s, 1H). MS (ES+) Found (M+1)=369; $C_{18}H_{16}N_4O_3S$ requires 368.

Intermediate B119

1-(4-Ethoxycarbonylphenyl)-2-(4-fluorobenzyl)thio-5-(pyrimid-5-ylmethyl)-2-thiouracil

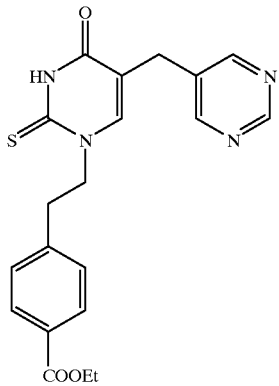

Prepared analogously to intermediate B45. ¹H NMR (CDCl₃) δ: 1.41 (t, 3H), 3.69 (s, 2H), 4.39 (q, 2H), 7.30 (s, 1H), 7.46 (d, 2H), 8.21 (d, 2H), 8.72 (s, 2H), 9.10 (s, 1H). MS (ES+) Found (M+1)=369; $C_{18}H_{16}N_4O_3S$ requires 368.

Intermediate B120

1-(5-(Ethoxycarbonyl)fur-2-yl)-2-(4-fluorobenzyl)thio-5-(pyrimid-5-ylmethyl)-2-thiouracil

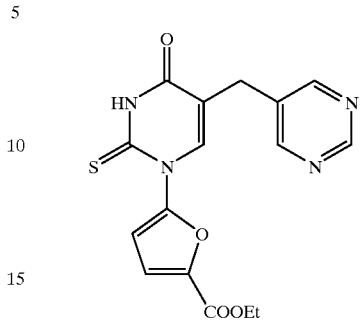

Prepared analogously to intermediate B45. ¹H NMR (CDCl₃) δ: 1.39 (t, 3H), 3.69 (s, 2H), 4.39 (q, 2H), 6.69 (d, 1H), 7.28 (d, 1H), 7.41 (s, 1H), 8.72 (s, 2H), 9.12 (s, 1H). MS (APCI+) Found (M+1)=359; $C_{16}H_{14}N_4O_4S$ requires 358.

Intermediate B121

1-Phenyl-2-(4-fluorobenzyl)thio-5-(pyrimid-5-ylmethyl)-2-thiouracil

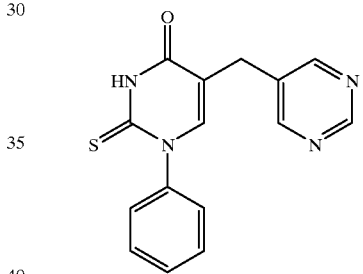

Prepared analogously to intermediate B45. ¹H NMR (CDCl₃) δ: 3.69 (s, 2H), 7.30 (m, 3H), 7.50 (m, 3H), 8.72 (s, 2H), 9.10 (s, 1H). MS (ES+) Found (M+1)=297; $C_{15}H_{12}N_4OS$ requires 296.

Intermediate B122

1-(4-(tert-Butoxycarbonylamino)but-1-yl)-2-(4-fluorobenzyl)thio-5-(pyrimid-5-ylmethyl)-2-thiouracil

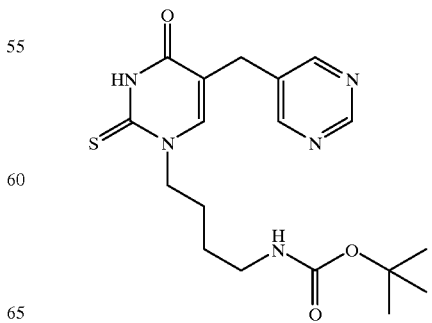

Prepared analogously to intermediate B45. ¹H NMR (DMSO-d$_6$) δ: 1.37 (s, 9H), 1.4 (m, 2H), 1.65 (m, 2H), 2.93 (m, 2H), 3.59 (s, 2H), 4.13 (t, 2H), 6.81 (br s, 1H), 7.49 (s, 1H), 8.70 (s, 2H), 9.04 (s, 1H), 13.45 (br s, 1H). MS (ES+) Found (M+1) 392; $C_{18}H_{25}N_5O_3S$ requires 391.

Intermediate B123

1-(3-(Ethoxycarbonylamino)prop-1-yl)-2-(4-fluorobenzyl)thio-5-(pyrimid-5-ylmethyl)-2-thiouracil

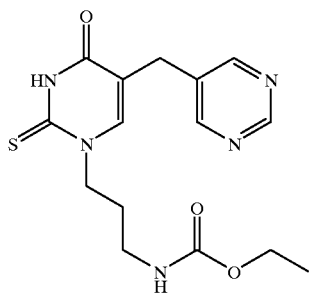

Prepared analogously to intermediate B45 as a pale buff solid. 1H NMR (DMSO-d$_6$) δ: 1.15 (t, 3H), 1.85 (m, 2H), 3.02 (m, 2H), 3.59 (s, 2H), 4.01 (q, 2H), 4.14 (t, 2H), 7.12 (br s, 1H), 7.93 (s, 1H), 8.69 (s, 2H), 9.00 (s, 1H), 13.55 (br s, 1H). MS (APCI+) Found (M+1)=350; $C_{15}H_{19}N_5O_3S$ requires 349.

Intermediate B124

1-(1-Undecyl)-5-(2-methoxypyrimid-5-ylmethyl)-2-thiouracil

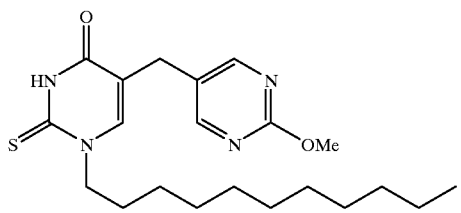

Prepared analogously to intermediate B45, except using sodium methoxide in place of ethoxide. ¹H-NMR (CDCl$_3$) δ 0.8–0.95 (3H, t), 1.1–1.85 (18H, m), 3.59 (2H, s), 4.01 (3H, s), 4.11 (2H, t), 7.04 (1H, s), 8.43 (2H, s); MS (APCI+) found (M+1)=405; $C_{21}H_{32}N_4O_2S$ requires 404.

Intermediate B125

1-(4-(Dec-1-yl)phenyl)-5-(pyrimid-5-ylmethyl)-2-thiouracil

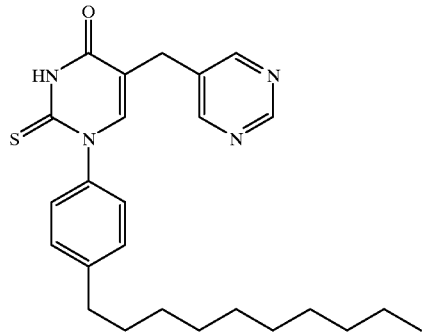

Prepared analogously to intermediate B45. The ethoxide cyclisation step failed to go to completion, but the crude thiouracil was used in the next step without purification.

Intermediate B126

1-(4-(Non-1-yloxyphenyl))-5-(pyrimid-5-ylmethyl)-2-thiouracil

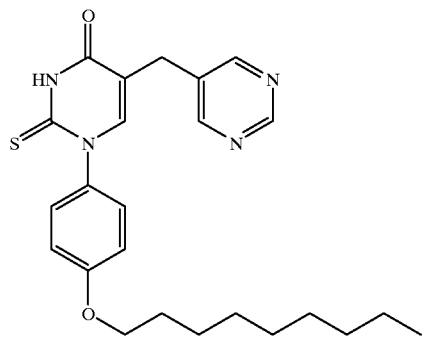

Prepared analogously to intermediate B125

Intermediate B127

1-(4-(Hex-1-yl)phenyl)-5-(pyrimid-5-ylmethyl)-2-thiouracil

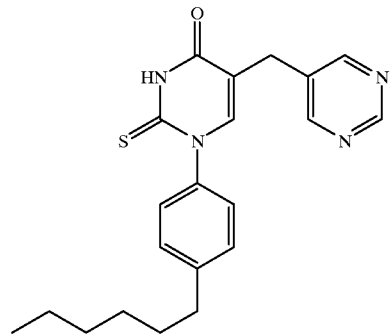

Prepared analogously to intermediate B125

Intermediate B128

1-(3-(Non-1-yloxy)phenyl)-5-(pyrimid-5-ylmethyl)-2-thiouracil

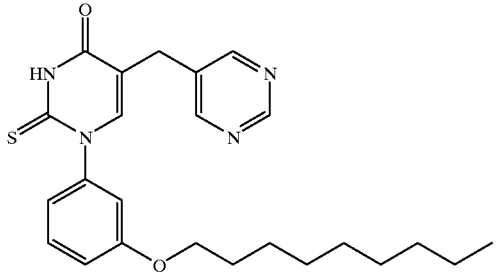

Prepared analogously to intermediate B125

Intermediate B129

1-(3-(Dec-1-yl)phenyl)-5-(pyrimid-5-ylmethyl)-2-thiouracil

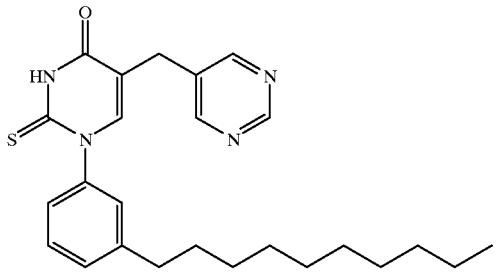

Prepared analogously to intermediate B125

Intermediate B130

1-(4-Iodophenyl)-5-(pyrimid-5-ylmethyl)-2-thiouracil

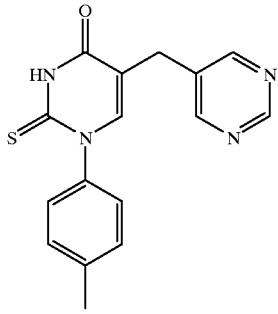

Prepared analogously to intermediate B125

Intermediate B131

1-(2-Fluorobenzyl)-5-(pyrimid-5-ylmethyl)-2-thiouracil

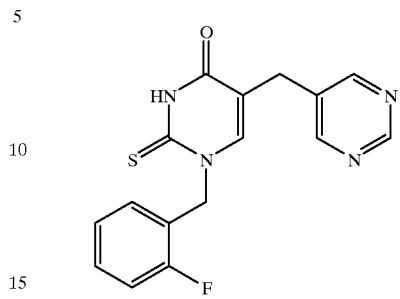

Prepared analogously to intermediate B45. $^1$H NMR (d$_6$-DMSO) δ 3.62 (2H, s), 5.45 (2H, s), 7.1–7.4 (4H, m), 7.98 (1H, s), 8.70 (2H, s), 9.04 (1H, s), 12.8 (1H, bs), MS (APCI−) M−1=327, C$_{16}$H$_{13}$FN$_4$OS requires 328

Intermediate B132

(S)-1-(Tetrahydrofur-2-ylmethyl)-5-(pyrimid-5-ylmethyl)-2-thiouracil

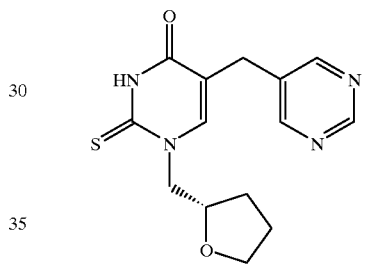

Prepared analogously to intermediate B45. $^1$H NMR (d$_6$-DMSO) δ 1.5–1.65 (1H, m), 1.75–2.05 (3H, m), 3.62 (2H, s), 3.65 (1H, m), 3.79 (1H, m), 3.95 (1H, m), 4.24 (1H, m), 4.47 (1H, dd), 7.83 (1H, s), 8.70 (2H, s), 9.04 (1H, s), 12.7 (1H, bs), MS (APCI−) M−1=303, C$_{14}$H$_{16}$N$_4$O$_2$S requires 304

Intermediate B133

(R)-1-(Tetrahydrofur-2-ylmethyl)-5-(pyrimid-5-ylmethyl)-2-thiouracil

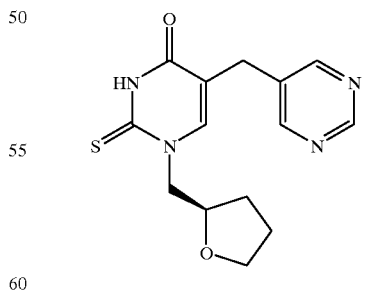

Prepared analogously to intermediate B45. $^1$H NMR (d$_6$-DMSO) δ 1.5–1.65 (1H, m), 1.75–2.05 (3H, m), 3.62 (2H, s), 3.65 (1H, m), 3.79 (1H, m), 3.95 (1H, m), 4.24 (1H, m), 4.47 (1H, dd), 7.83 (1H, s), 8.70 (2H, s), 9.04 (1H, s), 12.7 (1H, bs), MS (APCI−) M−1=303, C$_{14}$H$_{16}$N$_4$O$_2$S requires 304

Intermediate B134

1-(2-(4-Methoxyphenyl)ethyl)-5-(pyrimid-5-ylmethyl)-2-thiouracil

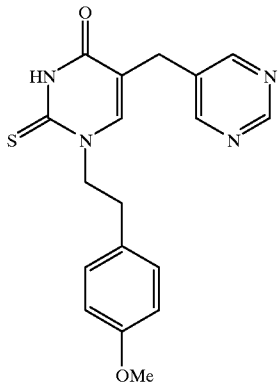

Prepared analogously to intermediate B45. $^1$H-NMR (d$_6$-DMSO) δ 2.97 (2H, t), 3.51 (2H, s), 3,74 (3H, s), 4.31 (2H, t), 6.85 (2H, m), 7.49 (2H, m), 7.14 (1H, s), 8.59 (2H, s), 9.03 (1H, s), 12.7 (1H, bs), MS (APCI+) M+1=355, C$_{18}$H$_{18}$N$_4$O$_2$S requires 354

Intermediate B135

1-(Undec-1-yl)-5-(2-methylpyrimid-5-ylmethyl)-2-thiouracil

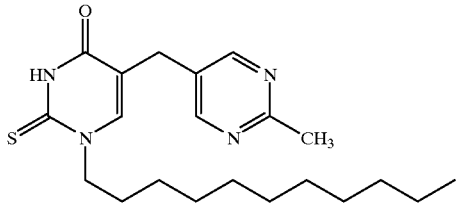

Prepared analogously to intermediate B45, except using sodium methoxide in place of ethoxide. $^1$H-NMR (CDCl$_3$) δ 0.8–0.9 (3H, t), 1.2–1.35 (16H, m), 1.75 (2H, m), 2.73 (3H, s), 3.62 (2H, s), 4.11 (2H, t), 7.05 (1H, s), 8.57 (2H, s), 9.7–9.8 (1H, br s); MS (APCI+) found (M+1)=389; C$_{21}$H$_{32}$N$_4$OS requires 388.

Intermediate B136

1-(4-Acetylphenyl)-5-(pyrimid-5-ylmethyl)-2-thiouracil

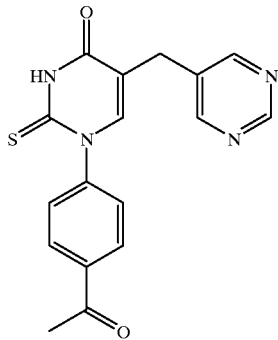

Prepared analogously to intermediate B125.

Intermediate B137

1-(trans-4-(Methoxycarbonyl)cyclohex-1-ylmethyl)-2-(4-fluorobenzyl)thio-5-(pyrimid-5-ylmethyl)-2-thiouracil

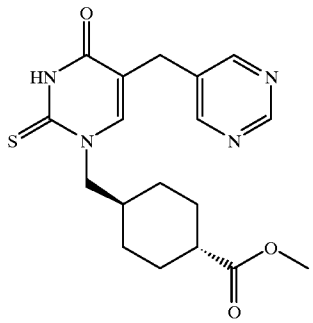

Prepared analogously to intermediate B45. $^1$H-NMR (d$_6$-DMSO) δ 1.0–1.4 (4H, m), 1.65 (2H, m), 1.92 (2H, m), 2.15–2.35 (1H, m), 3.58 (3H, s), 3.60 (2H, s), 4.01 (2H, m), 7.88 (1H, s), 8.70 (2H, s), 9.06 (1H, s), 12.6 (1H, br s); MS (APCI−) found (M−1)=373; C18H22N4O3S requires 374.

Intermediate B138

1-(2-(t-Butoxycarbonylamino)ethyl)-5-(pyrimid-5-ylmethyl)-2-thiouracil

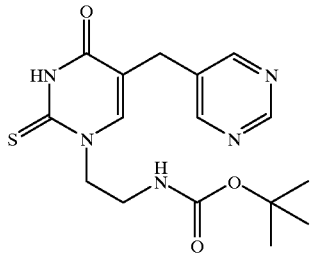

Prepared analogously to intermediate B45. $^1$H-NMR (d6-DMSO) δ 1.34 (9H, s), 3.32 (2H, m), 3.58 (2H, s), 4.19 (2H, m), 6.99 (1H, t), 7.69 (1H, s), 8.71 (2H, s), 9.03 (1H, s), 12.6 (1H, br s); MS (APCI−) found (M−1)=362; $C_{16}H_{21}N_5O_3S$ requires 363.

Intermediate B139

1-(3-(5-Phenylpent-1-yloxy)prop-1-yl)-5-(pyrimid-5-ylmethyl)-2-thiouracil

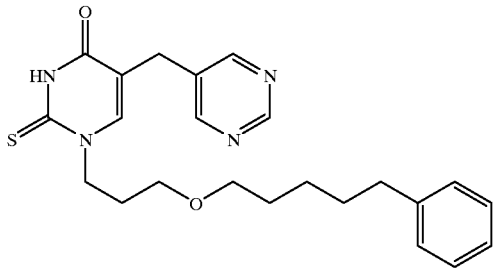

Prepared analogously to intermediate B45. $^1$H-NMR (d6-DMSO) δ 1.33 (2H, m), 1.4–1.7 (4H, m), 1.95 (2H, m), 2.55 (2H, t), 3.2–3.5 (4H, m), 3.60 (2H, s), 4.18 (2H, t), 7.1–7.3 (5H, m), 7.86 (1H, s), 8.71 (2H, s), 9.03 (1H, s), 12.6 (1H, br s); MS (APCI+) found (M+1)=425; $C_{23}H_{28}N_4O_2S$ requires 424.

General method A: S-Alkylation of thiouracils

A1 (N1-unsubstituted thiouracils). Sodium (2.2 equiv) was dissolved in ethanol to give a ca. 0.5M solution of sodium ethoxide. The appropriate thiouracil (1 equiv) was added, usually giving a clear solution, then the appropriate alkyating agent was added (1.0–1.25 equiv were used in various preparations, but no consistent advantage was seen with higher amounts) and the mixture was stirred at room temperature overnight. The ethanol was removed by evaporation, the residue was taken up in water, and the solution adjusted to pH 5 with acetic acid. In many cases the product precipitated, and was filtered off, washed with water and dried. When necessary, the aqueous solution was extracted with ethyl acetate, the organic layers dried and evaporated, and the residue triturated with ether or pet, ether to obtain the product.

A2. A mixture of thiouracil (1 equiv), the appropriate alkylating agent (1–1.1 equiv) and diisopropylethylamine (1–1.1 equiv) was stirred overnight at room temperature in dichloromethane (12 ml/mmol). The solution was diluted with dichloromethane and washed with saturated sodium bicarbonate solution. The organic layer was added directly to a silica gel column. Elution (ethyl acetate to methanol-:ethyl acetate) gave the desired product.

A3. A mixture of thiouracil (1 equiv), the appropriate alkylating agent (1–1.1 equiv) and diisopropylethylamine (1–1.1 equiv) was stirred for 1 h at between 64 and 72° C. in 1,2-dichloroethane (12 ml/mmol). The solution was diluted with dichloromethane and washed with saturated sodium bicarbonate solution. The organic layer was added directly to a silica gel column. Elution (ethyl acetate to methanol:ethyl acetate) gave the desired product.1

A4. A mixture of the appropriate thiouracil (1 equiv), the appropriate alkylating agent (1.1 equiv) and potassium carbonate (2–3 equiv) in dry dimethylformamide (ca 4 ml/mmol) was heated at 65° C. for 2.5 h. The mixture was cooled, the solvent was removed under reduced pressure and the residue partitioned between dichloromethane (50 ml) and 3% aqueous potassium carbonate solution. The organic layer was applied directly to a SepPak cartridge (10 g, Silica) and elution was continued with 2% to 8% methanol in ethyl acetate as eluent. This gave 1-(4 hydroxycyclohexyl)-2-(8-(4-chlorophenyl)-8-oxooct-1-yl) thio-5-(pyrimid-5-ylmethyl)pyrimidin-4-one (0.1 8 g)

A5. Array synthesis. This proceeded essentially as in method A1, except that parallel reactions were carried out in screw-capped polypropylene tubes. The appropriate thiouracil (1 equiv) was weighed into each tube, then 0.5M ethanolic sodium ethoxide (2 equiv) and the appropriate alkyl halide (1 equiv) as an 0.5M ethanol solution were dispensed in by pipette and the tubes capped and vortexed at room temperature overnight on an orbital shaker. After removal of solvent in a vacuum centrifuge, individual products were worked up in the usual way.

General method B: Displacement of 2-(nitroamino) pyrimidones with thiols

The appropriate 2-(nitroamino)pyrimidone (1 equiv) and thiol (2 equiv) in pyridine (ca 2 ml per mmol) were stirred at reflux for 2 days, then the pyridine was evaporated. Trituration with an appropriate solvent, as described in the individual examples, gave the desired product.

General method C: N1-Alkylation of pyrimidin-4-ones

C1. To a stirred solution of the pyrimidinone (1 equiv) in dry DMF (20 ml) was added sodium hydride (1 equiv). The mixture was stirred at room temperature for 30 min, then the appropriate alkylating agent (1–1.1 equiv) was added in portions over 15 min, and the mixture was stirred overnight. Ethyl acetate and dilute hydrochloric acid were added, the organic layer was separated and washed with water and brine, dried and evaporated. Flash chromatography (silica, 1–10% methanol in dichloromethane) gave first a mixture of the 3-alkyl and 4-alkoxypyrimidine byproducts, then the desired 1-alkylpyrimidin-4-one.

C2. A mixture of pyrimidinone (1 equiv), the appropriate alkylating agent (1–1.1 equiv) and diisopropylethylamine (1–1.5 equiv, usually 1.25–1.3 equiv) was stirred for between 20–72 h at room temperature in dichloromethane (12 ml/mmol) (if the pyrimidinone was only partially soluble in dichloromethane, dimethylformamide (2 ml/mmol) was also added). The solution was diluted with dichloromethane containing up to 2% methanol (if dimethylformamide was used, the solvent was first removed under reduced pressure) and washed with saturated ammonium chloride solution and sodium bicarbonate solution. The organic layer was separated and added directly to a silica gel column. Elution (ethyl acetate to methanol:dichloromethane:ethyl acetate) gave the desired product.

C3. Similar to method C2, except that the solvent was 1,2-dichloroethane in place of dichloromethane, and the pyrimidone was treated with tributyltin chloride (1 equiv) and stirred overnight to form the silyl ether before addition of the alkylating agent.

General method D: Ester hydrolysis

To a solution of the ester (1 equiv) in 1,4 dioxane (9 ml/mmol) under argon was added a solution of sodium hydroxide (0.95–1 equiv) in water (2–4.5 ml/mmol) whilst keeping the temperature below 25° C. After stirring for between 2–20 h at room temperature (the reaction was checked for completion), 75% of the solvent was removed under reduced pressure at <25° C. The residue was diluted with water and brought to pH3 with 5% aqueous sodium bisulphate. The solid so formed was filtered and dried in vacuo to give the desired material.

General method E: Amide coupling

To a slurry/solution of the carboxylic acid (1 equiv) in dichloromethane (or dimethylformamide) (12 ml/mmol) was added hydroxybenzotriazole (0.1 equiv), the amine (1 equiv) and 1-(3-dimethylaminopropyl)-3-ethylcarbodiimide hydrochloride (1.05 eq). After stirring under argon for 24 h, (the solvent removed under reduced pressure if dimethylformamide) the mixture was diluted with dichloromethane and washed with saturated sodium bicarbonate. Addition of the organic layer directly to a silica gel column and elution (ethyl acetate to methanol:ethyl acetate) gave the desired product. Alternatively, the crude product could be purified by solid phase extraction on a BondElut SCX cartridge, eluted with dichloromethane/methanol.

General method F: Urea synthesis

The appropriate BOC-protected amine was dissolved in neat TFA (ca 5 ml/g) at room temperature. After 5min the solution was concentrated to a brown gum and re-evaporated from ethyl acetate. The crude amine salt in dichloromethane (ca 15 ml/g) was treated with the isocyanate (1.1 equiv.) in dichloromethane, followed by the addition of triethylamine and the reaction mixture shaken overnight. The reaction mixture was centrifuged to remove any solid material and the supernatent washed with water. The organic layer was dried over anhydrous magnesium sulfate and the solution concentrated. The crude material was then purified by silica gel chromatography.

Example 1

2-(8-Phenyloct-1-yl)thio-5-((1-benzyl-2-oxo-pyrid-4-yl)methyl)pyrimidin-4-one

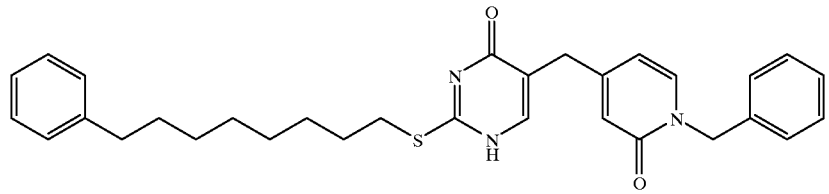

Prepared from intermediate B10 by general method A1 as a white solid. MPt 124–129° C.; $^1$H-NMR (d$_6$ DMSO) δ 1.2–1.5 (8H, m), 1.5–1.8 (4H, m), 2.59 (2H, t), 3.13 (2H, t), 3.54 (2H, s), 5.10 (2H, s), 6.14 (1H, dd), 6.50 (1H, bs), 7.15–7.4 (11H, m) and 7.68 (1H, s).

Example 2

2-(8-(4-Fluorophenyl)oct-1-yl)thio-5-((1-benzyl-2-oxo-pyrid-4-yl)methyl)pyrimidin-4-one

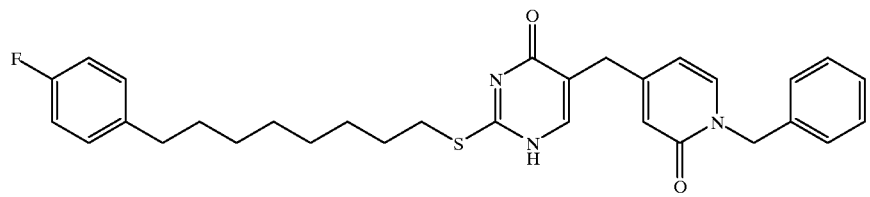

Prepared from intermediate B10 and A21 by general method A5 as a white solid. MPt 147–151° C.; $^1$H-NMR (CDCl$_3$) δ 1.2–1.5 (8H, m), 1.5–1.8 (4H, m), 2.58 (2H, t), 3.15 (2H, t), 3.55 (2H, s), 5.10 (2H, s), 6.15 (1H, dd), 6.47 (1H, m), 6.95 (2H, t), 7.05–7.2 (3H, m), 7.25–7.45 (5H, m) and 7.67 (1H, s); MS (EI) M=531; C$_{31}$H$_{34}$FN$_3$O$_2$S requires 531.

Example 3

2-(8-(4-Chlorophenyl)oct-1-yl)thio-5-((1-benzyl-2-oxo-pyrid-4-yl)methyl)pyrimidin-4-one

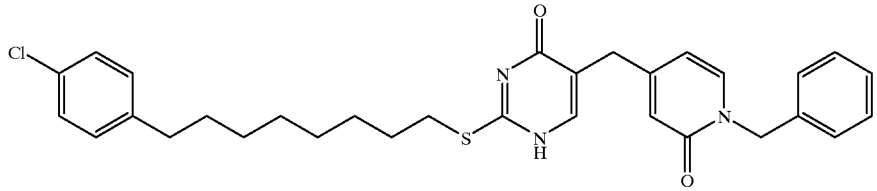

Prepared from intermediates B10 and A24 by general method A5 as a white solid. MPt 160–164° C.; $^1$H-NMR (CDCl$_3$) δ 1.2–1.8 (12H, m), 2.56 (2H, t), 3.13 (2H, t), 3.55 (2H, s), 5.10 (2H, s), 6.15 (1H, m), 6.48 (1H, bs), 7.0–7.45 (10H, m) and 7.67 (1H, s); MS (EI) M=547; C31H34ClN3O2S requires 547.

Example 4

2-(8-(4-Chlorophenyl)-8-oxooct-1-yl)thio-5-((1-benzyl-2-oxo-pyrid-4-yl)methyl)pyrimidin-4-one

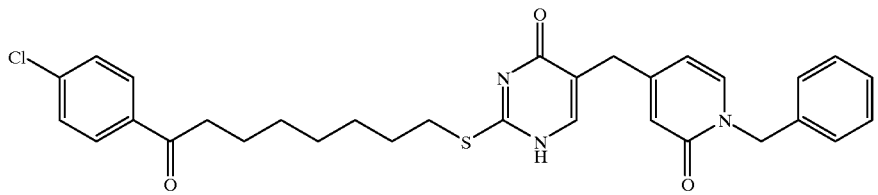

Prepared from intermediates B10 and A1 by general method A5 as a white solid. MPt 147–151° C.; $^1$H-NMR (CDCl$_3$) δ 1.2–1.8 (10H, m), 2.93 (2H, t), 3.13 (2H, t), 3.55 (2H, s), 5.10 (2H, s), 6.15 (1H, dd), 6.49 (1H, bs), 7.05–7.5 (8H, m), 7.68 (1H, s) and 7.89 (2H, d); MS (EI) M=561; $C_{31}H_{32}ClN_3O_3S$ requires 561.

Example 5

2-(8-(4-Fluorophenyl)-8-oxooct-1-yl)thio-5-((1-benzyl-2-oxo-pyrid-4-yl)methyl)pyrimidin-4-one

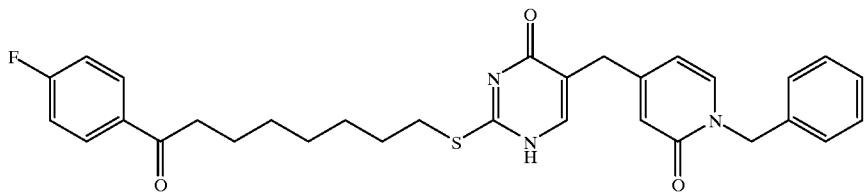

Prepared from intermediates B10 and A8 by general method A5 as a white solid. MPt 125–133° C.; $^1$H-NMR (CDCl$_3$) δ 1.2–1.8 (10H), 2.93 (2H, t), 3.13 (2H, t), 3.55

(2H, s), 5.10 (2H, s), 6.15 (1H, m), 6.48 (1H, bs), 7.05–7.45 (8H, m), 7.68 (1H, s) and 7.97 (2H, m); MS (EI) M=545; C$_{31}$H$_{32}$FN$_3$O$_3$S requires 545.

Example 6

2-(9-Phenylnon-1-yl)thio-5-((1-benzyl-2-oxo-pyrid-4-yl)methyl)pyrimidin-4-one

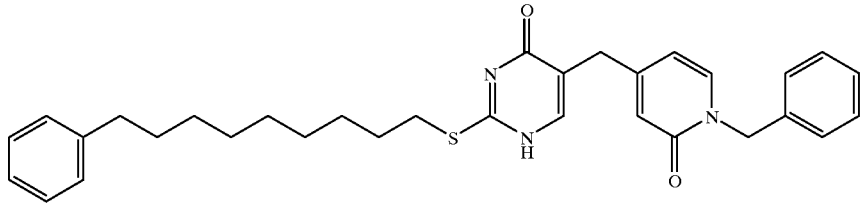

Prepared from intermediate B10 by general method A5 as a white solid. MPt 127–132° C,; $^1$H-NMR (CDCl$_3$) δ 1.2–1.9 (14H, m), 2.58 (2H, t), 3.14 (2H, t), 3.55 (2H, s), 5.10 (2H, s), 6.15 (1H, dd), 6.48 (1H, bd), 7.05–7.4 (10H, m) and 7.67 (1H, s); MS (EI) M=527; C$_{32}$H$_{37}$N$_3$O$_2$S requires 527.

Example 7

2-(6-Phenylhex-1-yl)thio-5-((1-methyl-2-oxo-pyrid-4-yl)methyl)pyrimidin-4-one

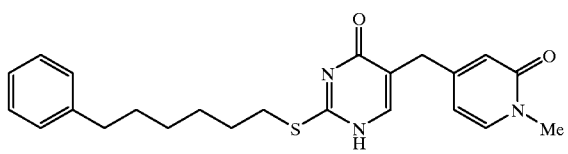

Prepared from intermediate B11 by general method A5. $^1$H-NMR (d$_6$-DMSO) δ 1.3 (4H, m), 1.6 (4H, m), 2.55 (2H, t), 3.08 (2H, t), 3.35 (3H, s), 3.41 (2H, s), 6.10 (1H, dd), 6.16 (1H, d), 7.1–7.3 (5H, m), 7.55 (1H, d), 7.78 (1H, s).

Example 8

2-(7-Phenylhept-1-yl)thio-5-((1-methyl-2-oxo-pyrid-4-yl)methyl)pyrimidin-4-one

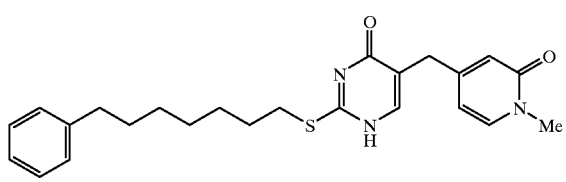

Prepared from intermediate B11 by general method A5. $^1$H-NMR (d$_6$-DMSO) δ 1.3 (6H, m), 1.6 (4H, m), 2.55 (2H, t), 3.07 (2H, t), 3.35 (3H, s), 3.41 (2H, s), 6.10 (1H, dd), 6.15 (1H, d), 7.1–7.3 (5H, m), 7.55 (1H, d), 7.77 (1H, s).

Example 9

2-(8-Phenyloct-1-yl)thio-5-((1-methyl-2-oxo-pyrid-4-yl)methyl)pyrimidin-4-one

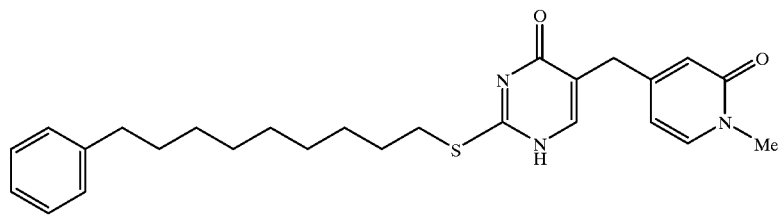

Prepared from intermediate B11 by general method A5. $^1$H-NMR (d$_6$-DMSO) δ 1.3 (8H, m), 1.6 (4H, m), 2.55 (2H, t), 2.97 (2H, t), 3.40 (3H, s), 3.42 (2H, s), 6.25 (1H, dd), 6.29 (1H, d), 7.1–7.3 (5H, m), 7.52 (1H, d), 7.58 (1H, s).

Example 10

2-(9-Phenylnon-1-yl)thio-5-((1-methyl-2-oxo-pyrid-4-yl)methyl)pyrimidin-4-one

Prepared from intermediate B11 by general method A5. ¹H-NMR (d₆-DMSO) δ 1.3 (10H, m), 1.6 (4H, m), 2.55 (2H, t), 3.06 (2H, t), 3.34 (3H, s), 6.10 (1H, dd), 6.15 (1H, d), 7.1–7.3 (5H, m), 7.55 (1H, d), 7.75 (1H, s).

Example 11

2-(6-Benzyloxyhex-1-yl)thio-5-((1-methyl-2-oxo-pyrid-4-yl)methyl)pyrimidin-4-one

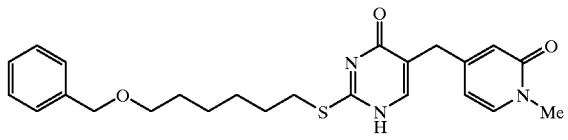

Prepared from intermediates B11 and A27 by general method A5. ¹H-NMR (d₆-DMSO) δ 1.3 (4H, m), 1.5 (2H, m), 1.6 (2H, m), 3.08 (2H, t), 3.40 (2H, t), 3.64 (2H, m), 4.43 (2H, s), 6.09 (1H, dd), 6.15 (1H, d), 7.1–7.3 (5H, m), 7.55 (1H, d), 7.75 (1H, s).

Example 12

2-(8-(4-Chlorophenyl)-8-oxooct-1-yl)thio-5-((1-methyl-2-oxo-pyrid-4-yl)methyl)pyrimidin-4-one

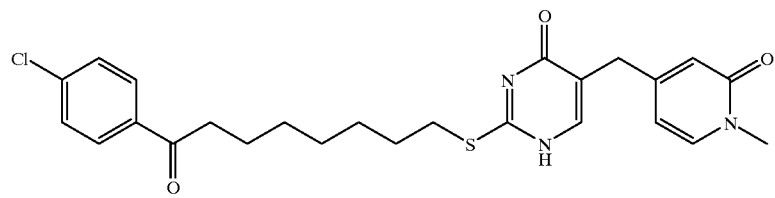

Prepared from intermediates B11 and A1 by general method A5 as a white solid. MPt 125–127° C.; ¹H-NMR (d₆-DMSO) δ 1.3 (6H, m), 1.6 (4H, m), 3.00 (2H, t), 3.08 (2H, t), 3.35 (3H, s), 3.41 (2H, s), 6.10 (1H, m), 6.15 (1H, s), 7.57 (3H, m), 7.79 (1H, s), 7.97 (1H, s), 7.97 (2H, d).

Example 13

2-(8-Phenyloct-1-yl)thio-5-((1-butyl-2-oxo-pyrid-4-yl)methyl)pyrimidin-4-one

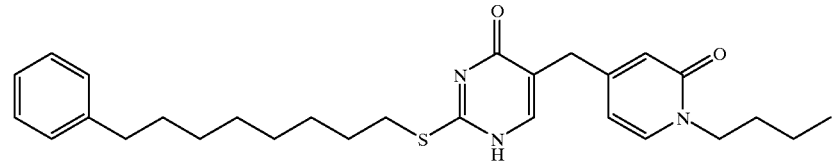

Prepared from intermediate B27 by general method B as a white solid from pet. ether. ¹H-NMR (d₆-DMSO) δ 0.87 (3H, t), 1.26 (10H, m), 1.5–1.7 (6H, m), 2.55 (2H, t), 3.08 (2H, t), 3.42 (2H, s), 3.79 (2H, t), 6.1 (2H, m), 7.2 (3H, m), 7.3 (2H, m), 7.54 (1H, d), 7.81 (1H, s), 12.8 (1H, br s).

Example 14

2-(8-Phenyloct-1-yl)thio-5-((2,3-dimethylpyrid-5-yl)methyl)pyrimidin-4-one

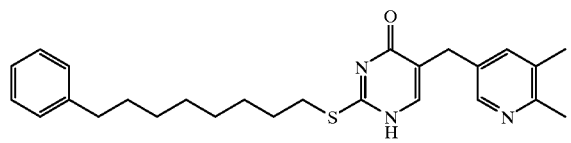

Prepared from intermediate B12 by general method A1 as a light brown solid. MPt 111–113° C.; ¹H-NMR (d₆-DMSO) δ 1.3 (8H, m), 1.6 (4H, m), 2.18 (3H, s), 2.35 (3H, s), 2.51 (2H, t), 3.05 (2H, t), 3.52 (2H, s), 7.1=7.3 (5H, m), 7.34 (1H, d), 7.74 (1H, s), 8.14 (1H, d).

Example 15

2-(6-Benzyloxyhex-1-yl)thio-5-((2,3-dimethylpyrid-5-yl)methyl)pyrimidin-4-one

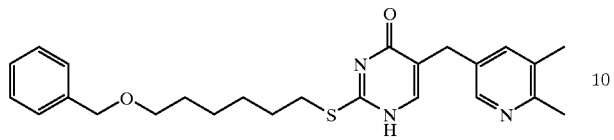

Prepared from intermediates B12 and A27 by general method A1 as a light brown solid. MPt 100–102° C.; $^1$H-NMR (d$_6$-DMSO) δ 1.3 (4H, m), 1.5 (2H, m), 1.6 (2H, m), 2.18 (3H, s), 2.35 (3H, s), 3.06 (2H, t), 3.36 (2H, t), 3.52 (2H, s), 4.43 (2H, s), 7.3 (6H, m), 7.74 (1H, s), 8.14 (1H, d).

Example 16

2-(8-Phenyloct-1-yl)thio-5-((2,4-dimethylpyrid-5-yl)methyl)pyrimidin-4-one

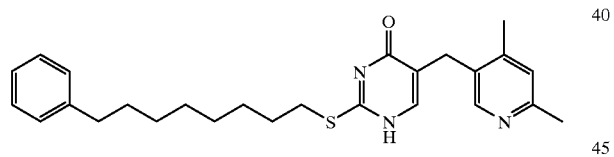

Prepared from intermediate B29 by general method B as a beige solid from ether/pet. ether. MPt 73–75° C.; $^1$H-NMR (d$_6$-DMSO) δ 1.2 (8H, m), 1.6 (4H, m), 2.21 (3H, s), 2.37 (3H, s), 2.57 (2H, t), 3.06 (2H, t), 3.57 (2H, s), 6.83 (1H, s), 7.1–7.3 (5H, m), 7.51 (1H, s), 8.15 (1H, s), 12.8 (1H, br s).

Example 17

2-(5Phenylpent-1-yl)thio-5-((2-methylpyrid-5-yl)methyl)pyrimidin-4-one

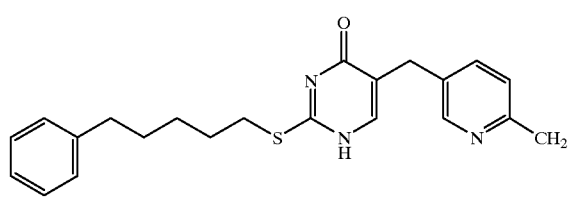

Prepared from intermediate B21 by general method A1 as a white solid. MPt 113–117° C.; $^1$H-NMR (d$_6$-DMSO) δ 1.35 (2H, m), 1.6 (4H, m), 2.40 (3H, s), 2.55 (2H, t), 3.07 (2H, t), 3.57 (2H, s), 7.1–7.3 (6H, m), 7.52 (1H, dd), 7.78 (1H, s), 8.33 (1H, d).

Example 18

2-(N-(6-(4-Fluorophenyl)hexyl)carboxamidomethyl)thio-5-((2-methylpyrid-5-yl)methyl)pyrimidin-4-one

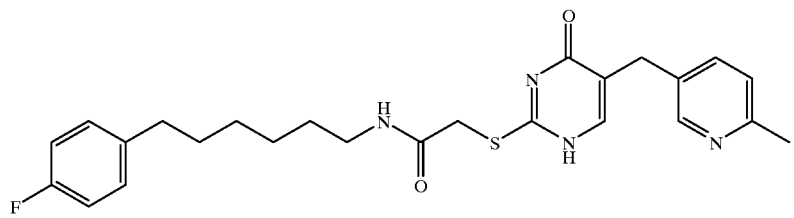

Prepared from intermediates B21 and A42 by general method A1. MPt 159–161° C.; $^1$H-NMR (d$_6$-DMSO) δ 1.2 (4H, m), 1.4 (2H, m), 1.5 (2H, m), 2.40 (3H, s), 2.52 (2 H, t), 3.04 (2H, m), 3.57 (2H, s), 3.81 (2H, s), 7.0–7.2 (5H, m), 7.49 (1H, dd), 7.75 (1H, s), 8.15 (1H, t), 8.33 (1H, dd).

Example 19

2-(6-Benzyloxyhex-1-yl)thio-5-((2-methylpyrid-5-yl)methyl)pyrimidin-4-one

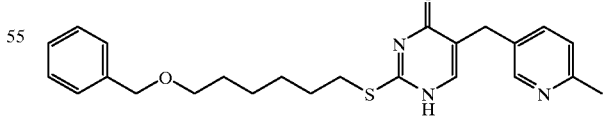

Prepared from intermediates B21 and A27 by general method A1. MPt 93–95° C.; $^1$H-NMR (d$_6$-DMSO) δ 1.3 (4H, m), 1.5 (2H, m), 1.6 (2H, m), 2.40 (3H, s), 3.07 (2H, t), 3.40 (2H, t), 3.57 (2H, s), 4.43 (2H, s), 7.13 (1H, d), 7.3 (5H, m), 7.51 (1H, dd), 7.80 (1H, s), 8.34 (1H, d).

Example 20

2-(8-Phenyloct-1-yl)thio-5-((2-methylpyrid-5-yl)methyl)pyrimidin-4-one

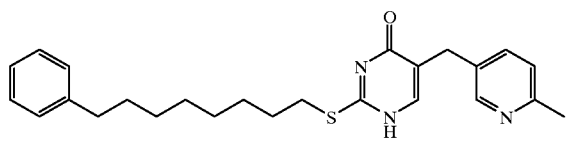

Prepared from intermediate B21 by general method A5 as a white solid. MPt 92–94° C.; $^1$H-NMR (d$_6$-DMSO) δ 1.3 (8H, m), 1.6 (4H, m), 2.40 (3H, s), 2.55 (2H, t), 3.02 (2H, t), 3.54 (2H, s), 7.11 (1H, d), 7.16 (3H, m), 7.25 (2H, m), 7.50 (1H, m), 7.69 (1H, s), 8.33 (1H, d).

Example 21

2-(7-Phenylhept-1-yl)thio-5-((2-methylpyrid-5-yl)methyl)pyrimidin-4-one

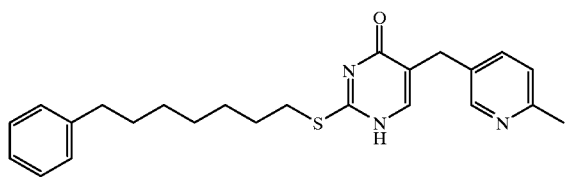

Prepared from intermediate B21 by general method A5 as a white solid. MPt 101–103° C.; $^1$H-NMR (d$_6$-DMSO) δ 1.3 (6H, m), 1.6 (4H, m), 2.40 (3H, s), 2.55 (2H, t), 3.02 (2H, t), 3.54 (2H, s), 7.11 (1H, d), 7.16 (3H, m), 7.25 (2H, m), 7.50 (1H, m), 7.68 (1H, s), 8.33 (1H, d).

Example 22

2-(6-Phenylhex-1-yl)thio-5-((2-methylpyrid-5-yl)methyl)pyrimidin-4-one

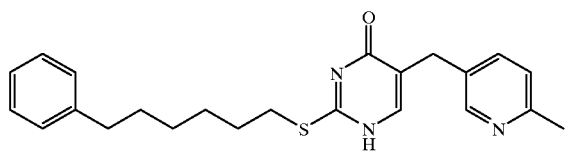

Prepared from intermediate B21 by general method A1 as a white solid. MPt 104–106° C.; $^1$H-NMR (d$_6$-DMSO) δ 1.3 (4H, m), 1.6 (4H, m), 2.40 (3H, s), 2.55 (2H, t), 3.05 (2H, t), 3.57 (2H, s), 7.1–7.3 (6H, m), 7.50 (1H, m), 7.78 (1H, s), 8.33 (1H, d).

Example 23

2-(9-Phenylnon-1-yl)thio-5-((2-methylpyrid-5-yl)methyl)pyrimidin-4-one

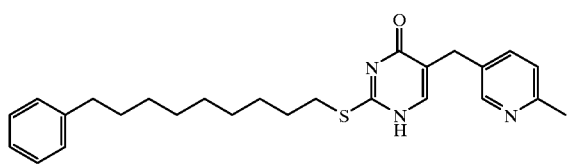

Prepared from intermediate B21 by general method A1 as a white solid. MPt 112–114° C.; $^1$H-NMR (d$_6$-DMSO) δ 1.3 (10H, m), 1.6 (4H, m), 2.40 (3H, s), 2.54 (2H, t), 3.05 (2H, t), 3.55 (2H, s), 7.1–7.3 (6H, m), 7.50 (1H, m), 7.88 (1H, s), 8.33 (1H, d).

Example 24

2-(6-(4-Chlorobenzyloxy)hex-1-yl)thio-5-((2-methylpyrid-5-yl)methyl)pyrimidin-4-one

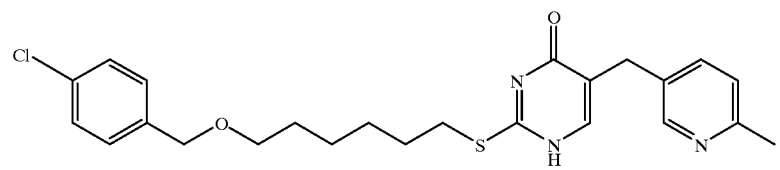

Prepared from intermediates B21 and A25 by general method A1 as a white solid. MPt 93–95° C.; $^1$H-NMR (d$_6$-DMSO) δ 1.3 (4H, m), 1.5 (2H, m), 1.6 (2H, m), 2.51 (3H, s), 3.13 (2H, t), 3.44 (2H, t), 3.70 (2H, s), 4.45 (2H, s), 7.06 (1H, d), 7.3 (3H, m), 7.53 (1H, dd), 7.64 (1H, s), 8.43 (1H, d).

Example 25

2-(6-(4-Fluorobenzyloxy)hex-1-yl)thio-5-((2-methylpyrid-5yl)methyl)pyrimidin-4-one

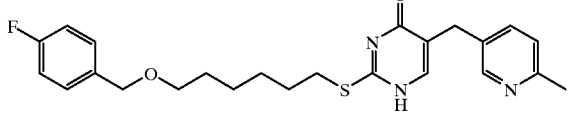

Prepared from intermediates B21 and A26 by general method A1 as a white solid. MPt 90–92° C.; $^1$H-NMR (d$_6$-DMSO) δ 1.3 (4H, m), 1.5 (2H, m), 1.6 (2H, m), 2.51 (3H, s), 3.13 (2H, t), 3.45 (2H, t), 3.70 (2H, s), 4.44 (2H, s), 7.0 (3H, m), 7.3 (2H, m), 7.53 (1H, dd), 7.64 (1H, s), 8.43 (1H, d).

Example 26

2-(8-(4-Methoxyphenyl)-8-oxooct-1-yl)thio-5-((2-methylpyrid-5-yl)methyl)pyrimidin-4-one

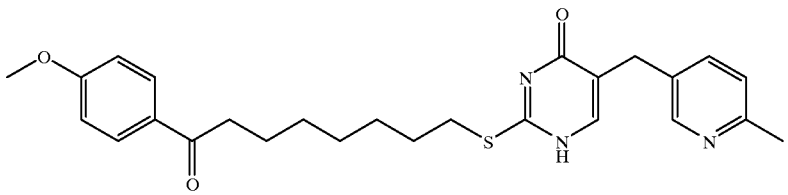

Prepared from intermediates B21 and A3 by general method A1 as a white solid. MPt 114–116° C.; $^1$H-NMR (d$_6$-DMSO) δ 1.3 (6H, m), 1.6 (4H, m), 2.40 (3H, s), 2.93 (2H, t), 3.08 (2H, t), 3.57 (2H, s), 3.83 (3H, s), 7.02 (2H, d), 7.13 (1H, d), 7.51 (1H, dd), 7.79 (1H, s), 7.93 (2H, d), 8.34 (1H, d), 12.7 (1H, br s).

Example 27

2-(8-(4-Methoxyphenyl)oct-1-yl)thio-5-((2-methylpyrid-5-yl)methyl)pyrimidin-4-one

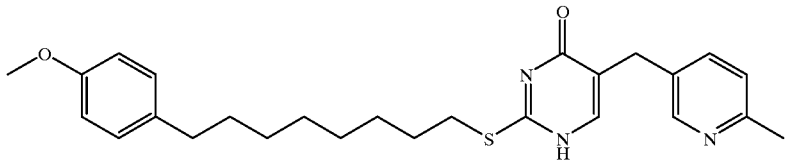

Prepared from intermediates B21 and A22 by general method A1 as a white solid. MPt 103–105° C.; $^1$H-NMR (d$_6$-DMSO) δ 1.3 (8H, m), 1.4–1.7 (4H, m), 2.40 (3H, s), 2.48 (2H, t), 3.07 (2H, t), 3.57 (2H, s), 3.84 (3H, s), 6.82 (2H, d), 7.07 (2H, d), 7.12 (1H, d), 7.51 (1H, dd), 7.78 (1H, s), 8.34 (1H, d), 12.7 (1H, br s).

Example 28

2-(8-(4-Fluorophenyl)oct-1-yl)thio-5-((2-methylpyrid-5-yl)methyl)pyrimidin-4-one

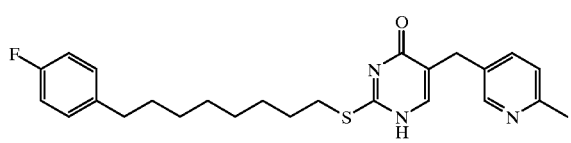

Prepared from intermediates B21 and A21 by general method A1. $^1$H-NMR (d$_6$-DMSO) δ 1.3 (8H, m), 1.6 (4H, m), 2.40 (3H, s), 2.53 (2H, t), 3.06 (2H, t), 3.56 (2H, s), 7.0–7.2 (5H, m), 7.5 (1H, m), 7.77 (1H, s), 8.33 (1H, m).

Example 29

2-(8-(4-Fluorophenyl)-8-oxooct-1-yl)thio-5-((2-methylpyrid-5-yl)methyl)pyrimidin-4-one

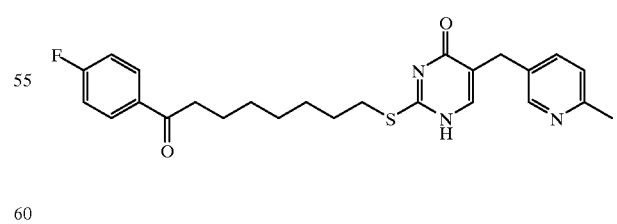

Prepared from intermediates B21 and A8 by general method A1. $^1$H-NMR (d$_6$-DMSO) δ 1.3 (6H, m), 1.6 (4H, m), 2.40 (3H, s), 3.00 (2H, t), 3.08 (2H, t), 3.57 (2H, s), 7.13 (1H, d), 7.34 (2H, m), 7.51 (1H, dd), 7.80 (1H, s), 8.04 (2H, m), 8.34 (1H, d), 12.7 (1H, br s).

Example 30

2-(8-(4-Chlorophenyl)oct-1-yl)thio-5-((2-methylpyrid-5-yl)methyl)pyrimidin-4-one

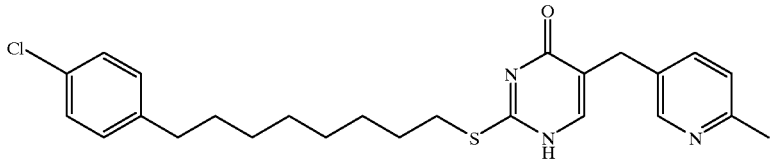

Prepared from intermediates B21 and A24 by general method A1 as a white solid. MPt 100–102° C.; ¹H-NMR (d₆-DMSO) δ 1.3 (8H, m), 1.6 (4H, m), 2.40 (3H, s), 2.57 (2H, t), 3.06 (2H, t), 3.56 (2H, s), 7.12 (1H, d), 7.20 (2H, d), 7.31 (2H, d), 7.50 (1H, dd), 7.76 (1H, s), 8.33 (1H, d).

Example 31

2-(8-(4-Chlorophenyl)-8-oxooct-1-yl)thio-5-((2-methylpyrid-5-yl)methyl)pyrimidin-4-one

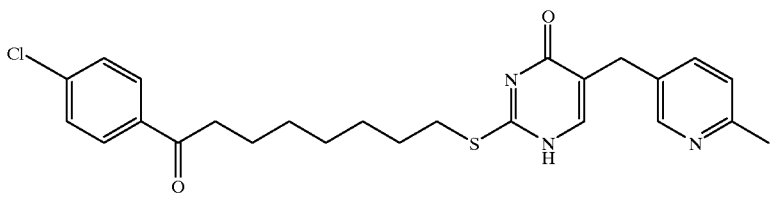

Prepared from intermediates B21 and A1 by general method A1 as a white solid. MPt 90–92° C.; ¹H-NMR (d₆-DMSO) δ 1.3 (6H, m), 1.6 (4H, m), 2.40 (3H, s), 3.00 (2H, t), 3.07 (2H, t), 3.56 (2H, s), 7.12 (1H, d), 7.51 (1H, dd), 7.58 (2H, d), 7.86 (1H, s), 7.97 (2H, d), 8.34 (1H, d).

Example 32

2-(8-Phenyl-8-oxooct-1-yl)thio-5-((2-methylpyrid-5-yl)methyl)pyrimidin-4-one

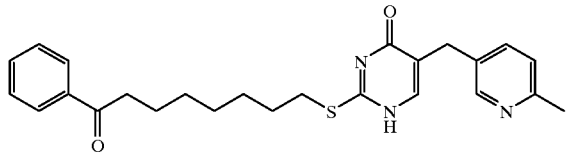

Prepared from intermediate B21 by general method A1 as a white solid. MPt 72–74° C.; ¹H-NMR (d₆-DMSO) δ 1.3 (6H, m), 1.6 (4H, m), 2.40 (3H, s), 3.00 (2H, t), 3.08 (2H, t), 3.57 (2H, s), 7.13 (1H, m), 7.5 (3H, m), 7.6 (1H, m), 7.80 (1H, s), 7.94 (1H, m), 8.33 (1H, d), 12.6 (1H, br s).

Example 33

2-(8-(4-Chlorophenyl)-8-hydroxyoct-1-yl)thio-5-((2-methylpyrid-5-yl)methyl)pyrimidin-4-one

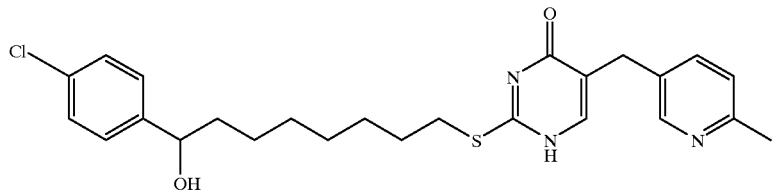

Prepared from intermediates B21 and A36 by general method A1. ¹H-NMR (d₆-DMSO) δ 1.3 (8H, m), 1.6 (4H, m), 2.40 (3H, s), 3.08 (2H, t), 3.58 (2H, s), 4.5 (1H, br t), 4.9 (1H, br s), 7.10 (1H, m), 7.31 (4H, m), 7.48 (1H, m), 7.71 (1H, s), 8.32 (1H, m), 12.4 (1H, br s).

Example 34

2-(8-(4-Methylphenyl)-8-oxooct-1-yl)thio-5-((2methylpyrid-5-yl)methyl)pyrimidin-4-one

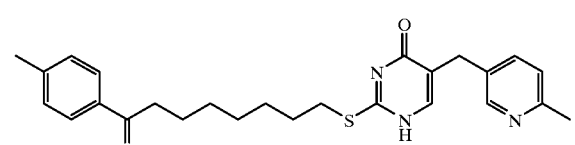

Prepared from intermediates B21 and A7 by general method A1 as a white solid. MPt 115–116° C.; ¹H-NMR (CDCl₃) δ 1.2–1.8 (10H, m), 2.41 (3H, s), 2.51 (3H, s), 2.93 (2H, t), 3.13 (2H, t), 7.06 (1H, m), 7.25 (2H, m), 7.26 (1H, s), 7.54 (1H, m), 7.85 (2H, m) and 8.43 (1H, d); MS (EI) M=449; C₂₆H₃₁N₃O₂S requires 449.

Example 35

2-(4-Phenylbut-1-yl)thio-5-((2-methylpyrid-5-yl)methyl)pyrimidin-4-one

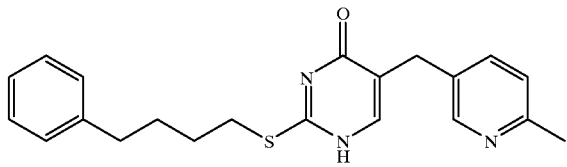

Prepared from intermediate B21 by general method A1. Mpt 129–30° C.; ¹H-NMR (d₆-DMSO) δ 1.6 (4H, m), 2.40 (3H, s), 2.58 (2H, m), 3.11 (2H, m), 3.57 (2H, s), 7.1–7.3 (6H, m), 7.52 (1H, dd), 7.80 (1H, s), 8.33 (1H, d).

Example 36

2-(8-Phenyloct-1-yl)thio-5-((1-oxo-2-methylpyrid-5-yl)methyl)pyrimidin-4-one

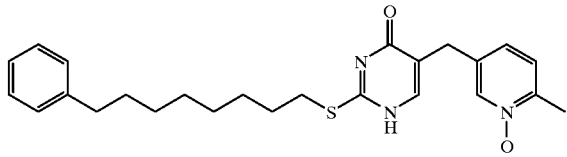

Prepared from intermediate B28 by general method B. Trituration with ether and recrystallisation from ethyl acetate gave the product as an off-white solid. MPt 93–95° C.; ¹H-NMR (d₆-DMSO) δ 1.3 (8H, m), 1.6 (4H, m), 2.55 (2H, t), 3.07 (2H, t), 3.56 (2H, s), 7.1–7.3 (6H, m), 7.52 (1H, dd), 7.78 (1H, s), 8.33 (1H, d).

Example 37

2-(8-Phenyloct-1-yl)thio-5-((2-methoxypyrid-4-yl)methyl)pyrimidin-4-one

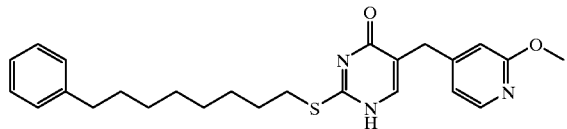

Prepared from intermediate B25 by general method B as a beige solid from ethanol. MPt 70–72° C.; ¹H-NMR (d₆-DMSO) δ 1.3 (8H, m), 1.6 (4H, m), 2.55 (2H, t), 3.08 (2H, t), 3.58 (2H, s), 3.80 (3H, s), 6.64 (1H, s), 6.84 (1H, d), 7.1–7.3 (5H, m), 7.80 (1H, s), 8.02 (1H, d).

Example 38

2-(8-(4-Chlorophenyl)-8-oxooct-1-yl)thio-5-(pyrazin-2-pyrimidin-4-one

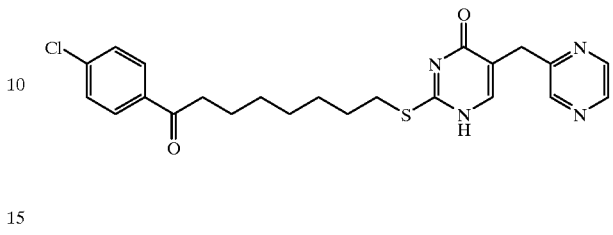

Prepared from intermediates B14 and A1 by general method A1 as a white solid. MPt 122.5–124° C.; ¹H-NMR (d₆ DMSO) δ 1.2–1.5 (6H, m), 1.5–1.8 (4H, m), 3.00 (2H, t), 3.10 (2H, t), 3.81 (2H, s), 7.59 (2H, d), 7.8 (1H, bs), 7.97 (2H, d), 8.46 (1H, m), 8.50 (1H, m) and 8.58 (1H, m); MS (FAB) M+1=457; C23H25ClN4O2S requires 456.

Example 39

2-(8-Phenyloct-1-yl)thio-5-(pyrid-2-ylmethyl)pyrimidin-4-one

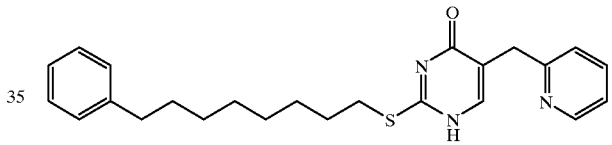

Prepared from intermediate B18 by general method A1. ¹H-NMR (d₆-DMSO) δ 1.3 (8H, m), 1.6 (4H, m), 2.55 (2H, t), 3.09 (2H, t), 3.76 (2H, s), 7.1–7.3 (7H, m), 7.67 (1H, m), 7.74 (1H, s), 8.44 (1H, m), 12.7 (1H, br s).

Example 40

2-(8-(4-Chlorophenyl)-8-oxooct-1-yl)thio-5-(thiazol-2-ylmethyl)pyrimidin-4-one

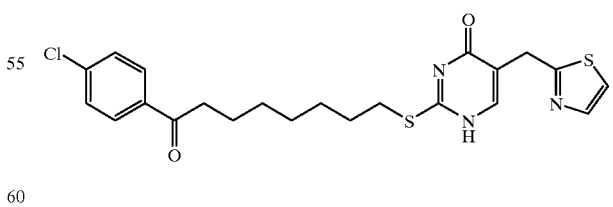

Prepared from intermediates B22 and A1 by general method A1 as a pale buff solid. MPt 112–114° C.; ¹H-NMR (CDCl₃) δ 1.2–1.85 (10H, m), 2.92 (2H, t), 3.15 (2H, t), 4.17 (2H, s), 7.22 (1H, d), 7.42 (2H, m), 7.69 (1H, d) and 7.8–8.0 (3H, m); MS (EI) M=461; C₂₂H₂₄ClN₃O₂S₂ requires 461.

Example 42

2-(6-Phenylhex-1-yl)thio-5-(pyrid-3-ylmethyl)pyrimidin-4-one

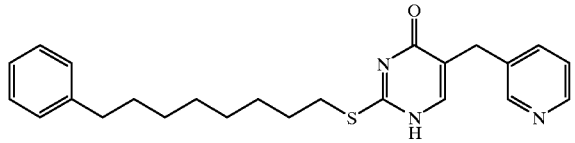

Prepared from intermediate B19 by general method A5. $^1$H-NMR (d$_6$-DMSO) δ 1.3 (4H, m), 1.6 (4H, m), 2.55 (2H, t), 3.07 (2H, t), 3.62 (2H, s), 7.1–7.3 (5H, m), 7.63 (1H, m), 7.81 (1H, s), 8.39 (1H, m), 8.48 (1H, d).

Example 43

2-(7-Phenylhept-1-yl)thio-5-(pyrid-3-ylmethyl)pyrimidin-4-one

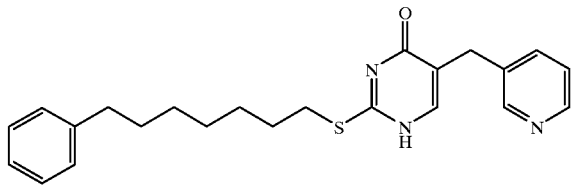

Prepared from intermediate B19 by general method A5. $^1$H-NMR (d$_6$-DMSO) δ 1.3 (6H, m), 1.6 (4H, m), 2.55 (2H, t), 3.07 (2H, t), 3.62 (2H, s), 7.1–7.3 (5H, m), 7.63 (1H, m), 7.82 (1H, s), 8.39 (1H, m), 8.48 (1H, d).

Example 44

2-(8-Phenyloct-1-yl)thio-5-(pyrid-3-ylmethyl)pyrimidin-4-one

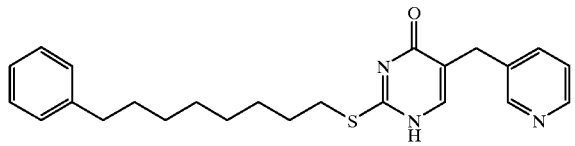

Prepared from intermediate B19 by general method A5. $^1$H-NMR (d$_6$-DMSO) δ 1.3 (8H, m), 1.6 (4H, m), 2.55 (2H, t), 2.97 (2H, t), 3.62 (2H, s), 7.1–7.3 (5H, m), 7.63 (1), m), 7.82 (1H, s), 8.39 (1H, m), 8.48 (1H, d).

Example 45

2-(9-Phenylnon-1-yl)thio-5-(pyrid-3-ylmethyl)pyrimidin-4-one

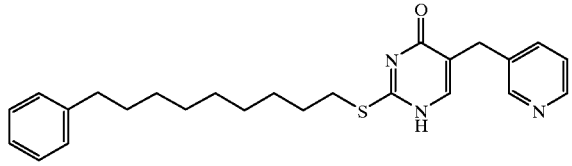

Prepared from intermediate B19 by general method A5. $^1$H-NMR (d$_6$-DMSO) δ 1.3 (10H, m), 1.6 (4H, m), 2.55 (2H, t), 3.07 (2H, t), 3.62 (2H, s), 7.1–7.3 (5H, m), 7.63 (1H, m), 7.81 (1H, s), 8.39 (1H, m), 8.48 (1H, d).

Example 46

2-(6-Benzyloxyhex-1-yl)thio-5-(pyrid-3-ylmethyl)pyrimidin-4-one

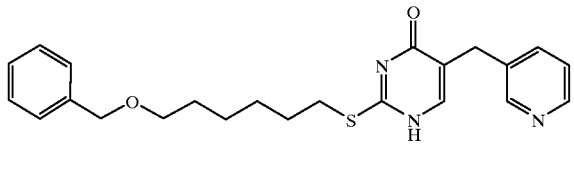

Prepared from intermediates B19 and A27 by general method A5. $^1$H-NMR (d$_6$-DMSO) δ 1.3 (4H, m), 1.5 (2H, m), 1.6 (2H, m), 3.08 (2H, t), 3.40 (2H, t), 3.62 (2H, s), 4.43 (2H, s), 7.1–7.3 (5H, m), 7.64 (6H, m), 7.82 (1H, s), 8.39 (1H, m), 8.49 (1H, d).

Example 47

2-(8-(4-Chlorophenyl)-8-oxooct-1-yl)thio-5-(pyrid-3-ylmethyl)-pyrimidin-4-one

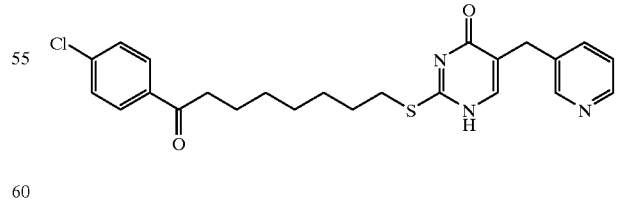

Prepared from intermediates B19 and A1 by general method A1 as a white solid. MPt 105–107° C.; $^1$H-NMR (d$_6$-DMSO) δ 1.3 (6H, m), 1.6 (4H, m), 3.00 (2H, t), 3.08 (2H, t), 3.62 (2H, s), 7.3 (1H, m), 7.58 (2H, d), 7.6 (1H, m), 7.82 (1H, s), 7.97 (2H, d), 8.39 (1H, m), 8.48 (1H, m).

Example 48

2-(8-(4-Fluorophenyl)non-8-en-1-yl)thio-5-(pyrid-3-ylmethyl)pyrimidin-4-one

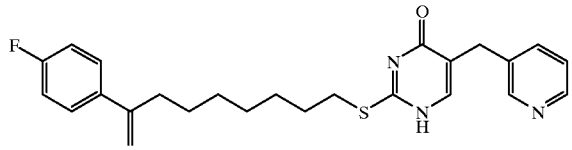

Prepared from intermediates B19 and A37 by general method A1 as a white powder. MPt 70–75° C.; $^1$H-NMR ($d_6$ DMSO) δ 1.2–1.8 (10H, m), 2.45 (2H, t), 3.06 (2H, m), 3.62 (2H, s), 5.04 (1H, s), 5.26 (1H, s), 7.16 (2H, t), 7.29 (1H, dxd), 7.4–7.55 (2H, m), 7.81 (1H, s), 8.38 (1H, m) and 8.48 (1H, d); MS (EI) Found M=437, $C_{25}H_{28}FN_3OS$ requires 437.

Example 49

2-(6-(4-Chlorobenzoylamino)hex-1-yl)thio-5-(pyrid-3-ylmethyl)pyrimidin-4-one

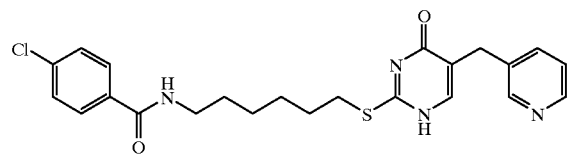

Prepared from intermediate B19 and A45 by general method A1 as a white solid. MPt 135–139° C.; $^1$H-NMR ($d_6$ DMSO) δ 1.2–1.8 (8H, m), 3.09 (2H, t), 3.23 (2H, q), 3.61 (2H, s), 7.28 (1H, s), 7.51 (2H, m), 7.62 (1H, m), 7.84 (3H, m), 8.38 (1H, m), 8.48 (1H, bs) and 8.53 (1H, bt).

Example 50

2-(8-(4-Bromophenyl)-8-oxooct-1-yl)thio-5-(pyrid-3-ylmethyl)pyrimidin-4-one

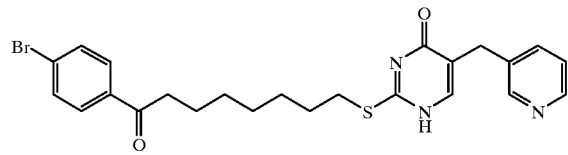

Prepared from intermediate B19 and A4 by general method A1 as a white solid. MPt 132–137° C.; $^1$H-NMR ($d_6$ DMSO) δ 1.2–1.5 (6H, m), 1.5–1.8 (4H, m), 2.98 (2H, t), 3.08 (2H, t), 3.62 (2H, t), 7.28 (1H, m), 7.5–7.95 (6H, m), 8.38 (1H, m) and 8.48 (1H, bd).

Example 51

2-(7-(4-Chlorophenoxy)hept-1-yl)thio-5-(pyrid-3-ylmethyl)pyrimidin-4-one

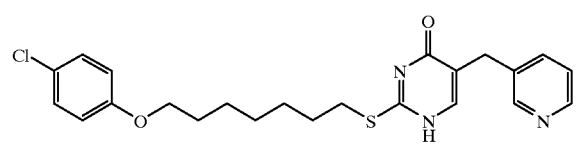

Prepared from intermediate B19 and A29 by general method A1. $^1$H-NMR ($d_6$ DMSO) δ 1.2–1.5 (6H, m), 1.5–1.8 (4H, m), 3.09 (2H, t), 3.62 (2H, s), 3.93 (2H, t), 6.94 (2H, m), 7.29 (2H, m), 7.63 (1H, m), 7.83 (1H, bs), 8.38 (1H, m) and 8.48 (1H, bd).

Example 52

2-(7-Phenoxyhept-1-yl)thio-5-(pyrid-3-ylmethyl)pyrimidin-4-one

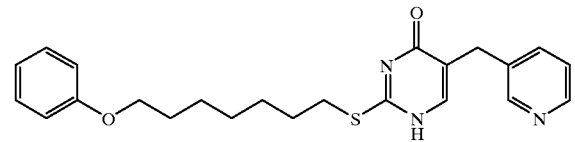

Prepared from intermediate B19 and A28 by general method A1. $^1$H-NMR ($d_6$ DMSO) δ 1.2–1.5 (6H, m), 1.5–1.8 (4H, m), 3.09 (2H, t), 3.62 (2H, s), 3.93 (2H, t), 6.90 (3H, m), 7.27 (3H, m), 7.63 (1H, m), 7.82 (1H, s), 8.39 (1H, m) and 8.48 (1H, m).

Example 53

2-(7-Phenylthiohept-1-yl)thio-5-(pyrid-3-ylmethyl)pyrimidin-4-one

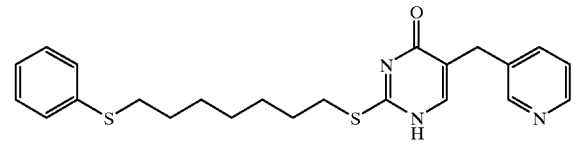

Prepared from intermediate B19 and A33 by general method A1. $^1$H-NMR ($d_6$ DMSO) δ 1.2–1.5 (6H, m), 1.5–1.8 (4H, m), 2.94 (2H, t), 3.06 (2H, t), 3.62 (2H, s), 7.16 (1H, m), 7.20–7.35 (5H, m), 7.62 (1H, m), 7.81 (1H, s), 8.38 (1H, m) and 8.48 (1H, bs).

Example 54

2-(7-(4-Chlorophenylthio)hept-1-yl)thio-5-(pyrid-3-ylmethyl)pyrimidin-4-one

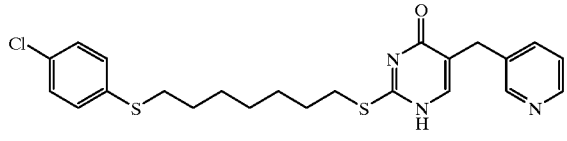

Prepared from intermediate B19 and A30 by general method A1. $^1$H-NMR (d$_6$ DMSO) δ 1.2–1.5 (6H, m), 1.5–1.8 (4H, m), 2.94 (2H, t), 3.07 (2H, t), 3.62 (2H, s), 7.2–7.5 (5H, m), 7.62 (1H, m), 7.82 (1H, s), 8.38 (1H, m) and 8.48 (1H, bs).

Example 55

2-(6-(3-Chlorophenyl)hex-1-yl)thio-5-(pyrid-3-ylmethylopyrimidin-4-one

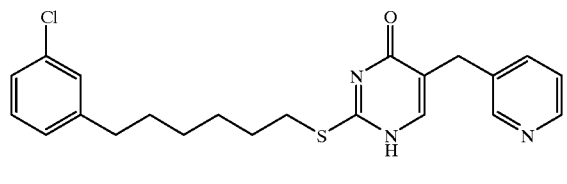

Prepared from intermediate B19 and A40 by general method A1 as a white solid. MPt 84–85° C.; $^1$H-NMR (CDCl$_3$) δ 1.2–1.8 (8H, m), 2.57 (2H, t), 3.13 (2H, t), 3.74 (2H, s), 7.03 (1H, m), 7.15–7.25 (4H, m), 7.65 (2H, m), 8.47 (1H, m),and 8.56 (1H, d); MS (EI) M=413; C$_{22}$H$_{24}$ClN$_3$OS requires 413.

Example 56

2-(7-Phenylsulfinylhept-1-yl)thio-5-(pyrid-3-ylmethyl)pyzimidin-4-one

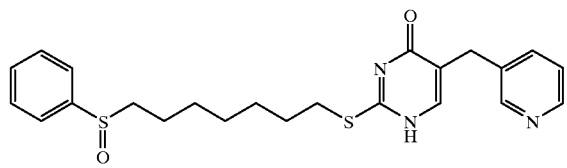

Prepared from intermediate B19 and A34 by general method A1. $^1$H-NMR (d$_6$ DMSO) δ 1.2–1.5 (6H, m), 1.5–1.8 (4H, m), 2.6–3.0 (4H, m), 3.55 (2H, s), 7.25 (1H, m), 7.45–7.7 (7H, m), 8.35 (1H, m) and 8.46 (1H, m).

Example 57

2-(7-(4-Chlorophenylsulfinyl)hept-1-yl)thio-5-(pyrid-3-ylmethyl)-pyrimidin-4-one

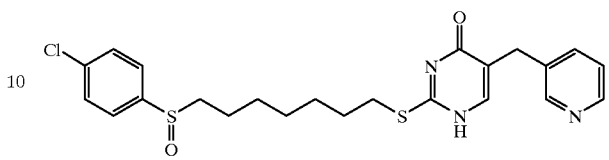

Prepared from intermediate B19 and A31 by general method A1. $^1$H-NMR (d6 DMSO) δ 1.2–1.5 (6H, m), 1.5–1.8 (4H, m), 2.7–3.2 (4H, m), 3.61 (2H, s), 7.28 (1H, m), 7.55–7.75 (5H, m), 7.80 (1H, s), 8.38 (1H, m) and 8.47 (1H, bs).

Example 58

2-(7-Phenylsulfonylhept-1-yl)thio-5-(pyrid-3-ylmethyl)pyrimidin-4-one

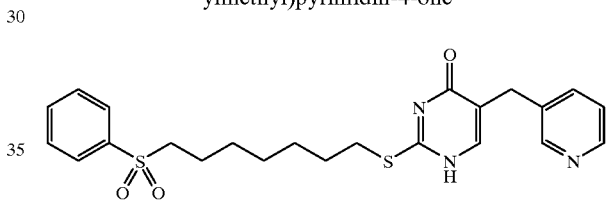

Prepared from intermediate B19 and A35 by general method A1. $^1$H-NMR (d$_6$ DMSO) δ 1.2–1.5 (6H, m), 1.5–1.8 (4H, m), 3.05 (2H, t), 3.29 (2H, t), 3.62 (2H, s), 7.29 (1H, m), 7.6–78.0 (7H, m), 8.44 (1H, m) and 8.49 (1H, m).

Example 59

2-(7-(4-Chlorophenylsulfonyl)hept-1-yl)thio-5-(pyrid-3-ylmethyl)pyrimidin-4-one

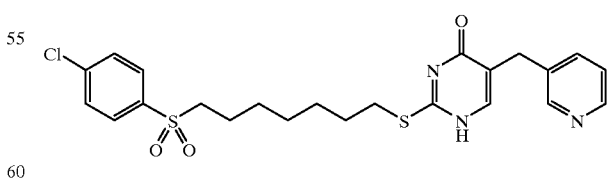

Prepared from intermediate B19 and A32 by general method A1. $^1$H-NMR (d$_6$ DMSO) δ 1.2–1.5 (6H, m), 1.5–1.8 (4H, m), 3.05 (2H, t), 3.62 (2H, s), 7.28 (1H, m), 7.6–80 (6H, m), 8.44 (1H, m) and 8.48 (1H, m).

Example 60

2-(8-(3-Chlorophenyl)oct-1-yl)thio-5-(pyrid-3-ylmethyl)pyrimidin-4-one

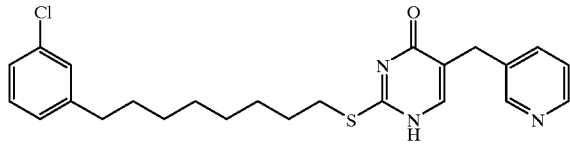

Prepared from intermediate B19 and A18 by general method A1 as a white solid. MPt 68–70° C.; $^1$H-NMR (CDCl$_3$) δ 1.2–1.5 (8H, m), 1.5–1.8 (4H, m), 2.56 (2H, t), 3.13 (2H, t), 3.74 (2H, t), 7.05 (1H, m), 7.15–7.25 (4H, m), 7.65 (2H, m), 8.46 (1H, m) and 8.57 (1H, m); MS (EI) M=441; C$_{24}$H$_{28}$ClN$_3$OS requires 441.

Example 61

2-(8-(3,4-Dichlorophenyl)oct-1-yl)thio-5-(pyrid-3-ylmethyl)pyrimidin-4-one

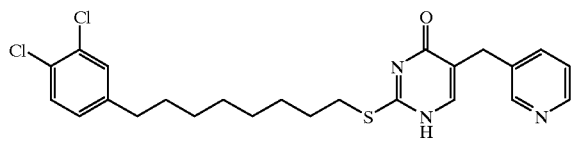

Prepared from intermediate B19 and A 15 by general method A1 as a white solid. MPt 96–99° C.; $^1$H-NMR (CDCl$_3$) δ 1.2–1.5 (8H, m), 1.5–1.8 (4H, m), 2.54 (2H, t), 3.13 (2H, t), 3.74 (2H, s), 7.0 (1H, m), 7.2–7.35 (3H, m), 7.65 (2H, m), 8.46 (1H, m) and 8.56 (1H, d); MS (EI) M=475; C$_{24}$H$_{27}$Cl$_2$N$_3$O requires 475.

Example 62

2-(8-(2-Thienyl)-8-oxooct-1-yl)thio-5-(pyrid-3ylmethyl)pyrimidin-4-one

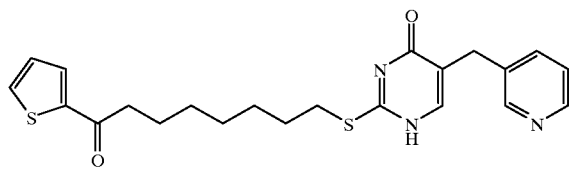

Prepared from intermediate B19 and A5 by general method A1 as a light brown solid. MPt 101–102° C.; $^1$H-NMR (d$_6$ DMSO) δ 1.2–1.45 (6H, m), 1.5–1.75 (4H, m), 2.79 (2H, t), 3.07 (2H, t), 3.61 (2H, s), 6.69 (1H, dd), 7.2–7.3 (1H, m), 7.45 (1H, d), 7.6–7.7 (1H, m), 7.81 (1H, s), 7.97 (1H, s), 8.3–8.4 (1H, m) and 8.47 (1H, d).

Example 63

2-(8-(2-Furyl)-8-oxooct-1-yl)thio-5-(pyrid-3-ylmethyl)pyrimidin-4-one

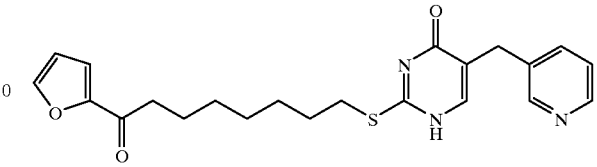

Prepared from intermediate B19 and A6 by general method A1 as a light brown solid. MPt 104–107° C.; $^1$H-NMR (d$_6$ DMSO) δ 1.2–1.45 (6H, m) 1.5–1.8 (4H, m), 2.79 (2H, t), 3.07 (2H, t), 3.61 (2H, s), 6.69 (1H, m), 7.28 (1H, m), 7.45 (1H, m), 7.63 (1H, m), 7.81 (1H, m), 7.97 (1H, m), 8.38 (1H, m) and 8.48 (1H, m).

Example 64

2-(8-(2-Pyridyl)oct-1-yl)thio-5-(pyrid-3-ylmethyl)pyrimidin-4-one

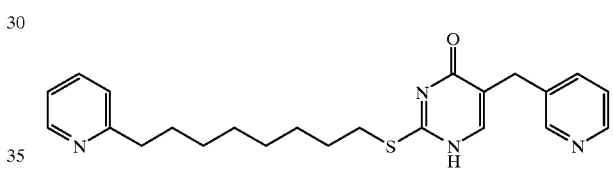

Prepared from intermediate B19 and A 11 by general method A1 as a light brown solid. MPt 76–79° C.; $^1$H-NMR (d$_6$ DMSO) δ 1.2–1.5 (8H, m), 1.55–1.8 (4H, m), 2.69 (2H, t), 3.07 (2H, t), 3.62 (2H, s), 7.05–7.4 (3H, m), 7.55–7.75 (2H, m), 7.82 (1H, s) and 8.35–8.55 (3H, m).

Example 65

2-(9-(4-Chlorophenyl)-9-oxonon-1-yl)thio-5-(pyrid-3-ylmethyl)-pyrimidin-4-one

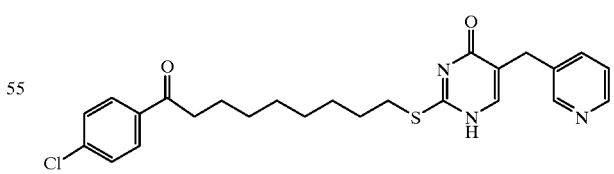

Prepared from intermediate B19 and A1 by general method A1 as a white solid. MPt 112–114° C.; $^1$H-NMR (CDCl$_3$) δ 1.2–1.8 (14H), 2.92 (2H, t), 3.11 (2H, t), 3.74 (2H, s), 7.2 (1H, m), 7.42 (2H, d), 7.6–7.75 (2H, m), 7.88 (2H, m), 8.45 (1H, m) and 8.55 (1H, m); MS (EI) M=469; C$_{25}$H$_{28}$ClN$_3$O$_2$S requires 469.

Example 66

2-(8-(3,4-Dichlorophenyl)oct-7-yn-1-yl)thio-5-(pyrid-3-ylmethyl)-pyrimidin-4-one

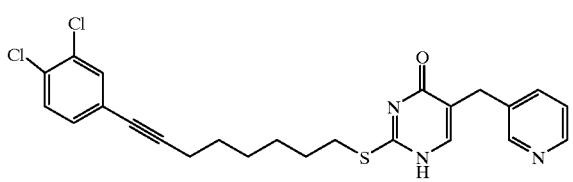

Prepared from intermediate B19 and A14 by general method A1 as a white solid. MPt 92–94° C.; $^1$H-NMR (CDCl$_3$) δ 1.4–1.9 (8H, m), 2.39 (2H, t), 3.15 (2H, t), 3.74 (2H, s), 7.1–7.4 (5H, m), 7.6–7.75 (2H, m), 8.45 (1H, m) and 8.57 (1H, m); MS (EI) M=471; C$_{24}$H$_{23}$Cl$_2$N$_3$OS requires 471.

Example 67

2-(8-(4-Acetylphenyl)oct-1-yl)thio-5-(pyrid-3-ylmethyl)pyrimidin-4-one

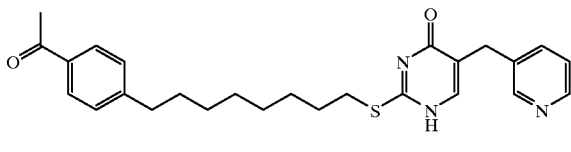

Prepared from intermediate B19 and A20 by general method A1 as a white solid. MPt 81–84° C.; $^1$H-NMR (CDCl$_3$) δ 1.2–1.8 (12H, m), 2.58 (3H, s), 2.65 (2H, t), 3.13 (2H, t), 3.74 (2H, s), 7.1–7.35 (3H, m), 7.6–7.75 (2H, m), 7.87 (2H, d) and 8.3–8.7 (2H, bd), MS (EI) M=449; C$_{26}$H$_{31}$N$_3$O$_2$S requires 449.

Example 68

2-(8-(4-Methylnaphth-1-yl)-8-oxooct-1-yl)thio-5-(pyrid-3-ylmethyl)-pyrimidin-4-one

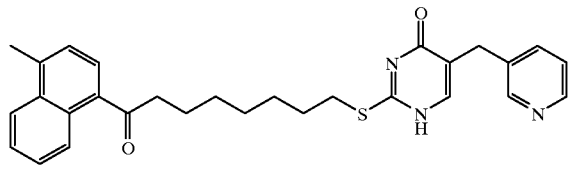

Prepared from intermediate B19 and A9 by general method A1 as a white solid. MPt 102–104° C.; $^1$H-NMR (CDCl$_3$) δ 1.2–1.5 (6H, m), 1.5–1.8 (4H, m), 2.73 (3H, s), 3.02 (2H, t), 3.13 (2H, t), 3.73 (2H, s), 7.25 (1H, m), 7.28 (1H, d), 7.45–7.75 (4H, m), 7.75 (1H, d), 8.02 (1H, m), 8.45 (1H, m) and 8.5–8.7 (2H, m); MS (EI) M=485; C$_{29}$H$_{31}$N$_3$O$_2$S requires 485.

Example 69

2-(8-(4-Pyridyl)oct-1-yl)thio-5-(pyrid-3-ylmethyl)pyrimidin-4-one

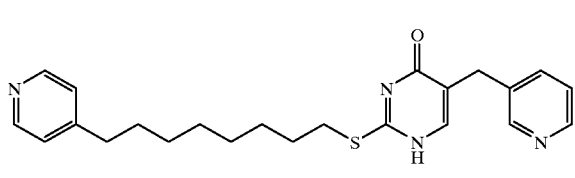

Prepared from intermediate B19 and A23 by general method A1 as a white solid. MPt 86–88° C.; $^1$H-NMR (d$_6$ DMSO) δ 1.2–1.5 (8H, m), 1.5–1.8 (4H, m), 2.57 (2H, t), 3.07 (2H, t), 3.62 (2H, s), 7.21 (2H, d), 7.25 (1H, m), 7.81 (1H, s) and 8.3–8.6 (4H, m).

Example 70

2-(8-(4-Chlorophenyloct-1-yl)thio-5(pyrid-3-ylmethyl)pyrimidin-4-one

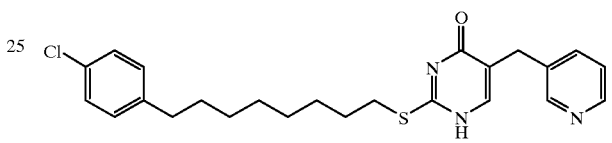

Prepared from intermediate B19 and A24 by general method A1. $^1$H-NMR (d$_6$ DMSO) δ 1.2–1.5 (6H, m), 1.5–1.8 (4H, m), 2.54 (2H, t), 3.07 (2H, t), 3.61 (2H, s), 7.1–7.4 (5H, m), 7.63 (1H, m), 7.80 (1H, s), 8.38 (1H, m) and 8.47 (1H, bs).

Example 71

2-(4-(3-Phenylprop-1-yloxy)but-1-yl)thio-5-(pyrid-3-ylmethyl)-pyrimidin-4-one

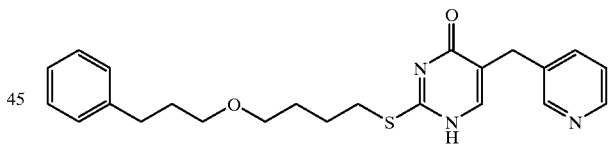

Prepared from intermediate B19 and A43 by general method A1. $^1$H-NMR (d6-DMSO) δ 1.5–1.9 (6H, m), 2.59 (2H, t), 3.12 (2H, t), 3.3 (4H, m), 3.61 (2H, s), 7.1–7.3(6H, m), 7.6 (1H, m), 7.81 (1H, s), 8.38 (1H, m), 8.48 (1H, d).

Example 72

2-(6-Benzyloxyhex-1-yl)thio-5-(quinolin-3-ylmethyl)pyrimidin-4-one

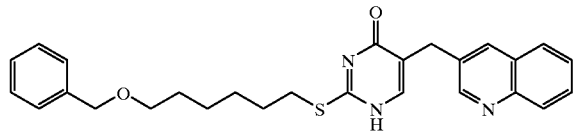

Prepared from intermediate B19 and A27 by general method A1 as a light brown solid. MPt 120–122° C.;

¹H-NMR (d₆-DMSO) δ 1.3 (4H, m), 1.5 (2H, m), 1.6 (2H, m), 3.08 (2H, t), 3.39 (2H, t), 3.82 (2H, s), 4.42 (2H, s), 7.3 (5H, m), 7.56 (1H, m), 7.70 (1H, m), 7.9–8.0 (3H, m), 8.13 (1H, d), 8.85 (1H, d), 12.7 (1H, br s).

Example 73

2-(8-Phenyloct-1-yl)thio-5-(quinolin-3-ylmethyl)pyrimidin-4-one

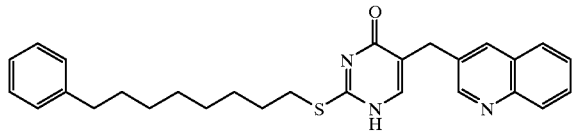

Prepared from intermediate B16 by general method A1 as a light brown solid. MPt 124–126° C.; ¹H-NMR (d₆-DMSO) δ 7.1–7.3 (5H, m), 7.56 (1H, m), 7.68 (1H, m), 7.9–8.0 (3H, m), 8.12 (1H, d), 8.85 (1H, d).

Example 74

2-(8-Phenyloct-1-yl)thio-5-((4-methoxypyrid-2-yl)methyl)pyrimidin-4-one

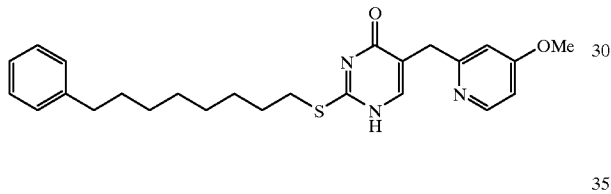

Prepared from intermediate B26 by general method B as a brown solid after trituration with ether and recrystallisation from ethyl acetate. MPt 58–60° C.; ¹H-NMR (d₆-DMSO) δ 1.3 (8H, m), 1.6 (4H, m), 2.55 (2H, t), 3.07 (2H, t), 3.69 (2H, s), 3.78 (3H, s), 6.8 (2H, m), 7.1–7.3 (5H, m), 7.70 (1H, s), 8.25 (1H, d).

Example 75

2-(8-Phenyloct-1-yl)thio-5-(2-oxopyrid-4-ylmethyl)pyrimidin-4-one

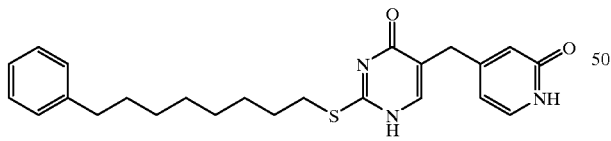

A mixture of 2-(8-phenyloct-1-yl)thio-5-(2-methoxypyrid-4-ylmethyl)pyrimidin-4-one (0.40 g, 0.9 mmol), chlorotrimethylsilane (0.23 ml, 1.8 mmol) and sodium iodide (0.27 g, 1.8 mmol) in acetonitrile (30 ml) was heated at reflux for 6 hours. The solvent was evaporated, the residue taken up in dichloromethane, and washed with water and aqueous sodium thiosulphate. Evaporation of the solvent and trituration with ether gave 2-(8-phenyloct-1-yl)thio-5-(2-oxopyrid-4-ylmethyl)pyrimidin-4-one as a white solid (0.03 g). ¹H-NMR (d₆-DMSO) δ 1.3 (8H, m), 1.6 (4H, m), 2.55 (2H, t), 3.07 (2H, t), 6.07 (2H, m), 7.1–7.3 (6H, m), 7.77 (1H, s); MPt indeterminate.

Example 76

2-(8-Phenyloct-1-yl)thio-5-(pyrid-4-ylmethyl)pyrimidin-4-one

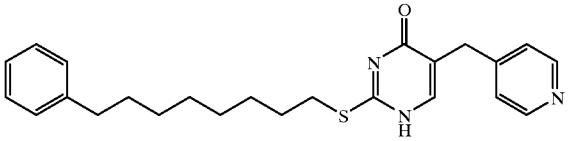

Prepared from intermediate B20 by general method A1 as a beige solid. MPt 124–125° C;, ¹H-NMR (d₆-DMSO) δ 1.3 (8H, m), 1.6 (4H, m), 2.55 (2H, t), 3.08 (2H, t), 3.63 (2H, s), 7.1–7.3 (7H, m), 7.83 (1H, s), 8.42 (2H, d).

Example 77

2-(6-Benzyloxyhex-1-yl)thio-5-(pyrid-4-ylmethyl)pyrimidin-4-one

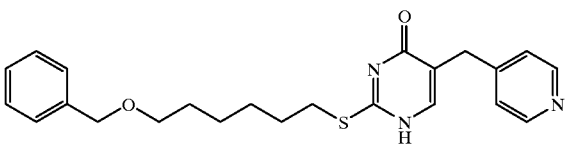

Prepared from intermediate B20 and A27 by general method A1 as a white solid. MPt 111–113° C.; ¹H-NMR (d₆-DMSO) δ 7.23 (2H, d), 7.3 (5H, m), 7.83 (1H, s), 8.43 (2H, d), 1.28 (1H, br s).

Example 78

2-(8-(4-Chlorophenyl)-8-oxooct-1-yl)thio-5-(pyrimid-5-ylmethyl)-pyrimidin-4-one

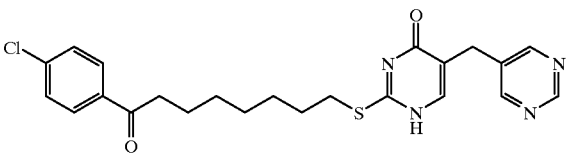

Prepared from intermediate B9 and A1 by general method A1 as a white solid. MPt 129–130° C.; ¹H-NMR (CDCl₃) δ 1.2–1.5 (6H, m), 1.5–1.8 (4H, m), 2.93 (2H, t), 3.15 (2H, t), 3.71 (2H, s), 7.43 (2H, d), 7.78 (1H, s), 7.89 (2H, d), 8.72 (2H, s) and 9.07 (1H, s); MS (EI) M=456; $C_{23}H_{25}ClN_4O_2S$ requires 456.

Example 79

2-(8-Phenyloct-1-yl)thio-5-(fur-2-ylmethyl)pyrimidin-4-one

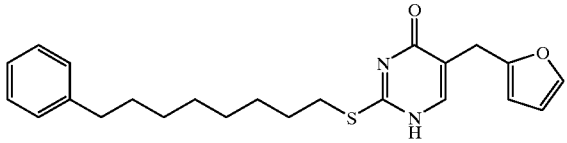

Prepared from intermediate B13 by general method A1 as a light brown solid. MPt 79–81° C.; $^1$H-NMR (d$_6$-DMSO) δ 1.3 (8H, m), 1.6 (4H, m), 2.55 (2H, t), 3.07 (2H, t), 3.64 (2H, s), 6.08 (1H, m), 6.34 (1H, m), 7.1–7.3 (5H, m), 7.51 (1H, m), 7.67 (1H, s).

Example 80

2-(6-Benzyloxyhex-1-yl)thio-5-(fur-2-ylmethyl)pyrimidin-4-one

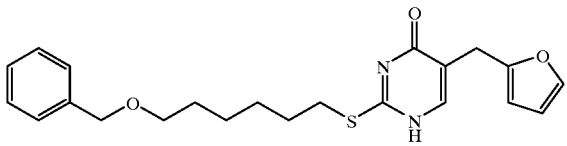

Prepared from intermediate B13 and A27 by general method A1 as a brown solid. MPt 63–65° C.; $^1$H-NMR (d$_6$-DMSO) δ 1.3 (4H, m), 1.5 (2H, m), 1.6 (2H, m), 3.08 (2H, t), 3.40 (2H, t), 3.64 (2H, s), 4.43 (2H, s), 6.08 (1H, m), 6.34 (1H, m), 7.3 (5H, m), 7.51 (1H, m), 7.68 (1H, s).

Example 81

2-(6Benzyloxyhex-1-yl)thio-5-(fur-3-ylmethyl)pyrimidin-4one

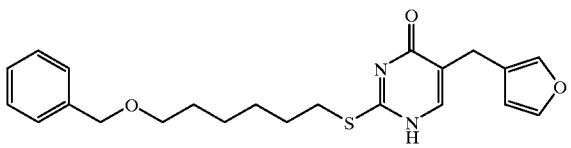

Prepared from intermediate B15 and A27 by general method A1 as a white solid. MPt 58–60° C.; $^1$H-NMR (d$_6$-DMSO) δ 1.3 (4H, m), 1.5 (2H, m), 1.6 (2H, m), 3.08 (2H, t), 3.4 (4H, m), 4.43 (2H, s), 6.37 (1H, m), 7.3 (5H, m), 7.44 (1H, m), 7.55 (1H, m), 7.68 (1H, s).

Example 82

2-(8-Phenyloct-1-yl)thio-5-(fur-3-ylmethyl)pyrimidin-4-one

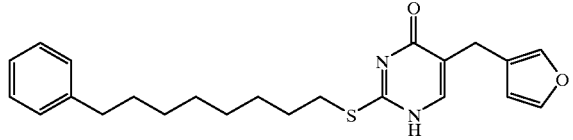

Prepared from intermediate B15 by general method A1 as a white solid. MPt 78–80° C.; $^1$H-NMR (d$_6$-DMSO) δ 6.37 (1H, s), 7.1–7.3 (5H, m), 7.44 (1H, m), 7.55 (1H, m), 7.65 (1H, s).

Example 83

2-Benzylthio-5-((1-methyl-2-oxo-pyrid-4-yl)methyl)pyrimidin-4-one

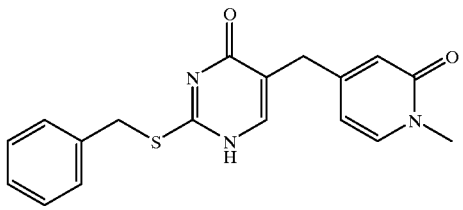

Prepared from intermediate B11 by general method A1 as a white solid. MPt 194–25 196° C.; $^1$H-NMR (d$_6$-DMSO) δ 3.35 (3H, s), 3.44 (2H, s), 4.39 (2H, s), 6.10 (1H, m), 6.16 (1H, s), 7.56 (1H, d), 7.86 (1H, s), 12.8 (1H, br s).

Example 84

2-Benzylthio-5-(fur-2-ylmethyl)pyrimidin-4-one

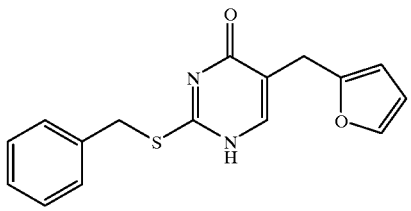

Prepared from intermediate B13 by general method A5. $^1$H-NMR (d$_6$-DMSO) δ 0.366 (2H, s), 4.38 (2H, s), 6.09 (1H, m), 6.35 (1H, m), 7.2–7.4 (5H, m), 7.52 (1H, m), 7.74 ()1H, s).

Example 85

2-(3-Chlorobenzyl)thio-5-(fur-2-ylmethyl)pyrimidin-4-one

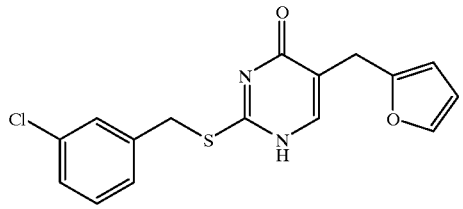

Prepared from intermediate B13 by general method A5. ¹H-NMR (d₆-DMSO) δ 3.66 (2H, s), 4.39 (2H, s), 6.09 (1H, m), 6.35 (1H, m), 7.3–7.4 (5H, m), 7.50 (1H, m), 7.74 (1H, s).

Example 86

2-(4-Chlorobenzyl)thio-5-(fur-2-ylmethyl)pyrimidin-4-one

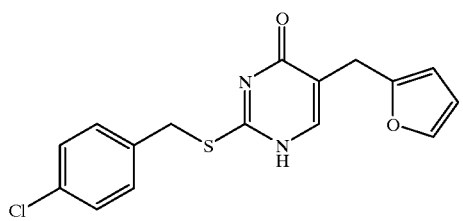

Prepared from intermediate B13 by general method A5. ¹H-NMR (d₆-DMSO) δ 3.63 (2H, s), 4.33 (2H, s), 6.07 (1H, m), 6.34 (1H, m), 7.35 (2H, d), 7.42 (2H, d), 7.50 (1H, m), 7.64 (1H, s).

Example 87

2-Benzylthio-5-((2-methylpyrid-5-yl)methyl)pyrimidin-4-one

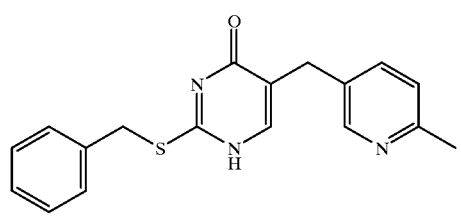

Prepared from intermediate B121 by general method A1 as a white solid. MPt 226–228° C.; ¹H-NMR (d₆-DMSO) δ 2.40 (3H, s), 3.59 (2H, s), 4.38 (2H, s), 7.14 (1H, d), 7.2–7.5 (5H, m), 7.52 (1H, dd), 7.84 (1H, s), 8.34 (1H, d).

Example 88

2-Benzylthio-5-((2-methoxypyrid-4-yl)methyl)pyrimidin-4-one

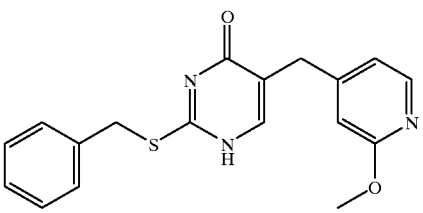

Prepared from intermediate B25 by general method B as a white solid. MPt 193–5° C.; ¹H-NMR (d₆-DMSO) δ 3.60 (2H, s), 3.81 (3H, s), 4.39 (2H, s), 6.65 (1H, s), 6.85 (1, m), 7.25–7.42 (5H, m), 7.87 (1H, s), 8.03 (1H, m).

Example 89

2-Benzylthio-5-(pyrazin-2-ylmethyl)pyrimidin-4-one

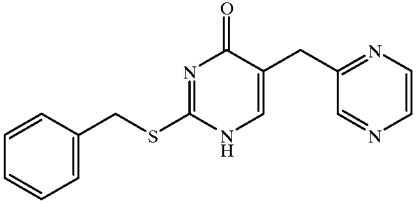

Prepared from intermediate B14 by general method A1 as a white solid. MPt 174–175° C.; ¹H-NMR (d₆ DMSO) δ 3.84 (2H, s), 4.40 (2H, s), 7.1–7.5 (5H, m), 7.89 (1H, bs), 8.47 (1H, d), 8.51 (1H, t) and 8.59 (1H, d); MS (FAB) M+1=311; C₁₆H₁₄N₄OS requires 310.

Example 90

2-Benzylthio-5-(thiazol-2-ylmethyl)pyrimidin-4-one

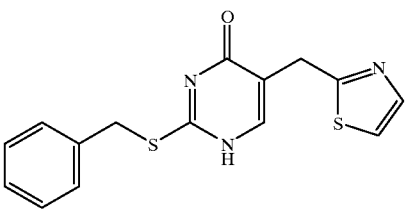

Prepared from intermediate B22 by general method A1 as light brown crystals; ¹H-NMR (d₆ DMSO) 4.02 (2H, s), 4.41 (2H, s), 7.2–7.45 (6H, m), 7.55 (1H, d), 7.67 (1H, d) and 7.95 (1H, bs); MS (EI) M=315; C₁₅H₁₃N₃OS₂ requires 315.

Example 91

2-(4-Chlorobenzyl)thio-5-(pyrid-3-ylmethyl)pyrimidin-4-one

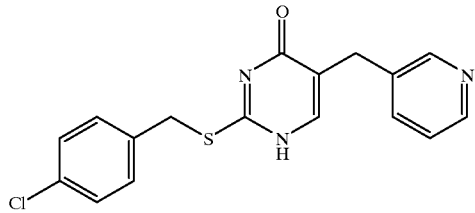

Prepared from intermediate B19 by general method A5. $^1$H-NMR (d$_6$-DMSO) δ 3.59 (2H, s), 4.30 (2H, s), 7.26 (1H, m), 7.31 (2H, d), 7.41 (2H, d), 7.63 (1H, m), 7.72 (1H, s), 8.37 (1H, m), 8.47 (1H, m).

Example 92

2-Benzylthio-5-(pyrid-3-ylmethyl)pyrimidin-4-one

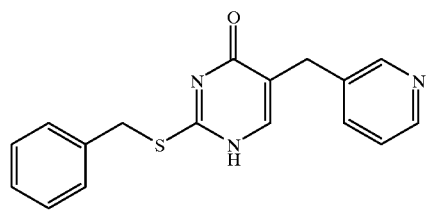

Prepared from intermediate B19 by general method A5. $^1$H-NMR (d$_6$-DMSO) δ 3.61 (2H, s), 4.33 (2H, s), 7.2–7.4 (5H, m), 7.64 (1H, m), 7.78 (1H, s), 8.38 (1H, m), 8.49 (1H, m).

Example 93

2-(3,4-Dichlorobenzyl)thio-5-(pyrid-3-ylmethyl)pyrimidin-4-one

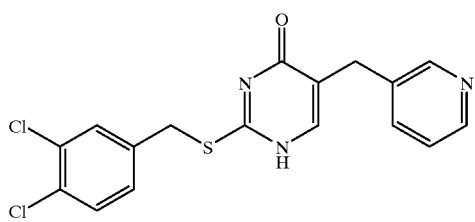

Prepared from intermediate B19 by general method A5. $^1$H-NMR (d$_6$-DMSO) δ 3.60 (2H, s), 4.31 (2H, s), 7.26 (1H, m), 7.39 (1H, m), 7.53 (1H, d), 7.65 (1H, m), 7.75 (1H, s), 8.37 (1H, m), 8.48 (1H, m).

Example 94

2-Benzylthio-5-(pyrid-4-ylmethyl)pyrimidin-4-one

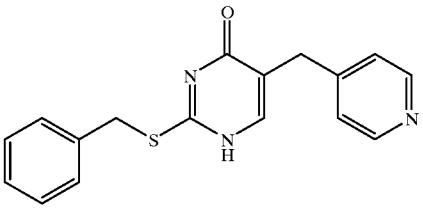

Prepared from intermediate B20 by general method A1 as a white solid. MPt 183–185° C.; $^1$H-NMR (d$_6$-DMSO) δ 3.64 (2H, s), 4.39 (2H, s), 7.24 (2H, d), 7.3–7.4 (5H, m) 7.89 (1H, s), 8.43 (2H, d).

Example 95

2-(4-Chlorobenzyl)thio-5-(pyrid-4-ylmethyl)pyrimidin-4-one

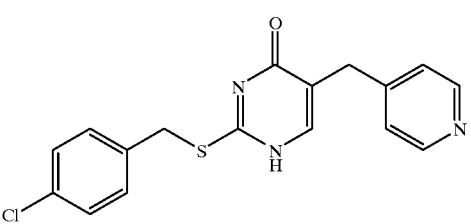

Prepared from intermediate B20 by general method A5. $^1$H-NMR (d$_6$-DMSO) δ 3.65 (2H, s), 4.38 (2H, s), 7.24 (2H, d), 7.37 (2H, d), 7.44 (2H, d), 7.88 (1H, s), 8.43 (2H, d).

Example 96

2-(3,4-Dichlorobenzyl)thio-5-(pyrid-4-ylmethyl)pyrimidin-4one

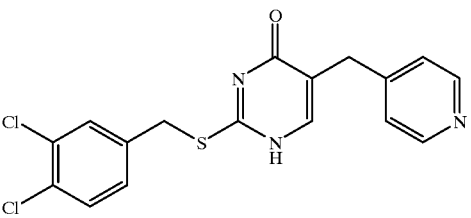

Prepared from intermediate B20 by general method A5. $^1$H-NMR (d$_6$-DMSO) δ 3.66 (2H, s), 4.39 (2H, s), 7.25 (2H, d), 7.42 (1H, dd), 7.57 (1H, d), 7.69 (1H, d), 7.89 (1H, s), 8.44 (2H, d).

Example 97

2-Benzylthio-5-(pyrimid-5-ylmethyl)pyrimidin-4-one

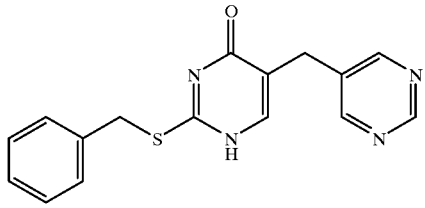

Prepared from intermediate B9 by general method A1 as a white solid. MPt 239–241° C.; $^1$H-NMR (d$_6$-DMSO) δ 3.65 (2H, s), 4.39 (2H, s), 7.1–7.5 (5H, m), 7.95 (1H, bs), 8.71 (2H, s) and 9.02 (1H, s); MS (EI) M=310; C$_{16}$H$_{14}$N$_4$OS requires 310.

Example 98

2-Benzylthio-5-(2-(pyrid-4-yl)ethyl)pyrimidin-4-one

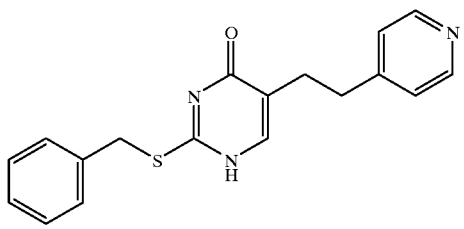

Prepared from intermediate B17 by general method A1 as a white solid. MPt 209–2105° C.; $^1$H-NMR (d$_6$-DMSO) δ 2.61 (2H, t), 2.81 (2H, t), 4.36 (2H, s), 7.1–7.5 (7H, m), 7.69 (1H, s) and 8.45 (2H, d); MS (FAB) M+1=324; C$_{18}$H$_{17}$N$_3$OS requires 323.

Example 99

2-Benzylthio-5-benzylpyrimidin-4-one

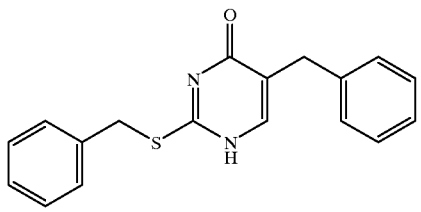

Prepared from intermediate B23 by general method A1 as a brown solid. MPt 156–158° C.; $^1$H-NMR (d$_6$-DMSO) δ 3.62 (2H, s), 4.38 (2H, s), 7.1–7.5 (10H, m), 7.8 (1H, s), 12.8 (1H, br s).

Example 100

2-(8-Phenyloct-1-yl)oxy-5(pyrid-3-ylmethyl)pyrimidin-4-one

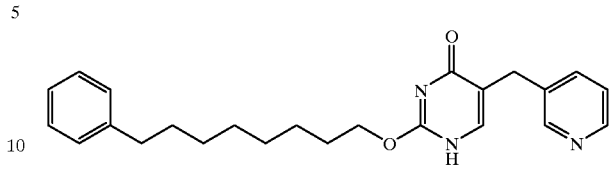

A mixture of 8-phenyl-1-octanol (1.5 g), 2-nitroamino-5-(pyrid-3-ylmethyl)pyrimidin-4-one (1.0 g) and pyridine (5 ml) was stirred at reflux for 24 hours, then the pyridine was removed by evaporation. Water was added, and the product extracted into dichloromethane, which was dried and evaporated. The residue was purified by chromatography (silica, 0–5% methanol in dichloromethane) and recrystallisation from ether to give 2-(8-phenyloct-1-yl)oxy-5-(pyrid-3-ylmethyl)pyrimidin-4-one as a pale buff solid (0.1 g). MPt 53–55° C.; $^1$H-NMR (CDCl$_3$) δ 1.32 (8H, m), 1.60 (2H, m), 1.74 (2H, m), 2.58 (2H, t), 3.72 (2H, t), 4.31 (2H, t), 7.1–7.3 (6H, m), 7.54 (1H, m), 7.63 (1H, m), 8.45 (1H, m) and 8.55 (1H, d); MS (EI) Found M=391; C$_{24}$H$_{29}$N$_3$O$_2$ requires 391.

Example 101

2-(8-(4-Chlorophenyl)-8-oxooct-1-yl)oxy-5-(pyrid-3-ylmethyl)-pyrimidin-4-one

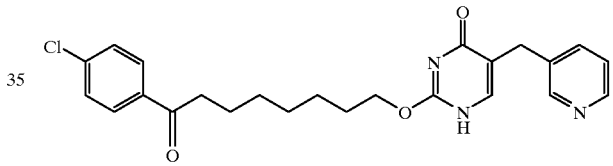

Prepared from intermediates B24 and A2 analogously to example 100. Recrystallisation from acetonitrile/ether gave the product as an off-white solid. MPt 116–7° C.; $^1$H-NMR (CDCl$_3$) δ 1.39 (6H, m), 1.74 (4H, m), 2.93 (2H, t), 3.72 (2H, t), 4.31 (2H, t), 7.2 (1H, m), 7.42 (2H, d), 7.55 (1H, s), 7.62 (1H, d), 7.88 (2H, d), 8.45 (1H, m) and 8.54 (1H, d); MS (FAB) M+1=440; C$_{24}$H$_{26}$ClN$_3$O$_2$ requires 439.

Example 102

2-(4-Phenylbut-1-yl)oxy-5-((2-methylpyrid-5-yl)methyl)pyrimidin-4-one

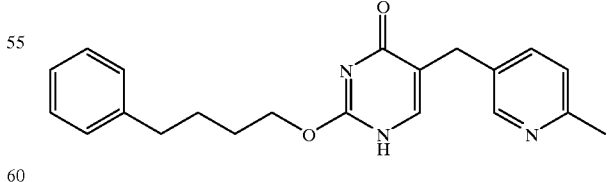

Finely ground cyanamide (1.68 g, 0.04 mol) and cyanamide dihydrochloride (2.26 g, 0.02 mol) were treated with 4-phenyl-1-butanol (3.24 g, 0.02 mol), occasionally stirring with a glass rod over a 20 day period. The white paste was dissolved in water, extracted with chloroform and the aqueous layer adjusted to pH 13 (conc. sodium hydroxide) with ice cooling. The oil which precipitated was extracted into ethyl acetate, dried (MgSO$_4$) and the solvent evaporated to give the isourea as a clear oil (3.88 g). A portion of this material (2.44 g) was converted to the hydrochloride salt by treatment with HCl/ethanol/ether, the solvents evaporated and the residue washed several times with ether and dried under high vacuum to yield 1.47 g.

This material (1.47 g, 0.00646 mol) was dissolved in ethanol (40 ml) together with ethyl 2-formyl-3-(6-methylpyrid-3-yl)propionate (0.95 g, 0.00431 mol) and triethylamine and heated under reflux for 6 h. The solvent was evaporated and the residue treated with water and extracted with ethyl acetate, dried (MgSO$_4$) and evaporated to an oil. Purification by chromatography (silica, methanol/chloroform) followed by crystallisation from ethyl acetate-petrol gave 2-(4-phenylbut-1-yl)thio-5-((2-methylpyrid-5-yl)methyl)-pyrimidin-4-one, yield 0.09 g (6%). MPt 88–90° C.; $^1$H-NMR (CDCl$_3$) δ 1.75 (4H, m), 2.49 (3H, s), 2.65 (2H, t), 3.64 (2H, s), 4.32 (2H, t), 6.90–7.60 (8H, m), 8.38 (1H, m).

Example 103

2-(2-Phenylethyl)thio-5-((2-methylpyrid-5-yl)methyl)pyrimidin-4-one

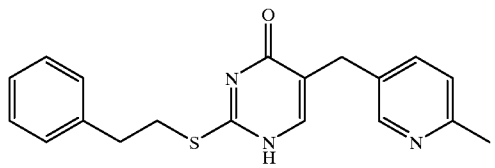

Prepared from intermediate B21 by general method B as white crystals, MPt 158–160° C. $^1$H-NMR (d$_6$-DMSO) δ 2.41 (3H, s), 2.93 (2H, t), 3.3 (2H+H$_2$O, t), 3.58 (2H, s), 7.14 (1H, d), 7.2–7.3 (5H, m), 7.52 (1H, dd), 7.83 (1H, s), 8.34 (1H, d), 12.7 (1H, br s).

Example 104

2-(2-Phenylethyl)thio-5-((2-methoxypyrid-4-yl)methyl)pyrimidin-4-one

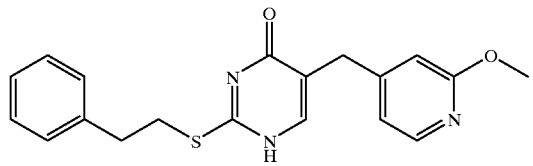

Prepared from intermediate B25 by general method B as white crystals; MPt 139–140° C. $^1$H-NMR (d$_6$-DMSO) δ 2.94 (2H, t), 3.3 (2H+H$_2$O, t), 3.59 (2H, s), 3.81 (3H, s), 6.65 (1H, s), 6.86 (1H, dd), 7.2–7.3 (5H, m), 7.85 (1H, br s), 8.03 (1H, d)

Example 105

2-Benzylthio-5-((1-methyipyrazol-4-yl)methyl)pyrimidin-4one

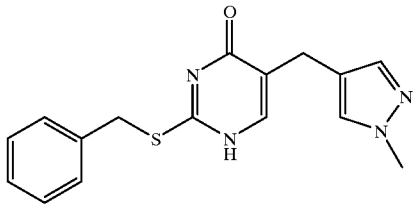

Prepared from intermediate B34 by general method A1 as a white crystalline solid. $^1$H-NMR (d$_6$-DMSO) δ 3.37 (2H, s), 3.71 (3H, s), 4.33 (2H, s), 7.2–7.4 (6H, m), 7.41 (1H, s), 7.67 (1H, br s), 12.7 (1H, br s); (APCI) M+H=313. C$_{16}$H$_{16}$N$_4$OS requires 312.

Example 106

2-(4-Fluorobenzylthio)-5-((pyrimid-5-yl)methyl)pyrimidin-4-one

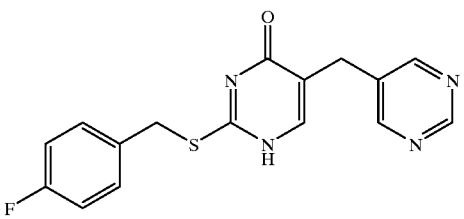

Prepared from intermediate B9 by general method A4. $^1$H-NMR (d$_6$-DMSO) δ 3.65 (2H, s), 4.38 (2H, s), 7.05–7.2 (2H, m), 7.35–7.5 (2H, m), 7.94 (1H, bs), 8.71 (2H, s), 9.06 (1H, s); MS (APCI–) found (M–1)=327; C$_{16}$H$_{13}$FN$_4$OS requires 328.

Example 107

2-(3,4-Difluorobenzylthio)-5-((2-methoxypyrimid-5-yl)methyl)pyrimidin-4-one

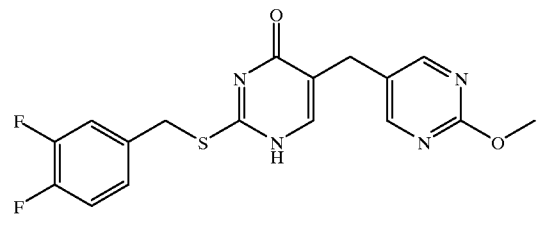

Prepared from intermediate B39 by general method A4. $^1$H-NMR (d6-DMSO) δ 3.57 (2H, s), 3.87 (3H, s), 4.37 (2H, s), 7.24–7.53 (3H, m), 7.88 (1H, br, s), 8.49 (2H, s), 12.88 (1H, br s); MS (APCI+) found (M+1)=377; C$_{17}$H$_{20}$F$_2$N$_4$O$_2$S requires 376.

Example 108

2-(4-Fluorobenzylthio)-5-((2-methoxypyrimid-5-yl)methyl)pyrimidin-4-one

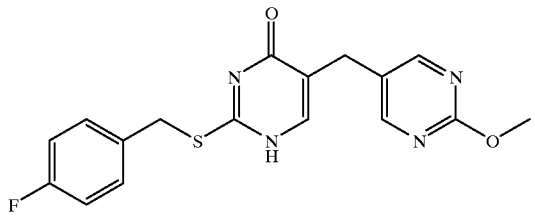

Prepared from intermediate B39 by general method A4. $^1$H-NMR (d$_6$ DMSO) δ 3.55 (2H, s), 3.85 (3H, s), 4.36 (2H, s), 7.0–7.2 (2H, m), 7.35–7.5 (2H, m), 7.86 (1H, bs), 8.48 (2H, s) 12.81 (1H, b); MS (APCI+) found (M+1)=359; $C_{17}H_{15}FN_4O_2S$ requires 358.

Example 109

2-(4-Fluorobenzylthio)-5-((2-benzyloxypyrimid-5-yl)methyl)pyrimidin-4-one

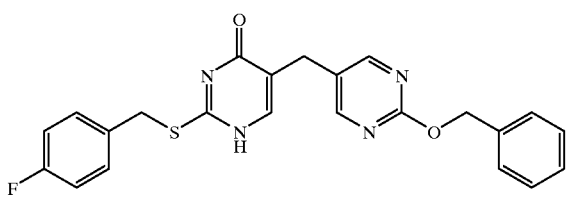

Prepared from intermediate B40 by general method A4. $^1$H-NMR (d$_6$-DMSO) δ 3.57 (2H, s), 4.38 (2H, s), 5.35 (2H, s), 7.0–7.2 (2H, m), 7.25–7.5 (7H, m), 7.87 (1H, bs), 8.51 (2H, s); MS (APCI+) found (M+1)=435; $C_{23}H_{19}FN_4O_2S$ requires 434.

Example 110

1-(4-Hydroxycyclohexyl)-2-(8-(4-chlorophenyl)-8-oxooct-1-yl)thio-5-(pyrimid-5-ylmethyl)pyrimidin-4-one

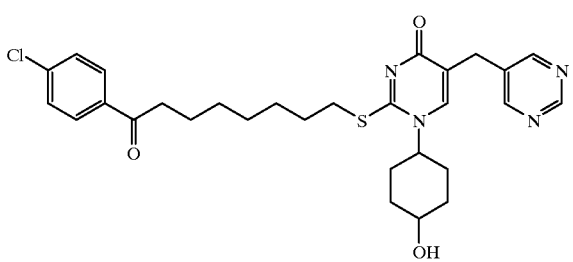

Prepared from intermediates B46 and A1 by general method A4. $^1$H-NMR (CDCl$_3$) δ 1.1–2.3(18H, m), 2.94(2H, t), 3.24(2H, t), 3.6–3.8(3H, m), 4.2 (1H, m), 7.12 (1H, s). 7.45(2H, m), 7.90(2H, m), 8.71(2H, s) and 9.09(1H, s); MS (APCI+) found (M+1)=555; $C_{29}H_{35}ClN_4O_3S$ requires 554.

Example 111

1-(2-Methoxyethyl)-2-(8-(4-chlorophenyl)-8-oxooct-1-yl)thio-5-(pyrimid-5-ylmethyl)pyrimidin-4one

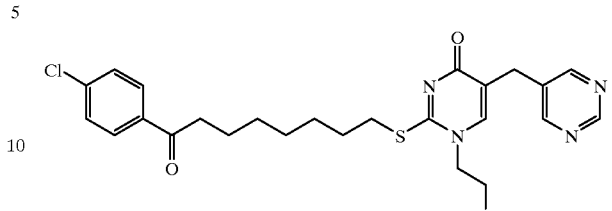

Prepared from intermediate B87 by general method A4. $^1$H-NMR (CDCl$_3$) δ 1.25–1.85(10H, m), 2.93(2H, t), 3.26 (2H, t), 3.32(3H, s), 3.62(2H, t), 3.69(2H, s), 7.08(1H, s), 7.43(2H, m), 7.90(2H, m), 8.70(2H, s) and 9.09(1H, s); MS (APCI+) found (M+1)=515; $C_{26}H_{31}ClN_4O_3S$ requires 514.

Example 112

1-(3-(1-Imidazolyl)prop-1-yl)-2-(8-(4-chlorophenyl)-8-oxooct-1-yl)thio-5-(pyrimid-5-ylmethyl)pyrimidin-4-one

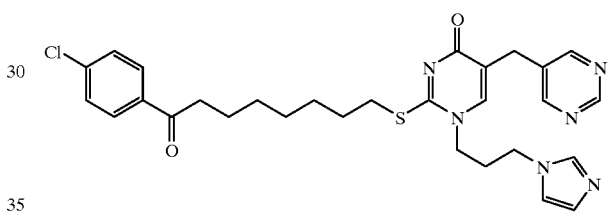

Prepared from intermediate B47 and A1 by general method A4, as a yellow oil. $^1$H-NMR (CDCl$_3$) δ 1.38 (6H, m), 1.70 (4H, m), 2.25 (2H, m), 2.91 (2H, t), 3.25 (2H, t), 3.69 (2H, s), 3.77 (2H, t), 4.07 (2H, t), 6.81 (1H, s), 6.92 (1H, s), 7 13 (1H, s), 7.43 (2H, d), 7.50 (1H, s), 7.89 (2H, d), 8.70 (2H, s), 9.10 (1H, s); MS APCI+) found (M+1)=565; $C_{29}H_{33}ClN_6O_2S$ requires 564.

Example 113

1-(3-(1-Morpholino)prop-1-yl)-2-(8-(4-chlorophenyl)-8-oxooct-1-yl)thio-5-(pyrimid-5-ylmethyl)pyrimidin-4-one

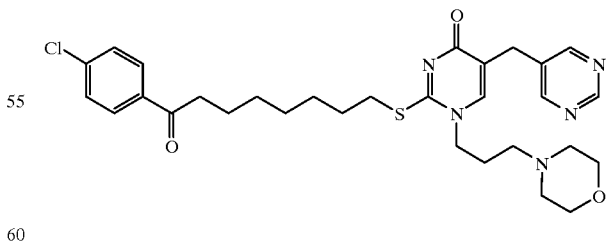

Prepared from intermediate B48 and A1 by general method A4, as a thick gum. $^1$H-NMR (CDCl$_3$) δ 1.2–1.8 (10H, m), 1.93(2H, m), 2.25–2.5(6H, m), 2.93(2H, t), 3.25 (2H, t), 3.55–3.8(6H, m), 3.90(2H, t), 7.07(1H, s), 7.45(2H, m), 7.90(2H, m), 8.72(2H, s) and 9.12(1H, s); MS (APCI+) found (M+1)=584, $C_{30}H_{38}ClN_5O_3S$ requires 583.

Example 114

1-(3-(2-Oxo-1-pyrrolidino)prop-1-yl)-2-(8-(4-chlorophenyl)-8-oxooct-1-yl)thio-5-(pyrimid-5-ylmethyl)pyrimidin-4-one

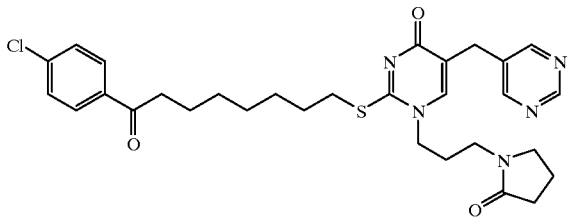

Prepared from intermediate B49 and A1 by general method A4, as a yellow oil. $^1$H-NMR (CDCl$_3$) δ 1.38 (6H, m), 1.74 (4H, m), 1.98 (2H, m), 2.10 (2H, m), 2.43 (2H, t), 2.93 (2H, m), 3.25 (2H, t), 3.34 (2H, t), 3.41 (2H, t), 3.70 (2H, s), 3.82 (2H, t), 7.43 (2H, m), 7.54 (1H, s), 7.89 (2H, m), 8.74 (2H, s), 9.07 (1H, s); MS APCI+) found (M+1)= 582; C$_{30}$H$_{36}$ClN$_5$O$_3$S requires 581.

Example 115

1-(3-Dimethylaminoprop-1-yl)-2-(8-(4-chlorophenyl)-8-oxooct-1-yl)thio-5-(pyrimid-5-ylmethyl)pyrimidin-4-one

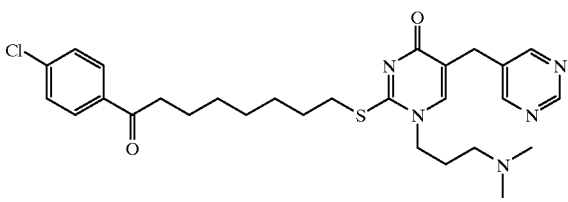

Prepared from intermediate B51 and A1 by general method A4, as a thick gum. $^1$H-NMR (CDCl$_3$) δ 1.2–1.8 (10H, m), 1.8–2.05(4H, m), 2.14(3H, s), 2.19(3H, s), 2.93 (2H, t), 3.24(2H, t), 3.70(2H, s), 7.42(2H, m), 7.88(2H, m) 8.72(2H, s) and 9.09(1H, s), MS (APCI+) found (M+1)= 542; C$_{28}$H$_{36}$ClN$_5$O$_2$S requires 541.

Example 116

1-(3-Hydroxyprop-1-yl)-2-(8-(4-chlorophenyl)-8-oxooct-1-yl)thio-5-(pyrimid-5-ylmethyl)pyrimidin-4-one

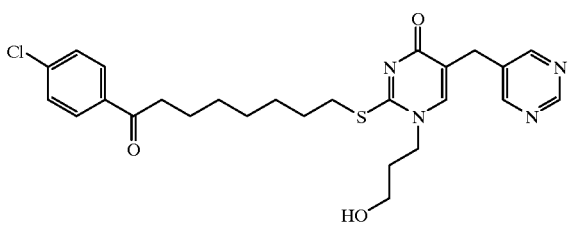

Prepared from intermediate B52 and A1 by general method A4. $^1$H-NMR (CDCl$_3$) δ 1.3–1.55 (6H, m), 1.6–1.85 (4H), 1.95–2.1(2H, m), 2.93(2H, t), 3.25(2H, t), 3.6–3.8 (4H, m), 4.01(2H, t), 7.11(1H, s) 7.45(2H, d), 7.89(2H, d), 8.70(2H, m) and 9.08(1H, s); MS (APCI+) found (M+1)= 515; C$_{26}$H$_{31}$ClN$_4$O$_3$S requires 514.

Example 117

1-(3-Hydroxyprop-1-yl)-2-(8-(4-chlorophenyl)oct-1-yl)thio-5-benzylpyrimidin-4-one

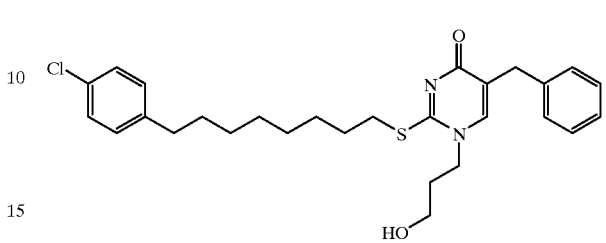

Prepared from intermediate B52 and A24 by general method A4, as a colourless powder. MPt 76–77° C.; $^1$H-NMR (CDCl$_3$) δ 1.2–2.0(14H, m), 2.56(2H, t), 3.25(2H, t), 3.61(2H, t ), 3.73(2H, s), 3.88(2H, t), 6.76(1H, s), 7.09(1H, d) and 7.15–7.4(7H, m), MS (FAB) found M+H= 499; C$_{28}$H$_{35}$ClN$_2$O$_2$S requires 498.

Example 118

1-(3-Methoxyprop-1-yl)-2-(8-(4-chlorophenyl)-8-oxooct-1-yl)thio-5-(pyrimid-5-ylmethyl)pyrimidin-4-one

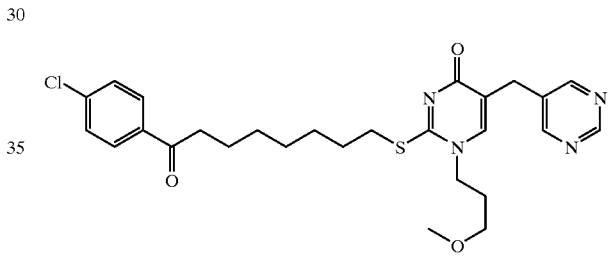

Prepared from intermediate B54 and A1 by general method A4. $^1$H-NMR (CDCl$_3$) δ 1.2–1.85(10H, m), 2.00 (2H, m), 2.94(2H, t), 3.2–3.4(7H, m), 3.70(2H, s), 3.92(2H, t), 6.99(1H, s), 7.44(2H, m), 7.90(2H, m), 8.71(2H, s) and 9.10(1H, s); MS (APCI+) found (M+1)=529; C$_{27}$H$_{33}$ClN$_4$O$_3$S requires 528.

Example 119

1-(3-Phenylprop-1-yl)-2-(8-(4-chlorophenyl)-8-oxooct-1-yl)thio-5-(pyrimid-5-ylmethyl)pyrimidin-4-one

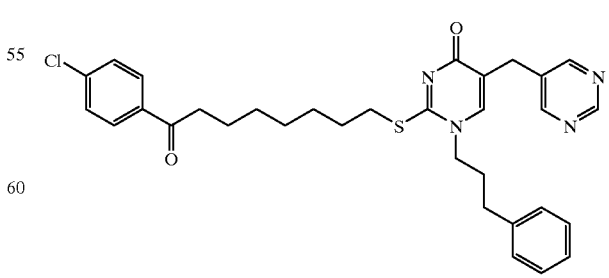

Prepared from intermediate B55 and A1 by general method A4. $^1$H-NMR (CDCl$_3$) δ 1.2–1.85(10H, m), 2.11

(2H, quintet), 2.69(2H, t), 2.93(2H, t), 3.24(2H, t), 3.67(2H, s), 3.78 (2H, t), 6.84(1H, s), 7.1–7.5(7H, m), 7.90(2H, m), 8.70(2H, s) and 9.10(1H, s); MS (APCI+) found (M+1)= 575; $C_{32}H_{35}ClN_4O_2S$ requires 574.

Example 120

1-(5-Hydroxypent-1-yl)-2-(8-(4-chlorophenyl)-8-oxooct-1-yl)thio-5-(pyrimid-5-ylmethyl)pyrimidin-4-one

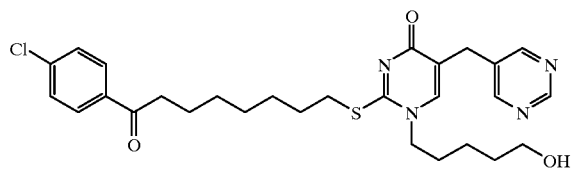

Prepared from intermediate B56 and A1 by general method A4. $^1$H-NMR (CDCl$_3$) δ 1.3–1.9(16H, m), 2.94(2H, t), 3.25(2H, t), 3.6–3.75(4H–m) 3.80(2H, t), 6.96(1H, m), 7.44 (2H, m), 7.90(2H, m), 8.71(2H, s) and 9.09(1H, s); MS (APCI+) found (M+1)=543; $C_{28}H_{35}ClN_4O_3S$ requires 542.

Example 121

1-(Pyrid-2-ylmethyl)-2-(8-(4-chlorophenyl)-8-oxooct-1-yl)thio-5-(pyrimid-5-ylmethyl)pyrimidin-4-one

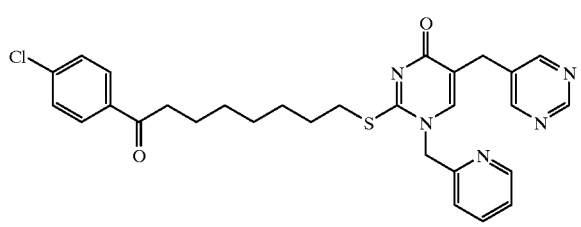

Prepared from intermediate B45 and A1 by general method A4, as a white solid. $^1$H-NMR (CDCl$_3$) δ 1.3–1.5 (6H, m), 1.6–1.8(4H, m), 2.92(2H, t), 3.25(2H, t), 3.71(2H, s), 5.06(2H, s), 7.2–7.35(3H, m), 7.6–7.8(1H, m), 8.5–8.6 (1H, m), 8.70(2H, s), and 9.10(1H, s); MS (APCI+) found (M+1)=548; $C_{29}H_{30}ClN_5O_2S$ requires 547.

Example 122

1-(Pyrid-2-ylmethyl)-2-(8-(4-chlorophenyl)oct-1-yl)thio-5-benzylpyrimidin-4-one

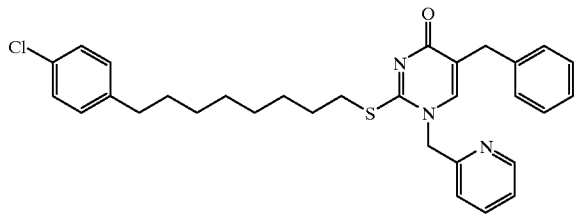

Prepared from intermediate B57 and A24 by general method A4, as a pale brown oil. $^1$H-NMR (CDCl$_3$) δ 1.2–1.5(8H, m), 1.5–1.85(4H, m), 2.55(2H, t), 3.24(2H, t), 3.77(2H, s), 5.00(2H, s), 6.88(1H, s), 7.09(2H, d), 7.25–7.4 (9H, m), 7.68(1H, m) and 8.57(1H, m); MS (EI) found M=531; $C_{31}H_{34}ClN_3OS$ requires 531.

Example 123

1-(Pyrid-3-ylmethyl)-2-(8-(4-chlorophenyl)-8-oxooct-1-yl)thio-5-((1-methyl-2-oxo-pyrid-4-yl)methyl)pyrimidin-4-one

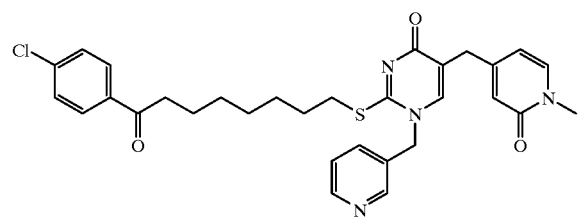

Prepared from intermediate B58 and A1 by general method A4, as a buff coloured solid. MPt 105–106° C.; $^1$H-NMR (CDCl$_3$) δ 1.36 (6H, m), 1.71 (4H, m), 2.96 (2H, t), 3.26 (2H, t), 3.49 (3H, s), 3.53 (2H, s), 5.02 (2H, s), 6.14 (1H, m), 6.34 (1H, s), 6.99 (1H, s), 7.17 (1H, m), 7.25–7.55 (4H, m), 7.91 (2H, d), 8.52 (1H, s), 8.64 (1H, m); MS (APCI+) found (M+1)=577; $C_{31}H_{33}ClN_4O_3S$ requires 576.

Example 124

1-(Pyrid-3-ylmethyl)-2-(8-(4-chlorophenyl)-8-oxooct-1-yl)thio-5-(pyrimid-5-ylmethyl)pyrimidin-4-one

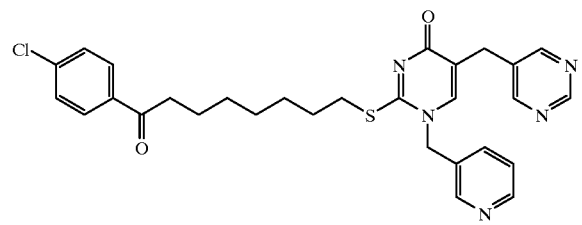

Prepared from intermediate B59 and A1 by general method A4, as a white solid. MPt 80–83° C.; $^1$H-NMR (CDCl$_3$) δ 1.40 (6H, m), 1.69 (4H, m), 2.93 (2H, t), 3.26 (2H, t), 3.69 (2H, s), 5.04 (2H, s), 7.04 (1H, s), 7.30–7.56 (4H, m), 7.91 (2H, d), 8.55 (1H, m), 8.68 (3H, m), 9.10 (1H, s); MS (APCI+) found (M+1)=548; $C_{29}H_{30}ClN_5O_2S$ requires 547.

Example 125

1-(Pyrid-3-ylmethyl)-2-(8-(4-chlorophenyl)oct-1-yl)thio-5-benzylpyrimidin-4-one

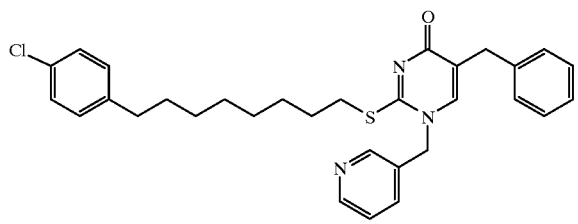

Prepared from intermediate B60 and A24 by general method A4, as a pale brown oil. $^1$H-NMR (CDCl$_3$) δ 1.2–1.5(8H, m), 1.5–1.85(4H, m), 2.56(2H, t), 3.26(2H, t), 3.75 (2H, s), 4.92(2H, s), 6.66(1H, s), 7.09(1H, d), 7.15–7.5 (9H, m), 8.45(1H, m) and 8.59(1H, m); MS (EI) found 531; C$_{31}$H$_{34}$ClN$_3$OS requires 531.

Example 126

1-(Pyrid-4-ylmethyl)-2-(8-(4-chlorophenyl)oct-1-yl)thio-5-((1-methyl-2-oxo-pyrid-4-yl)methyl)pyrimidin-4one

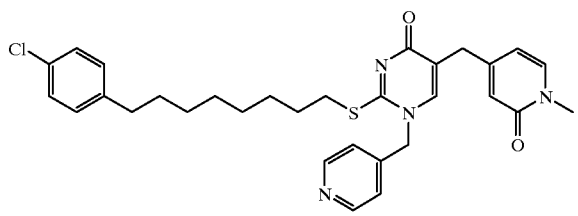

Prepared from intermediate B61 and A24 by general method A4, as an orange gum. $^1$H-NMR (CDCl$_3$) δ 1.2–1.5 (8H, m), 1.5–1.75(4H, m), 2.55(2H, t), 3.24(2H, t), 3.49(3H, s), 3.55(2H, s), 5.01(2H, s), 6.16(1H, m), 6.35(1H, bs), 6.9–7.35(8H, m) and 8.63(2H, m); MS (FAB) M+1=563; C$_{31}$H$_{35}$ClN$_4$O$_2$S requires 562.

Example 127

1(Pyrid-4ylmethyl)-2-(8-(4-chlorophenyl)-8-oxooct-1-yl)thio-5-((1-methyl-2-oxo-pyrid-4-yl)methyl)pyrimidin-4-one

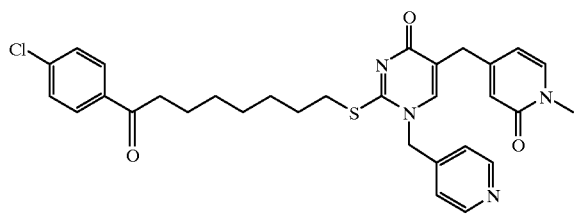

Prepared from intermediate B61 and A1 by general method A4, as an off-white solid. MPt 113–114° C.; $^1$H-NMR (CDCl$_3$) δ 1.29 (6H, m), 1.63 (4H, m), 2.86 (2H, t), 3.19 (2H, t), 3.43 (3H, s), 3.49 (2H, s), 4.95 (2H, s), 6.09 (1H, m), 6.29 (1H, m), 6.89 (1H, s), 6.99 (2H, m), 7.12 (1H, d), 7.36 (2H, d), 7.83 (2H, d), 8.58 (2H, m).

Example 128

1-(Pyrid-4-ylmethyl)-2-(8-(4-chlorophenyl)-8-oxooct-1-yl)thio-5-(pyrimid-5-ylmethyl)pyrimidin-4-one

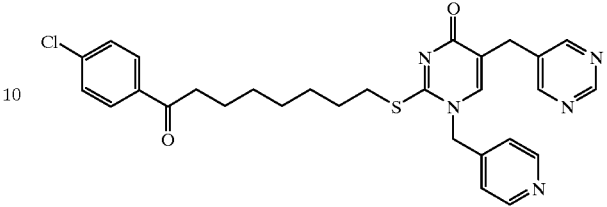

Prepared from intermediate B62 and A1 by general method A4, as a buff coloured solid. MPt 75–77° C.; $^1$H-NMR (CDCl$_3$) δ 1.35 (6H, m), 1.67 (4H, m), 2.92 (2H, t), 3.27 (2H, t), 3.72 (2H, s), 5.02 (2H, s), 6.99 (1H, s), 7.05 (2H, m), 7.43 (2H, d), 7.89 (2H, d), 8.64 (4H, m), 9.09 (1H, s); MS (APCI+) found (M+1)=548; C$_{29}$H$_{30}$ClN$_5$OS requires 547.

Example 129

1-(Pyrid-4-ylmethyl)-2-(8-(4-chlorophenyl)oct-1-yl)thio-5-benzylpyrimidin-4-one

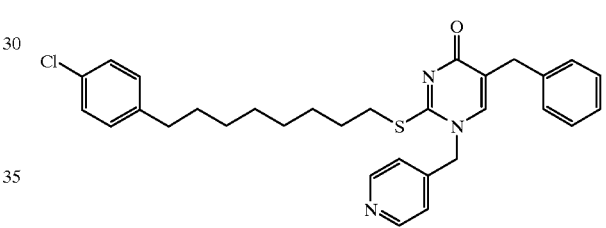

Prepared from intermediate B63 and A24 by general method A4, as a buff powder. MPt 108–110° C.; $^1$H-NMR (CDCl$_3$) δ 1.2–1.8(12H, m), 2.55(2H, t), 3.25(2H, t), 3.77 (2H, s), 4.91(2H, s), 6.62(1H, s), 6.68(2H, d), 7.08(2H, d), 7.15–7.4(7H, m) and 8.5–8.7(2H, m); MS (EI) found M=531; C$_{31}$H$_{34}$ClN$_3$OS requires 531.

Example 130

1-(Pyrid-4-ylmethyl)-2-(8-(4-chlorophenyl)oct-1-yl)thiopyrimidin-4-one

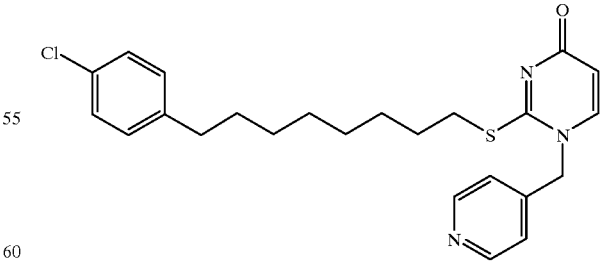

Prepared from intermediate B64 and A24 by general method A4, as a brown gum. $^1$H-NMR (CDCl$_3$) δ 1.2–1.5 (8H, m), 1.5–1.8(4H, m), 2.55(2H, t), 3.24(2H, t), 5.04(2H, s), 6.11(1H, d), 7.0–7.4(7H, m) and 8.65(2H, m); MS (EI) M=441; C$_{24}$H$_{28}$ClN$_3$OS requires 441.

Example 131

1-(2-(Pyrid-2-yl)ethyl)-2-(8-(4-chlorophenyl)-8-oxooct-1-yl)thio-5-(pyrimid-5-ylmethyl)pyrimidin-4-one

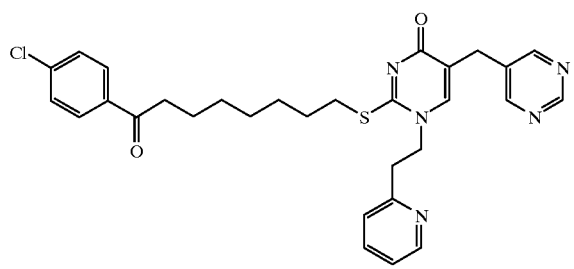

Prepared from intermediate B65 and A1 by general method A4. $^1$H-NMR (CDCl$_3$) δ 1.2–1.8(10H, m), 2.94(2H, t), 3.2–3.35(4H, m), 3.53(2H, s), 4.32(2H, t), 6.74(1H, s), 7.04(1H, m), 7.20(1H, m), 7.43(2H, m), 7.57(1H, m), 7.88 (2H, m), 8.4–8.55(3H, m) and 9.09(1H, s); MS (APCI+) found (M+1)=562; C$_{30}$H$_{32}$ClN$_5$O$_2$S requires 561.

Example 132

1-(2-(Pyrid-3-yl)ethyl)-2-(8-(4-chlorophenyl)-8-oxooct-1-yl)thio-5-((1-methyl-2-oxo-pyrid-4-yl)methyl)pyrimidin-4-one

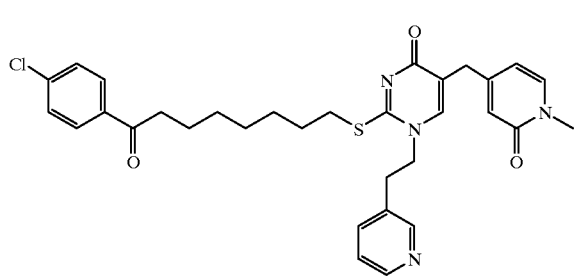

Prepared from intermediate B66 and A1 by general method A4, as a cream coloured crystalline solid. MPt 121–123° C.; $^1$H-NMR (CDCl$_3$) δ 1.42 (6H, m), 1.7 (4H, m), 2.94 (2H, t), 3.07 (2H, t), 3.29 (2H, t), 3.45 (2H, s), 3.51 (3H, s), 4.01 (2H, t), 6.05 (1H, m), 6.28 (1H, m), 6.64 (1H, s), 7.16 (1H, d), 7.26 (1H, m), 7.45 (3H, m), 7.89 (2H, d), 8.45 (1H, m), 8.54 (1H, m); MS (APCI+) found (M+1)=591; C$_{32}$H$_{35}$ClN$_4$O$_3$S requires 590.

Example 133

1-(2-(Pyrid-3-yl)ethyl)-2-(8-(4-chlorophenyl)-8-oxooct-1-yl)thio-5-(pyrimid-5-ylmethyl)pyrimidin-4-one

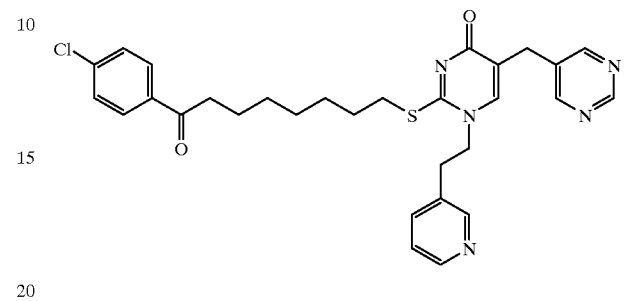

Prepared from intermediate B67 and A1 by general method A4. $^1$H-NMR (CDCl$_3$) δ 1.3–1.9 (10H, m), 2.94 (2H, t), 3.08 (2H, t), 3.58(2H, s), 4.03(2H, t), 6.57 (1H, s), 7.43 (2H, m), 7.90 (2H, m), 8.44 (1H, m), 8.55 (3H, m) and 9.09 (1H, m); MS (APCI+) found (M+1)=562; C$_{30}$H$_{32}$ClN$_5$O$_2$S requires 561.

Example 134

1-(2-(Pyrid-4-yl)ethyl)-2-(8-(4-chlorophenyl)-8-oxooct-1-yl)thio-5-((1-methyl-2-oxo-pyrid-4-yl)methyl)pyrimidin-4-one

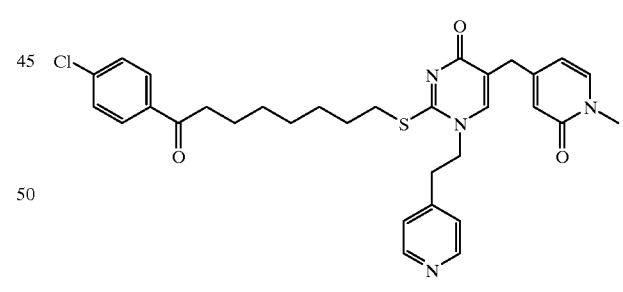

Prepared from intermediate B68 and A1 by general method A4, as a cream coloured crystalline solid. MPt 129–130° C.; $^1$H-NMR (CDCl$_3$) δ 1.40 (6H, m), 1.70 (4H, m), 2.95 (2H, t), 3.06 (2H, t), 3.30 (2H, t), 3.44 (2H, s), 3.51 (3H, s), 4.04 (2H, t), 5.95 (1H, m), 6.29 (1H, m), 6.56 (1H, s), 7.08 (2H, m), 7.17 (1H, d), 7.44 (2H, d), 7.90 (2H, d), 8.53 (2H, m); MS (APCI+) found (M+1)=591; C$_{32}$H$_{35}$ClN$_4$O$_3$S requires 590.

Example 135

1-(2-(Pyrid-4-yl)ethyl)-2-(8-(4-chlorophenyl)-8-oxooct-1-yl)thio-5-(pyrimid-5-ylmethyl)pyrimidin-4-one

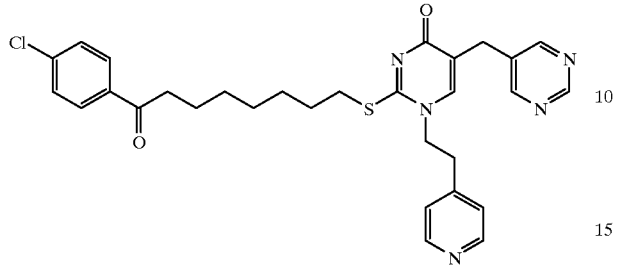

Prepared from intermediates B69 and A1 by general method A4. $^1$H-NMR (CDCl$_3$) δ 1.25–1.9(10H, m), 2.91 (2H, t), 3.06(2H, t), 3.29(2H, t), 3.59(2H, s), 4.04(2H, t), 6.62 (1H, s), 7.07(2H, m), 7.43(2H, m), 7.90(2H, m), 8.45–8.7(4H, m) and 9.10(1H, s); MS (APCI+) found (M+1)=562; C$_{30}$H$_{32}$ClN$_5$O$_2$S requires 561.

Example 136

1-(2-Phenylethyl)-2-(8-(4-chlorophenyl)oct-1-yl)thio-5-((1-methyl-2-oxo-pyrid-4-yl)methyl)pyrimidin-4-one

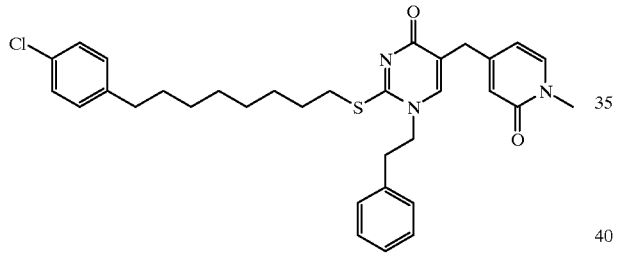

Prepared from intermediate B70 and A24 by general method A4, as a pale brown gum. $^1$H-NMR (d$_6$-DMSO) δ 1.2–1.5(8H, m), 1.5–1.8(4H, m), 2.54(2H, t), 3.01(2H, t), 3.11(2H, t), 3.26(2H, s), 3.35(3H+HOD), 4.09(2H, t), 5.94 (1H, dd), 6.10(1H, d), 7.1–7.4(9H, m) and 7.54(2H, m).

Example 137

1-(2-Phenylethyl)-2-(8-(4-chlorophenyl)oct-1-yl)thio-5-(pyrid-3-ylmethyl)pyrimidin-4-one

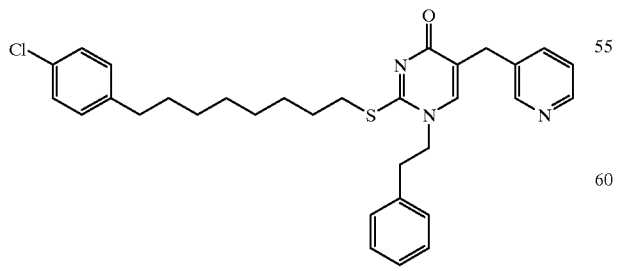

Prepared from Example 70 by general method C1, as a brown/green gum. $^1$H-NMR (CDCl$_3$) δ 1.2–1.8(12H, m), 2.56(2H, t), 3.01(2H, t), 3.26(2H, t), 3.51(2H, t), 3.97(2H, t), 6.27(1H, s), 7.0–7.5(11H, m), 8.30(1H, m) and 8.46(1H, m); MS (FAB) M+1=546; C$_{32}$H$_{36}$ClN$_3$OS requires 545.

Example 138

1-(2-Methylprop-1-yl)-2-(8-(4-chlorophenyl)-8-oxooct-1-yl)thio-5-pyrimid-5-ylmethyl)pyrimidin-4-one

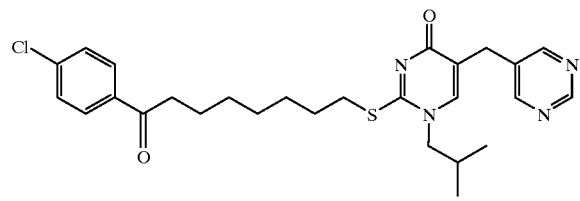

Prepared from intermediate B88 and A1 by general method A4. $^1$H-NMR (d$_6$-DMSO) δ 0.88 (6H, d), 1.2–1.4 (6H, m), 2.5–2.7 (4H, m), 2.08 (1H, m), 3.00 (2H, t), 3.11 (2H, t), 3.57 (2H, s), 3.69 (2H, d), 7.58 (2H, d), 7.82 (1H, s), 7.97 (2H, d), 8.70 (2H, s), 9.01 (1H, s); MS (APCI) M=513; C$_{27}$H$_{33}$ClN$_4$O$_2$S requires 513.

Example 139

1-Phenylsulfonyl-2-(8-(4-chlorophenyl)oct-1-yl)thio-5-(pyrid-3-ylmethyl)pyrimidin-4-one

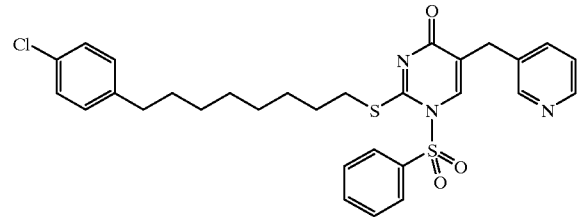

Benzenesulfonyl chloride (41 mg) was added to a solution of 2-(8-(4chlorophenyl)oct-1-yl)thio-5-(pyrid-3-ylmethyl)pyrimidin-4-one (103 mg) in pyridine (0.5 ml), and the mixture stirred overnight. Evaporation of the pyridine followed by chromatography (silica, 0–2% methanol in dichloromethane) gave 1-phenylsulfonyl-2-(8-(4-chlorophenyl)oct-1-yl)thio-5-(pyrid-3-ylmethyl)pyrimidin-4-one (25 mg). $^1$H-NMR (CDCl$_3$) δ 1.2–1.5(8H, m), 1.5–1.8 (4H, m), 2.56(2H, t), 2.92(2H, t), 3.87(2H, s), 7.08(2H, d), 7.15–7.8(7H, m), 7.95(2H, m), 8.29(1H, s) and 8.35–8.7 (2H, bm).

Example 140

1-Benzyl-2-(8-(4-chlorophenyl)oct-1-yl)thio-5-((1-methyl-2-oxo-pyrid-4-yl)methyl)pyrimidin-4-one

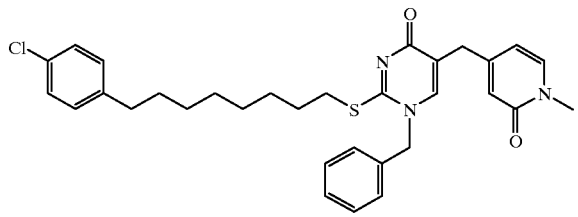

Prepared from intermediate B71 and A24 by general method A4, as a yellow/orange gum. $^1$H-NMR (CDCl$_3$) δ 1.2–1.5(8H, m), 1.5–1.8(4H, m), 2,56(2H, t), 3.25(2H, t), 3.49(3H, s), 3.52(2H, s), 4.99(2H, s), 6.16(1H, dd), 6.34(1H, m), 6.95(1H, s) and 7.0–7.5 (10H, m); MS (EI) M=561; C$_{32}$H$_{36}$ClN$_3$O$_2$S requires 561.

Example 141

1-Benzyl-2-(8-(4-chlorophenyl)-8-oxooct-1-yl)thio-5-((1-methyl-2-oxo-pyrid-4-yl)methyl)pyrimidin-4-one

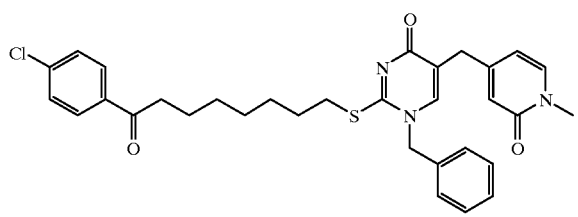

Prepared from intermediate B71 and A1 by general method A4, as a pale brown solid. $^1$H-NMR (CDCl$_3$) δ 1.38 (6H, m), 1.73 (4H, m), 2.93 (2H, t), 3.26 (2H, t), 3.49 (3H, s), 3.52 (2H, s), 4.99 (2H, s), 6.16 (1H, m), 6.33 (1H, m), 6.96 (1H, s), 7.16 (3H, m), 727–7.45 (5H, m), 7.90 (2H, d).

Example 142

1-Benzyl-2-(8-(4-chlorophenyl)oct-1-yl)thio-5-((2-methylpyrid-5-yl)methyl)pyrimidin-4-one

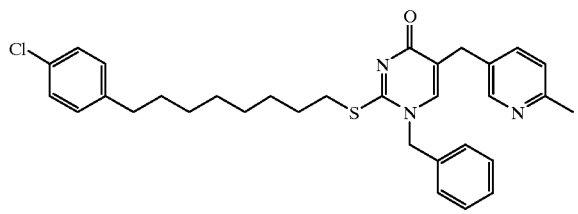

Prepared from Example 30 by general method C1, as a pale yellow gum. $^1$H-NMR (CDCl$_3$) δ 1.2–1.8(12H, m), 2.5–2.65(5H, m), 3.25(2H, t), 3.68(2H, s), 4.95(2H, s), 6.78(1H, s), 7.0–7.6(11H, m) and 8.31 (1H, d); MS (EI) found M=546; C$_{32}$H$_{36}$ClN$_3$OS requires 546.

Example 143

1-Benzyl-2-(8-phenyloct-1-yl)thio-5-((2-methylpyrid-5-yl)methyl)pyrimidin-4-one

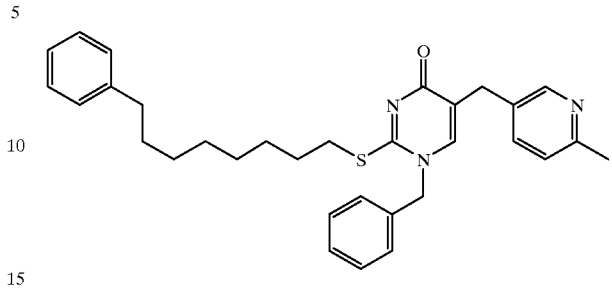

Prepared from Example 21 by general method C1, as a pale yellow oil. $^1$H-NMR (CDCl$_3$) δ 1.2–1.5(8H, m), 1.5–1.8(4H, m), 2.53(3H, s), 2.59(2H, t), 3.24(2H, t), 3.68 (2H, s), 4.95(2H, s), 6.78(1H, s), 7.0–7.5(11H, m), 7.52(1H, m) and 8.31 (1H, bs); MS (FAB) M+1=512; C$_{32}$H$_{37}$N$_3$OS requires 511.

Example 144

1-Benzyl-2-(8-phenyloct-1-yl)thio-5-((2-methoxypyrid-4-yl)methyl)pyrimidin-4-one

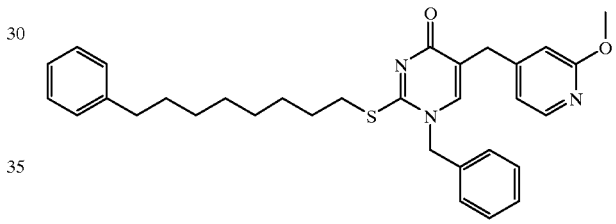

Prepared from Example 37 by general method C1, as a thick gum. $^1$H-NMR(CDCl$_3$) δ 1.2–1.8(10H, m), 2.59(2H, t), 3.26(2H, t), 3.66(2H, s), 3.91(3H, s), 4.95(2H, s), 6.56 (1H, bs), 6.73(1H, m), 6.78(1H, s), 7.05–7.45(10H, m) and 8.03(1H, m); MS (APCI+) Found (M+1)=528. C$_{32}$H$_{37}$N$_3$O$_2$S requires 527.

Example 145

1-Benzyl-2-(8-(4-chlorophenyl)-8-oxooct-1-yl)thio-5-(pyrid-3-ylmethyl)pyrimidin-4-one

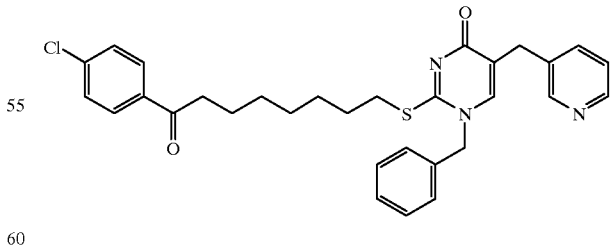

Prepared from Example 47 by general method C1, as a colourless oil. $^1$H-NMR (CDCl$_3$) δ 1.25–1.5(6H, m), 1.5–1.85(4H, m), 2.93(2H, t), 3.25(2H, t), 3.71(2H, s), 4.96(2H, s), 6.83(1H, s), 7.05–7.5(8H, m), 7.60(1H, txd), 7.88(2H, d) and 8.4–8.55(2H, m); MS (EI) found M=545; C$_{31}$H$_{37}$ClN$_3$O$_2$S requires 545.

Example 147

1-(2-Thienylmethyl)-2-(8-(4-chlorophenyl)-8-oxooct-1-yl)thio-5-(pyrimid-5-ylmethyl)pyrimidin-4-one

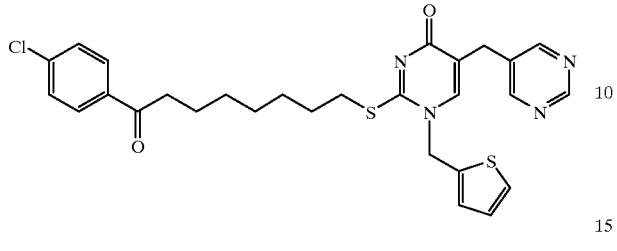

Prepared from intermediates B73 and A1 by general method A4, as a white crystalline solid. MPt 68–70° C.; $^1$H-NMR (CDCl$_3$) δ 1.38 (6H, m), 1.69 (4H, m), 2.93 (2H, t), 3.29 (2H, t), 3.67 (2H, s), 5.14 (2H, s), 7.04 (3H, m), 7.37 (1H, m), 7.43 (2H, m), 7.90 (2H, m), 8.67 (2H, s), 9.01 (1H, s); MS APCI+) found (M+1)=553, C$_{28}$H$_{29}$ClN$_4$O$_2$S$_2$ requires 552.

Example 148

1-(2,2-Dimethylprop-1-yl)-2-(8-(4-chlorophenyl)-8-oxooct-1-yl)thio-5-pyrimid-5-ylmethyl)pyrimidin-4-one

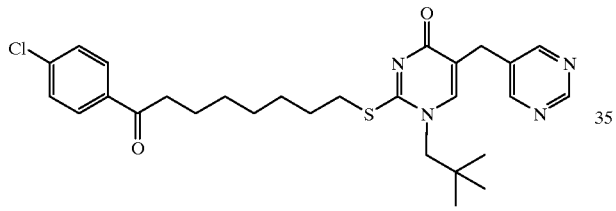

Prepared from intermediates B74 and A1 by general method A4. $^1$H-NMR (CDCl$_3$) δ 0.98(9H, s), 1.2–1.85(10H, m), 2.93(2H, t), 3.24(2H, t), 3.65(2H, s), 3.70(2H, s), 6.89(1H, s), 7.43(2H, m), 7.90(2H, m), 8.69(2H, s) and 9.09(1H, s); MS (APCI+) found (M+1)=527; C$_{28}$H$_{35}$ClN$_4$O$_2$S requires 526.

Example 149

1-(2-(1-Piperidino)ethyl)-2-(8-(4-chlorophenyl)-8-oxooct-1-yl)thio-5-(pyrimid-5-ylmethyl)pyrimidin-4-one

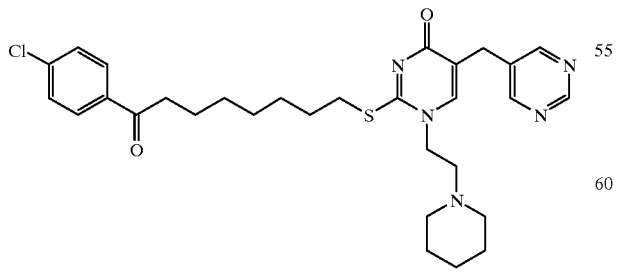

Prepared from intermediates B75 and A1 by general method A4, as a yellow oil. $^1$H-NMR (CDCl$_3$) δ 1.34–1.90 (16H, m), 2.30–2.55 (6H, m), 2.93 (2H, t), 3.25 (2H, t), 3.71 (2H, s), 4.40 (2H, m), 7.02 (1H, s), 7.42 (2H, m), 7.89 (2H, m), 8.70 (2H, s), 9.09 (1H, s); MS APCI+) found (M+1)= 568; C$_{30}$H$_{38}$ClN$_5$O$_2$S requires 567.

Example 150

1-(2-Hydroxyethyl)-2-(8-(4-chlorophenyl)-8-oxooct-1-yl)thio-5-(pyrimid-5-ylmethyl)pyrimidin-4-one

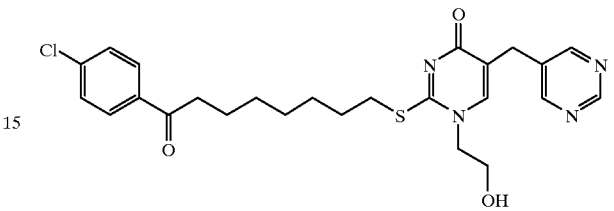

Prepared from intermediates B77 and A1 by general method A4. $^1$H-NMR (CDCl$_3$) δ 1.3–1.8(10H, m), 2.93(2H, t), 3.25(2H, t), 3.66(2H, s), 3.99(4H, m), 7.20(1H, s), 7.43(2H, m), 7.89(2H, m), 8.68(2H, s) and 9.05(1H, s); MS (APCI+) found (M+1)=501, C$_{25}$H$_{29}$ClN$_4$O$_3$S requires 500.

Example 151

1-(2-Hydroxyethyl)-2-(8-(4-chlorophenyl)oct-1-yl)thio-5-benzylpyrimidin-4-one

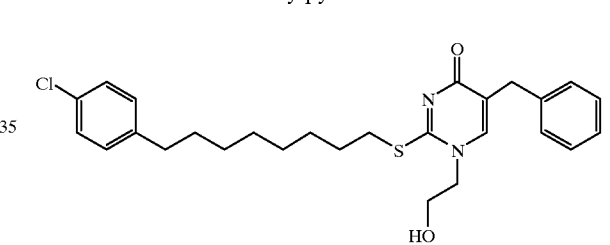

Prepared from intermediates B78 and A24 by general method A4, as a colourless gum. $^1$H-NMR (CDCl$_3$) δ 1.2–1.5(8H, m), 1.5–1.8(4H, m), 2.54(2H, t), 3.21(2H, t), 3.64(2H, s), 3.8–4.15(4H, m), 5.23(1H, bs), 6.97(1H, s), 7.08(2H, d) and 7.1–7.45(7H, m).

Example 152

1-Ethyl-2-(8-(4-chlorophenyl)-8-oxooct-1-yl)thio-5-(pyrimid-5-ylmethyl)pyrimidin-4-one

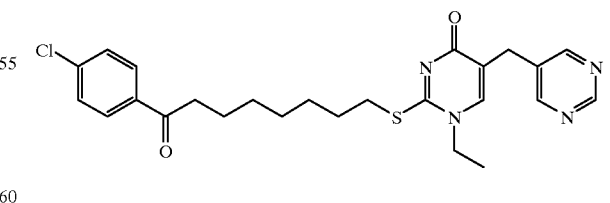

Prepared from intermediates B89 and A1 by general method A4. $^1$H-NMR (d$_6$-DMSO) δ 1.2–1.4 (9H, m), 2.5–2.7 (4H, m), 2.84 (2H, t), 3.11 (2H, t), 3.56 (2H, s), 3.89 (2H, q), 7.58 (2H, d), 7.85 (1H, s), 7.97 (2H, d), 8.70 (2H, s), 9.01 (1H, s); MS (APCI) M=485; C$_{25}$H$_{29}$ClN$_4$O$_2$S requires 485.

Example 153

1-(Fur-2-ylmethyl)-2-(8-(4-chlorophenyl)-8-oxooct-1-yl)thio-5-(pyrimid-5-ylmethyl)pyrimidin-4-one

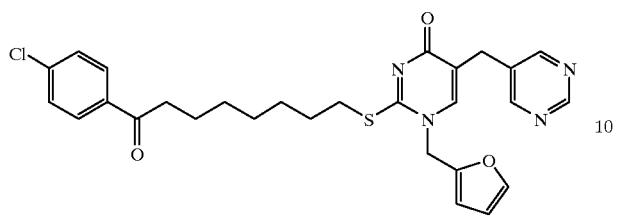

Prepared from intermediates B81 and A1 by general method A4, as a light brown oil. $^1$H-NMR (CDCl$_3$) δ 1.38 (6H, m), 1.70 (4H, m), 2.93 (2H, t), 3.27 (2H, t), 3.69 (2H, s), 4.94 (2H, s), 6.40 (2H, m), 7.06 (1H, s), 7.44 (3H, m), 7.90 (2H, m), 8.68 (2H, s), 9.09 (1H, s); MS APCI+) found (M+1)=537; C$_{28}$H$_{29}$ClN$_4$O$_3$S requires 536.

Example 154

1-(Fur-2-ylmethyl)-2-(8-(4-chlorophenyl)oct-1-yl)thio-5-benzylpyrimidin-4-one

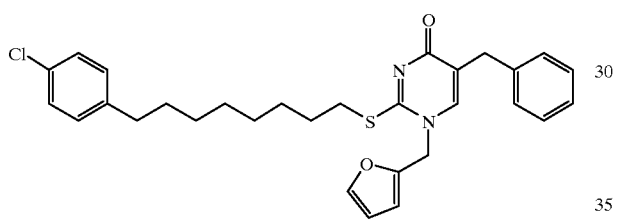

Prepared from intermediates B82 and A24 by general method A4, as a pale brown gum. $^1$H-NMR (CDCl$_3$) δ 1.2–1.5(8H, m), 1.5–1.8(4H, m), 2.56(2H, t), 3.27(2H, t), 3.73(2H, t), 4.85(2H, s), 6.33(2H, s), 6.73(1H, s), 7.09(2H, d) and 7.2–7.5(8H, m); MS (FAB) M+1=521; C$_{30}$H$_{33}$ClN$_2$O$_2$S requires 520.

Example 155

1-Methyl-2-(8-(4-chlorophenyl)-8-oxooct-1-yl)thio-5-bromopyrimidin-4-one

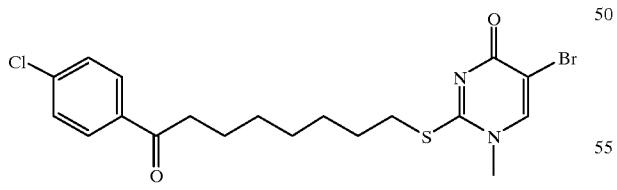

1-Methyl-2-(8-(4-chlorophenyl)-8-oxooct-1-yl)thiopyrimidin-4-one was prepared from 1-methyl-2-thiouracil by general method A4. A solution of bromine (0.05 ml) in dichloromethane (1 ml) was added to a slurry of 1-methyl-2-(8-(4-chlorophenyl)-8-oxooct-1-yl)thiopyrimidin-4-one (0.38 g) in dichloromethane (20 ml), and the mixture was stirred for 24 hours. The solution was washed with aqueous sodium carbonate, dried and evaporated. Chromatography (silica, 1–4% methanol in dichloromethane) gave 1-methyl-2-(8-(4-chlorophenyl)-8-oxooct-1-yl)thio-5-bromopyrimidin-4-one (0.18 g), as a white solid. $^1$H-NMR (CDCl$_3$) δ 1.3–1.5 (6H, m), 1.65–1.8 (4H, m), 2.94 (2H, t), 3.26(2H, t), 3.56(3H, s), 7.45(2H, d), 7.56(1H, s) and 7.90(2H, d); MS (APCI+) found (M+1)= 459; C$_{19}$H$_{22}$BrClN$_2$O$_2$S requires 458.

Example 156

1-Methyl-2-(8-(4-chlorophenyl)oct-1-yl)thio-5-((1-methyl-2-oxo-pyrid-4-yl)methyl)pyrimidin-4-one

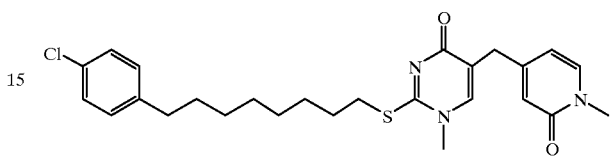

Prepared from intermediates B83 and A24 by general method A4, as a colourless solid. $^1$H-NMR (CDCl$_3$) δ 1.2–1.5(8H, m), 1.5–1.8(4H, m), 2.56(2H, t), 3.25(2H, t), 3.49(3H, s), 3.51(3H, s), 3.54(2H, s), 6.19(1H, m), 6.38(1H, m), 6.93(1H, s) and 7.0–7.35(5H, m); MS (EI) M=485; C$_{26}$H$_{32}$ClN$_3$O$_2$S requires 485.

Example 157

1-Methyl-2-(8-(4-chlorophenyl)-8-oxooct-1-yl)thio-5-((1-methyl-2-oxo-pyrid-4-yl)methyl)pyrimidin-4-one

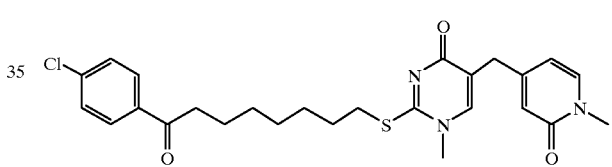

Prepared from intermediates B83 and A1 by general method A4, as a cream coloured crystalline solid. MPt 90–5° C.; $^1$H-NMR (CDCl$_3$) δ 1.38 (6H, m), 1.72 (4H, m), 2.91 (2H, t), 3.26 (2H, t), 3.49 (3H, s), 3.51 (3H, s), 3.54 (2H, s), 6.19 (1H, m), 6.38 (1H, s), 6.93 (1H, s), 7.19 (1H, m), 7.43 (2H, d), 7.90 (2H, d); MS (APCI+) Found (M+1)=500; C$_{26}$H$_{30}$N$_3$O$_3$S requires 499.

Example 158

1-Methyl-2-(8-(4-chlorophenyl)oct-1-yl)thio-5-(pyrid-3-ylmethyl)pyrimidin-4-one

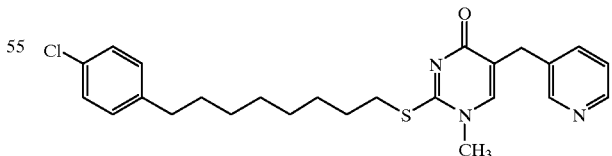

Prepared from Example 70 by general method C1, as a pale yellow oil. $^1$H-NMR (CDCl$_3$) δ 1.2–1.8(12H, m), 2.56(2H, t), 3.22(2H, t), 3.46(3H, s), 3.74(2H, s), 6.77(1H, s), 7.08(2H, d), 7.15–7.35(4H, m), 7.66(1H, txd) and 8.49 (2H, bs); MS (EI) found M=455; C$_{25}$H$_{30}$ClN$_3$OS requires 455.

Example 159

1-Methyl-2-(8-(4-chlorophenyl)-8-oxooct-1-yl)thio-5-(pyrimid-5-ylmethyl)pyrimidin-4-one

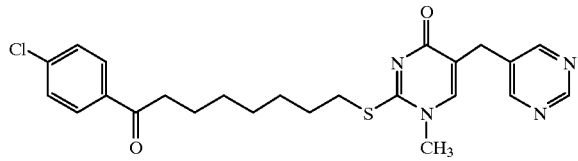

Prepared from intermediates B84 and A1 by general method A4, as a white solid. $^1$H-NMR (CDCl$_3$) δ 1.3–1.55 (6H, m), 1.6–1.85(4H, m), 2.93(2H, t), 3.26(2H, t), 3.51(3H, s), 3.70(2H, s), 6.94(1H, s), 7.45(2H, d), 7.89(2H, d), 8.70(2H, s) and 9.1(1H, s); MS (APCI+) found (M+1)=471; $C_{24}H_{27}ClN_4O_2S$ requires 470.

Example 160

1-Methyl-2-(8-(4-chlorophenyl)oct-1-yl)thio-5-benzylpyrimidin-4-one

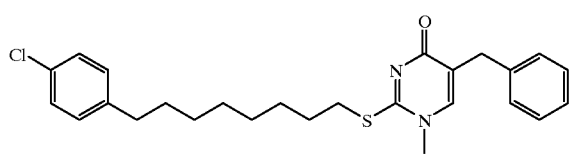

Prepared from intermediates B85 and A24 by general method A4, as a colourless powder. MPt 92–93° C.; $^1$H-NMR (CDCl$_3$) δ 1.2–1.8(12H, m), 2.56(2H, t), 3.26(2H, t), 3.40(3H, s), 3.76(2H, s), 6.59(1H, s), 7.09(2H, d) and 7.15–7.45(7H, m); MS (EI) found M=454; $C_{26}H_{31}ClN_2OS$ requires 454.

Example 161

1-Phenyl-2-(8-(4-chlorophenyl)oct-1-yl)thio-5-((1-methyl-2-oxo-pyrid-4-yl)methyl)pyrimidin-4-one

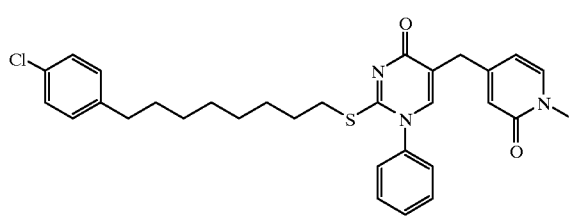

Prepared from intermediates B86 and A24 by general method A4, as a yellow/orange solid. $^1$H-NMR (CDCl$_3$) δ 1.2–1.5(8H, m), 1.5–1.8(4H, m), 2.54(2H, t), 3.14(2H, t), 3.49(3H, s), 3.57(2H, s), 6.22(1H, m), 6.38(1H, m), 7.00 (1H, s), 7.08(2H, d), 7.15–7.4(5H, m) and 7.5–7.6(3H, m); MS (EI) M=547; $C_{31}H_{34}ClN_3O_2S$ requires 547.

Example 162

1-Methylsulfonyl-2-(8-(4-chlorophenyl)oct-1-yl)thio-5-(pyrid-3-ylmethyl)pyrimidin-4-one

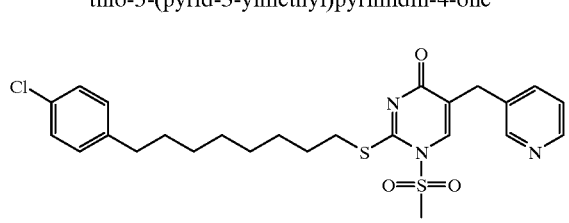

Prepared from Example 70, analogously to example 139. $^1$H-NMR (CDCl$_3$) δ 1.2–1.8(12H, m), 2.56(2H, t), 3.10(2H, t), 3.55(3H, s), 4.03(2H, s), 7.09(2H, m), 7.15–7.3(2H, m), 7.61(1H, m), 7.96(1H, m), 8.45(1H, s) and 8.60(2H, m).

Example 163

1-Benzyl-2-(8-phenyloct-1-yl)oxy-5-(pyrid-3-ylmethyl)pyrimidin-4-one

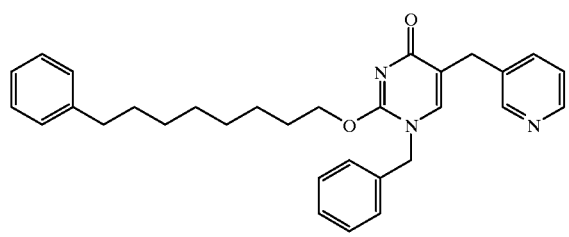

Prepared from Example 100 by general method C1, as a pale buff solid. MPt 74–78° C.; $^1$H-NMR (CDCl$_3$) δ 1.2–1.5 (8H, m), 1.5–1.85(4H, m), 2.58(2H, t), 3.72(2H, s), 4.40(2H, t), 4.83(2H, s), 6.76(1H, s), 7.0–7.4(11H, m), 7.6–7.7(1H, m) and 8.46(2H, m); IR 1655, 1621 cm−1.

Example 164

1-(2-Methoxyethyl)-2-benzylthio-5-(pyrimid-5-ylmethyl)pyrimidin-4-one

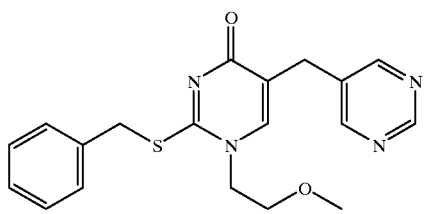

Prepared from intermediate B87 by general method A4. $^1$H-NMR (CDCl$_3$) δ 3.31(3H, s), 3.59(2H, t), 3.71(2H, s), 4.51(2H, s), 7.10(1H, s), 7.2–7.45(5H, m), 8.72(2H, s) and 9.10(1H, s); MS (APCI+) found (M+1)=369; $C_{19}H_{20}N_4O_2S$ requires 368.

Example 165

1-(3-Phenylprop-1-yl)-2-benzylthio-5-(pyrimid-5-ylmethyl)pyrimidin-4-one

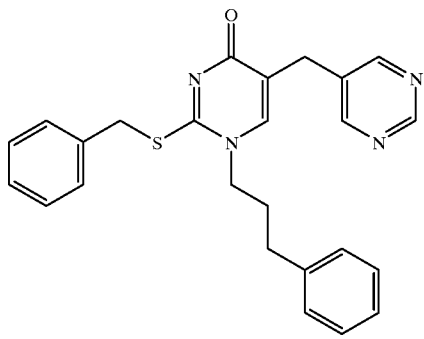

Prepared from intermediate B55 by general method A4. $^1$H-NMR (CDCl$_3$) δ 2.08(2H, quintet), 2.65(2H, t), 3.68(2H, s), 3.75(2H, t), 4.49(2H, s), 5.30(2H, s), 6.48(1H, s), 7.10 (2H, m), 7.15–7.5(8H, m), 8.69(2H, s) and 9.10(1H, s); MS (APCI+) found (M+1)=429; C$_{25}$H$_{24}$N$_4$OS requires 428.

Example 166

1-(5-Hydroxypent-1-yl)-2-benzylthio-5-(pyrimid-5-ylmethyl)pyrimidin-4-one

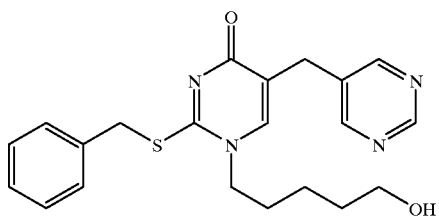

Prepared from intermediate B56 by general method A4. $^1$H-NMR (CDCl$_3$) δ 1.3–1.9(6H, m), 3.64(2H, t), 3.7–3.9 (4H, m), 4.50(2H, s), 6.98(1H, m), 7.2–7.5(5H, m), 8.72(2H, s) and 9.10(1H, s); MS (APCI+) found (M+1)=397; C$_{21}$H$_{24}$N$_4$O$_2$S requires 396.

Example 167

1-(Pyrid-2-ylmethyl)-2-benzylthio-5-(pyrimid-5-ylmethyl)pyrimidin-4-one

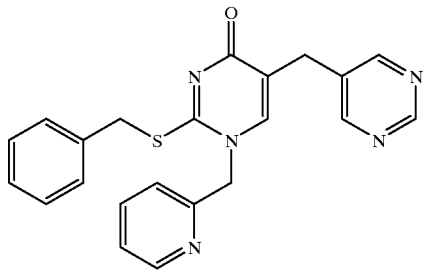

Prepared from intermediate B45 by general method A4. $^1$H-NMR (CDCl$_3$) δ 3.73(2H, s), 4.49(2H, s), 5.03(2H, s), 7.1–7.4(8H, m), 7.69(1H, m), 8.57(1H, m), 8.71(2H, s) and 9.09(1H, s); MS (APCI+) found (M+1)=402; C$_{22}$H$_{19}$N$_5$OS requires 401.

Example 168

1-(Pyrid-3-ylmethyl)-2-benzylthio-5-((1-methyl-2-oxo-pyrid-4-yl)methyl)pyrimidin-4-one

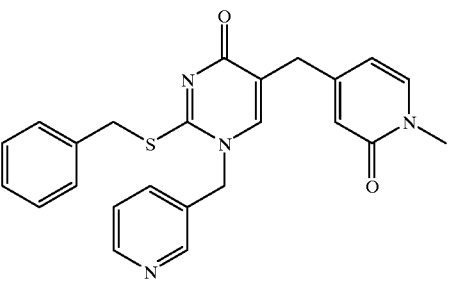

Prepared from intermediate B58 by general method A4, as a buff coloured solid. $^1$H-NMR (CDCl$_3$) δ 3.5 (3H, s), 3.55 (2H, s), 4.51 (2H, s), 4.99 (2H, s), 6.27 (1H, s), 7.01 (1H, s), 7.15–7.50 (8H, m), 8.50 (1H, s), 8.62 (1H, m); MS (APCI+) found (M+1)=431; C$_{24}$H$_{22}$N$_4$O$_2$S requires 430.

Example 169

1-(Pyrid-4-ylmethyl)-2-benzylthio-5-benzylpyrimidin-4-one

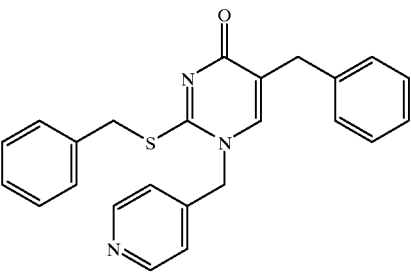

Prepared from intermediate B63 by general method A4, as a brown gum. $^1$H-NMR (CDCl$_3$) δ 3.78(2H, s), 4.50(2H, s), 4.89(2H, s), 6.64(1H, s), 6.94(2H, d), 7.1–7.5(10H, m) and 8.58(2H, d); MS (EI) found M=399; C$_{24}$H$_{21}$N$_3$OS requires 399.

Example 170

1-(2-(Pyrid-2-yl)ethyl)-2-benzylthio-5-(pyrimid-5-ylmethyl)pyrimidin-4-one

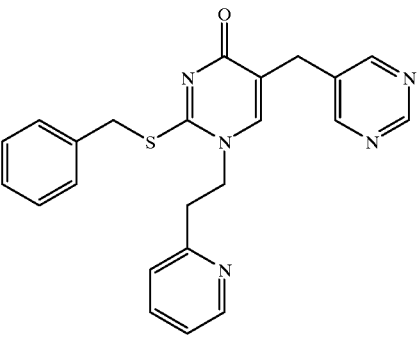

Prepared from intermediate B65 by general method A4. $^1$H-NMR (CDCl$_3$) δ 3.20(2H, t), 3.55(2H, s), 4.30(2H, t), 4.53(2H, s), 6.75(1H, s), 6.96(1H, m), 7.17(1H, m), 7.25–7.5 (5H, m), 7.56(1H, m), 8.4–8.55(3H, m) and 9.10(1H, s),; MS (APCI+) found (M+1)=416; $C_{23}H_{21}N_5OS$ requires 415.

Example 171

1-(2-(Pyrid-3-yl)ethyl)-2-benzylthio-5-(pyrimid-5-ylmethyl)pyrimidin-4-one

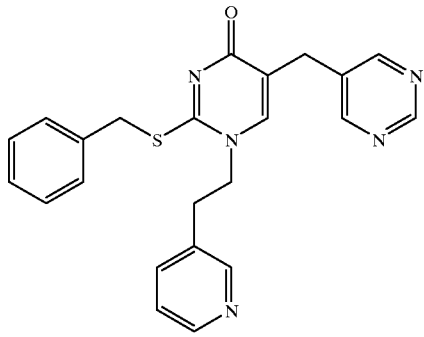

Prepared from intermediate B67 by general method A4. $^1$H-NMR (CDCl$_3$) δ 3.05(2H, t), 3.60(2H, s), 4.00(2H, t), 4.54(2H, s), 6.57(1H, s), 7.1–7.5(6H, m), 8.43(1H, m), 8.5–8.65(3H, m) and 9.10(1H, s); MS (APCI+) found (M+1)=416; $C_{23}H_{21}N_5OS$ requires 415.

Example 172

1-(2-(Pyrid-4-yl)ethyl)-2-benzylthio-5-(pyrimid-5-5 ylmethyl)pyrimidin-4-one

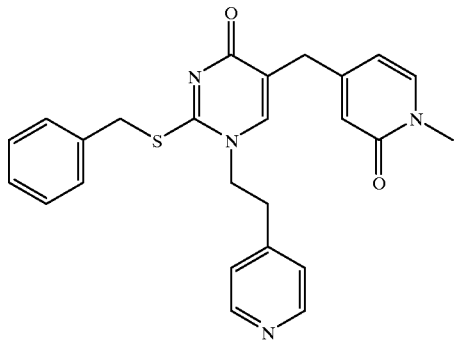

Prepared from intermediate B68 by general method A4, as a buff coloured solid. $^1$H-NMR (CDCl$_3$) δ 3.02 (2H, t), 3.45 (2H, s), 3.52 (3H, s), 4.00 (2H, t), 4.55 (2H, s), 5.95 (1H, m), 6.30 (1H, s), 6.57 (1H, s), 7.02 (2H, m), 7.18 (1H, m), 7.19–7.44 (5H, m), 8.50 (2H, m); MS (APCI+) Found (M+1)=445; $C_{25}H_{24}N_4O_2S$ requires 444.

Example 173

1-(2-(Pyrid-4-yl)ethyl)-2-benzylthio-5-(pyrimid-5-ylmethyl)pyrimidin-4-one

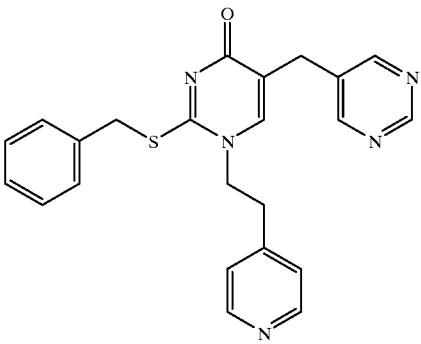

Prepared from intermediate B69 by general method A4. $^1$H-NMR (CDCl3) δ 3.03(2H, t), 3.60(2H, s), 4.01(2H, t), 4.54(2H, s), 6.61(1H, s), 7.01(2H, m), 7.25–7.5(5H, m), 8.45–8.65(4H, m) and 9.11(1H, s); MS (APCI+) found (M+1)=416; C23H21N5OS requires 415.

Example 174

1-(2-Phenylethyl)-2-benzylthio-5-((2-methoxypyrid-4-yl)methyl)pyrimidin-4-one

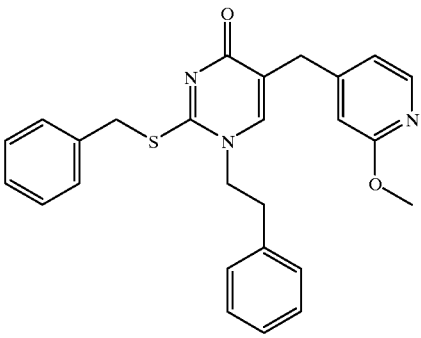

Prepared from Example 88 by general method C1. $^1$H-NMR (CDCl$_3$) δ 3.01(2H, t), 3.57(2H, s), 3.95(5H, m), 4.53(2H, m), 6.27(1H, s), 6.45(1H, s), 6.55(1H, m), 7.02 (2H, m ), 7.1–7.5(8H, m) and 8.02(1H, d); MS (APCI+) found M+H=444; $C_{26}H_{25}N_3O_2S$ requires 443.

Example 175

1-Benzyl-2-benzylthio-5-((2-methoxypyrid-4-yl)methyl)pyrimidin-4-one

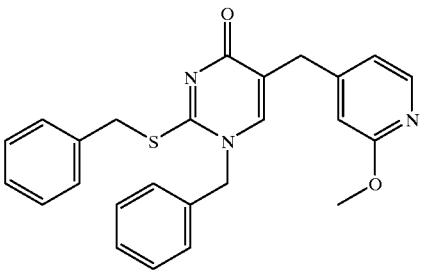

Prepared from intermediate Example 88 by general method C1, as a colourless stiff gum. $^1$H-NMR (CDCl$_3$) δ 3.67(2H, s), 3.90(3H, s), 4.51(2H, s), 4.93(2H, s), 6.57(1H, s), 6.73(1H, m), 6.81(1H, s), 7.10(1H, m), 7.25–7.45(9H, m) and 8.04(1H, d); MS (EI) M=429; C$_{25}$H$_{23}$N$_3$O$_2$S requires 429.

Example 176

1-(2-Thienylmethyl)-2-benzylthio-5-(pyrimid-1-ylmethyl)pyrimidin-4one

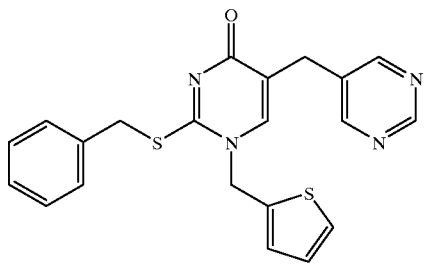

Prepared from intermediate B73 by general method A4, as a pale yellow crystalline solid. MPt 110–112° C.; $^1$H-NMR (CDCl$_3$) δ 3.69 (2H, s), 4.54 (2H, s), 5.11 (2H, s), 7.02 (3H, m), 7.30–7.42 (6H, m), 8.65 (2H, s), 9.09 (1H, s); MS APCI+) found (M+1)=407; C$_{21}$H$_{18}$N$_4$OS$_2$ requires 406.

Example 177

1-(2,2-Dimethylprop-1-yl)-2-benzylthio-5-(pyrimid-5-ylmethyl)pyrimidin-4-one

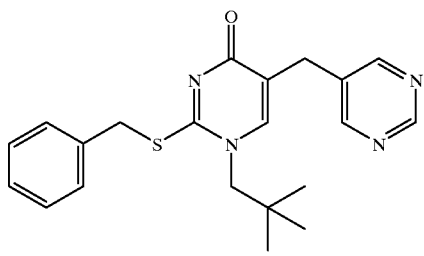

Prepared from intermediate B74 by general method A4. $^1$H-NMR (CDCl$_3$) δ 0.96(9H, s), 3.62(2H, s), 3.72(2H, s), 4.49(2H, s), 6.91(1H, s), 7.25–7.45(5H, m), 8.70(2H, s) and 9.11(1H, s); MS (APCI+) found (M+1)=381; C$_{21}$H$_{24}$N$_4$OS requires 380.

Example 178

1-(Fur-2-ylmethyl)-2benzylthio-5-(pyrimid-5-ylmethyl)pyrimidin-4-one

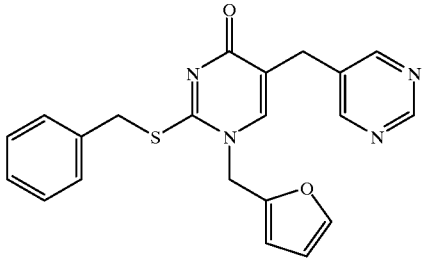

Prepared from intermediate B81 by general method A4, as a brown oil. $^1$H-NMR (CDCl$_3$) δ 3.70 (2H, s), 4.52 (2H, s), 4.91 (2H, s), 6.40 (2H, m), 7.06 (1H, s), 7.26–7.42 (6H, m), 8.70 (2H, s), 9.10 (1H, s); MS APCI+) found (M+1)=391; C$_{21}$H$_{18}$N$_4$O$_2$S requires 390.

Example 179

1-Methyl-2-benzylthio-5-((2-methoxypyrid-4-yl)methyl)pyrimidin-4-one

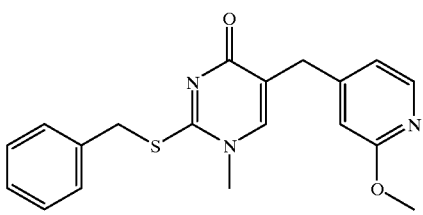

Prepared from Example 88 by general method C1, as a pale cream powder. MPt 119–120° C.; $^1$H-NMR (CDCl$_3$) δ 3.44(3H, s), 3.69(2H, s), 3.93(3H, s), 4.52(2H, s), 6.62(1H, bs), 6.78(2H, m), 7.2–7.5(5H, m) and 8.10(1H, m); MS (EI) M=353; C$_{19}$H$_{19}$N$_3$O$_2$S requires 353.

Example 180

1-Benzyl-2-(8-(4-chlorophenyl)oct-1-yl)thio-5-(pyrimid-5-ylmethyl)pyrimidin-4-one

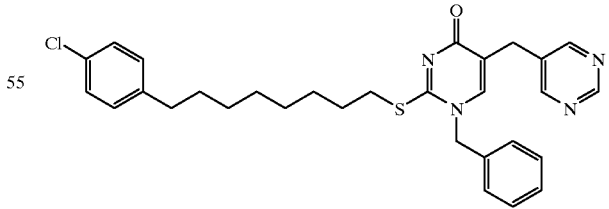

Prepared from intermediate B94 by general method A4. $^1$H-NMR (CDCl$_3$) δ 1.2–1.8 (12H, m), 2.55(2H, t), 3.25 (2H, t), 3.67 (2H, s), 5.00 (2H, s), 6.8–7.4 (10H, m), 8.7 (2H, s), 9.07 (1H, s); (APCI) M+H=533. C$_{30}$H$_{33}$ClN$_4$OS requires 532.

Example 181

1-(2-Phenylethyl)-2-(8-(4-chlorophenyl)oct-1-yl)thio-5-(pyrimid-5-ylmethyl)pyrimidin-4-one

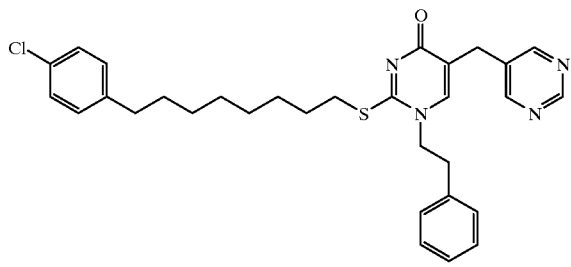

Prepared from intermediate B93 by general method A4, as a white crystalline solid. $^1$H-NMR (CDCl$_3$) δ 1.2–1.5(8H, m), 1.5–1.8(4H, m), 2.56(2H, t), 3.05 (2H, t), 3.29 (2H, t), 3.50(2H, s), 4.02 (2H, t), 6.36(1H, s), 7.0–7.1 (4H, m), 7.2–7.3 (5H, m), 8.47(2H, s) and 9.07(1H, s); (APCI) M+H=547. C$_{31}$H$_{35}$ClN$_4$OS requires 546.

Example 182

1-Methyl-2-(8-(4-chlorophenyl)oct-1-yl)thio-5-(pyrimid-5-ylmethyl)pyrimidin-4-one

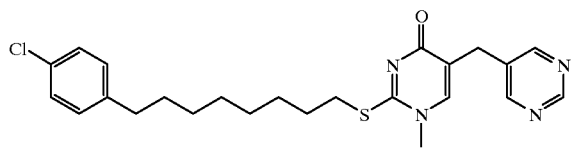

Prepared from intermediate B84 by general method A4 as a white crystalline solid. $^1$H-NMR (CDCl$_3$) δ 1.2–1.5(8H, m), 1.5–1.8(4H, m), 2.56(2H, t), 3.25 (2H, t), 3.50 (3H, st), 3.70(2H, s), 6.94(1H, s), 7.09 (2H, m), 7.23 (2H, m), 8.69(2H, s) and 9.09(1H, s); (APCI) M+H=457. C$_{24}$H$_{29}$ClN$_4$OS requires 456.

Example 183

1-Benzyl-2-(8-(4-chlorophenyl)-8-oxooct-1-yl)thio-5-(pyrid-4-yl)pyrimidin-4-one

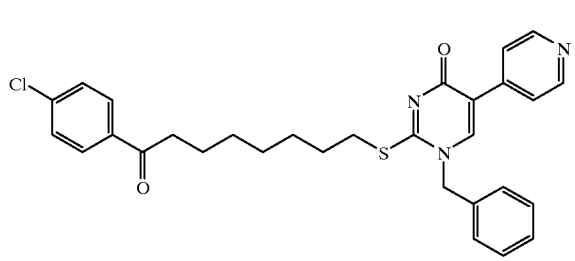

1-Benzyl-2-(8-(4-chlorophenyl)-8-oxooct-1-yl)thio-pyrimidin-4-one was prepared from 1-benzyl-2-thiouracil and intermediate A1 by general method A4, then iodinated with iodine (1.2 equiv) and silver trifluoromethanesulfonate (1 equiv) in chloroform at room temperature overnight, giving 1-benzyl-2-(8-(4-chlorophenyl)-8-oxooct-1-yl)thio-5-iodopyrimidin-4-one in 27% yield after chromatography. This compound (1 equiv) and 4-pyridylboronic acid (2 equiv) were suspended in dimethoxyethane, 2M aqueous sodium carbonate added, followed by tetrakis (triphenylphosphine)palladium (0.05 equiv). The mixture was refluxed for 16 hours, then the solvent evaporated. Aqueous workup, chromatography and crystallisation from ether gave the title compound as a white crystalline solid. $^1$H-NMR (CDCl$_3$) δ 1.3–1.5 (6H, m), 1.6–1.8 (4H, m), 2.94 (2H, t), 3.32 (2H, t), 5.13 (2H, s), 7.27 (2H, d), 7.4 (6H, m), 7.55 (2H, d), 7.90 (2H, d); (APCI) M+H=532. C$_{30}$H$_{30}$ClN$_3$O$_2$S requires 531.

Example 184

1-Benzyl-2-(8-(4-chlorophenyl)-8-oxooct-1-yl)thio-5-(pyrimid-5-ylmethyl)pyrimidin-4-one

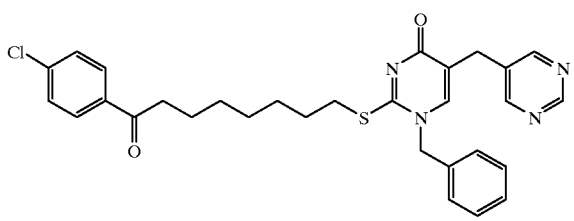

Prepared from intermediate B94 by general method A4. $^1$H-NMR (CDCl$_3$) δ 1.3–1.5 (4H, m), 1.6–1.8 (4H, m)2.93 (2H, t), 3.26 (2H, t), 3.67 (2H, s), 5.01 (2H, s), 6.98 (1H, s), 7.1–7.2 (2H, m), 7.4–7.5 (5H, m), 7.90 (2H, d), 8.7 (2H, s), 9.07 (1H, s); (APCI) M+H=547. C$_{30}$H$_{31}$ClN$_4$O$_2$S requires 546.

Example 185

1-(2-Phenylethyl)-2-(8-(4-chlorophenyl)-8-oxooct-1-yl)thio-5-(pyrimid-5-ylmethyl)pyrimidin-4-one

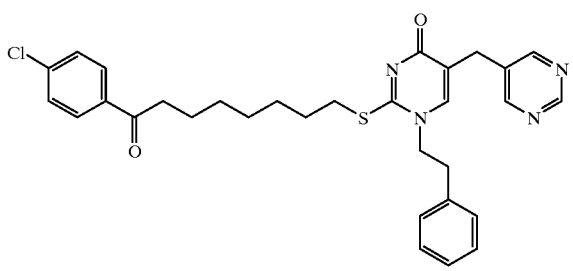

Prepared from intermediate B93 by general method A4 as a cream coloured crystalline solid. $^1$H-NMR (CDCl$_3$) δ 1.3–1.5(6H, m), 1.6–1.8(4H, m), 2.94(2H, t), 3.05 (2H, t), 3.30 (2H, t), 3.50(2H, s), 4.03 (2H, t), 6.37(1H, s), 7.05 (2H, m), 7.3 (3H, m), 7.43 (2H, d), 7.89 (2H, d), 8.47 (2H, s), 9.08 (1H, s); (APCI) M+H=561. C$_{31}$H$_{33}$ClN$_4$O$_2$S requires 560.

Example 186

1-(Fur-2-ylmethyl)-2-(2-phenylethyl)thio-5-(pyrimid-5-ylmethyl)pyrimidin-4-one

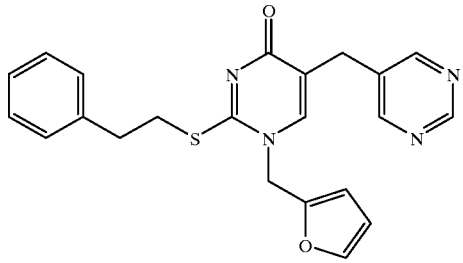

Prepared from intermediate B81 by general method A4. $^1$H-NMR (CDCl$_3$) δ 3.02 (2H, t), 3.54 (2H, t), 3.69 (2H, s), 4.91 (2H, s), 6.38 (2H, m), 7.06 (1H, s), 7.2–7.35 (5H, m), 7.4 (1H, m), 8.7 (2H, s), 9.09 (1H, s); (APCI) M+H=405. C$_{22}$H$_{20}$N$_4$O$_2$S requires 404.

Example 187

1-(2-Fluorobenzyl)-2-benzylthio-5-(pyrimid-5-ylmethyl)pyrimidin-4one

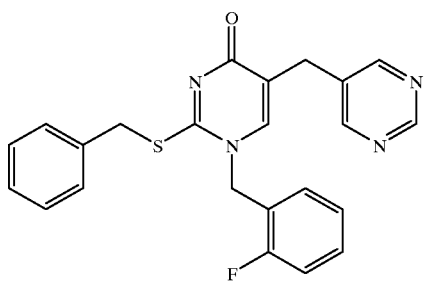

Prepared from intermediate B131 by general method A4. $^1$H-NMR (CDCl$_3$) δ 3.70 (2H, s), 4.51 (2H, s), 5.01 (2H, s), 7.08 (1H, s), 7.1–7.2 (3H, m), 7.2–7.4 (6H, m), 8.7 (2H, s), 9.09 (1H, s), (APCI) M+H=419. C$_{23}$H$_{19}$FN$_4$OS requires 418.

Example 188

1-(8-Phenloctyl)-2-benzylthio-5-(pyrimid-5-ylmethyl)pyrimidin-4-one

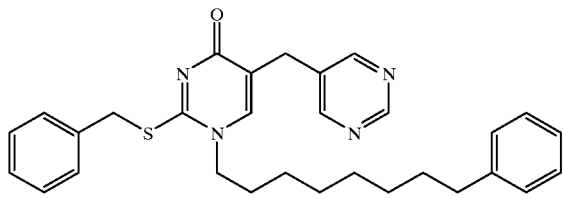

Prepared from intermediate B90 by general method A4. $^1$H-NMR (CDCl$_3$) δ 1.2–1.4(8H, m), 1.5–1.8(4H, m), 2.59 (2H, t), 3.6–3.8(4H, m), 4.50(2H, s), 6.93(1H, s), 7.1–7.5 (10H, m), 8.70(2H, s) and 9.10(1H, s); (APCI) M+H=499. C$_{30}$H$_{34}$N$_4$OS requires 498.

Example 189

(9-Phenylnonyl)-2-benzylthio-5-(pyrimid-5-ylmethyl pyrimidin-4-one

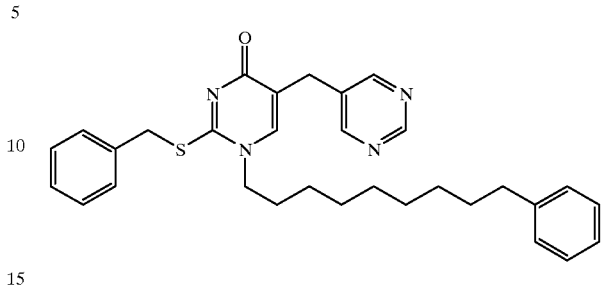

Prepared from intermediate B91 by general method A4 as a thick oil. $^1$H-NMR (CDCl$_3$) δ 1.2–1.4(10H, m), 1.5–1.85 (4H, m), 2.59(2H, t), 3.6–3.8(4H, m), 4.50(2H, s), 6.94(1H, s), 7.1–7.45(1H, m), 8.69(2H, s) and 9.10(1H, s); (APCI) M+H=513. C$_{31}$H$_{36}$N$_4$OS requires 512.

Example 190

1-Benzyl-2-benzylthio-5-(pyrimid-5-ylmethyl)pyrimidin-4-one

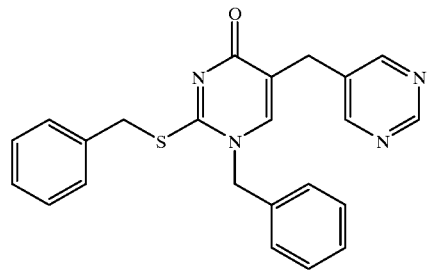

Prepared from intermediate B94 by general method A4. $^1$H-NMR (CDCl$_3$) δ 3.68 (2H, s), 4.51 (2H, s), 4.97 (2H, s), 7.00 (1H, s), 7.1 (2H, m), 7.2–7.4 (2H, m), 8.7(2H, s) and 9.08(1H, s); (APCI) M+H=401. C$_{23}$H$_{20}$N$_4$OS requires 400.

Example 191

1-Benzyl-2-benzylthio-5-((1-methylpyrazol-4-yl)methyl)pyrimidin-4-one

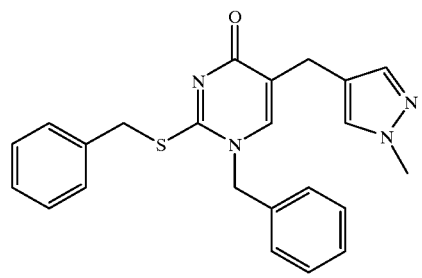

Prepared from Example 105 by general method C3, as a pale brown oil. $^1$H-NMR (CDCl$_3$) δ 3.57 (2H, s), 3.84 (3H, s), 4.52 (2H, s), 4.93 (2H, s), 6.90 (1H, s), 7.1 (2H, s), 7.2–7.4 (10H, m); (APCI) M+H=403. C$_{23}$H$_{22}$N$_4$OS requires 402.

Example 192

1-Benzyl-2-(4-fluorobenzyl)thio-5-(pyrimid-5-ylmethyl)pyrimidin-4-one

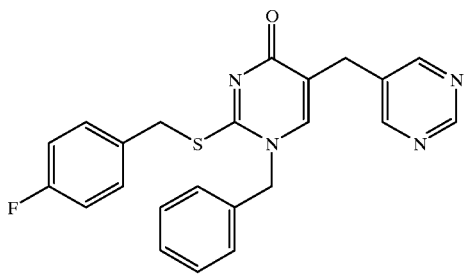

Prepared from intermediate B94 by general method A4. $^{1}$H-NMR (CDCl$_3$) δ 3.68 (2H, s), 4.48 (2H, s), 4.97 (2H, s), 7.0 (3H, m), 7.1 (2H, m), 7.3–7.4 (5H, m), 8.7 (2H, s), 9.08 (1H, s); (APCI) M+H=419. C$_{23}$H$_{19}$FN$_4$OS requires 418.

Example 193

1-(2,2-Dimethylprop-1-yl)-2-(4-fluorobenzyl)thio-5-(pyrimid-5-ylmethyl)pyrimidin-4-one

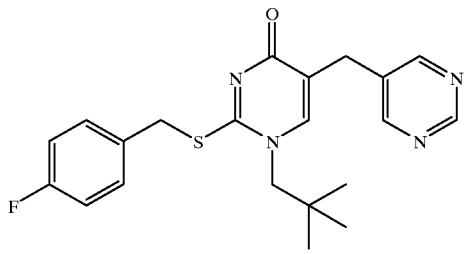

Prepared from intermediate B74 by general method A4 as a oil. $^{1}$H-NMR (CDCl$_3$) δ 0.96(9H, s), 3.61(2H, s), 3.72(2H, s), 4.46(2H, s), 6.85–7.1(3H, m), 7.3–7.45(2H, m), 8.70(2H, s) and 9.11(1H, s); (APCI) M+H=399. C$_{21}$H$_{23}$FN$_4$OS requires 398.

Example 194

1-(2-Phenylethyl)-2-benzylthio-5-(pyrimid-5-ylmethyl)pyrimidin-4-one

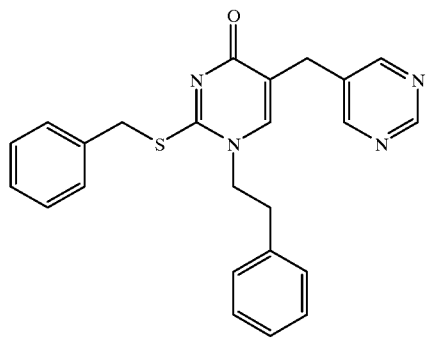

Prepared from intermediate B93, by general method A4, as a cream coloured crystalline solid. $^{1}$H-NMR (CDCl$_3$) δ 3.02 (2H, t), 3.51 (2H, s), 4.00 (2H, t), 4.55 (2H, s), 6.37 (1H, s), 7.0 (2H, m), 7.2–7.4 (8H, m), 8.47 (2H, s), 9.09 (1H, s); (APCI) M+H=415. C$_{24}$H$_{22}$N$_4$OS requires 414.

Example 195

1-(Fur-2-ylmethyl)-2-(4-methylbenzyl)thio-5-(pyrimid-5-ylmethyl)pyrimidin-4-one

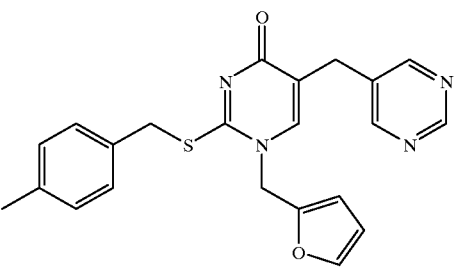

Prepared from intermediate B81 by general method A4. $^{1}$H-NMR (CDCl$_3$) δ 2.33 (3H, s), 3.70 (2H, s), 4.49 (2H, s), 4.90 (2H, s), 6.3–6.4 (2H, m), 6.84 (1H, s), 7.08 (2H, d), 7.33 (2H, d), 7.41 (1H, m), 8.7 (2H, s), 9.10 (1H, s); (APCI) M+H=405. C$_{22}$H$_{20}$N$_4$OS requires 404.

Example 196

1-(Fur-2-ylmethyl)-2-(2-fluorobenzyl)thio-5-(pyrimid-5-ylmethyl)pyrimidin-4-one

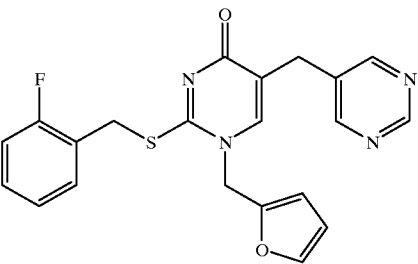

Prepared from intermediate B93 by general method A4. $^{1}$H-NMR (CDCl$_3$) δ 3.70 (2H, s), 4.56 (2H, s), 4.90 (2H, s), 6.37 (1H, m), 6.41 (1H–m), 7.1 (3H, m), 7.3 (1H, m), 7.41 (1, H, m), 7.55 (1H, m), 8.7 (2H, s), 9.10 (1H, s); (APCI) M+H=409. C$_{21}$H$_{17}$FN$_4$O$_2$S requires 408.

Example 197

1-(Fur-2-ylmethyl)-2-(4-chlorobenzyl)thio-5-(pyrimid-5-ylmethyl)pyrimidin-4-one

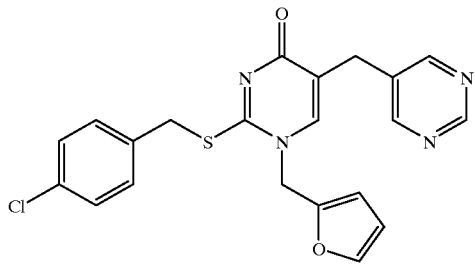

Prepared from intermediate B81 by general method A4. $^1$H-NMR (CDCl$_3$) δ 3.69 (2H, s), 4.48 (2H, s), 4.90 (2H, s), 6.38 (2H, m), 7.06 (1H, m), 7.28 (2H, d), 7.35 (2H, d), 7.42 (1H, m), 8.7 (2H, s), 9.10 (1H, s); (APCI) M+H=425, 2M+H=849. C$_{21}$H$_{17}$ClN$_4$O$_2$S requires 424.

Example 198

1-(Fur-2-ylmethyl)-2-(3-fluorobenzyl)thio-5-(pyrimid-5-ylmethyl)pyrimidin-4-one

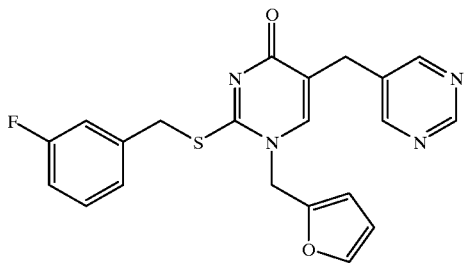

Prepared from intermediate B81 by general method A4. $^1$H-NMR (CDCl$_3$) δ 3.70 (2H, s), 4.51 (2H, s), 4.90 (2H, s), 6.38 (1H, m), 6.41 (1H, m), 7.0 (1H, m), 7.1–7.3 (5H, m), 7.42 (1H, m), 8.7 (2H, s), 9.10 (1H, s); (APCI) M+H=409. C$_{21}$H$_{17}$FN$_4$O$_2$S requires 408.

Example 199

1-(Fur-2-ylmethyl)-2-(3-chlorobenzyl)thio-5-(pyrimid-5-ylmethyl)pyrimidin-4-one

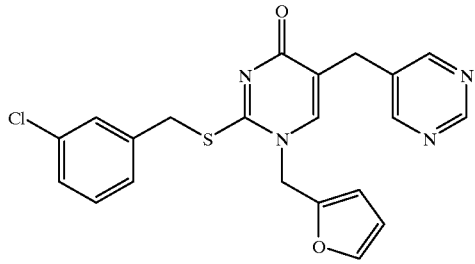

Prepared from intermediate B81 by general method A4, as an orange oil. $^1$H-NMR (CDCl$_3$) δ 3.69 (2H, s), 4.47(2H, s), 4.93 (2H, s), 6.38 (1H, m), 6.41 (1H, m), 7.12 (1H, s), 7.2–7.4 (5H, m), 8.7 (2H, s), 9.08 (1H, s); (APCI) M+H= 425. C$_{21}$H$_{17}$ClN$_4$O$_2$S requires 424.

Example 200

1-Methyl-2-benzylthio-5-(pyrimid-5-ylmethyl)pyrimidin-4-one

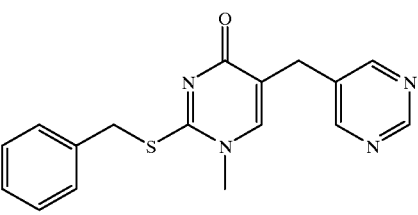

Prepared from intermediate B84 by general method A4, as an off-white crystalline solid. $^1$H-NMR (CDCl$_3$) δ 3.49 (3H, s), 3.71 (2H, s), 4.51 (2H, s), 6.96 (1H, s), 7.2–7.5 (5H, m), 8.70 (2H, s), 9.10 (1H, s); (APCI) M+H=325. C$_{17}$H$_{16}$N$_4$OS requires 324.

Example 201

1-((R)-Tetrahydofuran-2-ylmethyl)-2-benzylthio-5-(pyrimid-5-ylmethyl)pyrimidin-4-one

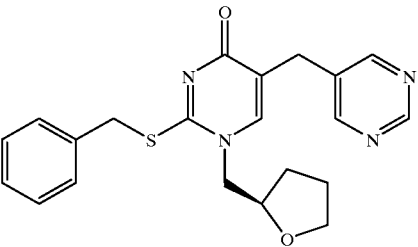

Prepared from intermediate B133 by general method A4. White solid. $^1$H-NMR (CDCl$_3$) δ 1.37–1.60 (1H, m), 1.81–2.14 (3H, m), 3.53–3.87 (5H, m), 3.99–4.18 (2H, m), 4.50 (1H, s), 7.18(1H, s), 7.28–7.44 (5H, m), 8.72 (2H, s), 9.09 (1H, s); MS (APCI$^+$) found (M+1)=395 C$_{21}$H$_{22}$N$_4$O$_2$S requires 394.

Example 202

1-((S)-Tetrahydrofuran-2-ylmethyl)-2-benzylthio-5-(pyrimid-5-ylmethyl)pyrimidin-4-one

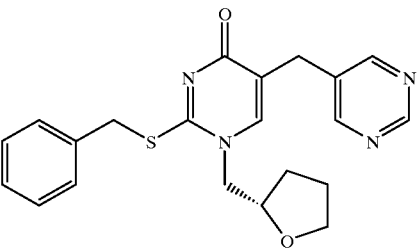

Prepared from intermediate B132 by general method A4, as a white solid. $^1$H-NMR (CDCl$_3$) δ 1.37–1.58 (1H, m), 1.8–2.12 (3H, m), 3.55–3.88 (5H, m), 3.98–4.19 (2H, m), 4.5 (2H, s), 7.17 (1H, s), 7.29–7.44 (5H, m), 8.70 (2H, s), 9.02(1H, s); MS (APCI$^+$) found (M+1)=395; C$_{21}$H$_{22}$N$_4$O$_2$S requires 394.

Example 203

1-(4-Fluorobenzyl)-2-(4-fluorobenzyl)thio-5-(pyrimid-5-ylmethyl)pyrimidin-4-one

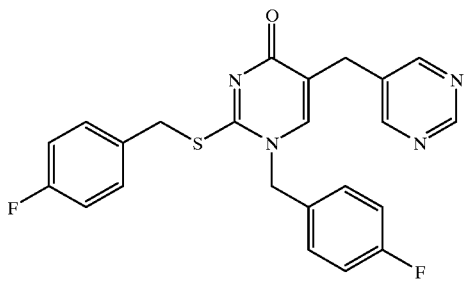

Prepared from intermediate B99 by general method A2, as an orange solid. $^1$H-NMR (CDCl$_3$) δ 3.68 (2H, s), 4.47 (2H, s), 4.94 (2H, s), 6.92–7.20 (7H, m), 7.28–7.41 (2H, m), 8.66 (2H, s), 9.08 (1H, s); MS (APCI$^+$) found (M+1)=437; C$_{23}$H$_{18}$F$_2$N$_4$OS requires 436.

Example 204

1-(4-Bromobenzyl)-2-(4-fluorobenzyl)thio-5-(pyrimid-5-ylmethyl)pyrimidin-4-one

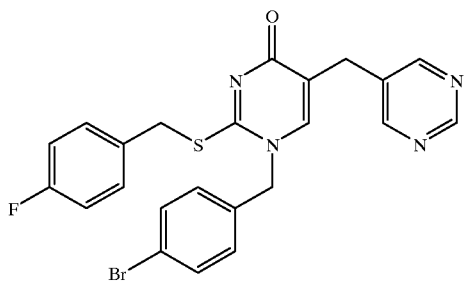

Prepared from intermediate B115 by general method A2. $^1$H-NMR (CDCl$_3$) δ 3.68 (2H, s), 4.46 (2H, s), 4.91 (2H, s), 7.01 (5H, m), 7.35 (2H, m), 7.50 (2H, m), 8.70 (2H, s), 9.09 (1H, s), MS(APCI$^+$) M+1=497, C$_{23}$H$_{18}$BrFN$_4$OS requires 496. MPt 162.2° C. (cream solid). MPt. 162.2

Example 205

1-(2-(6-(4-Fluorophenyl)hex-1-yloxy)ethyl)-2-(4-fluorobenzyl)thio-5-(pyrimid-5-ylmethyl)pyrimidin-4-one

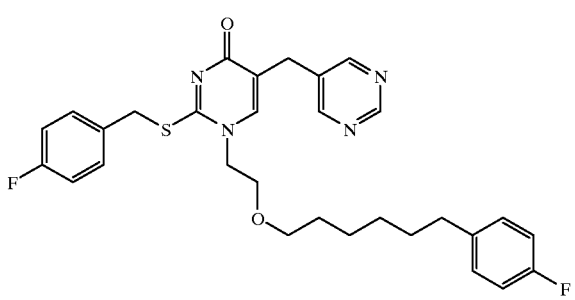

Prepared from intermediate B109 by general method A2 as an oil. $^1$H-NMR (CDCl$_3$) δ 1.15–1.72 (8H, m), 2.50–2.63 (2H, t), 3.28–3.30 (2H, t), 3.55–3.64 (2H, t), 3.69 (2H, ), 3.89–3.98 (2H, t), 4.47(2H, s), 6.88–7.43 (9H, m), 8.69 (2H, s), 9.08 (1H, s); MS (APCI$^+$) found (M+1)=551; C$_{30}$H$_{32}$F$_2$N$_4$O$_2$S requires 550.

Example 206

1-(2-Phenoxyethyl)-2-(3,4-difluorobenzyl)thio-5-(pyrimid-5-)pyrimidin-4-one

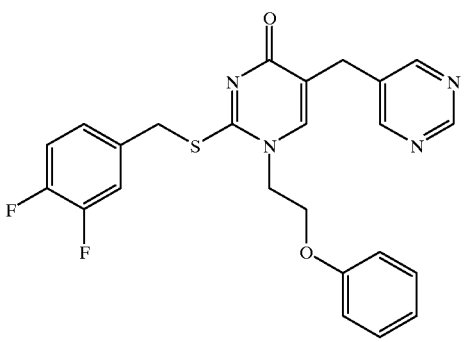

Prepared from intermediate B101 by general method A2 as a solid. $^1$H-NMR (CDCl$_3$) δ 3.72 (2H, s), 4.10–4.29 (4H, m), 4.47 (2H, s), 6.70–6.80 (2H, d), 6.95–7.39 (7H, m), 8.70 (2H, s), 9.12 (1H, s); MS (ES+) found (M+1)=467; C$_{24}$H$_{20}$F$_2$N$_4$O$_2$S requires 466.

Example 207

1-(3-(5-Phenylpent-1-yloxy)prop-1-yl)-2-benzylthio-5-(pyrimid-5-ylmethyl)pyrimidin-4-one

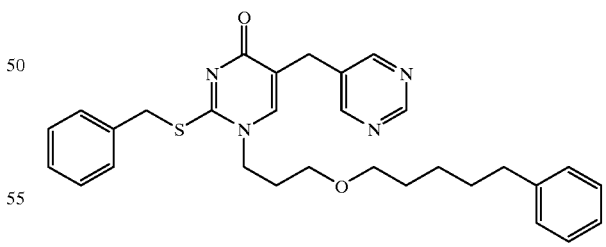

Prepared from intermediate B139 by general method A2. $^1$H-NMR (CDCl$_3$) δ 1.35 (2H, m), 1.59 (4H, m), 1.95 (2H, m), 2.60 (2H, t), 3.32 (4H, m), 3.68 (2H, s), 3.87 (2H, t), 4.50 (2H, s), 7.01 (1H, s), 7.14–7.38 (10H, m), 8.68(2H, s) 9.08 (1H, s); MS (APCI$^+$) found (M+1)=515; C$_{30}$H$_{34}$N$_4$O$_2$S requires 514.

Example 208

1-(9-Phenylnonyl)-2-furfurylthio-5-(pyrimid-5-ylmethyl)pyrimidin-4-one

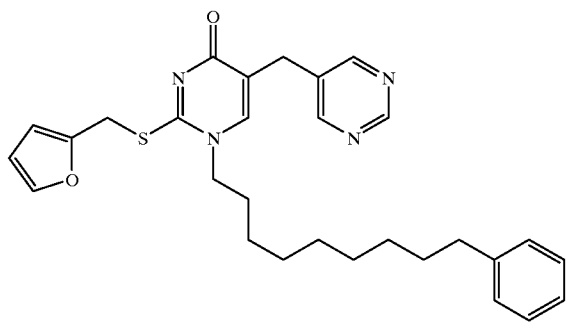

Prepared from intermediate B91 by general method A2.
$^1$H-NMR (CDCl$_3$) δ 1.28 (10H, m), 1.65 (4H, m), 2.60 (2H, t), 3.69 (4H, m), 4.56 (2H, s), 6.30 (1H, m), 6.40 (1H, m), 6.98 (1H, s), 7.14–7.36 (6H, m), 8.69 (2H, s), 9.10 (1H, s); MS (APCI$^+$) found (M+1)=503; C$_{29}$H$_{34}$N$_4$O$_2$S requires 502.

Example 209

1-(9-Phenylnonyl)-2-(thiazol-2-ylmethyl)thio-5-(pyrimid-5-ylmethyl)pyrimidin-4-one

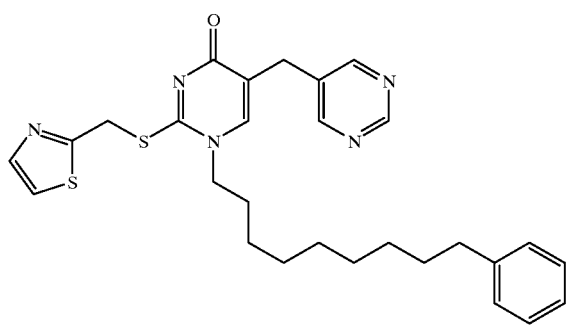

Prepared from intermediate B91 by general method A2.
$^1$H-NMR (CDCl$_3$) δ 1.28 (10H, m), 1.65 (4H, m), 2.60 (2H, t), 3.72 (2H, s), 3.75 (2H, t), 4.85 (2H, s), 6.97 (1H, s), 7.14–7.30 (6H, m), 7.71 (1H, d), 8.71 (2H, s), 9.11 (1H, s); MS (APCI$^+$) found (M+1)=520; C28H33N5OS2 requires 519.

Example 210

1-(9-Phenylnonyl)-2-(thien-2-ylmethyl)thio-5-(pyrimid-5-ylmethyl)pyrimidin-4-one

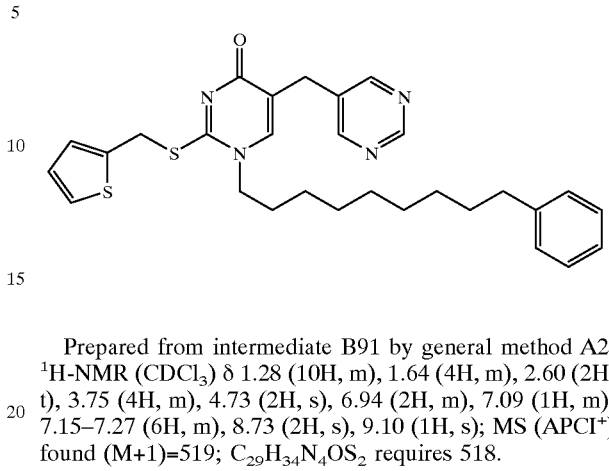

Prepared from intermediate B91 by general method A2.
$^1$H-NMR (CDCl$_3$) δ 1.28 (10H, m), 1.64 (4H, m), 2.60 (2H, t), 3.75 (4H, m), 4.73 (2H, s), 6.94 (2H, m), 7.09 (1H, m), 7.15–7.27 (6H, m), 8.73 (2H, s), 9.10 (1H, s); MS (APCI$^+$) found (M+1)=519; C$_{29}$H$_{34}$N$_4$OS$_2$ requires 518.

Example 211

1-(9-Phenylnonyl)-2-(3,4-difluorobenzyl)thio-5-(pyrimid-5-ylmethyl)pyrimidin-4-one

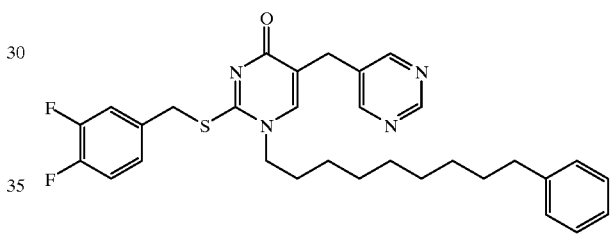

Prepared from intermediate B91 by general method A2.
$^1$H-NMR (CDCl$_3$) δ 1.28 (10H, m), 1.60 (4H, m), 2.59 (2H, t), 3.71 (4H, m), 4.44 (2H, s), 6.95 (1H, s), 7.10–7.27 (8H, m), 8.70 (2H, s), 9.10 (1H, s); MS (APCI$^+$) found (M+1)=549; C$_{31}$H$_{34}$F$_2$N$_4$OS requires 548.

Example 212

1-(2-(2-Pent-1-ylphenyl)ethyl)-2-(4-fluorobenzyl)thio-5-(pyrimid-5-ylmethyl)pyrimidin-4-one

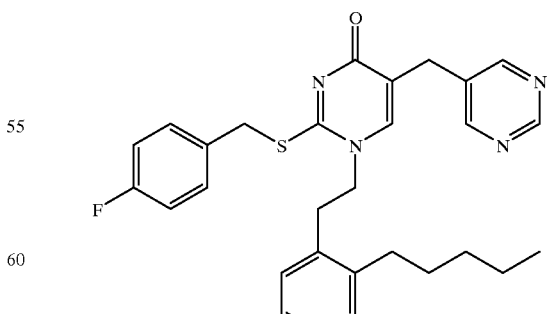

Prepared from intermediate B117 by general method A2.
$^1$H-NMR (CDCl$_3$) δ 0.87 (3H, t), 1.25 (4H, m), 1.45 (2H, m), 2.39 (2H, t), 3.04 (2H, t), 3.50 (2H, s), 3.97 (2H, t), 4.52 (2H, s), 6.31 (1H, s), 6.94–7.21 (8H, m), 7.40 (2H, m), 8.50 (2H, s), 9.09 (1H, s), MS (APCI$^+$) M+1=503, C$_{29}$H$_{31}$FN$_4$OS requires 502. MPt 112.3° C. (colourless solid).

Example 213

1-(2-(3-Pent-1-ylphenyl)ethyl)-2-(4-fluorobenzyl) thio-5-(pyrimid-5-ylmethyl)pyrimidin-4-one

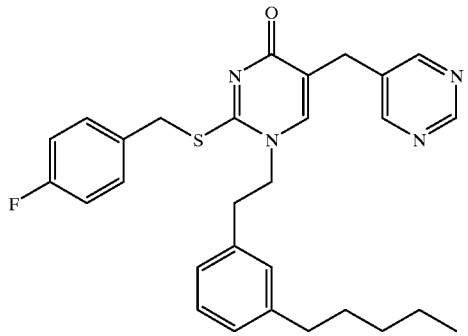

Prepared from intermediate B116 by general method A2. $^1$H-NMR (CDCl$_3$) δ 0.89 (3H, m), 1.30 (4H, m), 1.50 (2H, m), 2.52 (2H, t), 2.98 (2H, t), 3.51 (2H, s), 3.98 (2H, s), 3.98 (2H, t), 4.51 (2H, s), 6.41 (1H, s), 6.80–7.16 (6H, m), 7.41 (2H, m), 8.49 (2H, s), 9.08 (1H, s), MS(APCI$^+$) M+1=503, C$_{29}$H$_{31}$FN$_4$OS requires 502. MPt 93.2° C. (colourless solid).

Example 214

1-(2-(4-Bromophenyl)ethyl)-2-(4-fluorobenzyl)thio-5-(pyrimid-5-ylmethyl)pyrimidin-4-one

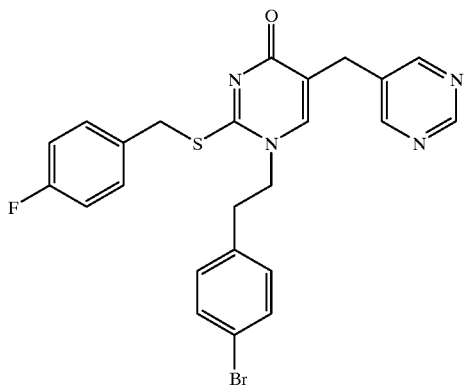

Prepared from intermediate B114 by general method A2. $^1$H-NMR (CDCl$_3$) δ 2.97 (2H, t), 3.59 (2H, s), 3.95 (2H, t), 4.49 (2H, s), 6.50 (1H, s), 6.89–7.05 (4H, m), 7.35–7.44 (4H, m), 8.58 (2H, s), 9.11 (1H, s), MS(APCI$^+$) M+1=511, C$_{24}$H$_{20}$BrFN$_4$OS requires 510. MPt 151.6° C. (cream solid).

Example 215

1-(5-Methylfuran-2-ylmethyl)-2-(4-fluorobenzyl) thio-5-(pyrimid-5-ylmethyl)pyrimidin-4-one

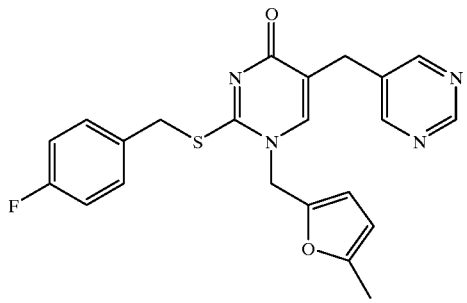

Prepared from intermediate B98 by general method A2 as a pale yellow solid. $^1$H-NMR (CDCl$_3$) δ 1.64 (3H, s), 3.70 (2H, s), 4.49 (2H, s), 4.83 (2H, s), 5.95 (1H, d), 6.28 (1H, d), 6.94–7.09 (3H, m), 7.33–7.45 (2H, m), 8.69 (2H, s), 9.09 (1H, s), MS (APCI$^+$) found (M+1)=423; C$_{22}$H$_{19}$FN$_4$O$_2$S requires 422.

Example 216

1-(2-(2-Chlorophenyl)ethyl)-2-(4-fluorobenzyl)thio-5-(pyrimid-5-ylmethyl)pyrimidin-4-one

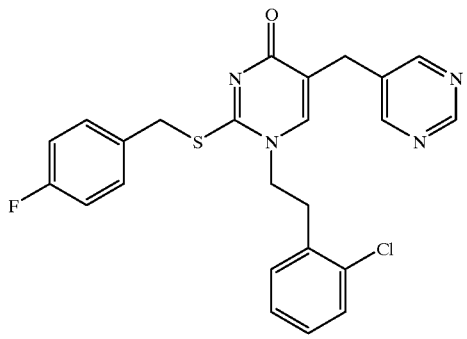

Prepared from intermediate B100 by general method A2 as a pale yellow solid. $^1$H-NMR (CDCl$_3$) δ 3.10–3.23 (2H, t), 3.51 (2H, s), 4.00–4.12 (2H, t), 4.51 (2H, t), 6.42 (1H, s), 6.90–7.48 (8H, m), 8.48 (2H, s), 9.09 (1H, s); MS (APCI$^+$) found (M+1) 467; C$_{24}$H$_{20}$ClFN$_4$OS requires 466.

Example 217

1-(2-(Thien-2-yl)ethyl)-2-(3,4-difluorobenzyl)thio-5-(pyrimid-5-ylmethyl)pyrimidin-4-one

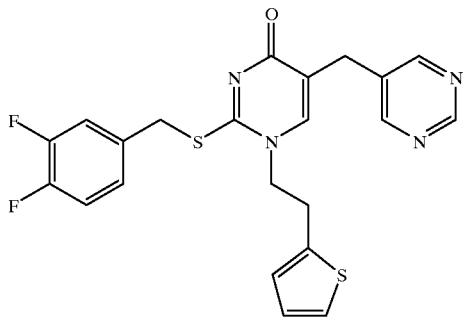

Prepared from intermediate B97 by general method A2. ¹H-NMR (CDCl₃) δ 3.26 (2H, t), 3.55 (2H, s), 4.02 (2H, t), 4.48 (2H, s), 6.51 (1H, s), 6.67 (1H, m), 6.91 (1H, m), 7.05–7.27 (4H, m), 8.53(2H, s) 9.09 (1H, s); MS (APCI⁺) found (M+1)=457; C₂₂H₁₈F₂N₄OS₂ requires 456.

Example 218

1-(2-Phenylethyl)-2-(2,3,4-trifluorobenzyl)thio-5-(pyrimid-5-ylmethyl)pyrimidin-4-one

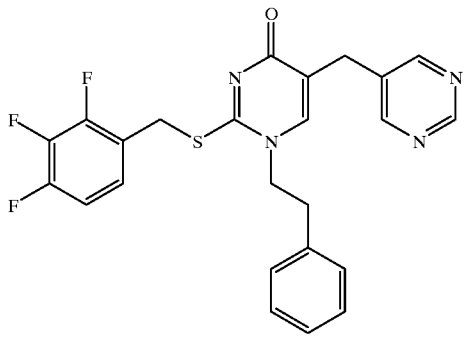

Prepared from intermediate B93 by general method A3 as a pale yellow foam ¹H-NMR (CDCl₃) δ 3.02 (2H, t), 3.51 (2H, s), 3.99 (2H, t), 4.55 (2H, s), 6.42 (1H, s), 6.8–7.1 (3H, m), 7.2–7.45 (4H, m), 8.48 (2H, s), 9.09 (1H, s); MS (APCI⁺) found (M+1)=469; C₂₄H₁₉F₃N₄OS requires 468.

Example 219

1-(2-Phenylethyl)-2-(2,3,5-trifluorobenzyl)thio-5-(pyrimid-5-ylmethyl)pyrimidin-4-one

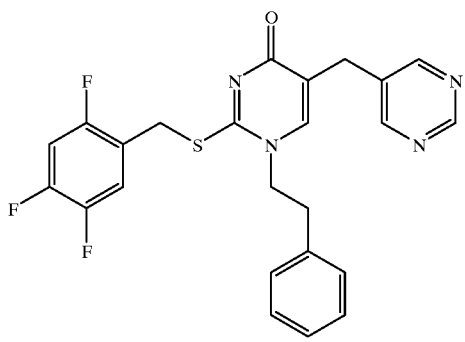

Prepared from intermediate B93 by general method A3 as a white solid ¹H-NMR (CDCl₃) δ 3.02 (2H, t), 3.52 (2H, s), 3.99 (2H, t), 4.51 (2H, s), 6.40 (1H, s), 6.85–7.1 (3H, m) 7.2–7.35 (3H, m), 7.4–7.55 (1H, m), 8.5 (2H, s), 9.09 (1H, s); MS (APCI⁺) found (M+1)=469; C₂₄₁₉F₃N₄OS requires 468.

Example 220

1-(2-Phenylethyl)-2-(2,4,6-trifluorobenzyl)thio-5-(pyrimid-5-ylmethyl)pyrimidin-4-one

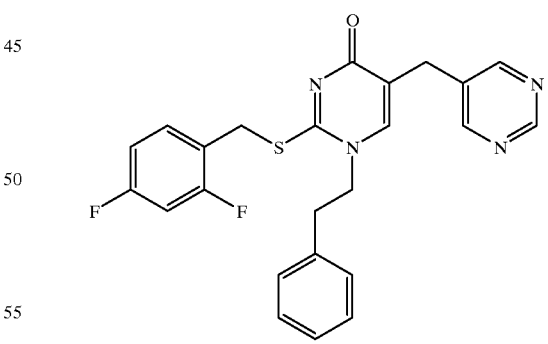

Prepared from intermediate B93 by general method A3 as a white solid ¹H-NMR (CDCl₃) δ 3.02 (2H, t), 3.51 (2H, s), 3.99 (2H, t), 4.60 (2H, s), 6.38 (1H, s), 6.6–6.8 (2H, m), 7.0–7.1 (2H, m), 7.2–7.3 (3H, m), 8.48 (2H, s), 9.09 (1H, s); MS (APCI⁺) found (M+1)=469; C₂₄H₁₉F₃N₄OS requires 468.

Example 221

1-(2-Phenylethyl)-2-(2,4-difluorobenzyl)thio-5-(pyrimid-5-ylmethyl)pyrimidin-4-one Prepared from intermediate B93 by general method A2 as a pale yellow solid. ¹H-NMR (CDCl₃) δ 2.95–3.08 (2H, t), 3.51 (2H, s), 3.94–4.05 (2H, t), 4.54 (2H, s), 6.39 (1H, s), 6.74–6.91 (2H, m), 6.95–7.06 (2H, m), 7.18–7.34 (3H, m), 7.52–7.67 (1H, m), 8.48 (2H, s), 9.09 (1H, s); MS (APCI⁺) found (M+1)=451; C₂₄H₂₀F₂N₄OS requires 450.

Example 222

1-(2-Phenylethyl)-2-(2-fluorobenzyl)thio-5-(pyrimid-5-ylmethyl)pyrimidin-4-one

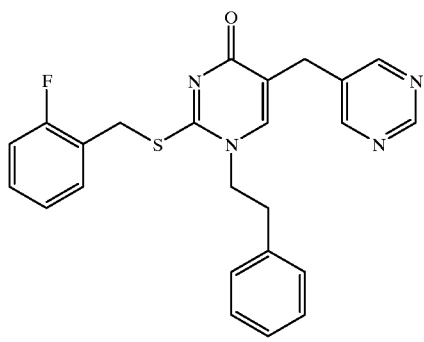

Prepared from intermediate B93 by general method A2. $^1$H-NMR (CDCl$_3$) δ 2.95–3.09 (2H, t), 3.49 (2H, s), 3.92–4.06 (2H, t), 4.59 (2H, s), 6.38 (1H, s), 6.94–7.37 (8H, m), 7.50–7.63 (1H, t), 8.49 (2H, s), 9.08 (1H, s), MS (APCI$^+$) found (M+1)=433; C$_{24}$H$_{21}$FN$_4$OS requires 432.

Example 223

1-(2-Phenylethyl)-2-furfurylthio-5-(pyrimid-5-ylmethyl)pyrimidin-4-one

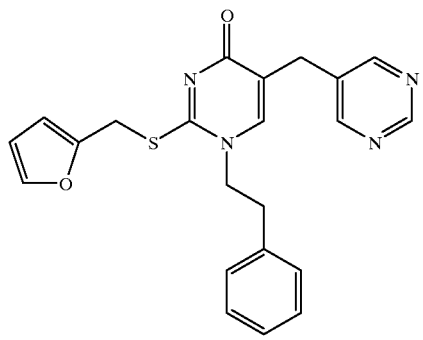

Prepared from intermediate B93 by general method A2. $^1$H-NMR (CDCl$_3$) δ 3.03 (2H, t), 3.51 (2H, s), 4.00 (2H, t), 4.62 (2H, s), 6.41 (3H, m), 7.03 (2H, m), 7.27 (3H, m), 7.38 (1H, m), 8.46 (2H, s), 9.09 (1H, s); MS (APCI$^+$) found (M+1)=405; C$_{22}$H$_{20}$N$_4$O$_2$S requires 404.

Example 224

1-(2-Phenylethyl)-2-(thien-2-ylmethyl)thio-5-(pyrimid-5-ylmethyl)pyrimidin-4-one

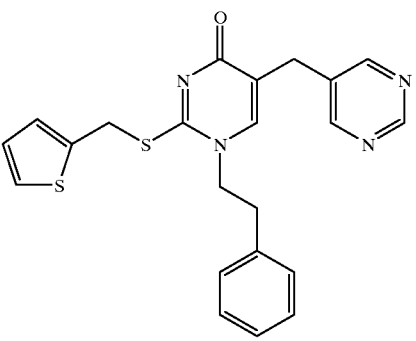

Prepared from intermediate B93 by general method A2. $^1$H-NMR (CDCl$_3$) δ 3.03 (2H, t), 3.51 (2H, s), 3.99 (2H, t), 4.78 (2H, s), 6.36 (1H, s), 6.93–7.02 (3H, m), 7.12 (1H, m), 7.22–7.28 (4H, m), 8.48 (2H, s), 9.09 (1H, s); MS (APCI$^+$) found (M+1)=421; C$_{22}$H$_{20}$N$_4$OS$_2$ requires 420.

Example 225

1-(2-Phenylethyl)-2-(3,4,5-trifluorobenzyl)thio-5-(pyrimid-5-ylmethyl)pyrimidin-4-one

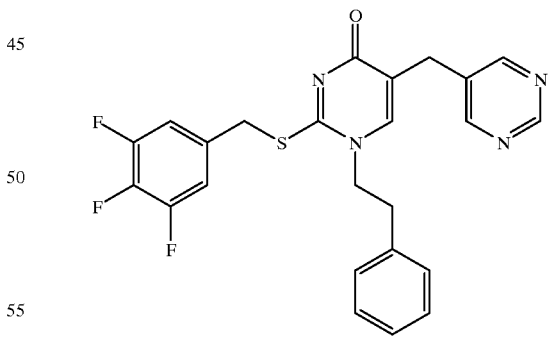

Prepared from intermediate B93 by general method A3 as a pale yellow foam. $^1$H-NMR (CDCl$_3$) δ 3.03 (2H, t), 3.52 (2H, s), 4.02 (2H, t), 4.45 (2H, s), 6.46 (1H, s), 6.95–7.2 (4H, m), 7.2–7.4 (3H, m), 8.49 (2H, s), 9.09 (1H, s); MS (APCI$^+$) found (M+1)=469; C$_{24}$H$_{19}$F$_3$N$_4$OS requires 468.

Example 226

1-(2-Phenylethyl)-2-(3,4-difluorobenzyl)thio-5-(pyrimid-5-ylmethyl)pyrimidin-4-one

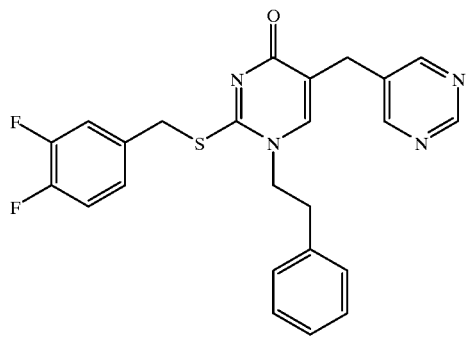

Prepared from intermediate B93 by general method A2. $^1$H-NMR (CDCl$_3$) δ 2.95–3.10 (2H, t), 3.52 (2H, s), 3.95–4.07 (2H, t), 4.49 (2H, s), 6.39 (1H, s), 6.96–7.36 (8H, m), 8.48 (2H, s), 9.09 (1H, s); MS (APCI$^+$) found (M+1)= 451; C$_{24}$H$_{20}$F$_2$N$_4$OS require 450.

Example 227

1-(2-Phenylethyl)-2-(3,5-difluorobenzyl)thio-5-(pyrimid-5-ylmethyl)pyrimidin-4-one

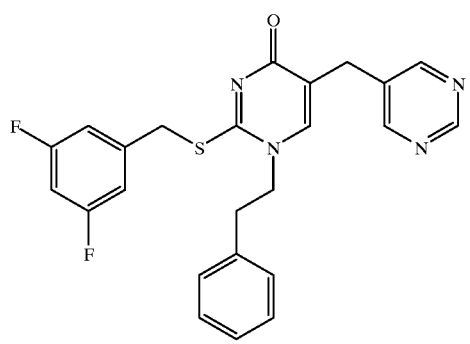

Prepared from intermediate B93 by general method A2 as a pale yellow solid. $^1$H-NMR (CDCl$_3$) δ 2.97–3.10 (2H, t), 3.52 (2H, s), 3.95–4.16 (2H, t), 4.51 (2H, s), 6.40 (1H, s), 6.66–6.80 (1H, m), 6.89–7.08 (4H, m), 7.18–7.37 (3H, m), 8.49 (2H, s), 9.09 (1H, s); MS (APCI$^+$) found (M+1)=451; C$_{24}$H$_{20}$F$_2$N$_4$OS requires 450.

Example 228

1-(2-Phenylethyl)-2-(3-fluorobenzyl)thio-5-(pyrimid-5-ylmethyl)pyrimidin-4-one

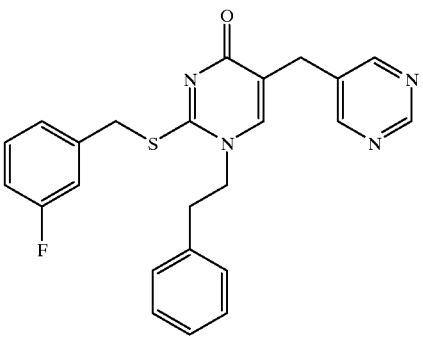

Prepared from intermediate B93 by general method A2 as a pale yellow solid. $^1$H-NMR (CDCl$_3$) δ 2.95–3.09 (2H, s), 3.52 (2H, s), 3.94–4.07 (2H, t), 4.53 (2H, s), 6,39 (1H, s), 6.90–7.38 (9H, m), 8.48 (2H, s), 9.09 (1H, s); MS (APCI$^+$) found (M+1)=433; C$_{24}$H$_{21}$FN$_4$OS. requires 432.

Example 229

1-(2-Phenylethyl)-2-(4-fluorobenzyl)thio-5-(pyrimid-5-ylmethyl)pyrimidin-4-one

Prepared from intermediate B93 by general method A2 as a pale yellow solid. $^1$H-NMR (CDCl$_3$) δ 2.98–3.10 (2H, t), 3.49 (2H, s), 3.944.06 (2H, s), 4.51 (2H, s), 6.39 (1H, s), 6.94–7.08 (4H, m), 7.20–7.33 (3H, m), 7.36–7.48 (2H, m), 8.48 (2H, s), 9.09 (1H, s); Ms (APCI$^+$) found (M+1)=433; C$_{24}$H$_{21}$FN$_4$OS requires 432.

Example 230

1-(2-Phenylethyl)-2-(1-phenylethyl)thio-5-(pyrimid-5-ylmethyl)pyrimidin-4one

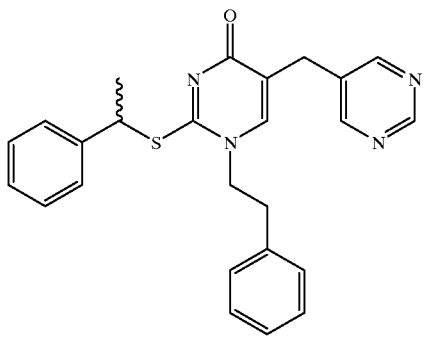

Prepared from intermediate B93 by general method A2 as a pale yellow solid. $^1$H-NMR (CDCl$_3$) δ 1.82 (2H, t), 2.99 (2H, t), 3.50 (2H, s), 3.85–4.1 (2H, m), 5.35 (1H, q), 6.34 (1H, s), 6.9–7.05 (2H, m), 7.15–7.5 (8H, m), 8.49 (2H, s), 9.09 (1H, s); MS (APCI$^+$) found (M+1)=429; C$_{25}$H$_{24}$N$_4$OS requires 428.

Example 231

1-(2-(4-Methoxyphenyl)ethyl)-2-(3,4-difluorobenzyl)thio-5-pyrimid-5-ylmethyl)pyrimidin-4-one

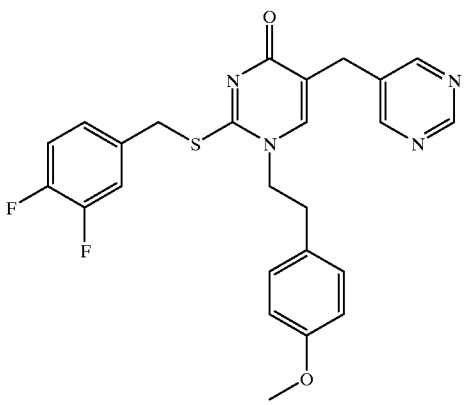

Prepared from intermediate B134 by general method A2 as a white solid. $^1$H-NMR (CDCl$_3$) δ 2.91–3.02 (2H, t), 3.59 (2H, s), 3.84 (3H, s), 3.90–4.02 (2H, t), 4.48 (2H, s), 6.42 (1H, s), 6.73–7.31 (7H, m), 8.51 (2H, s), 9.10 (1H, s); MS (APCI$^+$) found (M+1)=481; C$_{25}$H$_{22}$F$_2$N$_4$O$_2$S requires 480.

Example 232

1-(2-(4-Pent-1-ylphenyl)ethyl)-2-(4-fluorobenzyl)thio-5-(pyrimid-5-ylmethyl)pyrimidin-4-one

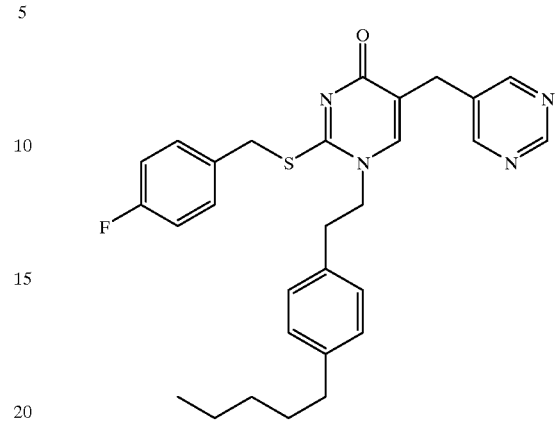

Prepared from intermediate B112 by general method A2. $^1$H-NMR (CDCl$_3$) δ 0.88 (3H, t), 1.32 (4H, m), 1.60 (2H, m), 2.60 (2H, m), 2.97 (2H, m), 3.52 (2H, s), 3.97 (2H, t), 4.51 (2H, s), 6.46 (1H, s), 6.84–7.11 (6H, m), 7.40 (2H, m), 8.50 (2H, s), 9.08 (1H, s); MS(APCI$^+$) M+1=503, C$_{29}$H$_{31}$FN$_4$OS requires 502. MPt 98.7° C. (colourless solid).

Example 233

1-(Cycloprop-1-yl)-2-(4-fluorobenzyl)thio-5-(pyrimid-5-ylmethyl)-pyrimidin-4-one

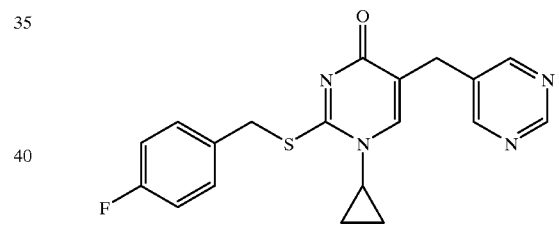

Prepared from intermediate B105 by general method A2. $^1$H-NMR (CDCl$_3$) δ 0.94–1.32 (4H, m), 3.03–3.18 (1H, m), 3.69 (2H, s), 4.42 (2H, s), 6.93–7.07 (2H, t), 7.14 (1H, s), 7.31–7.45 (2H, m), 8.70 (2H, s), 9.10 (1H, s); MS (APCI$^+$) found (M+1)=369; C$_{19}$H$_{17}$FN$_4$OS requires 368.

Example 234

1-(Dodec-1-yl)-2-(3,4-difluorobenzyl)thio-5-(pyrimid-5-ylmethyl)pyrimidin-4-one

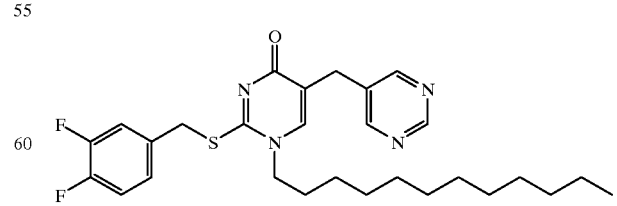

Prepared from intermediate B96 by general method A2 as an oil. $^1$H-NMR (CDCl$_3$) δ 0.78–0.85 (3H, t), 1.13–1.70 (20H, m), 3.65–3.80 (4H, m), 4.45 (2H, s), 6.92–7.27 (4H, s), 8.70 (2H, s), 9.11 (1H, s); MS (APCI⁺) found (M+1)= 515; $C_{28}H_{36}F_2N_4OS$ requires 514.

Example 235

1-Ethyl-2-(4-fluorobenzyl)thio-5-(pyrimid-5-ylmethyl)pyrimidin-4-one

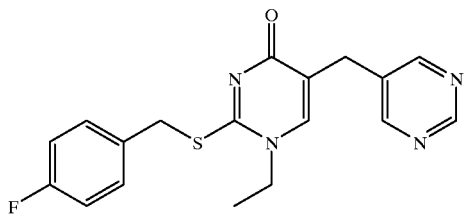

Prepared from intermediate B89 by general method A2 as a solid. ¹H-NMR (CDCl₃) δ 1.30–1.44 (3H, t). 3.72 (2H, s), 3.75–3.90 (2H, q), 4.47 (2H, s), 6.94–7.17 (3H, m), 7.33–7.45 (2H, m), 8.70 (2H, s), 9.10 (1H, s); MS (APCI⁺) found (M+1)=357; $C_{18}H_{17}FN_4OS$ requires 356.

Example 236

1-(1-Methylethyl)-2-(4-fluorobenzyl)thio-5-(pyrimid-5-ylmethyl)pyrimidin-4-one

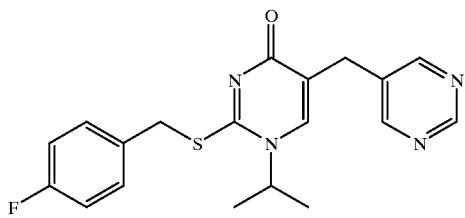

Prepared from intermediate B104 by general method A2 as a solid. ¹H-NMR (CDCl₃) δ 1.32–1.45 (6H, d), 3.73 (2H, s), 4.46 (2H, s), 4.49–4.65 (1H, m), 6.94–7.05 (2H, t), 7.17 (1H, s), 7.33–7.45 (2H, m), 8.72 (2H, s), 9.10 (1H, s); MS (APCI⁺) found (M+1)=371; $C_{19}H_{19}FN_4OS$ requires 370.

Example 237

1-Methyl-2-(4-fluorobenzyl)thio-5-(pyrimid-5-ylmethyl)pyrimidin-4-one

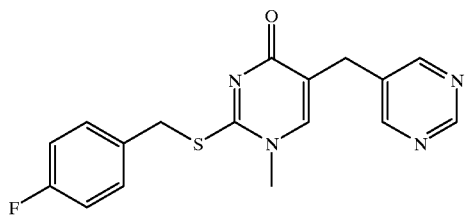

Prepared from intermediate B84 by general method A2 as a solid. ¹H-NMR (CDCl₃) δ 3.49 (3H, s), 3.71 (2H, s), 4.48 (2H, s) 6.93–7.07 (3H, m), 7.32–7.44 (2H, m), 8.70 (2H, s), 9.10 (1H, s); MS (APCI⁺) found (M+1)=343; $C_{17}H_{15}FN_4OS$ requires 342.

Example 238

1-(Undec-1-yl)-2-(4-fluorobenzyl)thio-5-(pyrimid-5-ylmethyl)pyrimidin-4-one

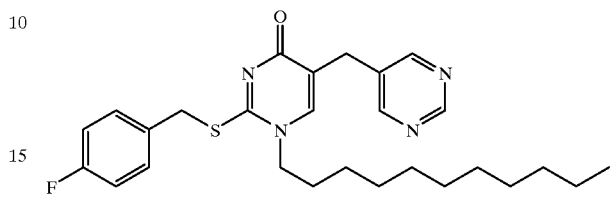

Prepared from intermediate B95 by general method A2 as an oil. ¹H-NMR (CDCl₃) δ 0.82–0.98 (3H, t), 1.13–1.80 (18H, m), 3.65–3.79 (4H, m), 4.47 (2H, s), 6.90–7.07 (3H, m), 7.31–7.43 (2H, m), 8.70 (2H, s), 9.10 (1H, s); MS (APCI⁺) found (M+1)=483; $C_{27}H_{35}FN_4OS$ requires 482.

Example 239

1-(Undec-1-yl)-2-(4-fluorobenzyl)thio-5-(2-oxopyrimid-5-ylmethyl)pyrimidin-4-one

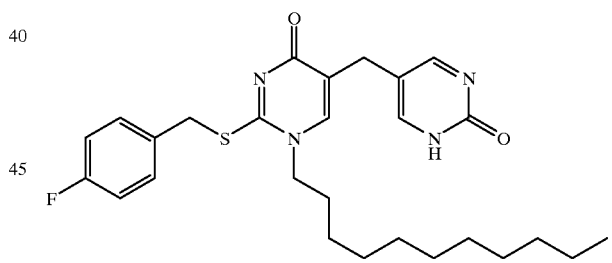

To a solution of either Example 243 or 244 (0.2 g) in dry methylene chloride (4 ml) at 4° C. was added boron tribromide (1M in methylene chloride, 2 ml). The mixture was stirred under argon for 24 h and poured into a mixture of ice (50 ml) and 0.880 ammonia (15 ml) with stirring. Extraction with 5% methanol:methylene chloride was followed by filtration through kieselguhr and drying the organic layer over sodium sulphate. Removal of the solvent in vacuo gave the desired material as a grey solid (0.15 g). ¹H-NMR (CDCl₃) δ 0.8–0.95 (3H, m), 1.1–1.4 (16H, m), 1.6–1.85 (2H, m), 3.49 (2H, s), 3.79 (2, t), 4.45 (2H, s), 6.9–7.1 (2H, m), 7.2–7.45 (3H, m), 8.32 (2H, s); MS (APCI⁺) found (M+1)=499; $C_{27}H_{35}FN_4O_2S$ requires 498.

Example 240

1-Benzyl-2-benzylthio-5-(2-methoxypyrimid-5-ylmethyl)pyrimidin-4-one

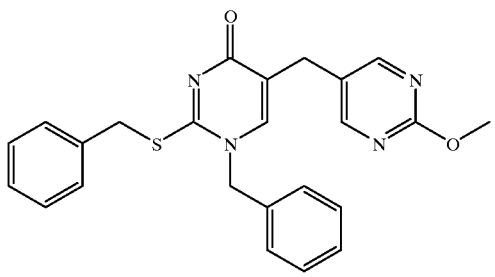

Prepared from Example B39 by alkylation with benzyl bromide using general method A4, followed by N-alkylation using general method C2. ¹H-NMR (CDCl₃) δ 3.62 (2H, s), 3.98 (3H, s), 4.51 (2H, s), 4.96 (2H, s), 6.92 (1H, s), 7.10 (1H, m), 7.23–7.40 (9H, m), 8.41 (2H, s); MS (APCI⁺) found (M+1)=431; $C_{24}H_{22}N_4O_2S$ requires 430.

Example 241

1-(2-Phenylethyl)-2-(3,4-difluorobenzyl)thio-5-(2-methoxypyrimid-5-ylmethyl)pyrimidin-4-one

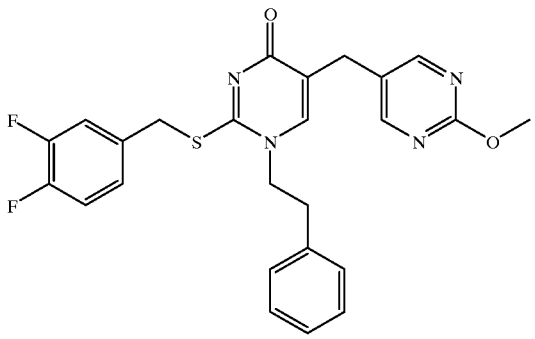

Prepared from Example 107 by general method C3. ¹H-NMR (CDCl₃) δ 3.01 (2H, t), 3.46 (2H, s), 3.99 (2H, t), 4.01 (3H, s), 4.49 (2H, s), 6.33 (1H, s), 6.99–7.29 (8H, m), 8.22 (2H, s); MS (APCI⁺) found (M+1)=481; $C_{25}H_{22}F_2N_4O_2S$ requires 480.

Example 242

1-(Furan-2-ylmethyl)-2-(3,4-difluorobenzyl)thio-5-(2-methoxypyrimid-5-ylmethyl)pyrimidin-4-one

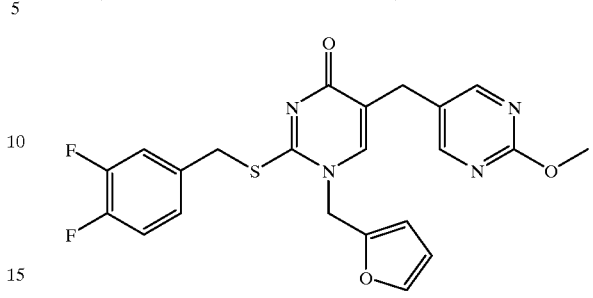

Prepared from Example 107 by general method C3. ¹H-NMR (CDCl₃) δ 3.63 (2H, s), 4.00 (3H, s), 4.46 (2H, s), 4.90 (2H, s), 6.38 (2H, m), 7.01 (1H, s), 7.07–7.26 (3H, m), 7.42 (1H, m), 8.44 (2H, s); MS (APCI⁺) found (M+1)=457; $C_{22}H_{18}F_2N_4O_3S$ requires 456.

Example 243

1-(Undec-1-yl)-2-(4-fluorobenzyl)thio-5-(2-methoxypyrimid-5-ylmethyl)pyrimidin-4-one

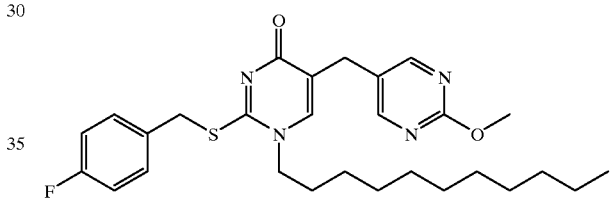

Prepared from intermediate B124 by general method A2. ¹H-NMR (CDCl₃) δ 0.88 (3H, t), 1.25 (16H, m), 1.68 (2H, m), 3.64 (2H, s), 3.71 (2H, t), 4.00 (3H, s), 4.47 (2H, s), 6.87 (1H, s), 7.00 (2H, m), 7.36 (2H, m), 8.46 (2H, s); MS (APCI⁺) found (M+1)=513; $C_{28}H_{37}N_4O_2S$ requires 512.

Example 244

1-(Undec-1-yl)-2-(4-fluorobenzyl)thio-5-(2-ethoxypyrimid-5-ylmethyl)pyrimidin-4-one

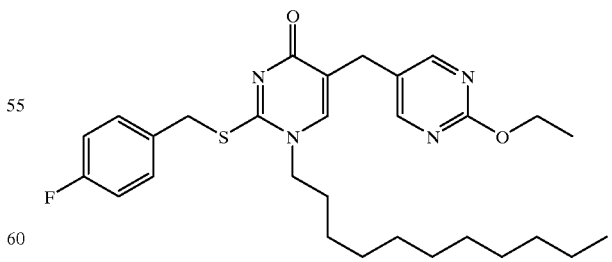

Prepared from intermediate B92 by general method A3 as an off-white solid. ¹H-NMR (CDCl₃) δ 0.8–0.95 (3H, m), 1.15–1.4 (16H, m), 1.43 (3H, t), 1.55–1.8 (2H, m), 3.68 (2H, s), 3.71 (2H, t), 4.41 (2H, q), 4.47 (2H, s), 6.86 (1H, s), 6.9–7.1 (2H, m), 7.3–7.45 (2H, m), 8.45 (2H, d); MS (APCI⁺) found (M+1)=527; $C_{29}H_{39}FN_4O_2S$ requires 526.

Example 245

1-(Undec-1-yl)-2-(4-fluorobenzyl)thio-5-(2-methylpyrimid-5-ylmethyl)pyrimidin-4-one

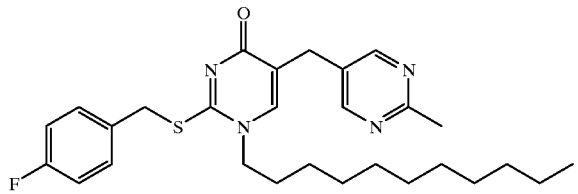

Prepared from intermediate B135 by general method A2.
¹H-NMR (CDCl₃) δ 0.88 (3H, t), 1.25 (16H, m), 1.68 (2H, m), 2.72 (3H, s), 3.68 (2H, s), 3.72 (2H, t), 4.47 (2H, s), 6.89 (1H, s), 6.97 (2H, m), 7.38 (2H, m), 8.58(2H, s); MS (APCI⁺) found (M+1)=497; $C_{28}H_{37}N_4OS$ requires 496.

Example 246

1-(2-Phenylethyl)-2-(4-fluorobenzyl)thio-5-((1-methyl-2-oxo-pyrid-4-yl)methyl)pyrimidin-4-one

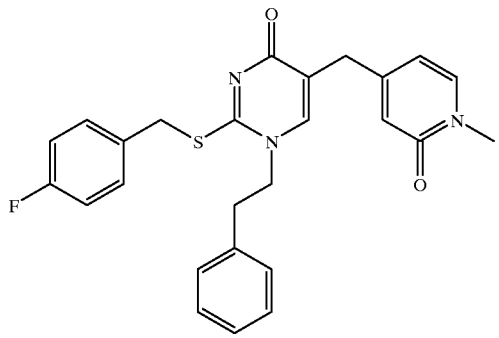

Prepared from intermediate B70 by general method A2.
¹H-NMR (CDCl₃) δ 3.01 (2H, t), 3.40 (2H, s), 3.51 (3H, s), 3.97 (2H, t), 4.51 (2H, s), 6.02 (1H, m), 6.24 (1H, s), 6.49 (1H, s), 6.98–7.43 (10H, m); MS (APCI⁺) M+1=462; $C_{26}H_{24}FN_3O_2S$ requires 461. MPt 69–75° C. (cream solid).

Example 247

1-(Undec-1-yl)-2-(4-fluorobenzyl)thio-5-((1-methyl-2-oxo-pyrid-4-yl)methyl)pyrimidin-4-one

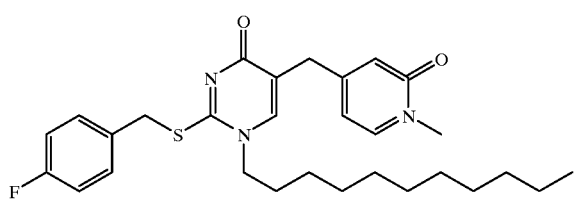

Prepared from intermediate B110 by general method A2.
¹H-NMR (CDCl₃) δ 0.88 (3H, t), 1.25 (16H, m), 1.69 (2H, m), 3.50 (3H, s), 3.55 (2H, s), 3.71 (2H, t), 4.78 (2H, s), 6.17 (1H, m), 6.38 (1H, d), 6.84 (1H, s), 6.96 (2H, m), 7.19 (1H, m), 7.39 (2H, m); MS (APCI⁺) M+1=512, $C_{29}H_{38}FN_3O_2S$ requires 511. MPt 78–79° C. (colourless solid).

Example 248

1-(Undec-1-yl)-2-(4-fluorobenzyl)thio-5-(1-methyl-2-oxopyrimid-5-ylmethyl)pyrimidin-4-one

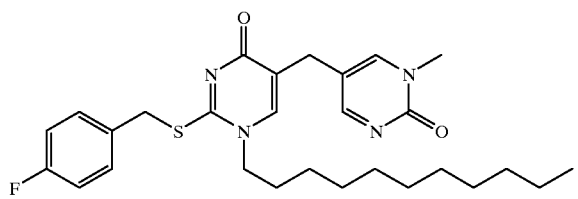

Prepared from Example 239 by treatment with methyl iodide (1 equiv) and potassium carbonate (2 equiv) in DMF. The misture was stirred at room temperature for 16 hours, then at 50° C. for 1 hour. Evaporation of the solvent, aqueous workup and chromatography gave the title compound in 72% yield. ¹H-NMR (CDCl₃) δ 0.8–0.95 (3H, m), 1.15–1.4 (16H, m), 1.6–1.85 (2H, m), 3.43 (2H, bs), 3.54 (3H, s), 3.78 (2H, t), 4.46 (2H, s), 6.9–7.1 (2H, m), 7.19 (1H, s), 7.25–7.45 (2H, m), 8.01 (1H, bd), 8.46 (1H, m).

Example 249

1-(Undec-1 -yl)-2-(4-fluorobenzyl)thio-5(1-benzyl-2-oxopyrimid-5-ylmethyl)pyrimidin-4-one

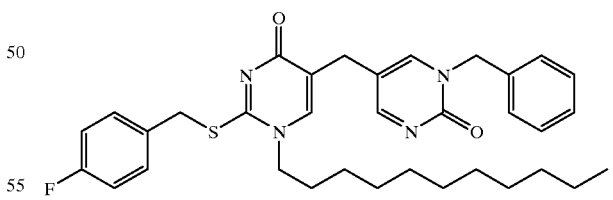

Prepared from Example 239 analogously to Example 248, using benzyl bromide in place of methyl iodide. ¹H-NMR (CDCl₃) δ 0.8–0.95 (3H, m), 1.15–1.4 (16H, m), 1.6–1.85 (2H, m), 3.39 (2H, s), 3.74 (2H, t), 4.46 (2H, s), 5.08 (2H, s), 6.9–7.1 (3H, m), 7.25–7.45 (7H, m), 7.94 (1H, d), 8.43 (1H, d); MS (APCI⁺) found (M+1)=589; $C_{34}H_{41}FN_4O_2S$ requires 588.

Example 250

1-(Undec-1-yl)-2-benzylthio-5-(pyrimid-5-ylmethyl)pyrimidin-4-one

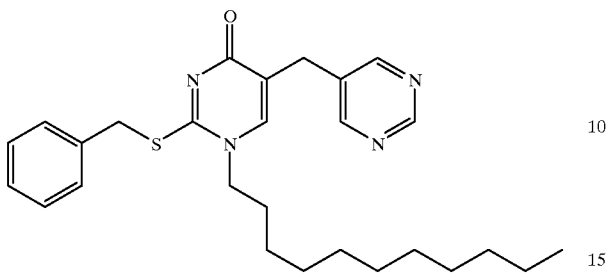

Prepared from intermediate B95 by general method A4.
$^1$H-NMR (CDCl$_3$) δ 0.88 (3H, t), 1.25 (16H, br s), 1.71 (2H, m), 3.71 (2H, s), 3.74 (2H, m), 4.49 (2H, s), 7.04 (1H, s), 7.26–7.41 (5H, m), 8.69 (2H, s), 9.09 (1H, s); MS (APCI) found (M+H)=465; C$_{27}$H$_{36}$N$_4$OS requires 464.

Example 251

1-Methyl-2-(4-fluorobenzyl)thio-5-(2-methoxypyrimid-5-ylmethyl)-pyrimidin-4-one

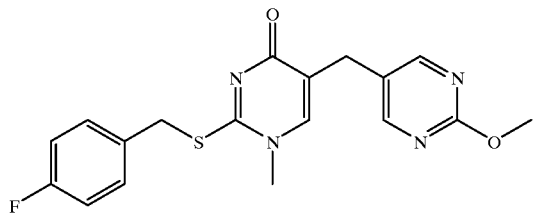

Prepared from Example 108 by general method C2.
$^1$H-NMR (CDCl3) δ 3.47 (3H, s), 3.64 (2H, t), 3.99 (3H, s), 4.47 (2H, s), 6.88 (1H, s), 6.9–7.1 (2H, m), 7.3–7.5 (2H, m), 8.44 (2H, s); MS (APCI+) found (M+1) 373; C$_{18}$H$_{17}$FN$_4$O$_2$S requires 372.

Example 252

1-Methyl-2-(4-fluorobenzyl)thio-5-(2-oxopyrimid-5-ylmethyl)pyrimidin-4-one

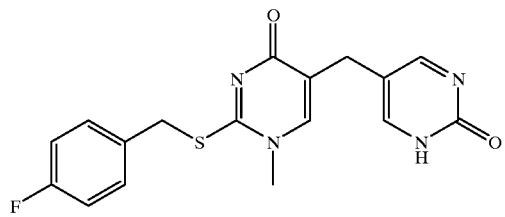

To a solution of Example 251 (5 g) in dry methylene chloride was added a solution of boron tribromide 1M in dichloromethane (50 ml) at 5° C. under argon with stirring. After 0.5 h, the mixture was allowed to warm to room temperature and was allowed to stir at room temperature for 72 h. The mixture was decanted into a mixture of ice (50 ml) and 0.880 ammonia (50 ml). The solid remaining in the flask was treated with some of the aqueous mixture and 10% methanol in methylene chloride. The entire mixture was filtered through kieselguhr and the organic layer was separated. The aqueous layer was reduced to one quarter volume in vacuo and the solid formed filtered off, washed with water and dried in vacuo to give the desired product (2.2 g).
$^1$H-NMR (d$_6$ DMSO) δ 3.30 (2H, s), 3.47 (3H, s), 4.41 (2H, s), 7.05–7.25 (2H, m), 7.4–7.55 (2H, m), 7.65 (1H, s), 7.85–8.3 (2H, b): MS (APCI+) found (M+1) 359; C$_{17}$H$_{15}$FN$_4$O$_2$S requires 358.

Example 253

1-(4-Acetylphenyl)-2-(4-fluorobenzyl)thio-5-(pyrimid-5-ylmethyl)-pyrimidin-4-one

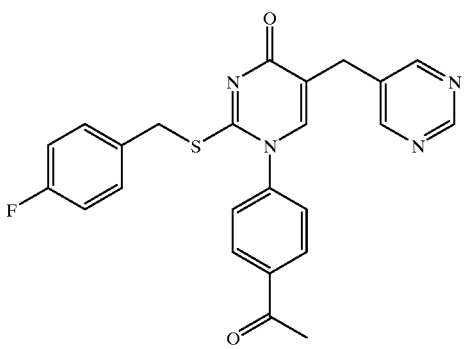

Prepared from intermediate B136 by general method A4.
$^1$H-NMR (CDCl$_3$) δ 2.64(3H, s), 3.79(2H, s), 4.39(2H, s), 6.95(2H, m), 7.05(1H, s), 7.29(2H, m), 7.43(2H, d, j=8.5 Hz), 8.08(2H, d, j=8.5), 8.75(2H, s), 9.09(1H, s): MS (APCI) found (M+H)=447; C$_{24}$H$_{19}$FN$_4$O$_2$S requires 446.

Example 254

1-(3-(Non-1-yloxy)phenyl)-2-(4-fluorobenzyl)thio-5-(pyrimid-5-ylmethyl)pyrimidin-4-one

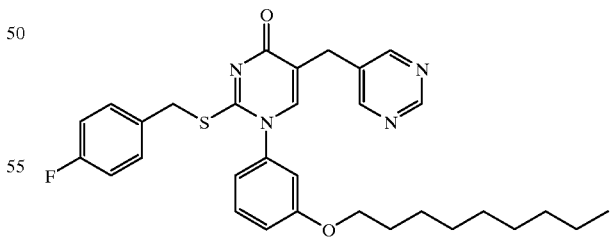

Prepared from intermediate B128 by general method A2.
$^1$H-NMR (CDCl$_3$) δ 9.08 (1H, s), 8.73 (2H, s), 7.41–7.28 (3H, m), 7.09 (1H, s), 7.03–6.78 (5H, m), 4.36 (2H, s), 3.95 (2H, t), 3.73 (2H, s), 1.78 (2H, quintet), 1.47–1.23 (12H, m), 0.88 (3H, t); MS (APCI+) found (M+1)=547, C$_{31}$H$_{35}$FN$_4$O$_2$S requires 546.

Example 255

1-(3-(Dec-1-yl)phenyl)-2-(4-fluorobenzyl)thio-5-(pyrimid-5-ylmethyl)pyrimidin-4-one

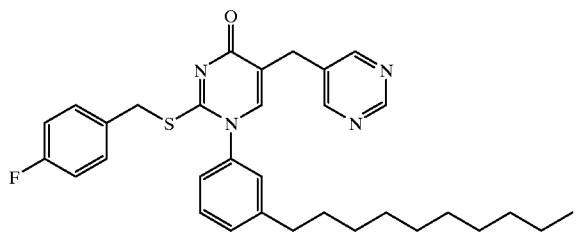

Prepared from intermediate B129 by general method A2. $^1$H-NMR (CDCl$_3$) δ 9.08 (1H, s), 8.73 (2H, s), 7.40–7.27 (4H, m), 7.11–7.08 (3H, m), 6.94 (2H, t), 4.35 (2H, s), 3.73 (2H, s), 2.65 (2H, t), 1.67–1.56 (2H, m), 1.30–1.22 (14H, m), 0.88 (3H, t); MS (APCI+) found (M+1)=545, C$_{32}$H$_{37}$FN$_4$OS requires 544.

Example 256

1-Methyl-2-(4-fluorobenzyl)thio-5-(1-undecyl-2-oxopyrimid-5-ylmethyl)pyrimidin-4-one

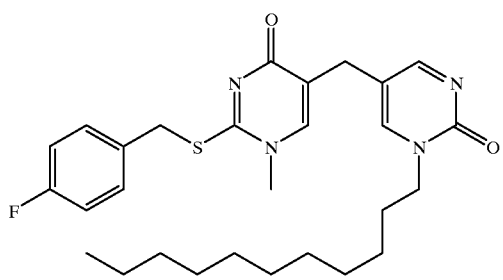

Prepared from Example 252 and undecyl iodide by the method of Example 248. $^1$H-NMR (CDCl3) δ 0.88 (3H, s), 1.2–1.4 (16H, m), 1.77 (2H, m), 3.43 (2H, s), 3.53 (3H, s), 3.86 (2H, t), 4.47 (2H, s), 6.9–7.1 (2H, m), 7.20 (1H, s), 7.3–7.45 (2H, m), 7.96 (1H, d), 8.44 (1H, d); MS (APCI+) found (M+1)=513; C$_{28}$H$_{37}$FN$_4$O$_2$S requires 512.

Example 257

1-Phenyl-2-(4-fluorobenzyl)thio-5-(pyrimid-5-ylmethyl)pyrimidin-4-one

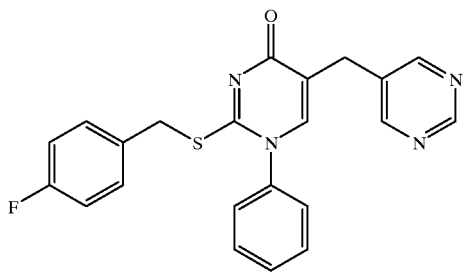

Prepared from intermediate B121 by general method A2. $^1$H NMR (CDCl$_3$) δ: 3.74 (s, 2H), 4.36 (s, 2H), 6.95 (t, 2H), 7.06 (s, 1H), 7.30 (m, 4H), 7.55 (m, 3H), 8.72 (s, 2H), 9.10 (s, 1H). MS (APCI+) Found (M+1)=405; C$_{22}$H$_{17}$FN$_4$OS requires 404.

Example 258

1-Phenyl-2-(8-(4-chlorophenyl)-8-oxooct-1-yl)thio-5-(pyrimid-5-ylmethyl)pyrimidin-4-one

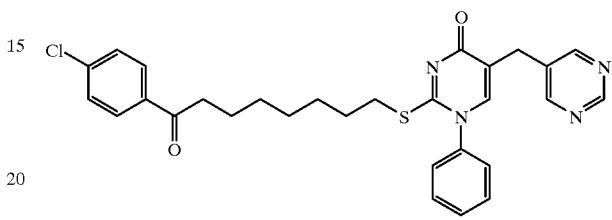

Prepared from intermediate B121 by general method A2. $^1$H NMR (CDCl$_3$) δ: 1.35 (m, 6H), 1.65 (m, 4H), 2.91 (t, 2H), 3.14 (t, 2H), 3.76 (s, 2H), 7.04 (s, 1H), 7.3 (m, 2H), 7.43 (d, 2H), 7.55 (m, 3H), 7.89 (d, 2H), 8.72 (s, 2H), 9.10 (s, 1H). MS (APCI+) Found (M+1)=533/535; C$_{29}$H$_{29}$ClN$_4$O$_2$S requires 533.

Example 259

1-(4-(Non-1-yloxyphenyl))-2-(4-fluorobenzyl)thio-5-(pyrimid-5-ylmethyl)pyrimidin-4-one

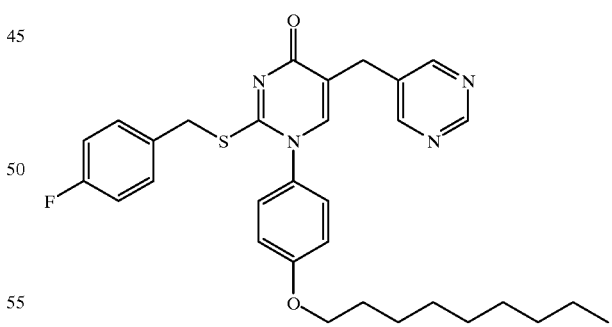

Prepared from intermediate B126 by general method A2. $^1$H-NMR (CDCl$_3$) δ 9.07 (1H, s), 8.73 (2H, s), 7.30 (2H, dd), 7.21 (2H, d), 7.13 (1H, s), 6.95 (2H, d), 6.94 (2H, t), 4.33 (2H, s), 3.97 (2H, t), 3.73 (2H, s), 1.79 (2H, quintet), 1.47–1.23 (12H, m), 0.88 (3H, t); MS (APCI+) found (M+1)=547, C$_{31}$H$_{35}$FN$_4$O$_2$S requires 546.

Example 260

1-(4-Iodophenyl)-2-(4-fluorobenzyl)thio-5-(pyrimid-5-ylmethyl)pyrimidin-4-one

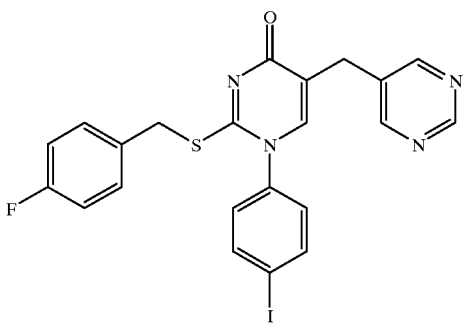

Prepared from intermediate B130 by general method A2. $^1$H-NMR (CDCl$_3$+CD$_3$OD) δ 9.08 (1H, s), 8.72 (2H, s), 7.85 (2H, d), 7.33–7.26 (2H, m), 7.07 (1H, s), 7.05 (2H, d), 6.98 (2H, t), 4.35 (2H, s), 3.73 (2H, s); MS (APCI+) found (M+1)=531, C$_{22}$H$_{16}$FIN$_4$OS requires 530.

Example 261

1-(4-(Hex-1-yl)phenyl)-2-(4-fluorobenzyl)thio-5-(pyrimid-5-ylmethyl)pyrimidin-4-one

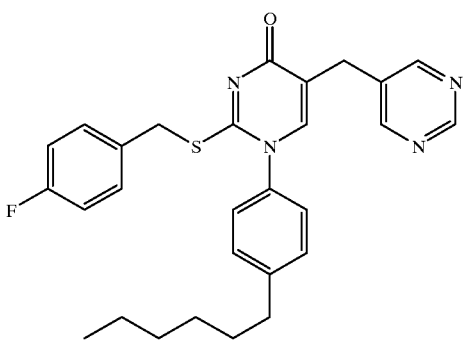

Prepared from intermediate B127 by general method A2. $^1$H-NMR (CDCl$_3$) δ 9.08 (1H, s), 8.73 (2H, s), 7.33–7.27 (4H, m), 7.19 (2H, d), 7.09 (1H, s), 6.94 (2H, t), 4.35 (2H, s), 3.73 (2H, s), 2.66 (2H, t), 1.62 (2H, quintet), 1.39–1.27 (6H, m), 0.87 (3H, t); MS (APCI+) found (M+1)=489, C$_{28}$H$_{29}$FN$_4$OS requires 488.

Example 262

1-(4-(Dec-1-yl)phenyl)-2-(4-fluorobenzyl)thio-5-(pyrimid-5-ylmethyl)pyrimidin-4-one

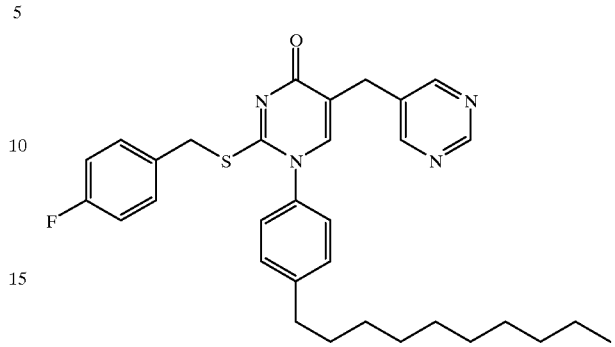

Prepared from intermediate B125 by general method A2. $^1$H-NMR (CDCl$_3$) δ 9.08 (1H, s), 8.73 (2H, s), 7.33–7.27 (4H, m), 7.19 (2H, d), 7.10 (1H, s), 6.94 (2H, t), 4.35 (2H, s), 3.73 (2H, s), 2.65 (2H, t), 1.67–1.56 (2H, m), 1.34–1.22 (14H, m), 0.88 (3H, t); MS (APCI+) found (M+1)=545, C$_{32}$H$_{37}$FN$_4$OS requires 544.

Example 263

1-Ethoxycarbonylmethyl-2-(8-(4-chlorophenyl)-8-oxooct-1-yl)thio-5-(pyrimid-5-ylmethyl)pyrimidin-4-one

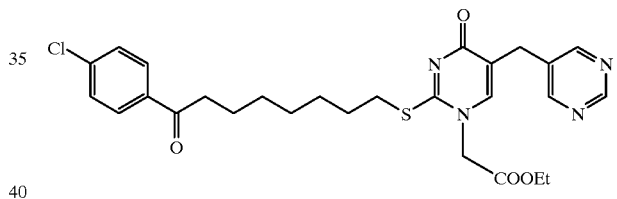

Prepared from intermediates B80 and A1 by general method A4, as a light brown crystalline solid. MPt 100–102° C.; $^1$H-NMR (CDCl$_3$) δ 1.30 (3H, t), 1.37 (6H, m), 1.70 (4H, m), 2.93 (2H, t), 3.26 (2H, t), 3.71 (2H, s), 4.28 (2H, q), 4.50 (2H, s), 6.90 (1H, s), 7.44 (2H, m), 7.90 (2H, m), 8.71 (2H, s), 9.10 (1H, s); MS APCI+) found (M+1)=543; C$_{27}$H$_{31}$ClN$_4$O$_4$S requires 542.

Example 264

1-(3-Ethoxycarbonylprop-1-yl)-2-(8-(4-chlorophenyl)-8-oxooct-1-yl)thio-5-(pyrimid-5-ylmethyl)pyrimidin-4-one

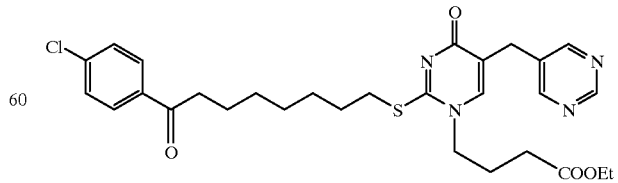

Prepared from intermediates B50 and A1 by general method A4, as a brown oil. $^1$H-NMR (CDCl$_3$) δ 1.27 (3H, t), 1.38 (6H, m), 1.69 (4H, m), 2.05 (2H, m), 2.38 (2H, t), 2.93 (2H, t), 3.25 (2H, t), 3.70 (2H, s), 3.88 (2H, t), 4.12 (2H, q), 7.05 (1H, s), 7.42 (2H, d), 7.91 (2H, d), 8.72 (2H, s), 9.09 (1H, s); MS (APCI+) found (M+1)=571; $C_{29}H_{35}ClN_4O_4S$ requires 570.

Example 265

1-(3-Ethoxycarbonylprop-1-yl)-2-benzylthio-5-(pyrimid-5-ylmethyl)pyrimidin-4-one

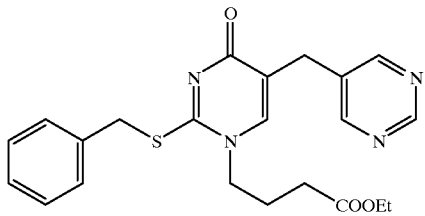

Prepared from intermediate B50 by general method A4, as a brown oil. $^1$H-NMR (CDCl$_3$) δ 1.24 (3H, t), 2.01 (2H, m), 2.35 (2H, m), 3.71 (2H, s), 3.86 (2H, t), 4.12 (2H, q), 4.50 (2H, s), 7.07 (1H, s), 7.27–7.41 (5H, m), 8.72 (2H, s), 9.12 (1H, s); MS (APCI+) found (M+1)=425; $C_{22}H_{24}N_4O_3S$ requires 424.

Example 266

1-(3-Ethoxycarbonylprop-1-yl)-2-(3,4-difluorobenzyl)thio-5-(pyrimid-5-ylmethyl)pyrimidin-4-one

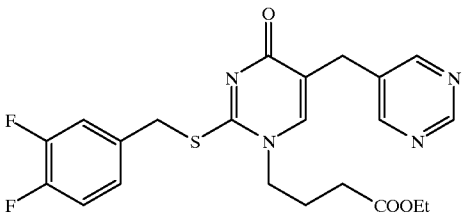

Prepared from intermediate B50 by general method A2 as an oil. $^1$H-NMR (CDCl$_3$) δ 1.17–1.30 (3H, m), 1.96–2.12 (2H, m), 2.30–2.41 (2H, t), 3.70 (2H, s), 3.70 (2H, s), 3.80–3.90 (2H, t), 4.06–4.20 (2H, q), 4.49 (2H, s), 7.01–7.26 (4H, m), 8.72 (2H, s), 9.10 (1H, s); MS (ES+) found (M+1)=461; $C_{22}H_{22}F_2N_4O_3S$ requires 460.

Example 267

1-(3-Ethoxycarbonylprop-1-yl)-2-(4-fluorobenzyl)thio-5-(pyrimid-5-ylmethyl)pyrimidin-4-one

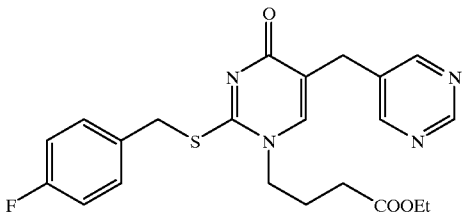

Prepared from intermediate B50 by general method A2. $^1$H-NMR (CDCl$_3$) δ 1.26 (3H, t), 2.03 (2H, m), 2.35 (2H, t), 3.70 (2H, s), 3.85 (2H, t), 4.12 (2H, m), 4.47 (2H, s), 6.71–7.07 (3H, m), 7.35–7.41 (2H, m), 8.70 (2H, s), 9.10 (1H, s); MS (APCI$^+$) M+1=443, $C_{22}H_{23}FN_4O_3S$ requires 442 (orange oil).

Example 268

1-(5-Ethoxycarbonylpent-1-yl)-2-(3,4-difluorobenzyl)thio-5-(pyrimid-5-ylmethyl)pyrimidin-4-one

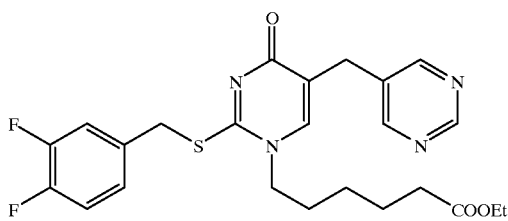

Prepared from intermediate B102 by general method A2 as an oil. $^1$H-NMR (CDCl$_3$) δ 1.14–1.87 (9H, m), 2.25–2.37 (2H, m), 3.63–3.82 (4H, m), 4.04–4.19 (2,q), 4.45 (2H, s), 6.97–7.30 (4H, m), 8.70 (2H, s), 9.10 (1H, s); MS (ES+) found (M+1)=489; $C_{24}H_{26}F_2N_4O_3S$ requires 488.

Example 269

1-(1-(Ethoxycarbonyl)cycloprop-1-yl)-2-(4-fluorobenzyl)thio-5-(pyrimid-5-ylmethyl)pyrimidin-4-one

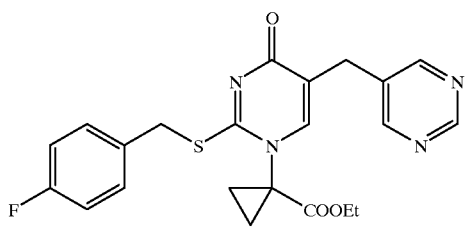

Prepared from intermediate B106 by general method A2 as a foam. $^1$H-NMR (CDCl$_3$) δ 1.08–1.20 (3H, t), 1.38–1.54 (1H, m), 1.58–1.85 (2H, m), 1.94–2.10 (1H, m), 3.71 (2H, s), 4.04–4.28 (2H, m), 4.35–4.52 (2H, q), 6.90–7.05 (2H, t), 7.08 (1H, s), 7.29–7.42 (2H, m), 8.70 (2H, s), 9.10 (1H, s); MS (APCI$^+$) found (M+1)=441; $C_{22}H_{21}FN_4O_3S$ requires 440.

Example 270

1-(4-Fluorobenzyloxycarbonylmethyl)-2-(4-fluorobenzyl)thio-5-(pyrimid-5-ylmethyl)pyrimidin-4-one

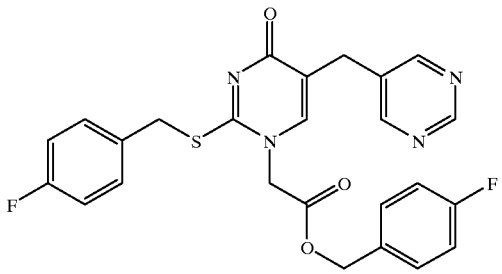

Prepared from intermediate B80 by alkaline hydrolysis as in general method D, followed by alkylation with 4-fluorobenzyl bromide by general method A2. $^1$H-NMR (CDCl$_3$) δ 3.71 (2H, s), 4.46 (4H, m), 5.16 (2H, s), 6.87 (1H, s), 6.94–7.06 (4H, m), 7.25–7.35 (4H, m) 8.68 (2H, s), 9.10 (1H, s); MS(APCI$^+$) M+1=495, C$_{25}$H$_{20}$F$_2$N$_4$O$_3$S requires 494. MPt 184–186° C. (colourless solid). MPt. 184–186

Example 271

1-Ethoxycarbonylmethyl-2-(4-fluorobenzyl)thio-5-(pyrimid-5-ylmethyl)pyrimidin-4-one

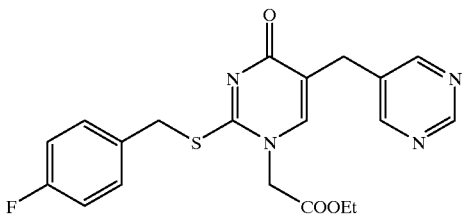

Prepared from intermediate B80 by general method A2. $^1$H-NMR (CDCl$_3$) δ 1.26 (3H, t), 3.71 (2H, s), 4.26 (2H, q), 4.46 (2H, s), 4.48 (2H, s), 6.91 (1H, s), 6.98 (2H, m), 7.35 (2H, m), 8.70 (2H, s), 9.09 (1H, s); MS(APCI$^+$) M+1=415, C$_{20}$H$_{19}$FN$_4$O$_3$S requires 414. MPt 145.1 ° C. (yellow solid).

Example 272

1-(1-(Methoxycarbonyl)ethyl)-2-(4-fluorobenzyl)thio-5-(pyrimid-5-ylmethyl)pyrimidin-4-one

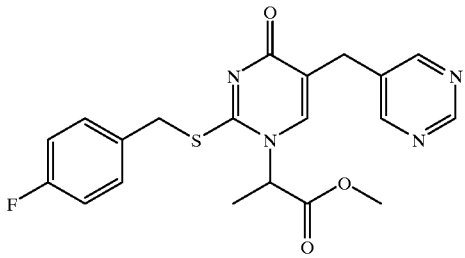

Prepared from intermediate B103 by general method A2 as a solid. $^1$H-NMR (CDCl$_3$) δ 1.68 (3H, d), 3.70 (2H, s), 3.78 (3H, s), 4.38–4.58 (2H, br.q), 4.98–5.10 (1H, q), 6.95–7.07 (2H, t), 7.19 (1H, s), 7.30–7.42 (2H, m), 8.72 (2H, s), 9.10 (1H, s); MS (APCI$^+$) found (M+1)=429, C$_{20}$H$_{19}$FN$_4$O$_3$S requires 428.

Example 273

1-(trans-4-(Methoxycarbonyl)cyclohex-1-ylmethyl)-2-(4-fluorobenzyl)thio-5-(pyrimid-5-ylmethyl)pyrimidin-4-one

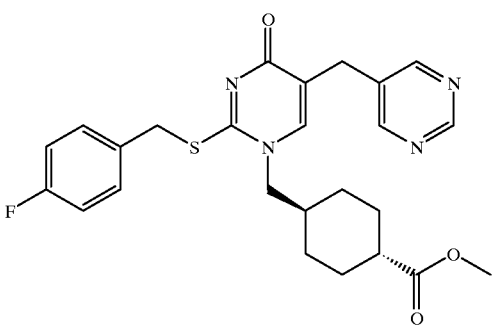

Prepared from intermediate B137 by general method A2 as a solid. $^1$H-NMR (CDCl$_3$) δ 0.88–1.11 (2H, m), 1.30–1.54 (2H, m), 1.60–1.82 (4H, m), 1.94–2.13 (1H, m), 2.14–2.34 (1H, m), 3.53–3.74 (7H, m), 4.46 (2H, s), 6.90 (1H, s), 6.94–7.08 (2H, t), 7.30–7.44 (2H, m), 8.70 (2H, s), 9.11 (1H, s); MS (APCI$^+$) found (M+1)=483; C$_{25}$H$_{27}$FN$_4$O$_3$S requires 482.

Example 274

1-(trans-4-(Methoxycarbonyl)cyclohex-1-yl)-2-(4-fluorobenzyl)thio-5-(pyrimid-5-ylmethyl)pyrimidin-4-one

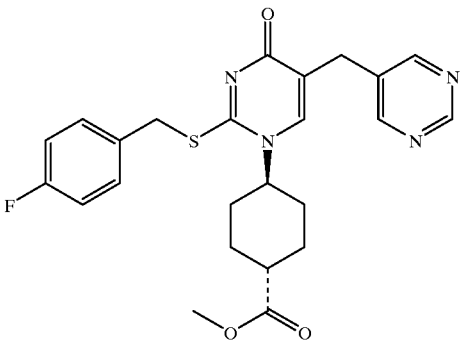

Prepared from intermediate B108 by general method A2 as a solid. $^1$H-NMR (CDCl$_3$) δ 1.54–1.97 (6H, m), 2.22–2.39 (2H, d), 2.68–2.79 (1H, br.s), 3.70 (2H, s), 3.73 (3H, s), 4.03–4.25 (1H, m), 4.45 (2H, s), 6.93–7.08 (2H, m), 7.21 (1H, s), 7.30–7.43 (2H, m), 8.71 (2H, s), 9.08 (1H, s). MS (APCI$^+$) found (M+1)=469; C$_{24}$H$_{25}$FN$_4$O$_3$S requires 468.

Example 275

1-(3-Ethoxycarbonylprop-1-yl)-2-(4-fluorobenzyl)thio-5-(((1-methyl-2-oxo-pyrid-4-yl)methyl)pyrimidin-4-one

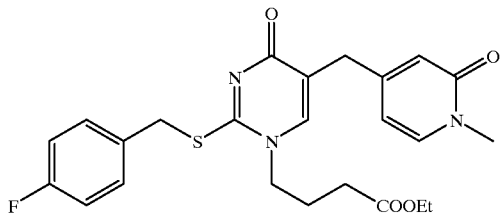

Prepared from intermediate B111 by general method A2. $^1$H-NMR (CDCl$_3$) δ 1.25 (3H, t), 2.02 (2H, m), 2.35 (2H, t), 3.50 (3H, s), 3.54 (2H, s), 3.83 (2H, t), 4.12 (2H, q), 4.47 (2H, s), 6.19 (1H, m), 6.37 (1H, s), 6.84–7.41 (6H, m). MS (APCI$^+$) M+1=472; C$_{24}$H$_{26}$FN$_3$O$_4$S requires 471. MPt 109–111° C. (colourless solid). MPt. 109–111

Example 276

1-(Ethoxycarbonylmethyl)-2-(4-fluorobenzyl)thio-5-(2-methoxypyrimid-5-ylmethyl)pyrimidin-4-one

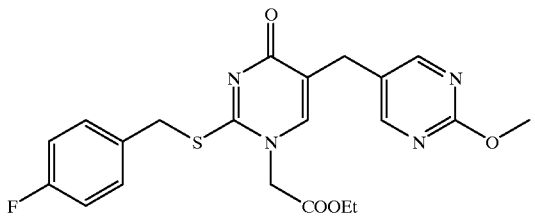

Prepared from Example 108 by general method C2. $^1$H-NMR (CDCl$_3$) δ 1.26 (3H, t), 3.66 (2H, s), 3.99 (3H, s), 4.23 (2H, q), 4.47 (2H, s), 4.48 (2H, s), 6.84 (1H, s), 6.98 (2H, m), 7.34 (2H, m), 8.44 (2H, s); MS (APCI+) found (M+1)=445; C$_{21}$H$_{21}$FN$_4$O$_4$S requires 444.

Example 277

1-(4-(Ethoxycarbonyl)benzyl)-2-(4-fluorobenzyl)thio-5-(pyrimid-5-methyl)pyrimidin-4-one

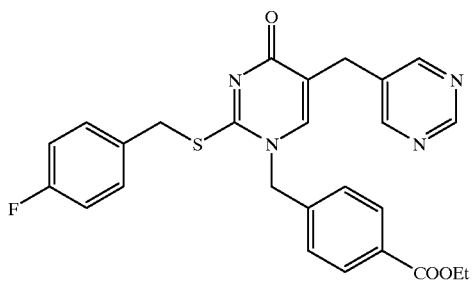

Prepared from intermediate B107 by general method A2 as a solid. $^1$H-NMR (CDCl$_3$) δ 1.35–1.47 (3H, t), 3.70 (2H, s), 3.93 (1H, s), 4.32–4.52 (3H, m), 5.02 (2H, s), 6.90–7.06 (3H, m), 7.13–7.40 (4H, m), 7.98–8.10 (2H, d), 8.67 (2H, s), 9.09 (1H, s); MS (APCI$^+$) found (M+1)=491; C$_{26}$H$_{23}$FN$_4$O$_3$S requires 490.

Example 278

1-(4-Methoxycarbonylbenzyl)-2-(8-(4-chlorophenyl)oct-1-yl)thio-5-(pyrid-3-ylmethyl)pyrimidin-4-one

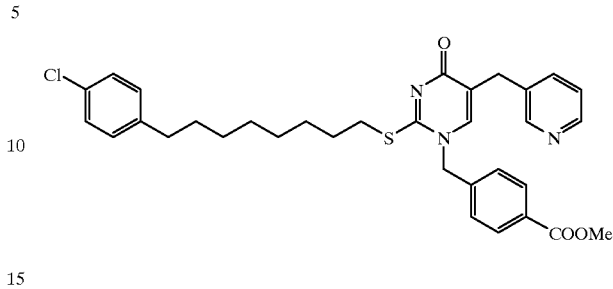

Prepared from Example 70 by general method C1. $^1$H-NMR (CDCl$_3$) δ 1.2–1.45(8H, m), 1.45–1.75(4H, m), 2.55(2H, t), 3.24(2H, t), 3.73(2H, s), 3.92(3H, s), 5.01(2H, s), 6.81(1H, s), 7.05–7.3(7H, m), 7.61(1H, txd), 8.03(2H, d) and 8.46(2H, bs); MS (EI) found M=589; C$_{33}$H$_{36}$ClN$_3$O$_3$S requires 589.

Example 279

1-(3-Carboxyprop-1-yl)-2-(4-fluorobenzyl)thio-5-(pyrimid-5-ylmethyl)pyrimidin-4-one

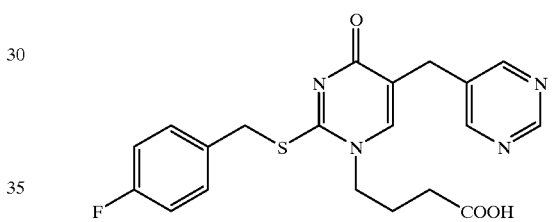

Prepared from Example 267 by general method D. $^1$H-NMR (d$_6$-DMSO) δ 1.93 (2H, m), 2.29 (2H, t), 3.58 (2H, s), 3.87 (2H, t), 4.40 (2H, s), 7.14 (2H, m), 7.48 (2H, m), 7.81 (1H, s), 8.70 (2H, s), 9.02 (1H, s); MS (APCI−) M−1=413, C$_{20}$H$_{19}$FN$_4$O$_3$S requires 414. MPt 188–190° C. (colourless solid).

Example 280

1-Carboxymethyl-2-(4-fluorobenzyl)thio-5-(pyrimid-5-ylmethyl)pyrimidin-4-one

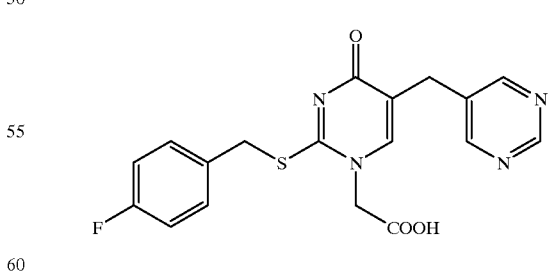

Prepared from Example 271 by general method D. $^1$H-NMR (d$_6$-DMSO) δ 3.59 (2H, s), 4.41 (2H, s), 4.67 (2H, s), 7.11 (2H, m), 7.45 (2H, m), 7.72 (1H, s), 8.70 (2H, s), 9.03 (1H, s), 13.55 (1H, bs); MS (APCI−) M−1=385, C$_{18}$H$_{15}$FN$_4$O$_3$S requires 386. MPt 206–207° C. (colourless solid).

Example 281

1-(3-Carboxyprop-1-yl)-2-(4-fluorobenzyl)thio-5-((1-methyl-2-oxo-pyrid-4-yl)methyl)pyrimidin-4-one

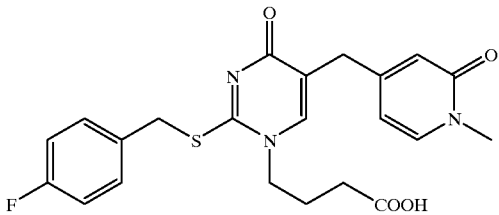

Prepared from Example 275 by general method D. $^1$H-NMR (d$_6$-DMSO) δ 1.90 (2H, m), 2.28 (2H, t), 3.37 (5H, m), 3.86 (2H, t), 4.41 (2H, s), 6.12 (1H, m), 6.18 (1H, s), 7.14 (2H, m), 7.50 (3H, m), 7.73 (1H, s), 12.2 (1H, bm); MS (APCI$^+$) M+1=444, C$_{22}$H$_{22}$FN$_3$O$_4$S requires 443. MPt 245–249° C. (colourless solid).

Example 282

1-(3-Carboxyprop-1-yl)-2-(3,4-difluorobenzyl)thio-5-(pyrimid-5-ylmethyl)pyrimidin-4-one

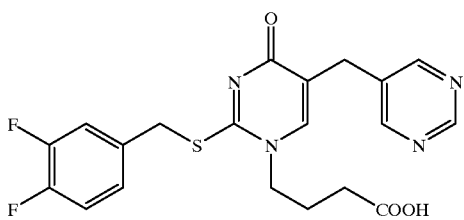

Prepared from Example 266 by general method D as a white solid. $^1$H-NMR (DMSO) δ 1.83–2.03 (2H, m), 2.24–2.37 (2H, t), 3.58 (2H, s), 3.81–3.93 (2H, t), 4.41 (2H, s), 7.23–7.59 (3H, m), 7.81 (1H, s), 8.71 (2H, s), 9.02 (1H, s), 12.13–12.20 (1H, s); MS (APCI−) found (M−1) 431; C$_{20}$H$_{18}$F$_2$N$_4$O$_3$S requires 432.

Example 283

1-(5-Carboxypent-1-yl)-2-(3,4-difluorobenzyl)thio-5-(pyrimid-5-ylmethyl)pyrimidin-4-one

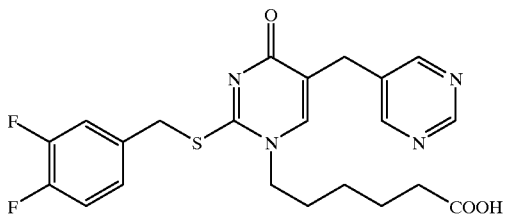

Prepared from Example 268 by general method D as a white solid. $^1$H-NMR (DMSO) δ 1.18–1.81 (6H, m), 2.14–2.29 (2H, t), 3.59 (2H, s), 3.76–3.90 (2H, t), 4.41 (2H, s), 7.23–7.60 (3H, m), 7.85 (1H, s), 8.70 (2H, s), 9.02 (1H, s), 11.92–12.10 (1H, s); MS (APCI−) found (M−1)=459; C$_{22}$H$_{22}$F$_2$N$_4$O$_3$S requires 460.

Example 284

1-(4-Carboxybenzyl)-2-(4-fluorobenzyl)thio -5-(pyrimid-5-ylmethyl)-2-thiouracil

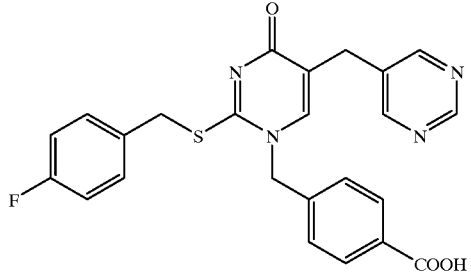

Prepared from Example 277 by general method D. $^1$H-NMR (DMSO) δ 3.60 (2H, s), 4.39 (2H, s), 5.21 (2H, s), 7.03–7.19 (2H, t), 7.26–7.49 (4H, m), 7.38–8.02 (3H, m), 8.72 (2H, s), 9.03 (1H, s), 12.92–13.10 (1H, br.s); MS (APCI+) found (M+1)=463; C$_{24}$H$_{19}$FN$_4$O$_3$S requires 462.

Example 285

1-(4-Carboxycyclohex-1-yl)-2-(4-fluorobenzyl)thio-5-(pyrimid-5-ylmethyl)-2-thiouracil

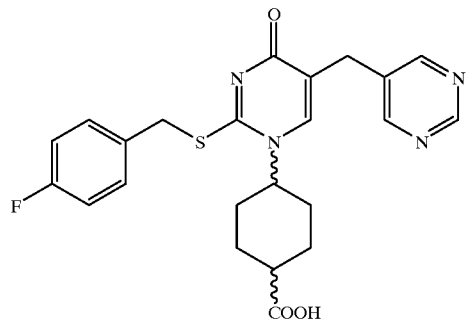

Prepared from Example 274 by general method D. $^1$H-NMR (DMSO) δ 1.57–1.88 (6H, m), 2.13–2.26 (2H, d), 2.60 (1H, s), 3.62 (2H, s), 3.98–4.10 (1H, m), 4.40 (2H, s), 7.09–7.19 (2H, t), 7.44–7.53 (2H, m), 8.00 (1H, s), 8.72 (2H, s), 9.00 (1H, s), 12.27 (1H, s); MS (APCI+) found (M+1)= 455; C$_{23}$H$_{23}$FN$_4$O$_3$S requires 454.

Example 286

1-(3-Ethoxycarbonylphenyl)-2-(4-fluorobenzyl)thio-5-(pyrimid-5-ylmethyl)pyrimidin-4-one

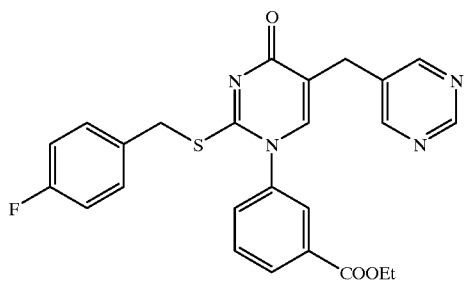

Prepared from intermediate B118 by general method A2. H NMR (CDCl$_3$) δ: 1.41 (t, 3H), 3.75 (s, 2H), 4.37 (s, 2H), 4.41 (q, 2H), 6.95 (t, 2H), 7.05 (s, 1H), 7.30 (m, 2H), 7.50 (m, 1H), 7.60 (t, 1H), 7.97 (m, 1H), 8.21 (d, 1H), 8.72 (s, 2H), 9.10 (s, 1H); MS (APCI+) Found (M+1)=477; C$_{25}$H$_{21}$FN$_4$O$_3$S requires 476.

Example 287

1-(3-Ethoxycarbonylphenyl)-2-(8-(4-chlorophenyl)-8-oxooct-1-yl)thio-5-(pyrimid-5-ylmethyl)pyrimidin-4-one

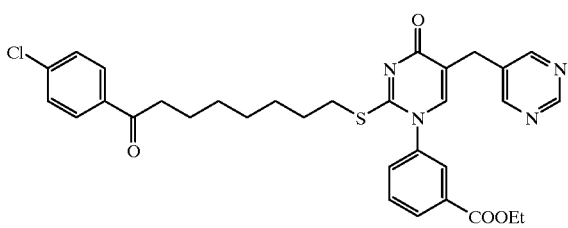

Prepared from intermediate B118 by general method A4. $^1$H NMR (CDCl$_3$) δ: 1.3 (m, 6H), 1.42 (t, 3H), 1.65 (m, 4H), 2.91 (t, 2H), 3.15 (t, 2H), 3.73 (s, 2H), 4.42 (q, 2H), 7.03 (s, 1H), 7.42 (d, 2H), 7.5 (m, 1H), 7.62 (t, 1H), 7.88 (d, 2H), 7.98 (s, 1H), 8.22 (d, 1H), 8.72 (s, 2H), 9.09 (s, 1H); MS (APCI+) Found (M+1)=605/607; C$_{32}$H$_{33}$ClN$_4$O$_4$S requires 605.

Example 288

1-(3-Carboxyphenyl)-2-(4-fluorobenzyl)thio-5-(pyrimid-5-ylmethyl)pyrimidin-4-one

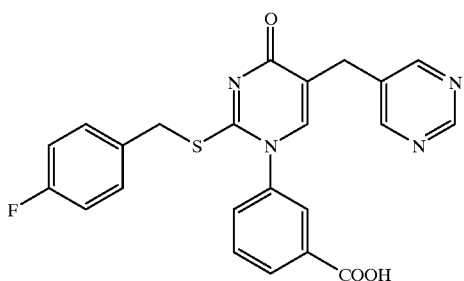

Prepared from Example 286 by general method D as a white solid, m.p 157–160. $^1$HNMR (DMSO-d$_6$) δ: 3.62 (s, 2H), 4.31 (s, 2H), 7.10 (t, 2H), 7.40 (m, 2H), 7.70 (t, 1H), 7.87 (d, 1H), 7.94 (s, 1H), 8.10 (m, 2H), 8.77 (s, 2H), 9.01 (s, 1H), 13.4 (br s, 1H); MS (APCI+) Found (M+1)=449; C$_{23}$H$_{17}$FN$_4$O$_3$S requires 448.

Example 289

1-(3-Carboxyphenyl)-2-(8-(4-chlorophenyl)-8-oxooct-1-yl)thio-5-(pyrimid-5-ylmethyl)pyrimidin-4-one

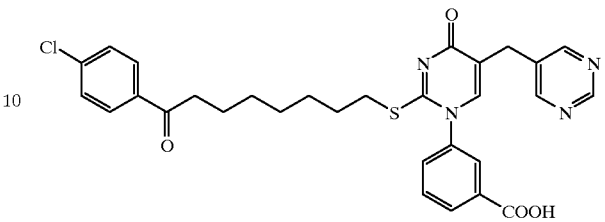

Prepared from Example 287 by general method D as a white solid, m.p 109–112°. $^1$H NMR (DMSO-d$_6$) δ: 1.3 (m, 6H), 1.65 (m, 4H), 2.9–3.1 (m, 4H), 3.60 (s, 2H), 7.57 (d, 2H), 7.71 (t, 1H), 7.8–8.0 (m, 4H), 8.13 (m, 2H), 8.75 (s, 2H), 9.02 (s, 1H) 13.35 (br s, 1H). MS (APCI+) Found (M+1)=577/579; C$_{30}$H$_{29}$ClN$_4$O$_4$S requires 577.

Example 290

1-(4-Ethoxycarbonylphenyl)-2-(4-fluorobenzyl)thio-5-(pyrimid-5-ylmethyl)pyrimidin-4-one

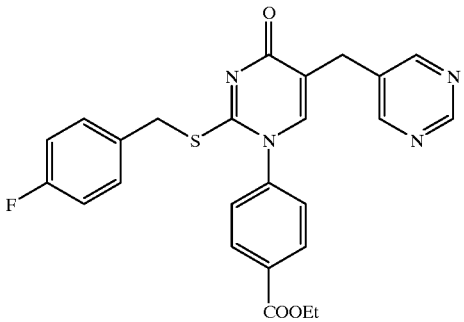

Prepared from intermediate B119 by general method A2. $^1$H NMR (CDCl$_3$) δ: 1.40 (t, 3H), 3.74 (s, 2H), 4.37 (s, 2H), 4.41 (q, 2H), 6.95 (t, 2H), 7.05 (s, 1H), 7.30 (m, 2H), 7.40 (d, 2H), 8.20 (d, 2H), 8.72 (s, 2H), 9.11 (s, 1H). MS (APCI+) Found (M+1)=477; C$_{25}$H$_{21}$FN$_4$O$_3$S requires 476.

Example 291

1-(4-Ethoxycarbonylphenyl)-2-(8-(4-chlorophenyl)-8-oxooct-1-yl)thio-5-(pyrimid-5-ylmethyl)pyrimidin-4-one

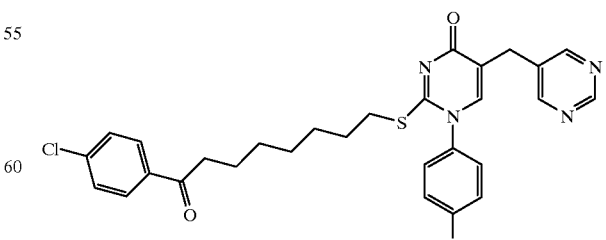

Prepared from intermediate B119 by general method A4. $^1$H NMR (CDCl$_3$) δ: 1.3 (m, 6H), 1.42 (t, 3H), 1.65 (m, 4H), 2.91 (t, 2H), 3.15 (t, 2H), 3.73 (s, 2H), 4.44 (q, 2H), 7.03 (s, 1H), 7.4 (m, 4H), 7.88 (d, 2H), 8.20 (d, 2H), 8.71 (s, 2H), 9.10 (s, 1H). MS (APCI+) Found (M+1)=605/607; $C_{32}H_{33}ClN_4O_4S$ requires 605.

Example 292

1-(4-Carboxyphenyl)-2-(4-fluorobenzyl)thio-5-(pyrimid-5-ylmethyl)pyrimidin-4-one

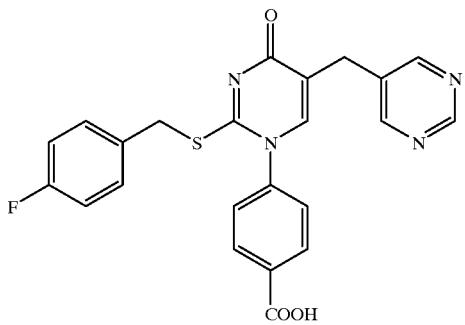

Prepared from Example 290 by general method D as a white solid, m.p.258–262° dec. ¹HNMR (DMSO-$d_6$) δ: 3.63 (s, 2H), 4.31 (s, 2H), 7.10 (t, 2H), 7.40 (m, 2H), 7.74 (d, 2H), 7.95 (s, 1H), 8.10 (d, 2H), 8.77 (s, 2H), 9.01 (s, 1H), 13.3 (br s, 1H). MS (APCI+) Found (M+1)=449; $C_{23}H_{17}FN_4O_3S$ requires 448.

Example 293

1-(4-Carboxyphenyl)-2-(8-(4-chlorophenyl)-8-oxooct-1-yl)thio-5-(pyrimid-5-ylmethyl)pyrimidin-4-one

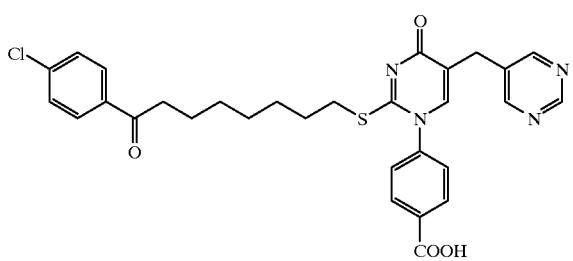

Prepared from Example 291 by general method D as a white solid, m.p 92–96° C. ¹H NMR (DMSO-$d_6$) δ: 1.3 (m, 6H), 1.6 (m, 4H), 2.9–3.1 (m, 4H), 3.61 (s, 2H), 7.57 (d, 2H), 7.74 (d, 2H), 7.95 (m, 3H), 8.10 (d, 2H), 8.75 (s, 2H), 9.02 (s, 1H) 13.35 (br s, 1H). MS (APCI+) Found (M+1)=577/579; $C_{30}H_{29}ClN_4O_4S$ requires 577.

Example 294

1-(5-(Ethoxycarbonyl)fur-2-yl)-2-(4-fluorobenzyl)thio-5-(pyrimid-5-ylmethyl)pyrimidin-4-one

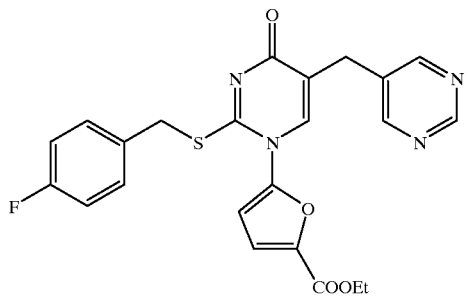

Prepared from intermediate B120 by general method A2. ¹H NMR (CDCl₃) δ: 1.38 (t, 3H), 3.72 (s, 2H), 4.38 (s, 2H), 4.39 (q, 2H), 6.60 (d, 1H), 6.97 (t, 2H), 7.08 (s, 1H), 7.20 (d, 1H), 7.3 (m, 2H), 8.71 (s, 2H), 9.11 (s, 1H). MS (APCI+) Found (M+1) 467; $C_{23}H_{19}FN_4O_4S$ requires 466.

Example 295

1-(3-Ethoxycarbonyl-4-iodobenzyl)-2-(4-fluorobenzyl)thio-5-(pyrimid-5-ylmethyl)pyrimidin-4-one

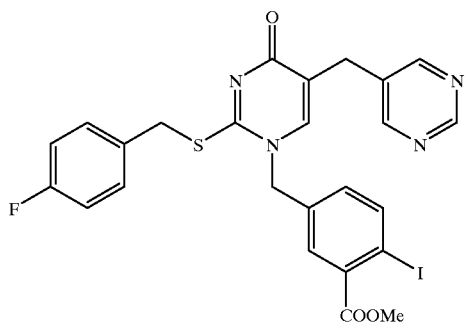

Prepared from Example 106 by general method C2 as a yellow solid. ¹H-NMR (250 MHz, DMSO) 9.03 (s, 1H), 8.82 (s, 2H), 8.00 (m, 2H), 7.57 (s, 1H), 7.42 (m, 2H), 7.11 (m, 3H), 5.14 (s, 2H), 4.39 (s, 2H), 3.87 (s, 3H), 3.62 (s, 2H). MS (AP+) 603 (M+H⁺, 100%).

Example 296

1-(3-(Hept-1-yloxy)-4-methoxycarbonylbenzyl)-2-(4-fluorobenzyl)thio-5-(pyrimid-5-ylmethyl) pyrimidin-4-one

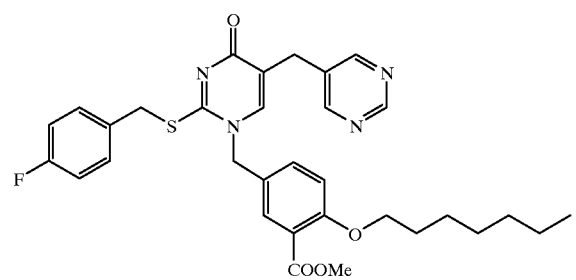

Prepared from Example 106 by general method C2 as a yellow solid. $^1$H-NMR (400 MHz, CDCl$_3$) 9.00 (s, 1H), 8.61 (s, 2H), 7.53 (d, 1H), 7.30 (d, 1H), 7.28 (d, 1H), 7.15 (dd, 1H), 6.90 (m, 4H), 4.82 (s, 2H), 4.40 (s, 2H), 3.96 (t, 2H), 3.82 (s, 3H), 3.60 (s, 2H), 1.73 (m, 2H), 1.42 (m, 2H), 1.29 (m, 6H), 0.83 (t, 3H). MS (AP+) 591 (M+H$^+$, 100%).

Example 297

1-(3-(Hept-1-yloxy)-4-methoxycarbonylbenzyl)-2-(4-fluorobenzyl)thio-5-(pyrimid-5-ylmethyl)pyrimidin-4-one

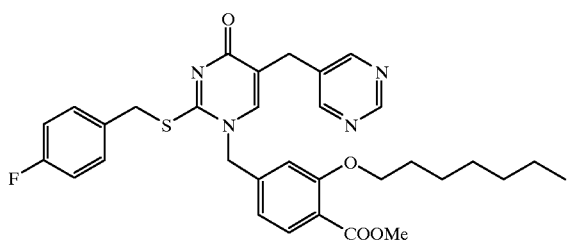

Prepared from Example 106 by general method C2 as a yellow solid. $^1$H-NMR (400 MHz, CDCl$_3$) 9.00 (S, 1H), 8.59 (s, 2H), 7.68 (d, 1H), 7.29 (d, 1H), 7.28 (d, 1H), 6.91 (m, 3H), 6.59 (s, 2H), 4.88 (s, 2H), 4.40 (s, 2H), 3.81 (m, 5H), 3.62 (s, 2H), 1.72 (m, 2H), 1.40 (m, 2H), 1.28 (6H) 0.83 (t, 3H). MS (AP+) 591 (M+H$^+$, 100%).

Example 298

1-(3-Carboxy-4-(hept-1-yloxy)benzyl)-2-(4-fluorobenzyl)thio-5-(pyrimid-ylmethyl)pyrimidin-4-one

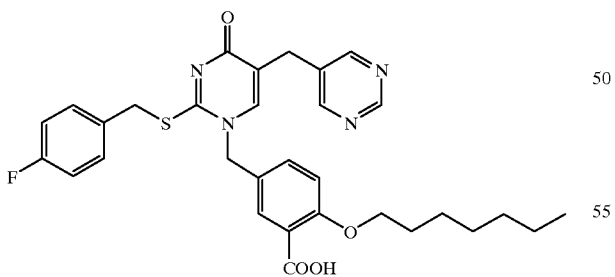

Prepared from Example 296 by general method D as a colourless solid. $^1$H-NMR (250 MHz, CDCl$_3$) 9.05 (s, 1H), 8.75 (s, 2H), 8.65 (br s, 1H), 8.02 (d, 1H), 7.32 (m, 4H), 6.98 (m, 3H), 4.99 (s, 2H), 4.40 (s, 2H), 4.21 (t, 2H), 3.70 (s, 2H), 1.88 (m, 2H), 1.50–1.20 (m, 8H), 1.20 (m, 8H), 0.87 (t, 3H). MS (AP+) 577 (M+H$^+$, 100%).

Example 299

1-(3-(Hept-1-yloxy)4-carboxybenzyl)-2-(4-fluorobenzyl)thio-5-(pyrimid-5-ylmethyl)pyrimidin-4-one

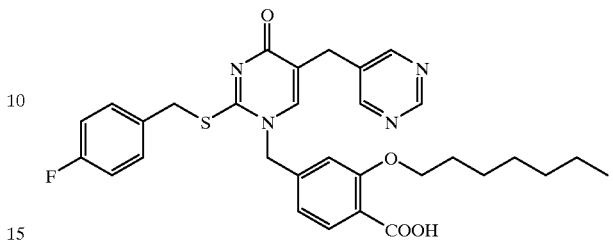

Prepared from Example 297 by general method D as a colourless solid. $^1$H-NMR (400 MHz, CDCl$_3$) 9.04 (s, 1H), 8.67 (s, 2H), 8.11 (d, 1H), 7.33 (d, 1H), 7.31 (d, 1H), 7.05 (s, 1H), 6.95 (t, 2H), 6.82 (d, 1H), 6.68 (s, 1H), 4.99 (s, 2H), 4.44 (s, 2H), 4.05 (t, 2H), 3.69 (s, 2H), 1.87 (m, 2H), 1.50–1.25 (m, 8H), 0.87 (t, 3H). MS (AP+) 577 (M+H$^+$, 55%).

Example 300

1-(3-Methoxycarbonyl-4-hydroxybenzyl)-2-(4-fluorobenzyl)thio-5-(pyrimid-5-ylmethyl)pyrimidin-4-one

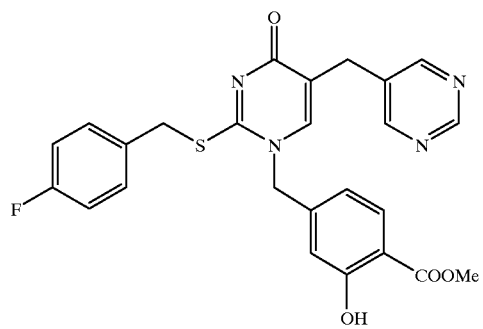

Prepared from Example 106 by general method C2 as a yellow solid. 1H-NMR (250 MHz, CDCl$_3$) 10.82 (s, 1H) 9.03 (s, 1H), 8.64 (s, 2H), 7.77 (d, 1H), 7.30 (m, 2H), 6.93 (m, 3H), 6.68 (d, 1H), 6.53 (dd, 1H), 4.88 (s, 2H), 4.41 (s, Example 301

1-(3-Methoxycarbonylbenzyl)-2-(4-fluorobenzyl)thio-5-(pyrimid-5-ylmethyl)pyrimidin-4-one

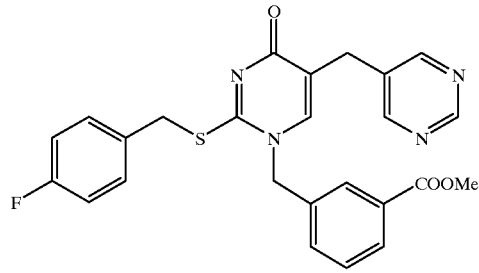

2H), 3.91 (s, 3H), 3.64 (s, 2H).

Prepared from Example 106 by general method C2 as a yellow solid. 1H-NMR (400MHz, CDCl$_3$) 9.10 (s, 1H), 8.71 (s, 2H), 8.07 (d, 1H), 7.86 (s, 1H), 7.50 (t, 1H), 7.30 (m, 3H), 7.07 (s, 1H), 7.01 (t, 2H), 5.05 (s, 2H), 4.50 (s, 2H), 3.97 (s, 3H), 3.72 (s, 2H). MS (AP+) 477 (M+H$^+$, 25%).

Example 302

1-(3-Carboxybenzyl)-2-(4-fluorobenzyl)thio-5-(pyrimid-5-ylmethyl)-pyrimidin-4-one

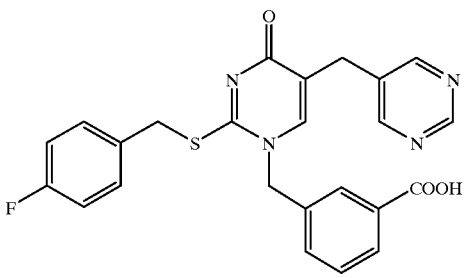

Prepared from Example 301 by general method D as colourless crystals. $^1$H-NMR (400 MHz, DMSO) 13.20 (br s, 1H), 9.07 (s, 1H), 8.78 (s, 2H), 8.06 (s, 1H), 7.95 (d, 1H), 7.85 (s, 1H), 7.50 (m, 4H), 7.16 (t, 2H), 5.26 (s, 2H), 4.44 (s, 2H), 3.68 (s, 2H).

Example 303

1-(3,4-Di-(methoxycarbonyl)benzyl)-2-(4-fluorobenzyl)thio-5-(pyrimid-5-ylmethyl)pyrimidin-4-one

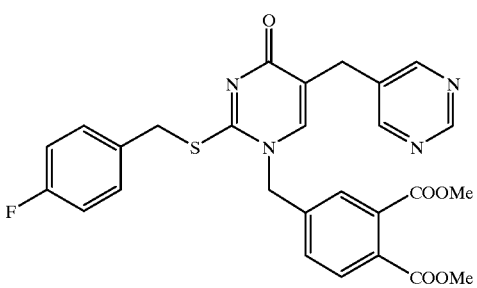

Prepared from Example 106 by general method C2 as a yellow solid. 1H-NMR (250 MHz, CDCl$_3$) 9.05 (s, 1H), 8.65 (s, 2H), 7.69 (m, 1H), 7.44 (s, 1H), 7.27 (m, 3H), 6.96 (m, 3H), 4.99 (s, 2H), 4.62 (s, 2H), 4.09 (s, 6H), 3.87 (s, 2H). MS (AP+) 535 (M+H$^+$, 100%).

Example 304

1-Carboxamidomethyl-2-(8-(4-chlorophenyl)oct-1-yl)thio-5-(pyrid-3-ylmethyl)pyrimidin-4-one

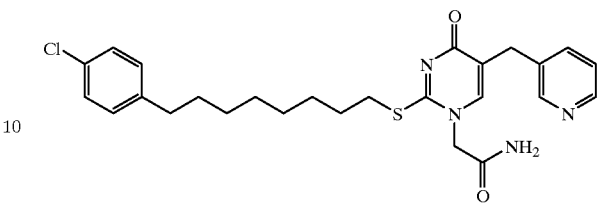

Prepared from Example 70 by general method C1, as a buff powder. MPt 147–152° C.; $^1$H-NMR (d$_6$ DMSO) δ 1.2–1.5(8H, m), 1.5–1.8(4H, m), 2.54(2H, t), 3.08(2H, t), 3.56 (2H, s), 4.53(2H, s),7.1–7.9(9H, m), 8.38(1H, m) and 8.48(1H, bs); MS (EI) M=498; C$_{26}$H$_{31}$ClN$_4$O$_2$S requires 498.

Example 305

1-Dimethylaminocarbonylmethyl-2-(8-(4-chlorophenyl)-8-oxooct-1-yl)thio-5-(pyrimid-5-ylmethyl)pyrimidin-4-one

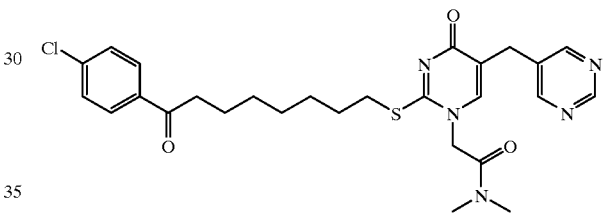

Prepared from intermediates B79 and A1 by general method A4, as a light brown crystalline solid. MPt 57–59° C.; $^1$H-NMR (CDCl$_3$) δ 1.37 (6H, m), 1.69 (4H, m), 2.92 (2H, t), 3.01 (3H, s), 3.16 (3H, s), 3.68 (2H, s), 4.43 (2H, m), 5.06 (2H, s), 7.11 (1H, s), 7.42 (2H, m), 7.89 (2H, m), 8.71 (2H, s), 9.11(1H, s).

Example 306

1-Carboxamidomethyl-2-benzylthio-5-((2-methoxypyrid-4-yl)methyl)pyrimidin-4-one

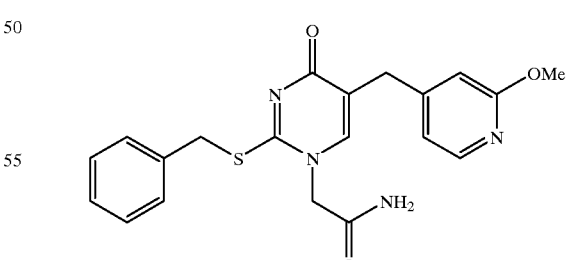

Prepared from Example 88 by general method C1, as a cream solid. MPt 126–132° C.; $^1$H-NMR (d$_6$ DMSO) δ 3.53(2H, s), 3.81(3H, s), 4.40(2H, s), 4.53), 6.66(1H, s), 6.85(1H, dd), 7.2–7.5(6H, m), 7.63(1H, s), 7.75(1H, bs) and 8.03(1H, d); MS (EI) found M=396; C$_{20}$H$_{20}$N$_4$O$_3$S requires 396.

Example 307

1-(3-(Octadec-1ylaminocarbonyl)prop-1-yl)-2-(4-fluorobenzyl)thio-5-(pyrimid-5-ylmethyl)pyrimidin-4-one

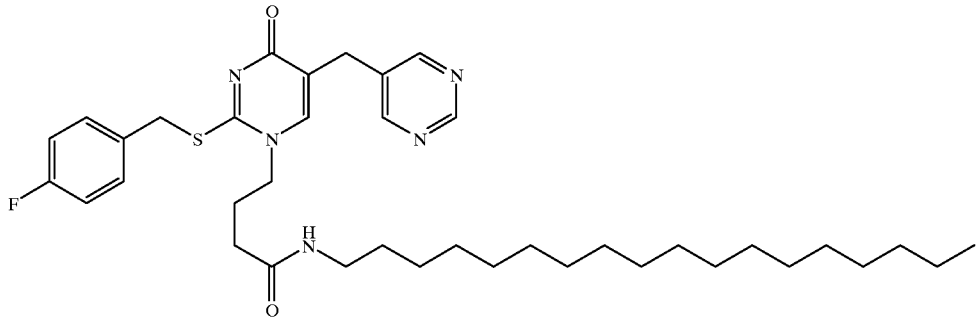

Prepared from Example 279 by general method E. $^{1}$H-NMR (CDCl$_3$) δ 0.88 (3H, m), 1.25 (30H, m), 1.47 (2H, m), 2.05 (2H, m), 2.18 (2H, m), 3.21 (2H, m), 3.69 (2H, s), 3.92 (2H, m), 4.46 (2H, s), 5.42 (1H, m), 6.98 (2H, m), 7.27 (1H, m), 7.37 (2H, m), 8.71 (2H, s), 9.09 (1H, s), MS(APCI$^+$) M+1=666, C$_{38}$H$_{56}$FN$_5$O$_2$S requires 665. MPt 115.1° C. (colourless solid).

Example 308

1-(3-(Octadec-9-(Z)-en-1ylaminocarbonyl)prop-1-yl)-2-(4-fluorobenzyl)thio-5-(pyrimid-5-ylmethyl)pyrimidin-4-one

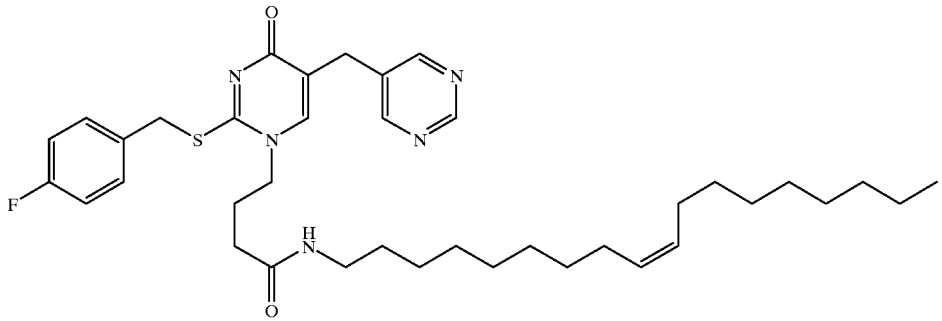

Prepared from Example 279 by general method E. $^{1}$H-NMR (CDCl$_3$) δ 0.88 (3H, m), 1.27 (22H, m), 1.47 (2H, m), 1.99–2.20 (8H, m), 3.20 (2H, m), 3.69 (2H, s), 3.92 (2H, m), 4.46 (2H, s), 5.32 (2H, m), 5.42 (1H, m), 6.99 (2H, m), 7.26 (1H, s), 7.37 (2H, m), 8.71 (2H, s), 9.08 (1H, s), MS(APCI$^+$) M+1=664, C$_{38}$H$_{54}$FN$_5$O$_2$S requires 663 (waxy solid).

Example 309

1-(3-(Octadec-9-(E)-en-1ylaminocarbonyl)prop-1-yl)-2-(4-fluorobenzyl)thio-5-(pyrimid-5-ylmethyl)pyrimidin-4-one

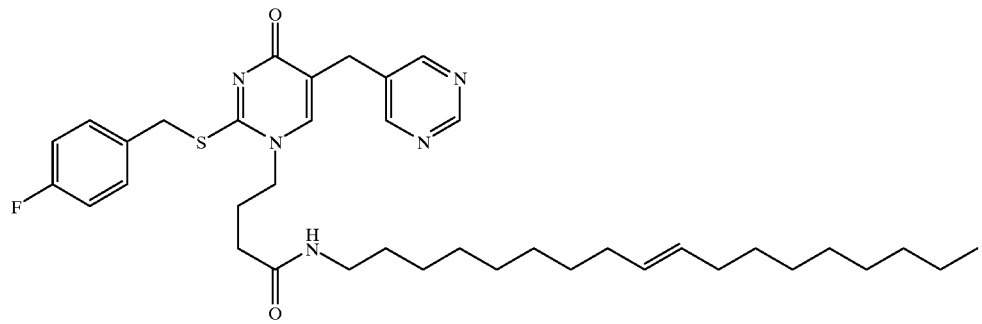

Prepared from Example 279 by general method E.
$^1$H-NMR (CDCl$_3$) δ 0.88 (3H, t), 1.27 (22H, m), 1.47 (2H, m), 1.99–2.20 (8H, m), 3.20 (2H, m), 3.69 (2H, s), 3.92 (2H, m), 4.46 (2H, s), 5.37 (2H, m), 5.44 (1H, m), 6.99 (2H, m), 7.26 (1H, s), 7.37 (2H, m), 8.71 (2H, s), 9.08 (1H, s), MS(APCI$^+$) M+1=664, C$_{38}$H$_{54}$FN$_5$O$_2$S requires 663. MPt 108.4° C. (colourless solid).

Example 310

1(3-(N-Dodec-1yl-N-methylaminocarbonyl)prop-1-yl)-2-(4-fluorobenzyl)thio-5-(pyrimid-5-ylmethyl)pyrimidin-4-one

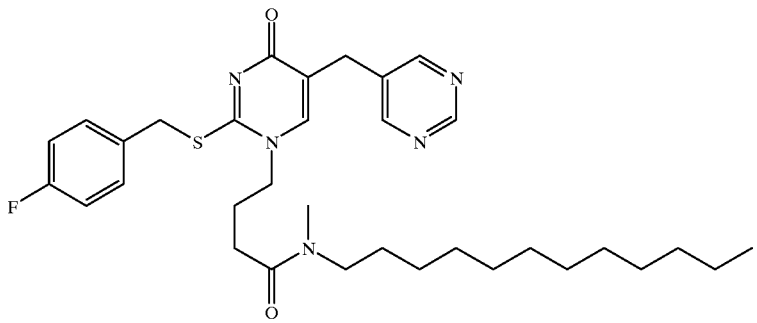

Prepared from Example 279 by general method E.
$^1$H-NMR (CDCl$_3$) δ 0.88 (3H, m), 1.26 (18H, m), 1.49 (2H, m), 2.02 (2H, m), 2.30 (2H, m), 2.90 (3H, s), 3.17, 3.32 (each 1H, m), 3.69 (2H, s), 3.92 (2H, t), 4.46 (2H, s), 6.98 (2H, m), 7.24 (1H, m), 7.35 (2H, m), 8.70 (2H, s), 9.08 (1H, s), MS(APCI$^+$) M+1=596, C$_{33}$H$_{46}$FN$_5$O$_2$S requires 595. MPt 76.9° C. (colourless solid).

Example 311

1-(3-(N-Non-1-yl-N-methylaminocarbonyl)prop-1-yl)-2-(4-fluorobenzyl)thio-5-(pyrimid-5-ylmethyl)pyrimidin-4one

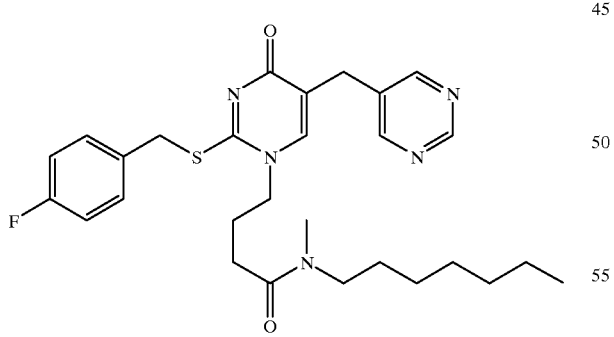

Prepared from Example 279 by general method E.
$^1$H-NMR (CDCl$_3$) δ 0.88 (3H, m), 1.26 (8H, m), 1.48 (2H, m), 2.05 (2H, m), 2.30 (2H, m), 2.90 (3H, s), 3.18, 3.32 (each 1H, m), 3.69 (2H, s), 3.91 (2H, t), 4.46 (2H, s), 6.99 (2H, m), 7.25 (1H, m), 7.35 (2H, m), 8.71 (2H, s), 9.08 (1H, s), MS(APCI$^+$) M+1=526, C$_{28}$H$_{36}$FN$_5$O$_2$S requires 525. (coloured oil).

Example 312

1-(4-(Pent-1-ylaminocarbonyl)benzyl)-2-(4-fluorobenzyl)thio-5-(pyrimid-5-ylmethyl)pyrimidin-4-one Prepared from Example 284 by general method E as a solid. $^1$H-NMR (CDCl$_3$) δ 0.82–1.05 (3H, t), 1.21–1.48 (3H, m), 1.52–1.77 (3H, m), 3.38–3.54 (2H, q), 3.69(2H, s), 4.49(2H, s), 5.01 (2H, s), 6.14–6.27 (1H, br.t), 6.90–7.05 (3H, m), 7.10–7.21 (2H, d), 7.28–7,39(2H, m), 7.70–7.80 (2H, d), 8.65 (2H, s), 9.07 (1H, s); MS (APCI$^+$) found (M+1)=532; C$_{29}$H$_{30}$FN$_5$O$_2$S requires 531.

Example 315

1-(1-(6-(4-Fluorophenyl)hex-1-ylaminocarbonyl)ethyl)-2-(4-fluorobenzyl)thio-5-(pyrimid-5-ylmethyl)pyrimidin-4-one

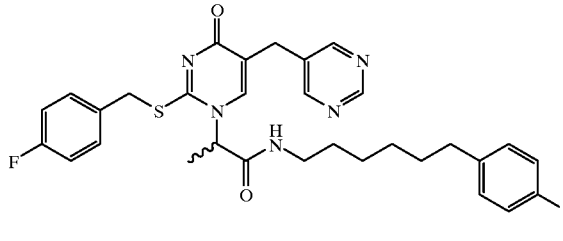

Prepared from Example 272 by hydrolysis using general method D, followed by amide coupling using general method E. $^1$H-NMR (CDCl$_3$) δ 1.15–1.72 (11H, m), 2.47–2.60 (2H, t), 3.17–3.35 (2H, m), 3.52–3.70 (2H, m), 4.25–4.49 (2H, br.q), 4.74–4.89 (1H, q), 6.53–6.66 (1H, br.t), 6.87–7.16 (6H, m), 7.21–7.40 (2H, m), 7.53 (1H, s), 8.69 (2H, s), 9.08 (1H, s); MS (APCI$^+$) found (M+1)=578; C$_{31}$H$_{33}$F$_2$N$_5$O$_2$S requires 577.

Example 316

1-(3-(11-Dimethylaminoundec-1-ylaminocarbonyl)prop-1-yl)-2-(4-fluorobenzyl)thio-5-(pyrimid-5-ylmethyl)pyrimidin-4-one

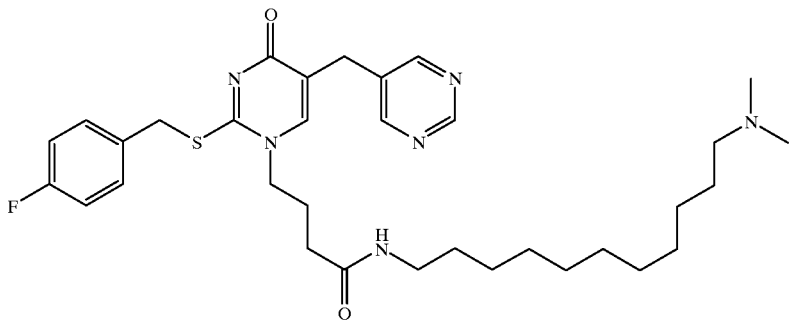

Prepared from Example 279 by general method E. $^1$H-NMR (CDCl$_3$) δ 1.27 (10H, m), 1.47 (4H, m), 1.99–2.20 (4H, m), 2.30 (6H, m), 3.20 (2H, m), 3.69 (2H, s), 3.92 (2H, m), 4.46 (2H, s), 5.49 (1H, bm), 6.99 (2H, m), 7.26 (1H, s), 7.37 (2H, m), 8.71 (2H, s), 9.08 (1H, s), MS(APCI$^+$) M+1=611, C$_{33}$H$_{47}$FN$_6$O$_2$S requires 610 (gum).

Example 317

1-(3-(3-Ethoxyprop-1ylaminocarbonyl)prop-1-yl)-2-(3,4-difluorobenzyl)thio-5-(pyrimid-5-ylmethyl)pyrimidin-4-one

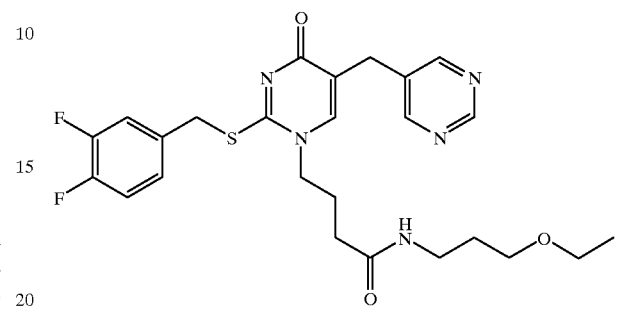

Prepared from Example 282 by general method E. $^1$H-NMR (CDCl$_3$) δ 1.14–1.35 (5H, m), 1.70–1.88 (2H, m), 2.11–2.23 (2H, t), 3.70–3.43 (2H, q), 3.435–3.60 (4H, m), 3.70 (2H, s), 3.87–4.01 (2H, t), 4.44 (2H, s), 6.23–6.38 (1H, br.t), 7.01–7.33 (4H, m), 8.71 (2H, s), 9.09 (1H, s); MS (APCI$^+$) found (M+1)=518; C$_{25}$H$_{29}$F$_2$N$_5$O$_3$S requires 517.

Example 318

1-(3-(5-(Methoxycarbonyl)-5-(benzykloxycarbonylamino)pent-1ylaminocarbonyl)prop-1-yl)-2-(4-fluorobenzyl)thio-5-(pyrimid-5-ylmethyl)pyrimidin-4-one

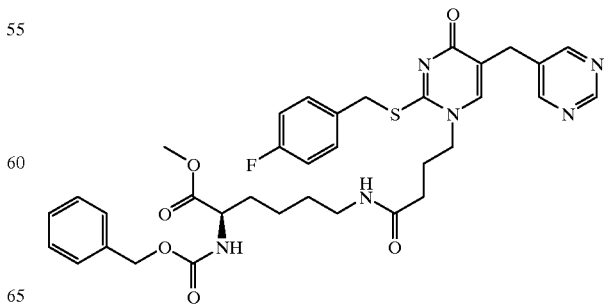

Prepared from Example 279 by general method E. ¹H-NMR (CDCl₃) δ 1.2–2.2 (10H, m), 3.19 (2H, m), 3.67 (2H, s), 3.74 (3H, s), 3.85 (2H, t), 4.35 (1H, m), 4.45 (2H, s), 5.09 (2H, s), 5.55 (2H, m), 6.99 (2H, m), 7.22–7.37 (8H, m), 8.71 (2H, s), 9.08 (1H, s), MS(APCI⁺) M+1=691, $C_{35}H_{39}FN_6O_6S$ requires 690 (colourless foam).

Example 319

1-(3-(5-(Methoxycarbonyl)pent-1ylaminocarbonyl)prop-1-yl)-2-(4-fluorobenzyl)thio-5-(pyrimid-5-ylmethyl)pyrimidin-4-one

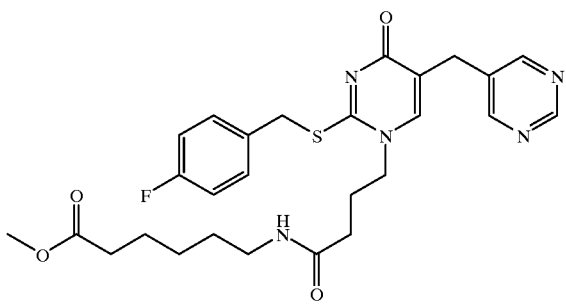

Prepared from Example 279 by general method E. ¹H-NMR (CDCl₃) δ 1.2–1.7 (6H, m), 1.98–2.21 (4H, m), 2.31 (2H, t), 3.22 (2H, m), 3.66 (3H, s), 3.70 (2H, s), 3.92 (2H, t), 4.45 (2H, s), 5.57 (1H, bm), 6.99 (2H, m), 7.26 (1H, s), 7.36 (2H, m), 8.71 (2H, s), 9.08 (1H, s); MS(APCI⁺) M+1=542, $C_{27}H_{32}FN_5O_4S$ requires 541. (oil).

Example 320

1-(3-(Hex-1ylaminocarbonyl)prop-1-yl)-2-(3,4-difluorobenzyl)thio-5-(pyrimid-5-ylmethyl)pyrimidin-4-one

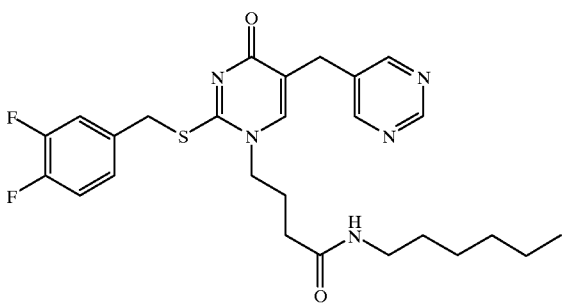

Prepared from Example 279 by general method E as a solid. ¹H-NMR (CDCl₃) δ 0.83–0.98 (3H, t), 1.20–1.59 (8H, m), 1.97–2.28 (4H, m), 3.15–3.29 (2H, q), 3.69 (2H, s), 3.87–4.01 (2H, t), 4.43 (2H, s), 5.49–5.64 (1H, br.t), 6.99–7.32 (4H, m), 8.71 (2H, s), 9.08 (1H, s); MS (APCI⁺) found (M+1)=516; $C_{26}H_{30}F_2N_5O_2S$ requires 515.

Example 321

1-(3-(5-(t-Butoxycarbonylamino)pent-1ylaminocarbonyl)prop-1-yl)-2-(4-fluorobenzyl)thio-5-(pyrimid-5-ylmethyl)pyrimidin-4-one

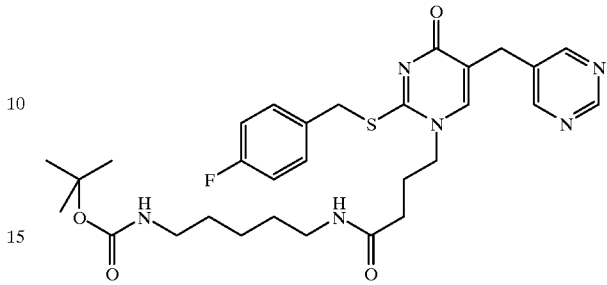

Prepared from Example 279 by general method E. ¹H-NMR (CDCl₃) δ 1.18–1.5 (15H, m), 2.05 (2H, m), 2.19 (2H, m), 3.16 (4H, m), 3.70 (2H, s), 3.92 (2H, t), 4.52 (2H, s), 4.64(1H, bm), 5.71 (1H, bm), 6.99 (2H, m), 7.28 (1H, s), 7.37 (2H, m), 8.72 (2H, s), 9.08 (1H, s); MS(APCI⁺) M+1=599, $C_{30}H_{39}FN_6O_4S$ requires 598. (colourless foam).

Example 322

1-(3-(6-(t-Butoxycarbonylamino)hex-1ylaminocarbonyl)prop-1-yl)-2-(4-fluorobenzyl)thio-5-(pyrimid-5-ylmethyl)pyrimidin-4-one

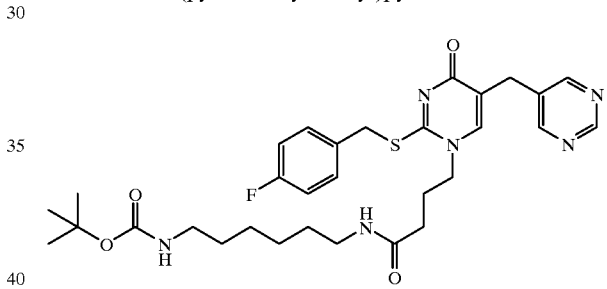

Prepared from Example 279 by general method E. ¹H-NMR (CDCl₃) δ 1.18–1.5 (17H, m), 2.04 (2H, m), 2.20 (2H, m), 3.15 (4H, m), 3.69 (2H, s), 3.92 (2H, t), 4.45 (2H, s), 4.59 (1H, bm), 5.80 (1H, bm), 6.96 (2H, s), 7.28 (1H, s), 7.36 (2H, m), 8.71 (2H, s), 9.08 (1H, s); MS(APCI⁺) M+1=613, $C_{31}H_{41}FN_6O_4S$ requires 612. MPt 90–98° C. (colourless foam).

Example 323

1-(3-(Dec-1ylaminocarbonyl)prop-1-yl)-2-(4-fluorobenzyl)thio-5-(pyrimid-5-ylmethyl)pyrimidin-4-one

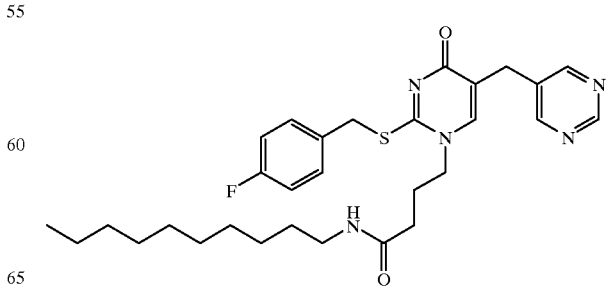

Prepared from Example 279 by general method E. ¹H-NMR (CDCl₃) δ 0.88 (3H, t), 1.26 (14H, m), 1.47 (2H, m), 1.98–2.20 (4H, m), 3.20 (2H, m), 3.69 (2H, s), 3.92 (2H, t), 4.46 (2H, s), 5.39 (1H, bm), 6.98 (2H, m), 7.24 (1H, s), 7.37 (2H, m), 8.70 (2H, s), 9.08 (1H, s); s); MS(APCI⁺) M+1=554, C₃₀H₄₀FN₅O₂S requires 553. MPt 90–98° C. (colorurless solid).

Example 324

1-(3-(Dec-1ylaminocarbonyl)prop-1-yl)-2-(4-fluorobenzyl)thio-5-(pyrimid-5-ylmethyl)pyrimidin-4-one

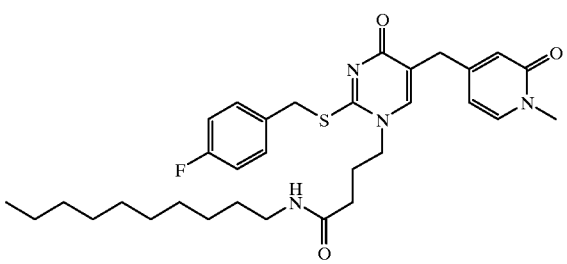

Prepared from Example 279 by general method E. ¹H-NMR (d₆-DMSO) δ 0.85 (3H, m), 1.22 (14H, m), 1.31 (2H, m), 1.87 (2H, m), 2.12 (2H, m), 2.98 (2H, m), 3.35 (3H, s), 3.37 (2H, s), 3.84 (2H, m), 4.41 (2H, s), 6.13 (2H, m), 7.13 (2H, m), 7.51 (3H, m), 7.77 (2H, m); MS (APCI⁺) M+1=583, C₃₂H₄₃FN₄O₃S requires 582. MPt 133.3° C. (colourless solid).

Example 325

1-(3-(Hept-1ylaminocarbonyl)prop-1-yl)-2-(4-fluorobenzyl)thio-5-(pyrimid-5-ylmethyl)pyrimidin-4-one

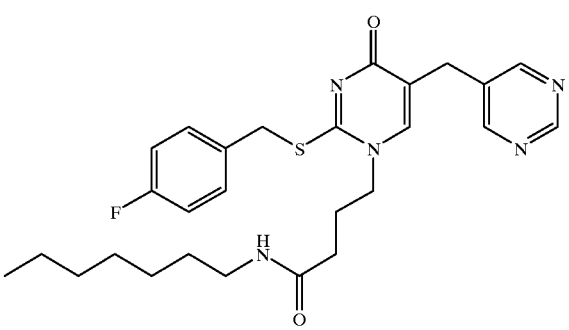

Prepared from Example 279 by general method E. ¹H-NMR (CDCl₃) δ 0.88 (3H, t), 1.27 (8H, m), 1.47 (2H, m), 1.98–2.25 (4H, m), 3.20 (2H, m), 3.69 (2H, s), 3.92 (2H, t), 4.52 (2H, s), 5.42 (1H, bm), 6.98 (2H, m), 7.25 (1H, s), 7.37 (2H, m), 8.68 (2H, s), 9.08 (1H, s); MS(APCI⁺) M+1=512, C27H34FN5O2S requires 511. MPt 84–89° C. (colourless solid). MPt. 84–89

Example 326

1-(3-(Hex-1ylaminocarbonyl)prop-1-yl)-2-(4-fluorobenzyl)thio-5-(pyrimid-5-ylmethyl)pyrimidin-4-one

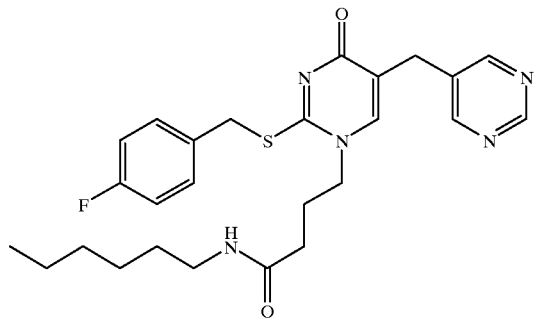

Prepared from Example 279 by general method E. ¹H-NMR (CDCl₃) δ 0.89 (3H, m), 1.20–1.55 (8H, m), 1.98–2.20 (4H, m), 3.19 (2H, m), 3.69 (2H, s), 3.92 (2H, t), 4.45 (2H, s), 5.44 (1H, bm), 6.96 (2H, m), 7.25 (1H, s), 7.37 (2H, m), 8.68 (2H, s), 9.08 (1H, s); MS(APCI=)M+1=498, C₂₆H₃₂FN₅O₂S requires 497. MPt 106–109° C. (colourless solid).

Example 327

1-(3-(Non-1ylaminocarbonyl)prop-1-yl)-2-(4-fluorobenzyl)thio-5-(pyrimid-5-ylmethyl)pyrimidin-4-one

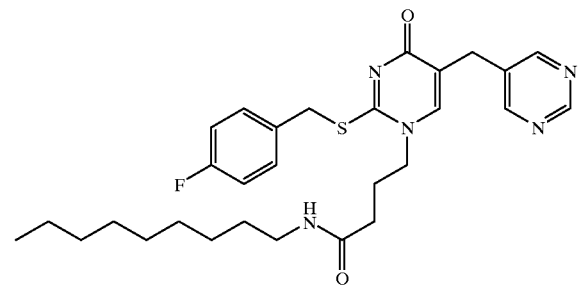

Prepared from Example 279 by general method E. ¹H-NMR (CDCl₃) δ 0.87 (3H, t), 1.26 (12H, m), 1.47 (2H, m), 1.98–2.25 (4H, m), 3.20 (2H, m), 3.69 (2H, s), 3.91 (2H, t), 4.46 (2H, s), 5.39 (1H, bm), 6.98 (2H, m), 7.24 (1H, s), 7.37 (2H, m), 8.70 (2H, s), 9.08 (1H, s); MS(APCI⁺) M+1=540, C₂₉H₃₈FN₅O₂S requires 539. MPt 92–97° C. (colourless solid).

Example 328

1-(3-(Oct-1ylaminocarbonyl)prop-1-yl)-2-(4-fluorobenzyl)thio-5-(pyrimid-5-ylmethyl)pyrimidin-4-one

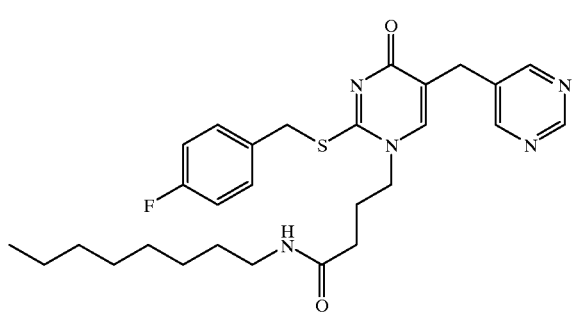

Prepared from Example 279 by general method E. $^1$H-NMR (CDCl$_3$) δ 0.88 (3H, t), 1.27 (10H, m), 1.47 (2H, m), 1.98–2.20 (4H, m), 3.22 (2H, m), 3.69 (2H, s), 3.92 (2H, t), 4.45 (2H, s), 5.43 (1H, bm), 6.98 (2H, m), 7.25 (1H, s), 7.37 (2H, m), 8.70 (2H, s), 9.08 (1H, s); MS(APCI$^+$) M+1=526, C$_{28}$H$_{36}$FN$_5$O$_2$S requires 525. MPt 72–83° C. (colourless solid).

Example 329

1-(3-(Pent-1ylaminocarbonyl)prop-1-yl)-2-(4-fluorobenzyl)thio-5-(pyrimid-5-ylmethyl)pyrimidin-4-one

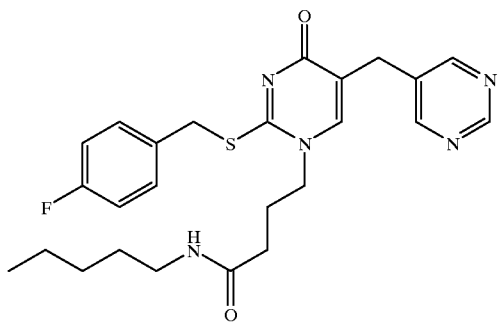

Prepared from Example 279 by general method E. $^1$H-NMR (CDCl$_3$) δ 0.90 (3H, m), 1.17–1.61 (6H, m), 1.98–2.26 (4H, m), 3.20 (2H, m), 3.69 (2H, s), 3.92 (2H, t), 4.45 (2H, s), 5.44 (1H, bm), 6.97 (2H, m), 7.25 (1H, s), 7.38 (2H, m), 8.68 (2H, s), 9.08 (1H, s); MS(APCI$^+$) M+1=484, C$_{25}$H$_{30}$FN$_5$O$_2$S requires 483. MPt 64–69° C. (colourless solid).

Example 330

1-(3-(N-Hex-1yl-N-methylaminocarbonyl)prop-1-yl)-2-(3,4-difluorobenzyl)thio-5-(pyrimid-5-ylmethyl)pyrimidin-4-one

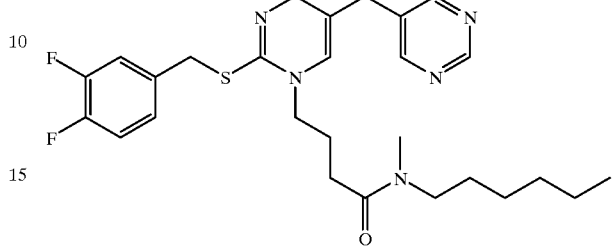

Prepared from Example 282 by general method E. $^1$H-NMR (CDCl$_3$) δ 0.78–0.99 (3H, m), 1.19–1.77 (8H, m), 1.95–2.14 (2H, m), 2.25–2.44 (2H, q), 2.92 (3H, d), 3.12–3.27 (1H, t), 3.29–3.42 (1H, t), 3.70 (2H, s), 3.84–4.00 (2H, t), 4.44 (2H, t), 7.01–7.31 (4H, m), 8.71 (2H, s), 9.10 (1H, s); MS (APCI$^+$) found (M+1)=530; C$_{27}$H$_{33}$F$_2$N$_5$O$_2$S requires 529.

Example 331

1-(5-(2-mEthoxyethylaminocarbonyl)pent-1-yl)-2-(3,4-difluorobenzyl)thio-5-(pyrimid-5-ylmethyl)pyrimidin-4-one

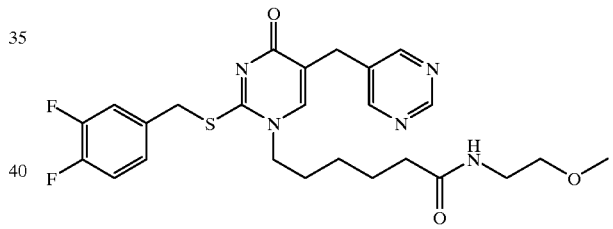

Prepared from Example 283 by general method E. $^1$H-NMR (CDCl$_3$) δ 1.22–1.85 (6H, m), 2.13–2.25 (2H, t), 3.29–3.38 (3H, s), 3.39–3.53 (4H, s), 3.68–3.85 (4H, m), 4.44 (2H, s), 5.90–6.04 (1H, br.s), 7.01–7.29 (4H, m), 8.72 (2H, s), 9.09 (1H, s); MS (APCI$^+$) found (M+1)=518; C$_{25}$H$_{29}$F$_2$N$_5$O$_3$S requires 517.

Example 332

1-(5-(2-Phenylethylaminocarbonyl)pent-1-yl)-2-(3,4-difluorobenzyl)thio-5-(pyrimid-5-ylmethyl)pyrimidin-4-one

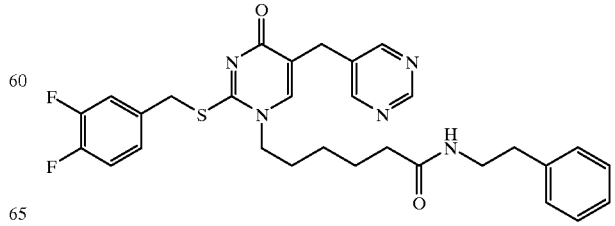

Prepared from Example 283 by general method E as a foam. $^1$H-NMR (CDCl$_3$) δ 1.17–1.38 (2H, m), 1.56–1.84 (4H, m), 2.04–2.19 (2H, t), 2.77–2.89 (2H, t), 3.41–3.60 (2H, m), 3.64–3.86 (4H, m), 4.43 (2H, s), 5.68–5.85 (1H, m), 7.00–7.38 (9H, M), 8.67 (2H, s), 9.06 (1H, s); MS (APCI$^+$) found (M+1)=564; C30H31F2N5O2S requires 563.

Example 333

1-(5-(But-1-ylaminocarbonyl)pent-1-yl)-2-(3,4-difluorobenzyl)thio-5-(pyrimid-5-ylmethyl)pyrimidin-4-one

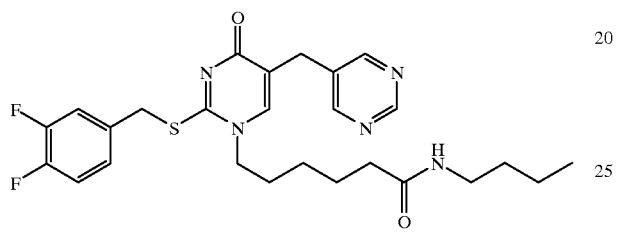

Prepared from Example 283 by general method E. $^1$H-NMR (CDCl$_3$) δ 0.88–1.00 (3H, t), 1.17–1.76 (10H, m), 2.11–2.22 (2H, t), 3.18–3.30 (2H, q), 3.67–3.88 (4H, m), 4.43 (2H, s), 5.52–5.70 (1H, br.t), 7.00–7.30 (4H, m), 8.71 (2H, s), 9.09 (1H, s); MS (APCI$^+$) found (M+1)=516; C$_{26}$H$_{31}$F$_2$N$_5$O$_2$S requires 515.

Example 334

1-(5-(N-(2-Phenylethyl)-N-methylaminocarbonyl)pent-1-yl)-2-(3,4-difluorobenzyl)thio-5-(pyrimid-5-ylmethyl)pyrimidin-4-one

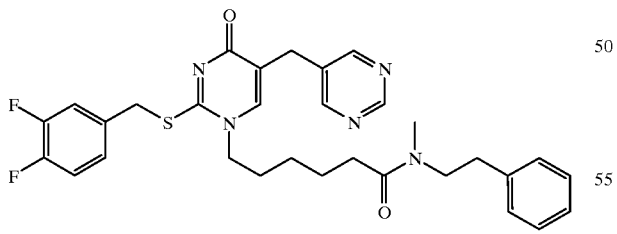

Prepared from Example 283 by general method E. $^1$H-NMR (CDCl$_3$) δ 1.01–1.86 (6H, m), 1.98–2.09 (1H, t), 2.21–2.35 (1H, t), 2.76–2.99 (5H, m), 3.44–3.87 (6H, M), 4.44 (2H, s), 7.00–7.35 (9H, m), 8.71 (2H, d), 9.09 (1H, s); MS (APCI$^+$) found (M+1)=578; C31H33F2N5O2S requires 577.

Example 335

1-(5-(N-But-1-yl-N-methylaminocarbonyl)pent-1-yl)-2-(3,4-difluorobenzyl)thio-5-(pyrimid-5-ylmethyl)pyrimidin-4-one

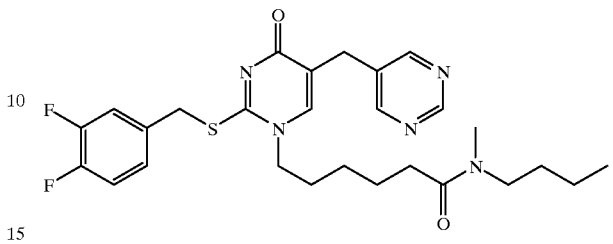

Prepared from Example 283 by general method E. $^1$H-NMR (CDCl$_3$) δ 1.20–1.87 (13H, m), 2.24–2.39 (2H, q), 2.88–2.99 (3H, d), 3.18–3.42 (2H, m), 3.68–3.88 (4H, m) 4.44 (2H, s), 7.00–7.29 (4H, m), 8.72 (2H, s), 9.09 (1H, s); MS (APCI$^+$) found (M+1)=530; C$_{27}$H$_{33}$F$_2$N$_5$O$_2$S requires 529.

Example 336

1-((R)-1-(Hex-1-ylaminocarbonyl)ethylaminocarbonylmethyl)-2-(4-fluorobenzyl)thio-5-(pyrimid-5-ylmethyl)pyrimidin-4-one

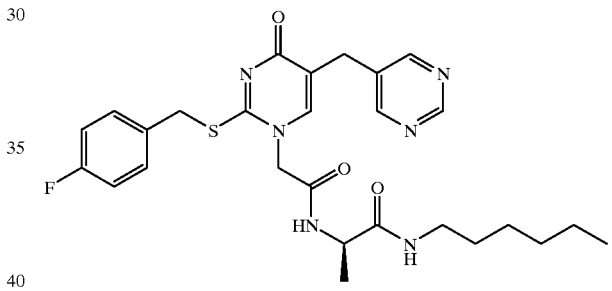

Prepared from Example 280 by general method E. $^1$H-NMR (d6 DMSO) δ 0.8–0.95 (3H, m), 1.15–1.5 (11H, m), 2.95–3.2 (2H, m), 3.64 (2H, s), 4.3–4.5 (3H, m), 4.64 (2H, s), 6.95–7.1 (2H, m), 7.3–7.5 (2H, m), 7.71 (1H, d), 8.47 (1H, bd), 8.7 (2H, s), 8.97 (1H, s); MS (APCI$^+$) found (M+1)=541; C$_{27}$H$_{33}$FN$_6$O$_3$S requires 540.

Example 337

1-((S)-1-(Hex-1-ylaminocarbonyl)ethylaminocarbonylmethyl)-2-(4-fluorobenzyl)thio-5-(pyrimid-5-ylmethyl)pyrimidin-4-one

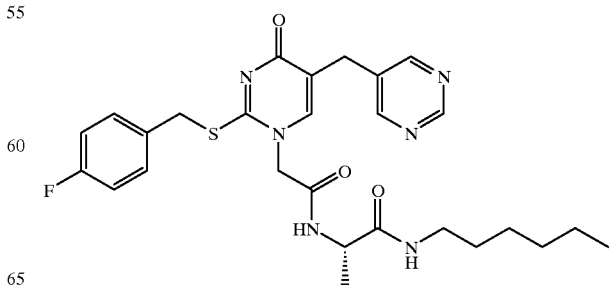

Prepared from Example 280 by general method E. ¹H-NMR (d6 DMSO) δ 0.8–0.95 (3H, m), 1.2–1.55 (11H, m), 3.0–3.25 (2H, m), 3.64 (2H, s), 4.35–4.5 (3H, m), 4.60 (2H, s), 6.90–7.05 (2H, m), 7.25–7.45 (4H, m), 8.3 (1H, bd), 8.71 (2H, s), 9.01 (1H, s); MS (APCI⁺) found (M+1)=541; $C_{27}H_{33}FN_6O_3S$ requires 540.

Example 338

1-((S)-2-(Hex-1-ylaminocarbonyl)pyrrolidin-1-ylcarbonylmethyl)-2-(4-fluorobenzyl)thio-5-(pyrimid-5-ylmethyl)pyrimidin-4-one

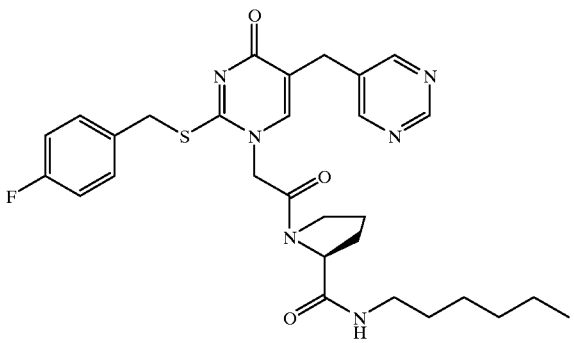

Prepared from Example 280 by general method E. ¹H-NMR (CDCl₃) δ 0.8–0.95 (3H, m), 1.15–1.55 (8H, m), 1.75–2.45 (4H, m), 3.0–3.8 (6H, m), 3.72 (2H, bd), 4.35–4.60 (5H, m), 6.43 (1H, m), 6.90–7.05 (2H, m), 7.26 (1H, s), 7.27–7.45 (2H, m), 8.71 (2H, s), 9.09 (1H, s); MS (APCI⁺) found (M+1) 567; $C_{29}H_{35}FN_6O_3S$ requires 566.

Example 339

1-(1-Pyrrolidinocarbonylmethyl)-2-(4-fluorobenzyl)thio-5-(pyrimid-5-ylmethyl)pyrimidin-4-one

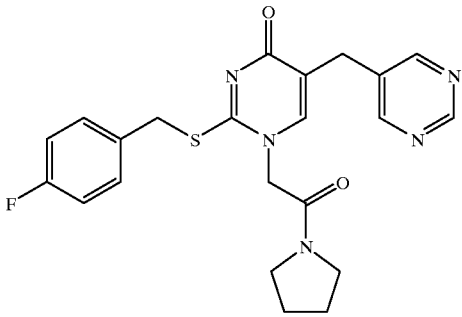

Prepared from Example 280 by general method E. ¹H-NMR,(CDCl₃) δ 1.87–2.08 (4H, m), 3.44–3.52 (4H, m), 3.72 (2H, s), 4.46 (2H, s), 4.49 (2H, s), 6.95 (3H, m), 7.34 (2H, m), 8.73 (2H, s), 9.10 (1H, s); MS (APCI⁺) found (M+1)=440; $C_{22}H_{22}FN_5O_2S$ requires 439.

Example 340

1-(3-Butoxyprop-1-ylaminocarbonylmethyl)-2-(4fluorobenzyl)thio-5-(pyrimid-5-ylmethyl)pyrimidin-4-one

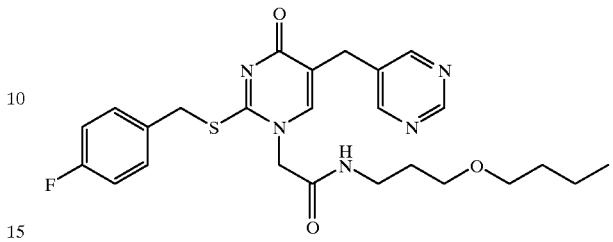

Prepared from Example 280 by general method E. ¹H-NMR (CDCl₃) δ 0.89 (3H, t), 1.32 (2H, m), 1.47 (2H, m), 1.75 (2H, m), 3.32–3.44 (4H, m), 3.51 (2H, t), 3.71 (2H, s), 4.31 (2H, s), 4.47 (2H, s), 6.73 (1H, br.t), 6.98(3H, m), 7,32 (2H, m), 8.71 (2H, s), 9.11 (1H, s); MS (APCI⁺) found (M+1)=500; $C_{25}H_{30}FN_5O_3S$ requires 499.

Example 341

1-(6-Hydroxyhex-1-ylaminocarbonylmethyl)-2-(4-fluorobenzyl)thio-5-(pyrimid-5-ylmethyl)pyrimidin-4-one

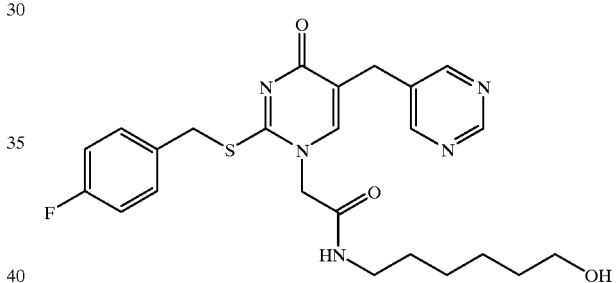

Prepared from Example 280 by general method E. ¹H-NMR (CDCl₃/d6 DMSO) δ 1.2–1.6 (8H, m), 3.14 (2H, q), 3.5 (2H, q), 3.67 (2H, s), 3.95 (1H, t) 4.44 (2H, s), 4.52 (2H, s), 6.9–7.1 (2H, m), 7.3–7.5 (2H, m), 7.51(1H, s), 8.04 (1H, bt), 8.73 (2H, s), 9.01 (1H, s); MS (APCI⁺) found (M+1)=486; $C_{24}H_{28}FN_5O_3S$ requires 485.

Example 342

1-(6-(4-Fluorophenyl)hex-1-ylaminocarbonylmethyl)-2-(4-fluorobenzyl)thio-5-(pyrimid-5-ylmethyl)pyrimidin-4-one

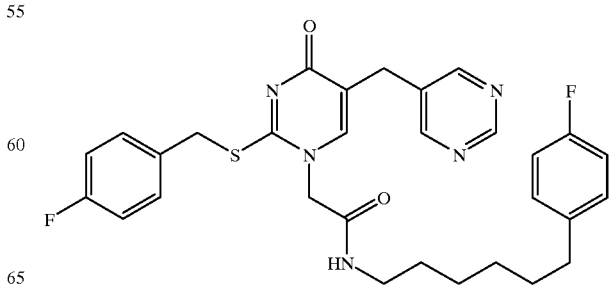

Prepared from Example 280 by general method E.
$^1$H-NMR (d$_6$-DMSO) δ 1.20–1.55 (8H, m), 2.51 (2H, m), 3.05 (2H, m), 3.59 (2H, s), 4.38 (2H, s), 4.53 (2H, s), 7.03–7.22 (6H, m), 7.43 (2H, m), 7.69 (1H, s), 8.21 (1H, m), 8.71 (2H, s), 9.02 (1H, s); MS (APCI$^+$) M+1=564, C$_{30}$H$_{31}$F$_2$N$_5$O$_2$S requires 563. MPt 170.8° C. (cream solid). MPt. 170.8

Example 343

1-(Tridec-1-ylaminocarbonylmethyl)-2-(4-fluorobenzyl)thio-5-(pyrimid-5-ylmethyl)pyrimidin-4-one

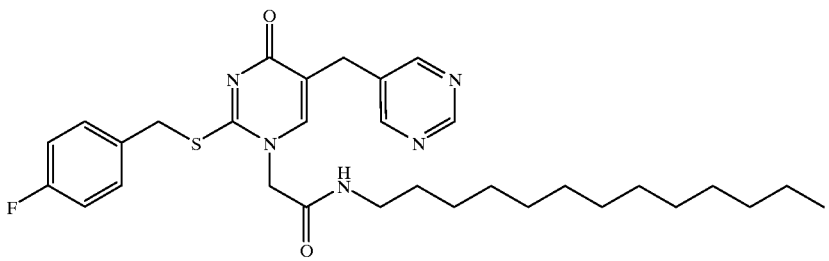

Prepared from Example 280 by general method E.
$^1$H-NMR (d$_6$-DMSO) δ 0.85 (3H, m), 1.20 (20H, m), 1.37 (2H, m), 3.06 (2H, m), 3.59 (2H, s), 4.39 (2H, s), 4.53 (2H, s), 7.12 (2H, m), 7.44 (2H, m), 7.69 (1H, s), 8.21 (1H, m), 8.70 (2H, s), 9.05 (1H, s); MS (APCI$^+$) M+1=568, C$_{31}$H$_{42}$FN$_5$O$_2$S requires 567. MPt 191.5° C. (colourless solid).

Example 344

1-(Tetradec-1-ylaminocarbonylmethyl)-2-(4-fluorobenzyl)thio-5-(pyrimid-5-ylmethyl)pyrimidin-4-one

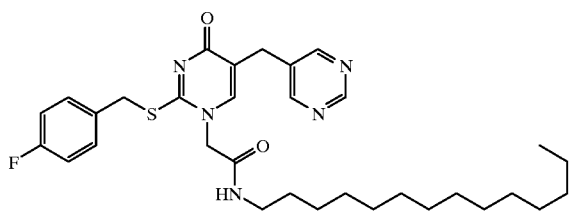

Prepared from Example 280 by general method E.
$^1$H-NMR (d$_6$-DMSO) δ 0.85 (3H, m), 1.23 (2H, m), 1.36 (2H, m), 3.05 (2H, m), 3.59 (2H, s), 4.38 (2H, s), 4.53 (2H, s), 7.12 (2H, m), 7.44 (2H, m), 7.69 (1H, s), 8.25 (1H, m), 8.70 (2H, s), 9.02 (1H, s); MS (APCI$^+$) M+1=582, C$_{32}$H44FN$_5$O$_2$S requires 581. MPt 191.7° C. (colourless solid).

Example 345

1-(Octadec-1-ylaminocarbonylmethyl)-2-(4-fluorobenzyl)thio-5-(pyrimid-5-ylmethyl)pyrimidin-4-one

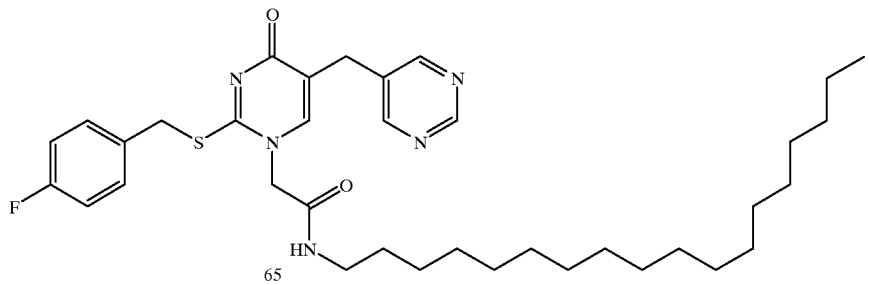

Prepared from Example 280 by general method E.
$^1$H-NMR (CDCl$_3$) δ 0.87 (3H, m), 1.25 (30H, m), 1.47 (2H, m), 3.26 (2H, m), 3.70 (2H, s), 4.37 (2H, s), 4.45 (2H, s), 5.95 (1H, m), 6.99 (3H, m), 7.32 (2H, m), 8.70 (2H, s), 9.09 (1H, s), MS(APCI$^+$) M+1=638, C$_{36}$H$_{52}$FN$_5$O$_2$S requires 637. MPt 189.8° C. (pale yellow solid).

Example 346

1-(Octadec-9-(Z)-en-1ylaminocarbonylmethyl)-2-(4-benzyl)thio-5-(pyrimid-5-ylmethyl)pyrimidin-4-one

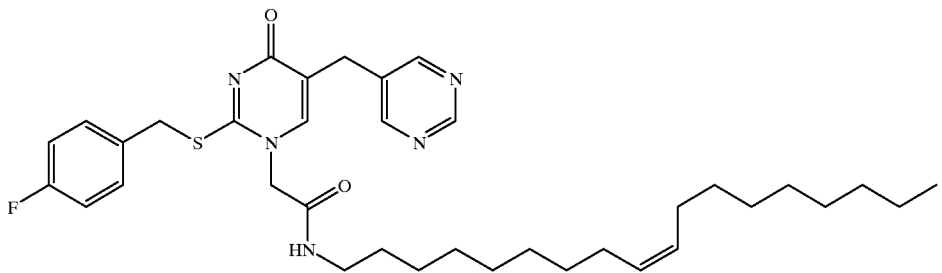

Prepared from Example 280 by general method E.
$^1$H-NMR (CDCl$_3$) δ 0.88 (3H, s), 1.26 (22H, m), 1.47 (2H, m), 2.01 (4H, m), 3.26 (2H, m), 3.71 (2H, s), 4.35 (2H, s), 4.46 (2H, s), 5.33 (2H, m), 5.73 (1H, m), 6.98 (3H, m), 7.34 (2H, m), 8.70 (2H, s), 9.09 (1H), MS(APCI$^+$) M+1=636, C$_{36}$H$_{50}$FN$_5$O$_2$S requires 635. MPt 179.7° C. (cream solid).

Example 347

1-(Octadec-9-(E)-en-1ylaminocarbonylmethyl)-2-(4-fluorobenzyl)thio-5-(pyrimid-5-ylmethyl)pyrimidin-4-one

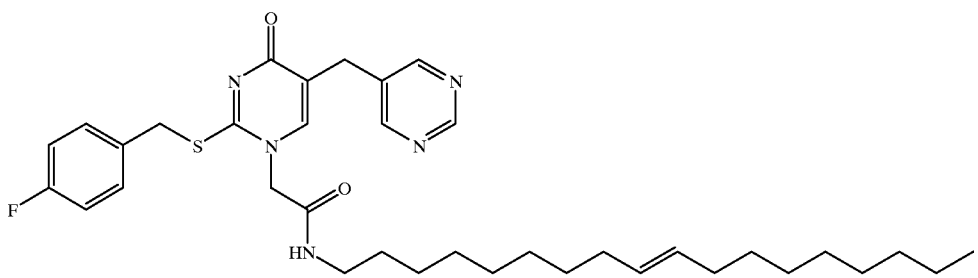

Prepared from Example 280 by general method E.
$^1$H-NMR (CDCl$_3$) δ 0.88 (3H, s), 1.26 (22H, m), 1.47 (2H, m), 1.95 (4H, m), 3.26 (2H, m), 3.70 (2H, s), 4.36 (2H, s), 4.45 (2H, s), 5.38 (2H, m), 5.87 (1H, m), 6.98 (3H, m), 7.32 (2H, m), 8.70 (2H, s), 9.08 (1H, s), MS(APCI$^+$) M+1=636, C$_{36}$H$_{50}$FN$_5$O$_2$S requires 635. MPt 184.6° C. (yellow solid). MPt. 184.6

Example 348

1-(Dec-1-ylaminocarbonylmethyl)-2-(4-fluorobenzyl)thio-5-pyrimid-5-ylmethyl)pyrimidin-4-one

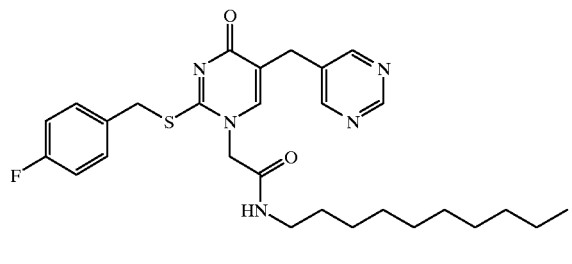

Prepared from Example 280 by general method E. $^1$H-NMR (d$_6$-DMSO) δ 0.85 (3H, m), 1.21 (14H, m), 1.37 (2H, m), 3.06 (2H, m), 3.59 (2H, s), 4.39 (2H, s), 4.53 (2H, s), 7.12 (2H, m), 7.42 (2H, m), 7.69 (1H, s), 8.26 (1H, m), 8.70 (2H, s), 9.03 (1H, s); MS (APCI$^+$) M+1=526, C$_{28}$H$_{36}$FN$_5$O$_2$S requires 525. MPt 187.7° C. (colourless solid). MPt. 187.7

Example 349

1-(Dodec-1-ylaminocarbonylmethyl)-2-(4-fluorobenzyl)thio-5-(pyrimid-5-ylmethyl)pyrimidin-4-one

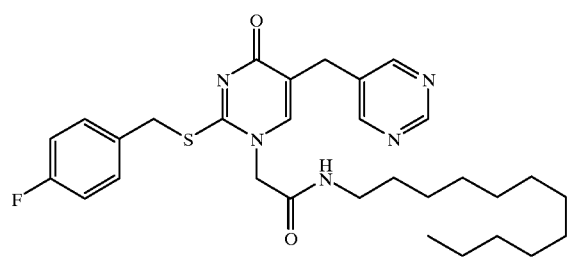

Prepared from Example 280 by general method E. $^1$H-NMR (d$_6$-DMSO) δ 0.85 (3H, m), 1.23 (18H, m), 1.35 (2H, m), 3.05 (2H, m), 3.59 (2H, s), 4.39 (2H, s), 4.53 (2H, s), 7.12 (2H, m), 7.43 (2H, m), 7.69 (1H, s), 8.20 (1H, m), 8.71 (2H, s), 9.03 (1H, s); MS (APCI$^+$) M+1=554, C$_{30}$H$_{40}$FN$_5$O$_2$S requires 553. MPt 191.1° C. (colourless solid).

Example 350

1-(Hept-1-ylaminocarbonylmethyl)-2-(4-fluorobenzyl)thio-5-(pyrimid-5-ylmethyl)pyrimidin-4-one

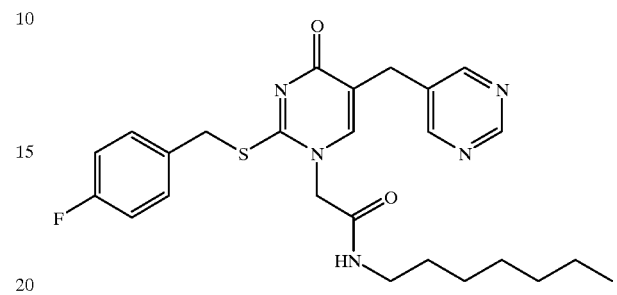

Prepared from Example 280 by general method E. $^1$H-NMR (d$_6$-DMSO) δ 0.84 (3H, m), 1.20 (8H, m), 1.37 (2H, m), 3.06 (2H, m), 3.59 (2H, s), 4.38 (2H, s), 4.54 (2H, s), 7.13 (2H, m), 7.42 (2H, m), 7.70 (1H, s), 8.26 (1H, m), 8.70 (2H, s), 9.03 (1H, s); MS (APCI$^+$) M+1=484, C$_{25}$H$_{30}$FN$_5$O$_2$S requires 483. MPt 189.1° C. (colourless solid). 189.1

Example 351

1-(Oct-1-ylaminocarbonylmethyl)-2-(4-fluorobenzyl)thio-5-(pyrimid-5-ylmethyl)pyrimidin-4-one

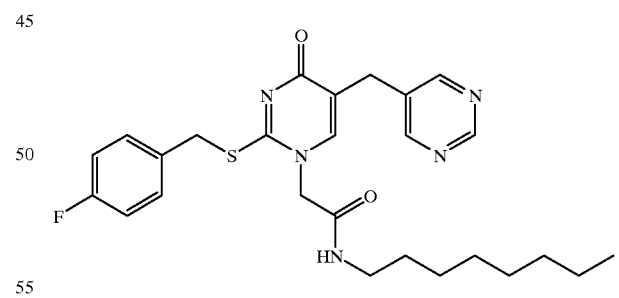

Prepared from Example 280 by general method E. $^1$H-NMR (CDCl$_3$) δ 0.88 (3H, t), 1.25 (10H, m), 1.48 (2H, m), 3.26 (2H, m), 3.70 (2H, s), 4.35 (2H, s), 4.46 (2H, s), 5.81 (1H, m), 6.93–7.03 (3H, m), 7.34 (2H, m), 8.71 (2H, s), 9.08 (1H, s); MS(APCI$^+$) M+1=498, C$_{26}$H$_{32}$FN$_5$O$_2$S requires 497. MPt 191–192° C. (colourless solid). MPt. 190–192

Example 352

1-(Undec-1-ylaminocarbonylmethyl)-2-(4-fluorobenzyl)thio-5-(pyrimid-5-ylmethyl)pyrimidin-4one

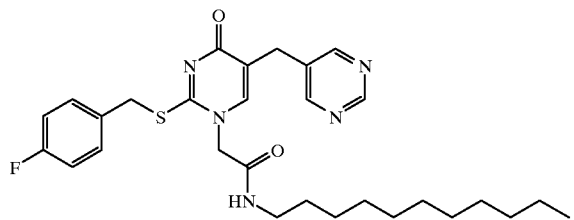

Prepared from Example 280 by general method E. $^1$H-NMR (d6-DMSO) δ 0.85 (3H, m), 1.20 (16H, m), 1.37 (2H, m), 3.06 (2H, m), 3.59 (2H, s), 4.39 (2H, s), 4.53 (2H, s), 7.12 (2H, m), 7.42 (2H, m), 7.69 (1H, s), 8.26 (1H, m), 8.70 (2H, s), 9.03 (1H, s); MS (APCI$^+$) M+1=540. C29H38FN5O2S requires 539. MPt 190.1° C. (colourless solid). MPt. 190.1

Example 353

1-(2-Hydroxyethylaminocarbonylmethyl)-2-(4-fluorobenzyl)thio-5-(pyrimid-5-ylmethyl)pyrimidin-4-one

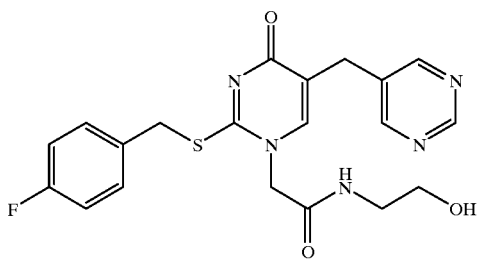

Prepared from Example 280 by general method E as a white solid $^1$H-NMR (d$_6$ DMSO) δ 3.15 (2H, q), 3.4 (2H, q), 3.58 (2H, s), 4.37 (2H, s), 4.57 (2H, s), 4.68 (1H, t), 7.05–7.2 (2H, m), 7.4–7.55 (2H, m), 7.70 (1H, s), 8.33 (1H, bt), 8.70 (2H, s), 9.03 (1H, s); MS (APCI$^+$) found (M+1)=430; C$_{20}$H$_{20}$FN$_5$O$_3$S requires 429.

Example 354

1-(2-Methoxyethylaminocarbonylmethyl)-2-(4-fluorobenzyl)thio-5-(pyrimid-5-ylmethyl)pyrimidin-4-one

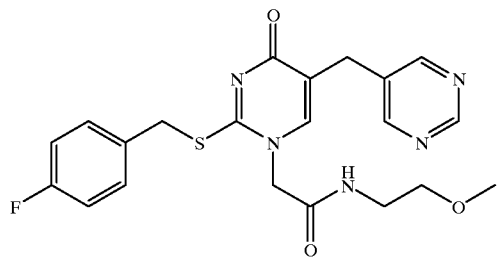

Prepared from Example 280 by general method E as a white solid $^1$H-NMR (CDCl$_3$/d6DMSO) δ 3.2–3.45 (7H, m), 3.63 (2H, s), 4.41 (2H, s), 4.59 (2H, s), 6.95–7.1 (2H, m), 7.35–7.5 (2H, m), 7.69 (1H, s), 8.37 (1H, bt), 8.70 (2H, s), 9.06 (1H, s); MS (APCI$^+$) found (M+1)=444; C$_{21}$H$_{22}$FN$_5$O$_3$S requires 443.

Example 355

1-(2-Phenylethylaminocarbonylmethyl)-2-(4-fluorobenzyl)thio-5-(pyrimid-5-ylmethyl)pyrimidin-4-one

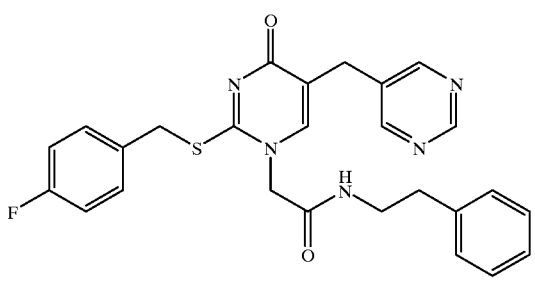

Prepared from Example 280 by general method E. $^1$H-NMR (CDCl$_3$) δ 2.80 (2H, t), 3.55 (2H, q), 3.66 (2H, s), 4.32 (2H, s), 4.41 (2H, s), 6.08 (1H, bt), 6.9–7.4 (10H, m), 8.66 (2H, s), 9.05 (1H, s); MS (APCI$^+$) found (M+1)=490; C$_{26}$H$_{24}$FN$_5$O$_2$S requires 489.

Example 356

1-(2-(4-Pent-1-ylphenyl)ethylaminocarbonylmethyl)-2-(4-fluorobenzyl)thio-5-(pyrimid-5-ylmethyl)pyrimidin-4-one

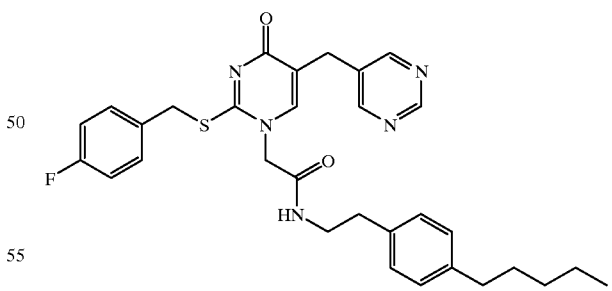

Prepared from Example 280 by general method E. $^1$H-NMR (d$_6$-DMSO) δ 0.86 (3H, m), 1.25 (4H, m), 1.51 (2H, m), 2.46 (2H, m), 2.66 (2H, m), 3.24 (2H, m), 3.59 (2H, s), 4.39 (2H, s), 4.53 (2H, s), 7.0–7.17 (6H, m), 7.46 (2H, m), 7.69 (1H, s), 8.32 (1H, m), 8.71 (2H, s), 9.02 (1H, s); MS (APCI$^+$) M+1=560, C$_{31}$H$_{34}$FN$_5$O$_2$S requires 559. MPt 170.6° C. (colourless solid).

Example 357

1-(Hex-1-ylaminocarbonylmethylaminocarbonylmethyl)-2-(4-fluorobenzyl)thio-5-(pyrimid-5-ylmethyl)pyrimidin-4-one

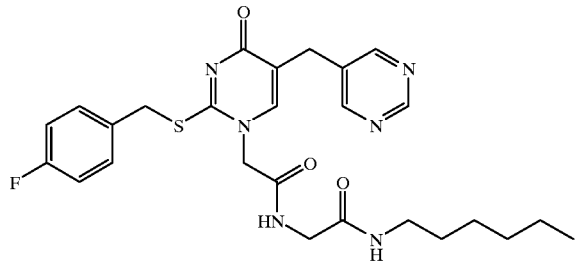

Prepared from Example 280 by general method E. white solid $^1$H-NMR (d6 DMSO) δ 0.8–0.95 (3H, m), 1.2–1.45 (8H, m), 2.95–3.10 (2H, m), 3.58 (2H, s), 3.72 (2H, bd), 4.38 (2H, m), 4.64 (2H, s), 7.05–7.2 (2H, m), 7.40–7.55 (2H, m), 7.70 (1H, s), 7.75–7.9 (1H, m), 8.5–8.6 (1H, m), 8.70 (2H, s), 9.01 (1H, s); MS (APCI$^+$) found (M+1)=527; $C_{26}H_{31}FN_6O_3S$ requires 526.

Example 358

1-(N-(Dodec-1-yl)-N-methylaminocarbonylmethyl)-2-(4-fluorobenzyl)thio-5-(pyrimid-5-ylmethyl)pyrimidin-4-one

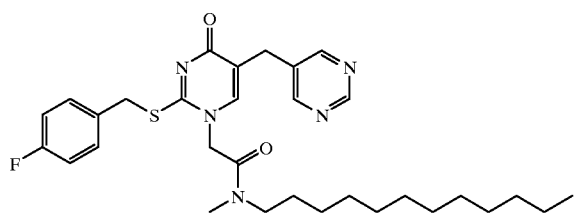

Prepared from Example 280 by general method E. $^1$H-NMR (CDCl$_3$) δ 0.88 (3H, m), 1.25 (18H, m), 1.50 (2H, m), 2.98 (3H, d), 3.21, 3.37 each 1H, m), 3.73 (2H, s), 4.52 (4H, m), 6.88 (1H, s), 6.99 (2H, m), 7.33 (2H, m), 8.71 (2H, s), 9.10 (1H, s), MS(APCI$^+$) M+1=568, $C_{31}H_{42}FN_5O_2S$ requires 567. MPt 145.3° C. (cream solid).

Example 359

1-(N-(2-Phenylethyl)-N-methylaminocarbonylmethyl)-2-(4-fluorobenzyl)thio-5-(pyrimid-5-ylmethyl)pyrimidin-4-one

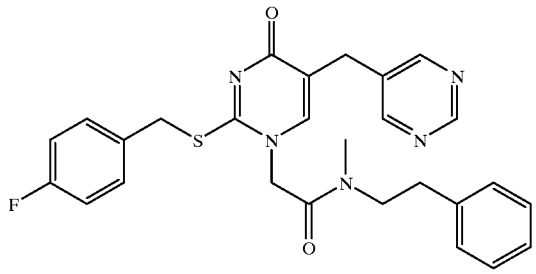

Prepared from Example 280 by general method E as a solid. $^1$H-NMR (CDCl$_3$) δ 2.78–2.97 (3H, m), 3.05 (2H, s), 3.42–3.57 (1H, m), 3.58–3.69 (2H, m), 3.73 (2s), 4.35–4.53 (3H, m), 6.12 (1H, s), 6.90–7.43 (9H, m), 8.62–8.75 (2H, d), 9.06–9.18 (1H, d); MS (APCI$^+$) found (M+1)=504; $C_{27}H_{26}FN_5O_2S$ requires 503.

Example 360

1-(4-(But-1-ylaminocarbonyl)cyclohex-1-yl)-2-(4-fluorobenzyl)thio-5-(pyrimid-5-ylmethyl)pyrimidin-4-one

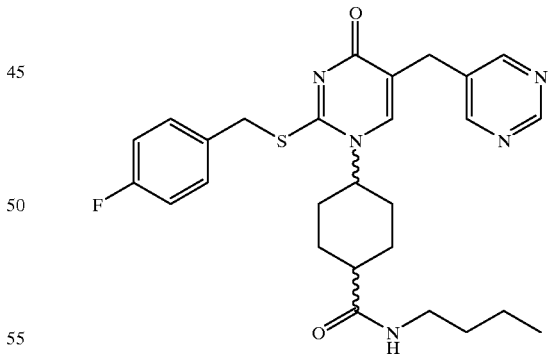

Prepared from Example 285 by general method E as a solid. $^1$H-NMR (CDCl$_3$) δ 0.85–1.04 (3H, t), 1.20–2.50 (13H, m), 3.18–3.33 (2H, q), 3.70 (2H, s), 4.01–4.20 (1H, m), 4.44 (2H, s), 5.47–5.63 (1H, br.t), 6.93–7.07 (2H, t), 7.32–7.43 (2H, m), 7.44 (1H, ), 8.72 (2H, s), 9.08 (1H, s); MS (APCI$^+$) found (M+1)=510; $C_{27}H_{32}FN_5O_2S$ requires 509.

Example 361

1-(4-(Hex-1-ylaminocarbonyl)cyclohex-1-yl)-2-(4-fluorobenzyl)thio-5-pyrimid-5-ylmethyl)pyrimidin-4-one

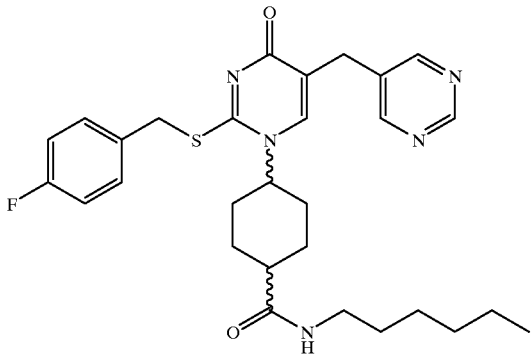

Prepared from Example 285 by general method E as a solid. $^1$H-NMR (CDCl$_3$) δ 0.78–0.97 (3H, t), 1.20–2.50 (17H, m), 3.17–3.32 (2H, q), 3.70 (2H, s), 4.03–4.20 (1H, m), 4.44 (2H, s), 5.47–5.60 (1H, br.t), 6.92–7.06 (2H, t), 7.30–7.40 (2H, m), 7.44 (1H, s), 8.71(2H, s), 9.09 (1H, s); MS (APCI$^+$) found (M+1)=538; C$_{29}$H$_{36}$FN$_5$O$_2$S requires 537.

Example 362

1-(4-(2-Methoxyethylaminocarbonyl)cyclohex-1-yl)-2-(4-fluorobenzyl)thio-5-(pyrimid-5-ylmethyl)pyrimidin-4-one

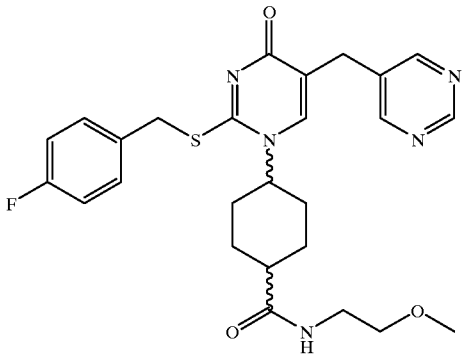

Prepared from Example 285 by general method E as a solid. $^1$H-NMR (CDCl$_3$) δ 1.58–1.90 (4H, m), 2.02–2.30 (4H, m), 2.48 (1H, br.s), 3.36 (3H, s), 3.47 (4H, s), 3.64 (2H, s), 4.03–4.20 (1H, m), 4.44 (2H, s), 5.91 (1H, br.s), 6.92–7.06 (2H, t), 7.31–7.45 (3H, m), 8.72 (2H, s), 9.06 (1H, s); MS (APCI$^+$) found (M+1)=512; C$_{26}$H$_{30}$FN$_5$O$_3$S requires 511.

Example 363

1-(1-(6-(4-Fluorophenyl)hex-1-yl)aminocarbonyl)cycloprop-1-yl)-2-(4-fluorobenzyl)thio-5-(pyrimid-5-ylmethyl)pyrimidin-4-one

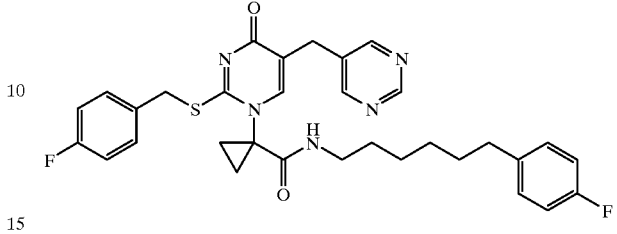

Prepared from Example 269, analogously to Example 315. $^1$H-NMR (CDCl$_3$) δ 1.15–1.71 (10H, m), 1.73–1.89 (1H, m), 1.94–2.01 (1H, m), 2.47–2.52 (2H, t), 2.98–3.18 (1H, m), 3.20–3.39 (1H, m), 3.60–3.69 (2H, d), 4.38 (2H, s), 5.64–5.78 (1H, br.t), 6.88–7.01 (4H, m), 7.03–7.20 (3H, m), 7.28–7.40 (2H, m), 8.68 (2H, s), 9.07 (1H, s); MS (APCI$^+$) found (M+1)=590; C$_{32}$H$_{33}$F$_2$N$_5$O$_2$S requires 589.

Example 364

1-(1-(Non-1-ylaminocarbonyl)cycloprop-1-yl)-2-(4-fluorobenzyl)thio-5-(pyrimid-5-ylmethyl)pyrimidin-4-one

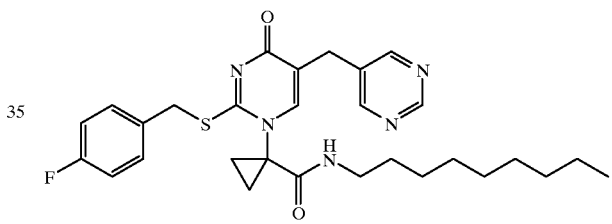

Prepared from Example 269, analogously to Example 315. $^1$H-NMR (CDCl$_3$) δ 0.78–0.98 (3H, t), 1.11–1.69 (16H, m), 1.73–1.89 (1H, m), 1.95–2.11 (1H, m), 3.00–3.19 (1H, m), 3.22–3.41 (1H, m), 3.55–3.78 (2H, br.q), 4.40 (2H, s), 5.52–5.65 (1H, br.t), 6.92 7.07 (2H, t), 7.26 (1H, s), 7.29–7.40 (2H, m), 8.69 (2H, s), 9.09 (1H, s); MS (APCI$^+$) found (M+1)=538; C$_{29}$H$_{36}$FN$_5$O$_2$S requires 537.

Example 365

1-((R)-1-(Non-1-ylaminocarbonyl)ethyl)-2-(4-fluorobenzyl)thio-5-(pyrimid-5-ylmethyl)pyrimidin-4-one

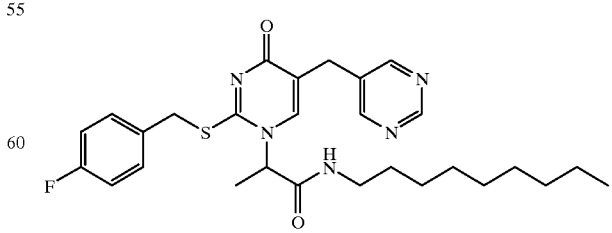

Prepared from Example 272, analogously to Example 315. $^1$H-NMR (CDCl$_3$) δ 0.80–0.94 (3H, t), 1.15–1.37 (12H, m), 1.38–1.54 (2H, m), 1.55–1.66 (3H, d), 3.10–3.36 (2H, m), 3.58–3.80 (2H, br.q), 4.32–4.55 (2H, br.q), 4.72–4.88 (1H, q), 6.08–6.20 (1H, br.t), 6.41–7.06 (2H, t), 7.29–7.39 (2H, m), 7.50 (1H, s), 8.70 (2H, s), 9.07 (1H, s); MS (APCI$^+$) found (M+1)=526; $C_{28}H_{36}FN_5O_2S$ requires 525.

Example 366

1-(11-(Dimethylamino)undec-1-ylaminocarbonylmethyl)-2-(4-fluorophorobenzyl)thio-5(pyrimid-5-ylmethyl)pyrimidin-4-one

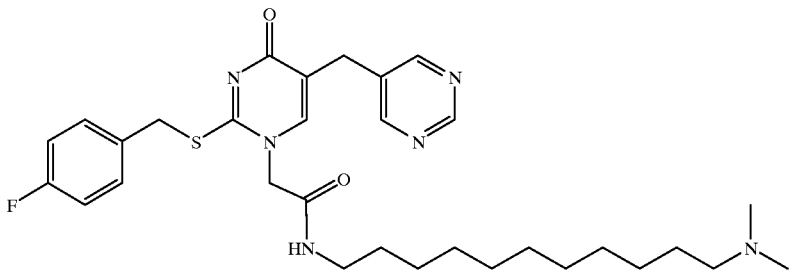

Prepared from Example 280 by general method E. $^1$H-NMR (d$_6$-DMSO) δ 1.20 (16H, m), 1.37 (2H, m), 2.15 (6H, s), 2.22 (2H, m), 3.07 (2H, m), 3.59 (2H, s), 4.38 (2H, s), 4.54 (2H, s), 7.13 (2H, m), 7.43 (2H, m), 7.70 (1H, s), 8.26 (1H, m), 8.70 (2H, s), 9.03 (1H, s); MS (APCI$^+$) M+1=583, $C_{31}H_{43}FN_6O_2S$ requires 582. MPt 152–155° C. (colourless solid). MPt. 152–155

Example 367

1-(2-(6-(4-Fluorophenyl)hex-1-yloxy)ethylaminocabonylmethyl)-2-(4-fluorobenzyl)thio-5-(pyrimid-5-ylmethyl)pyrimidin-4-one

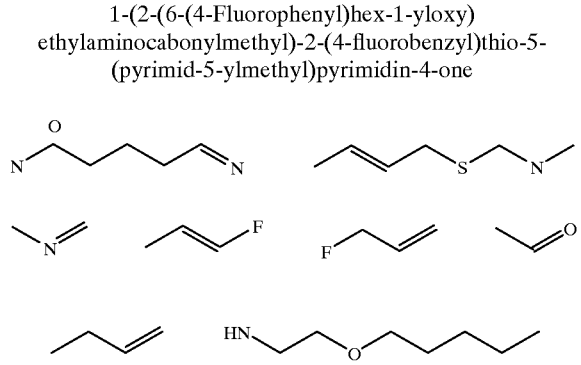

Prepared from Example 280 by general method E. $^1$H-NMR (d$_6$-DMSO) δ 1.26 (4H, m), 1.47 (4H, m), 2.56 (2H, m), 3.23 (2H, m), 3.40 (4H, m), 3.59 (2H, s), 4.38 (2H, s), 4.56 (2H, s), 7.03–7.21 (6H, m), 7.43 (2H, m), 7.69 (1H, s), 8.26 (1H, m), 8.70 (2H, s), 9.03 (1H, s); MS (APCI$^+$) M+1=608, $C_{32}H_{35}F_2N_5O_3S$ requires 607. MPt 155–159° C. (colourless solid). MPt. 155–159

Example 368

1-(5-(Methoxycarbonyl)-5-(benzyloxycarbonylamino)pent-1-ylaminocarbonylmethyl)-2-(4-fluorobenzyl)thio-5-(pyrimid-5-ylmethyl)pyrimidin-4-one

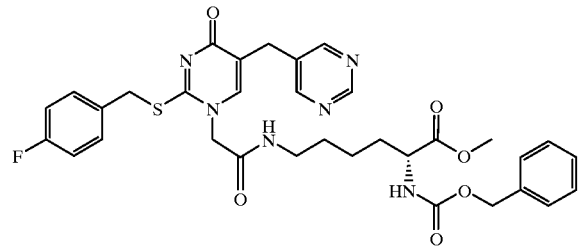

Prepared from Example 280 by general method E. $^1$H-NMR (d$_6$-DMSO) δ 1.35 (4H, m), 1.61 (2H, m), 3.05 (2H, m), 3.61 (5H, m), 3.99 (1H, m), 4.38 (2H, s), 4.52 (2H, s), 5.03 (2H, s), 7.11 (2H, m), 7.34 (5H, m), 7.44 (2H, m), 7.69 (2H, m), 8.24 (1H, m), 8.71 (2H, s), 9.02 (1H, s); MS (APCI$^+$) M+1=663, $C_{33}H_{35}FN_6O_6S$ requires 662. (colourless solid).

Example 369

1-(5-(Methoxycarbonyl)pent-1-ylaminocarbonylmethyl)-2-(4-fluorobenzyl)thio-5-(pyrimid-5-ylmethyl)pyrimidin-4-one

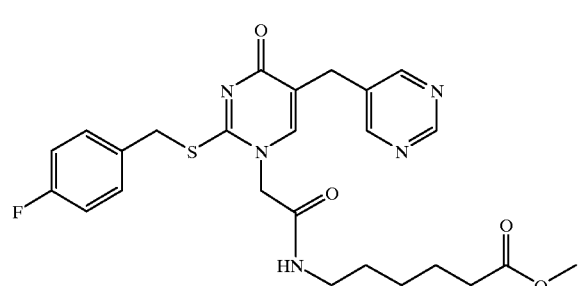

Prepared from Example 280 by general method E. $^1$H-NMR (d$_6$-DMSO) δ 1.19–1.55 (6H, m), 2.24 (2H, m), 3.06 (2H, m), 3.58 (3H, s), 3.60 (2H, s), 4.39 (2H, s), 4.53 (2H, s), 7.12 (2H, m), 7.44 (2H, m), 7.69 (1H, s), 8.26 (1H, m), 8.70 (2H, s), 9.03 (1H, s); MS (APCI$^+$) M+1=514, C$_{25}$H$_{28}$FN$_5$O$_4$S requires 513. MPt 166.8° C. (colourless solid). MPt. 166–172

Example 370

1-(Non-1-ylaminocarbonylmethyl)-2-(4-fluorobenzyl)thio-5-(pyrimid-5-ylmethyl)pyrimidin-4-one

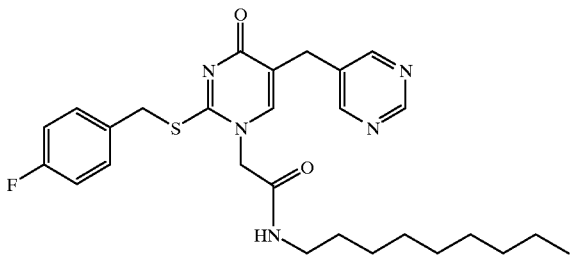

Prepared from Example 280 by general method E. $^1$H-NMR (d$_6$-DMSO) δ 0.85 (3H, m), 1.21 (12H, bs), 1.35 (2H, m), 3.07 (2H, m), 3.60 (2H, s), 4.39 (2H, s), 4.53 (2H, s), 7.14 (2H, m), 7.45 (2H, m), 7.69 (1H, s), 8.22 (1H, m), 8.68 (2H, s), 9.06 (1H, s); MS (APCI$^+$) M+1=512, C$_{27}$H$_{34}$FN$_5$O$_2$S requires 511. MPt 200–202° C. (colourless solid).

Example 371

1-Dimethylaminocarbonylmethyl-2-(4-fluorobenzyl)thio-5-(pyrimid-5-ylmethyl)pyrimidin-4-one

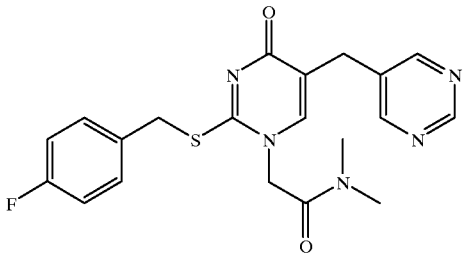

Prepared from Example 280 by general method E as a solid. $^1$H-NMR (DMSO) δ 2.86 (3H, s), 2.97 (3H, s), 3.59 (2H, s), 4.39 (2H, s), 4.86 (2H, s), 7.06–7.20 (2H, t), 7.49–7.52 (2H, m), 7.59 (1H, s), 8.70 (2H, s), 9.04 (1H, s); MS (APCI$^+$) found (M+1)=414; C$_{20}$H$_{20}$FN$_5$O$_2$S requires 413.

Example 372

1-(N-(2-Hydroxyethyl)-N-methylaminocabonylmethyl)-2-(4-fluorobenzyl)thio-5-(pyrimid-5-ylmethyl)pyrimidin-4-one

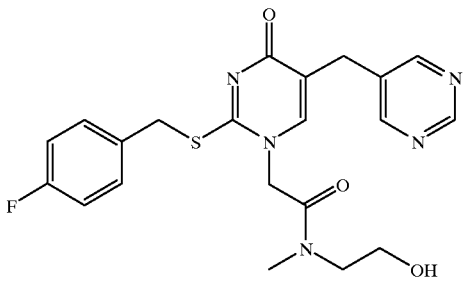

Prepared from Example 280 by general method E. pale yellow solid $^1$H-NMR (d6 DMSO) δ 2.86+3.02 (2H, 2xs), 3.2–3.65 (6H, m), 4.39 (2H, s), 4.6–5.05 (3H, m), 7.05–7.2 (2H, m), 7.35–7.55 (2H, m), 8.70 (2H, s), 9.03 (1H, s); MS (APCI$^+$) found (M+1)=444; C$_{21}$H$_{22}$FN$_5$O$_3$S requires 443.

Example 373

1-(trans-4-(4-Fluorobenzylaminocarbonyl)cyclohex-1-ylmethyl)-2-(4-fluorobenzyl)thio-5-(pyrimid-5-ylmethyl)pyrimidin-4-one

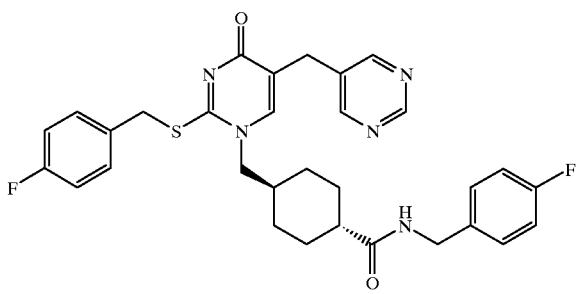

Prepared from Example 273, analogously to Example 315. $^1$H-NMR (CDCl$_3$) δ 0.80–2.15 (10H, m), 3.51–3.65 (2H, d), 3.71 (2H, s), 4.33–4.43 (2H, d), 4.47 (2H, s), 5.64–5.78 (1H, br.t), 6.89 (1H, s), 6.92–7.08 (4H, t), 7.15–7.44 (4H, m), 8.69 (2H, s), 9.10 (1H, s); MS (APCI$^+$) found (M+1)=576; C$_{31}$H$_{31}$F$_2$N$_5$O$_2$S requires 575.

Example 374

1-(trans4-(Pent-1-ylaminocarbonyl)cyclohex-1-ylmethyl)-2-(4-fluorobenzyl)thio-5-(pyrimid-5-ylmethyl)pyrimidin-4-one

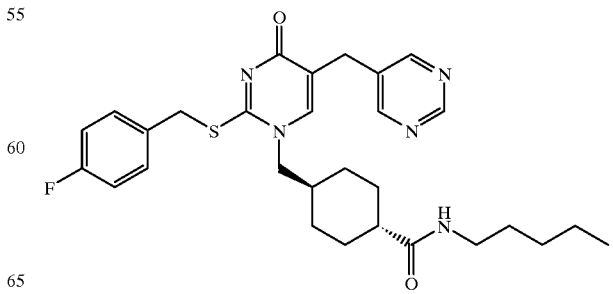

Prepared from Example 273, analogously to Example 315. $^1$H-NMR (CDCl$_3$) δ 0.81–2.09 (19H, m), 3.16–3.40 (2H, q), 3.52–3.65 (2H, d), 3.71 (2H, s), 4.46 (2H, s), 5.32–5.45 (1H, br.t), 6.89 (1H, s), 6.95–7.08 (2H, t), 7.30–7.45 (2H, m), 8.70 (2H, s), 9.11 (1H, s); MS (APCI$^+$) found (M+1)=538; C$_{29}$H$_{36}$FN$_5$O$_2$S requires 537.

Example 375

1-(3-(Hex-1ylaminocarbonyl)prop-1-yl)-2-(4-fluorobenzyl)thio-5-((1-methyl-2-oxo-pyrid-4-yl)methyl)pyrimidin-4-one

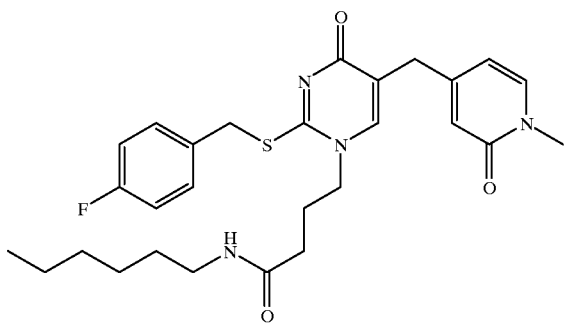

Prepared from Example 281 by general method E. $^1$H-NMR (CDCl$_3$) δ 0.88 (3H, t), 1.28 (6H, m), 1.45 (2H, m), 2.04 (2H, m), 2.20 (2H, m), 3.19 (2H, m), 3.50 (3H, s), 3.54 (2H, s), 3.86 (2H, t), 4.47 (2H, s), 5.69 (1 h, bm), 6.21 (1H, m), 6.34 (1H, s), 7.01 (2H, m), 7.09 (1H, s), 7.19 (1H, d), 7.39 (2H, ml): MS (APCI$^+$) M+1=527, C$_{28}$H$_{35}$FN$_4$O$_3$S requires 526. MPt 134–136° C. (colourless solid). MPt. 134–136

Example 376

1-(N-(N'-Hex-1-yl-N'-methylaminocarbonylmethyl)-N-methyl-aminocarbonylmethyl)-2-(4-fluorobenzyl)thio-5-(pyrimidyl-5-ylmethylopyrimidin-4-one

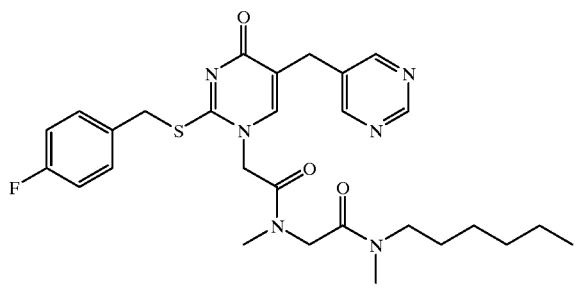

Prepared from Example 280 by general method E. $^1$H-NMR (CDCl$_3$) δ 0.88 (3H, m), 1.28 (6H, m), 1.4–1.65 (2H, m), 2.92–3.09 (6H, m), 3.17–3.36 (2H, m), 3.70 (2H, s), 4.05–4.19 (2H, m), 4.48–4.67 (4H, m), 6.97 (2H, m) 7.07 (1H, s), 7.35 (2H, m), 8.71 (2H, s), 9.08 (1H, s); MS (APCI+) found (M+1)=555; C$_{28}$H$_{35}$FN$_6$O$_3$S requires 554.

Example 377

1-(N-(N'-Hex-1-ylaminocarbonylmethyl)-N-methylaminocarbonyl-methyl)-2-(4-fluorobenzyl)thio-5-(pyrimid-5-ylmethyl)pyrimidin-4-one

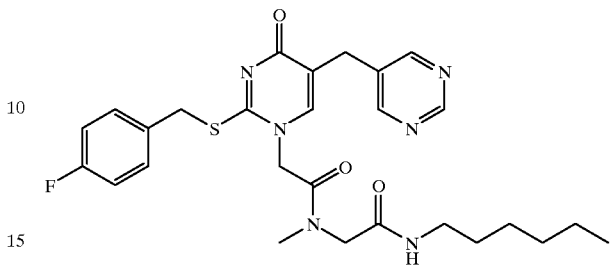

Prepared from Example 280 by general method E. $^1$H-NMR (CDCl$_3$) δ 0.87 (3H, m), 1.26 (6H, m), 1.44 (2H, m), 2.98 and 3.14 (3H, 2Xs), 3.19 (2H, m), 3.70 (2H, s), 3.87 and 3.97 (2H, 2Xs), 4.46 (2H, m), 4.64 (2H, m), 5.98 and 6.16 (1H, 2Xt), 6.98 (3H, m), 7.33 (2H, m), 8.70 (2H, s), 9.08 (1H, s); MS (APCI+) found (M+1)=541; C$_{27}$H$_{33}$FN$_6$O$_3$S requires 554.

Example 378

1-(N-(N'-Hex-1-yl-N'-methylaminocarbonylmethyl)aminocarbonyl-methyl)-2-(4-fluorobenzyl)thio-5-(pyrimid-5-ylmethyl)pyrimidin-4-one

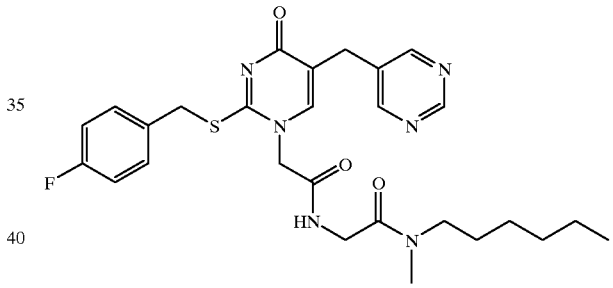

Prepared from Example 280 by general method E. $^1$H-NMR (CDCl$_3$) δ 0.88 (3H, m), 1.28 (6H, m), 1.52 (2H, m), 2.94 (3H, m), 3.18 and 3.38 (2H, 2Xt), 3.72 (2H, s), 4.03 (2H, m), 4.47 (4H, m), 6.98 (3H, m), 7.34 (2H, m), 8.71 (2H, s), 9.09 (1H, s); MS (APCI+) found (M+1)=541; C$_{27}$H$_{33}$FN$_6$O$_3$S requires 540.

Example 379

1-Phenylaminocarbonylmethyl-2-(4-fluorobenzyl)thio-5-(pyrimid-5-ylmethyl)pyrimidin-4-one

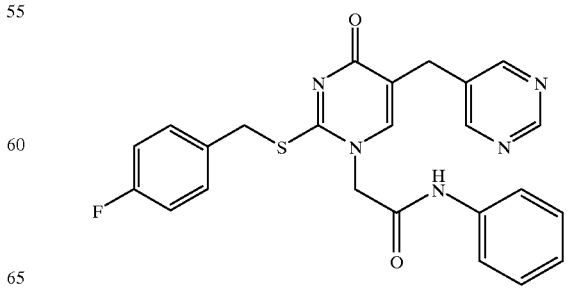

Prepared from Example 280 by general method E. ¹H-NMR (d₆-DMSO) δ 3.62 (2H, s), 4.41 (2H, s), 4.79 (2H, s), 7.0–7.2 (3H, m), 7.25–7.4 (2H, m), 7.4–7.6 (4H, m), 7.76 (1H, bs), 8.72 (2H, s), 9.04 (1H, s); MS (APCI+) found (M+1)=462; $C_{24}H_{20}FN_5O_2S$ requires 461.

Example 380

1-(4-Methoxycarbonylbenzylaminocarbonylmethyl)-2(4-fluorobenzyl)thio-5-(pyrimid-5-ylmethyl)pyrimidin-4-one

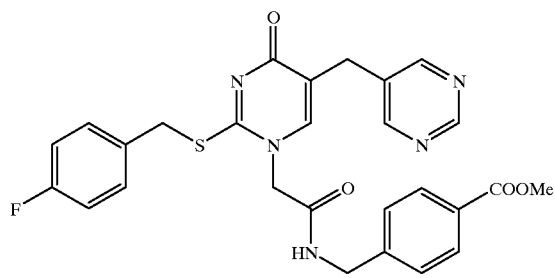

Prepared from Example 280 by general method E. ¹H-NMR (d₆-DMSO) δ 3.60 (2H, s), 3.86 (3H, s), 4.38 (2H, s), 4.40 (2H, s), 4.67 (2H, s), 7.05–7.25 (2H, m), 7.3–7.55 (4H, m), 7.74 (1H, s), 7.84 (2H, d), 8.70 (2H, s), 8.93 (1H, t), 9.03 (1H, s); MS (APCI+) found (M+1))=532; $C_{27}H_{24}FN_5O_4S$ requires 533.

Example 381

1-(N-Benzylaminocarbonylmethyl)-2-(4-fluorobenzyl)thio-5-(pyrimid-5-ylmethyl)pyrimidin-4-one

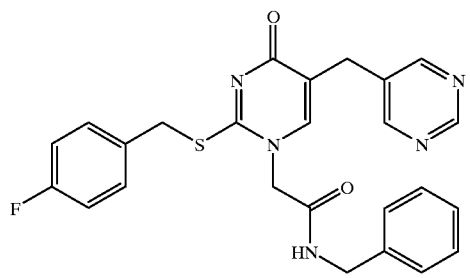

Prepared from Example 280 by general method E. ¹H-NMR (CDCl₃) δ 3.66(2H, s), 4.41(4H, s), 4.45(2H, d, j=5.7 Hz), 6.40(1H, brs), 6.94(1H, t, j=8.6 Hz), 7.03(1H, s), 7.23(8H, m), 8.66(2H, s), 9.06(1H, s): MS (APCI) found (M+H)=476; $C_{25}H_{22}FN_5O_2S$ requires 475.

Example 382

1-(N,N-Di-(but-1-yl)aminocarbonylmethyl)-2-(4-fluorobenzyl)thio-5-(pyrimid-5-ylmethyl)pyrimidin-4-one

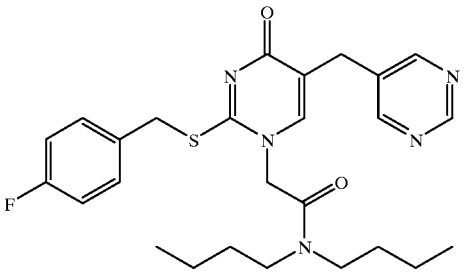

Prepared from Example 280 by general method E. ¹H-NMR (CDCl3) δ 0.8–1.05 (6H, m), 1.1–1.75 (8H, m), 3.19 (2H, t), 3.33 (2H, t), 3.72 (2H, s), 4.49 (2H, s), 4.52 (2H, s), 6.85–7.1 (3H, m), 7.3–7.45 (2H, m), 8.70 (1H, s), 9.09 (1H, s); MS (APCI+) found (M+1)=498; $C_{28}H_{32}FN_5O_2S$ requires 497

Example 383

1-(N-Methyl-N-(dodec-1-yl)aminocarbonylmethyl)-2-(4-fluorobenzyl)thio-5-(2-methoxypyrimid-5-ylmethyl)pyrimidin-4-one

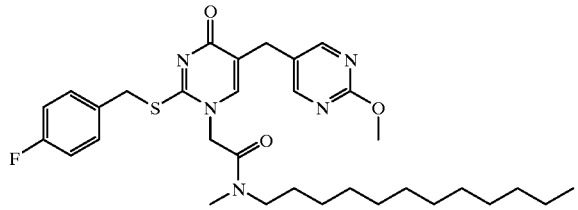

Prepared from Example 108 by general method C2. ¹H-NMR (CDCl₃) δ 0.85 (3H, t), 1.2 (18H, m), 1.5 (2H, m,), 2.92 and 2.95 (3H, 2xs), 3.17 and 3.33 (2H, 2xs), 3.63 (2H, s), 3.96 (3H, s), 4.45 (2H, s), 4.49 and 4.52 (2H, 2×s), 6.79 (1H, s), 6.95 (2H, m), 7.30 (2H, m), 8.42 (2H, s); MS (APCI+) found (M+1)=598, $C_{32}H_{44}FN_5O_3S$ requires 597.

Example 384

1-(N-Methyl-N-(oct-1-yl)aminocarbonylmethyl)-2-(4-fluorobenzyl)thio-5-(2-methoxypyrimid-5-ylmethyl)pyrimidin-4-one

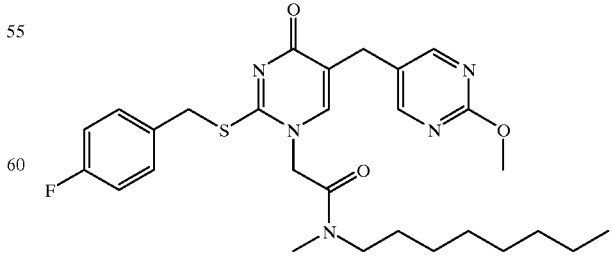

Prepared from Example 108 by general method C2. ¹H-NMR (CDCl₃) δ 0.8–0.95 (3H, m), 1.1–1.7 (12H, m), 2.95 and 2.99 (3H, 2xs), 3.21 and 3.36 (2H, 2xt), 3.66 (2H, s), 3.99 (3H, s), 4.48 (2H, s), 4.51 and 4.55 (2H, d), 6.80 (1H, s), 6.9–7.1 (2H, m), 7.3–7.45 (2H, m), 8.45 (2H, s); MS (APCI+) found (M+1)=542; $C_{28}H_{36}FN_5O_3S$ requires 541.

Example 385

1-(N-Methyl-N-(oct-1-yl)aminocarbonylmethyl)-2-(4-fluorobenzyl)thio-5-(2-etboxypyrimid-5-ylmethyl)pyrimidin-4-one

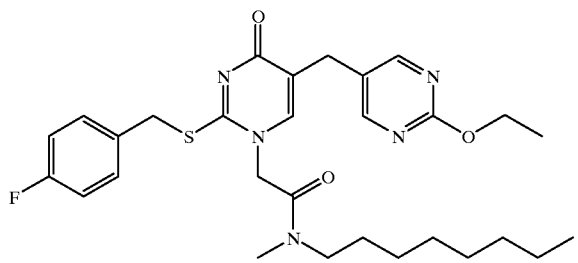

Isolated as an impurity from one of the batches of Example 384, which had in turn been made from an impure batch of Example 108. $^1$H-NMR (CDCl$_3$) δ 0.8–0.95 (3H, t), 1.1–1.7 (12H, m), 1.42 (3H, t), 2.95 and 2.99 (3H, 2xs), 3.23 and 3.36 (2H, 2xt), 3.65 (2H, s), 4.39 (2H, q), 4.49 (2H, s), 4.50 and 4.54 (2H, d), 6.77 (1H, s), 6.9–7.1 (2H, m), 7.3–7.4 (2H, m), 8.43 (2H, s); MS (APCI+) found (M+1)=556; $C_{29}H_{38}FN_5O_3S$ requires 555.

Example 386

1-(N-Methyl-N-(oct-1-yl)aminocarbonylmethyl)-2-(4-fluorobenzyl)thio-5-(2-benzyloxypyrimid-5-ylmethyl)pyrimidin-4-one

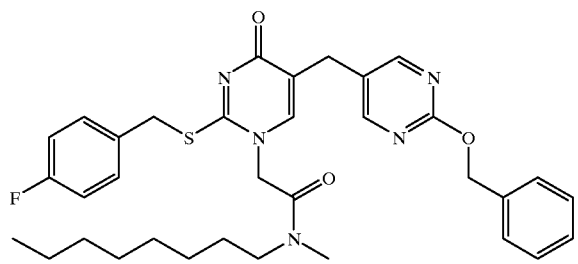

Prepared from Example 109 by general method C2. $^1$H-NMR (CDCl$_3$) δ 0.75–1.0 (3H, t), 1.05–1.75 (12H, m), 2.95 and 2.98 (3H, 2xs), 3.20 and 3.36 (2H, 2xs), 3.65 (2H, s), 4.4–4.6 (4H, m), 5.42 (2H, s), 6.80 (1H, s), 6.9–7.1 (2H, m), 7.05–7.2 (2H, m), 7.15–7.55 (7H, m), 8.45 (2H, s); MS (APCI−) found (M+1)=618; $C_{34}H_{40}FN_5O_3S$ requires 617.

Example 387

1-(N-Methyl-N-(dodec-1-yl)aminocarbonylmethyl)-2-(4-fluorobenzyl)thio-5-(2-oxopyrimid-5-ylmethyl)pyrimidin-4-one

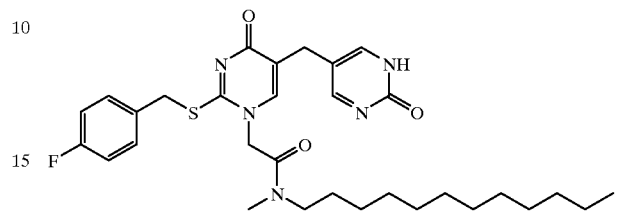

To a stirring solution of Example 383 (7.05 g) in dichloromethane (200 ml) was added in one portion B-bromocatecholborane (10 g). After stirring for 16 h at room temperature, the mixture was poured into water with stirring, diluted with more dichloromethane, shaken, and the phases allowed to separate slowly. The organic layer was purified by flash chromatography (silica, methanol-dichloromethane) and trituration with pet. ether. $^1$H-NMR (CDCl$_3$) δ 0.87 (3H, m), 1.2–1.4 (20, m), 2.88 and 2.96 (3H, 2xs), 3.15–3.4 (4H, m), 3.43 (2H, s), 4.41 (2H, m), 4.88 (2H, m), 6.9–7.0 (2H, m), 7.25–7.4 (2H, m), 7.50 (1H, m), 8.15 (2H, b); MS (APCI+) found (M+1)=584; $C_{31}H_{42}FN_5O_3S$ requires 583.

Example 388

1-(N-Methyl-N-(oct-1-yl)aminocarbonylmethyl)-2-(4-fluorobenzyl)thio-5-(2-oxopyrimid-5-ylmethyl)pyrimidin-4-one

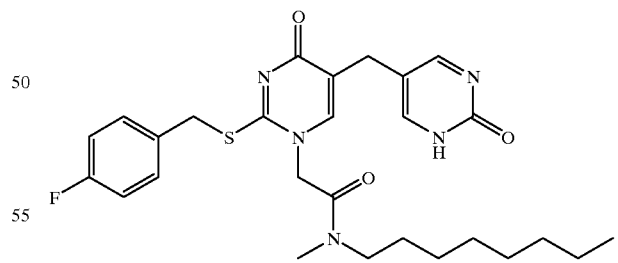

Prepared analogously to Example 387, from Example 384. 1H-NMR (d$_6$ DMSO) δ 0.8–0.95 (3H, m), 1.05–1.65 (12, m), 2.81 and 2.94 (3H, 2xs), 3.15–3.4 (4H, m), 4.39 (2H, s), 4.83 and 4.85 (2H, 2xd), 7.05–7.2 (2H, m), 7.35–7.55 (3H, m), 7.95–8.35 (2H, b); MS (APCI+) found (M+1)=526. $C_{27}H_{35}FN_5O_3S$ requires 525.

Example 389

1-(3-(N-(Hept-1-yl)-N-methylaminocarbonyl)phenyl)-2-(4-fluorobenzyl)thio-5-(pyrimid-5-ylmethyl)pyrimidin-4one

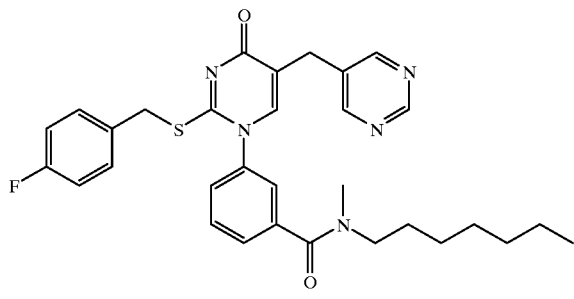

Prepared from Example 288 by general method E. 1H NMR (DMSO-d6) δ: 0.7–1.05 (m, 6H), 1.3 (m, 5H), 1.41 (m, 1H), 1.56 (br s, 1H), 2.9 (d, 3H), 3.15 (m, 1H), 3.4 (m, 1H), 3.63 (s, 2H), 4.30 (s, 2H), 7.10 (t, 2H), 7.41 (m, 2H), 7.55 (m, 1H), 7.60–7.85 (m, 3H), 7.95 (m, 1H), 8.78 (s, 2H), 9.02 (s, 1H). MS (APCI+) Found (M+1) 560; $C_{31}H_{34}FN_5O_2S$ requires 559.

Example 390

1-(3-(N-Ethyl-N-methylaminocarbonyl)phenyl)-2-(4-fluorobenzyl)thio-5-(pyrimid-5-ylmethyl)pyrimidin-4-one

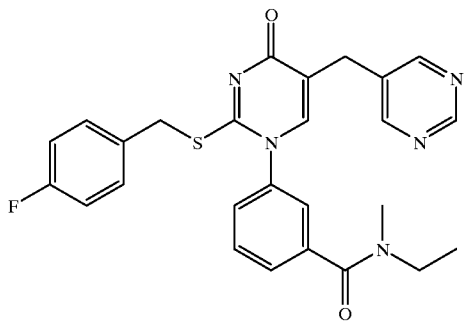

Prepared from Example 288 by general method E. $^1$H NMR (DMSO-d$_6$) δ: 1.0–1.2 (m, 3H), 2.9 (d, 3H), 3.18 (m, 1H), 3.45 (m, 1H), 3.62 (s, 2H), 4.31 (s, 2H), 7.10 (t, 2H), 7.40 (m, 2H), 7.60–7.85 (m, 4H), 7.96 (s, 1H), 8.78 (s, 2H), 9.01 (s, 1H). MS (APCI+) Found (M+1)=490; $C_{26}H_{24}FN_5O_2S$ requires 489.

Example 391

1-(4-(Prop-1-ylaminocarbonyl)phenyl)-2-(4-fluorobenzyl)thio-5-(pyrimid-5-ylmethyl)pyrimidin-4-one

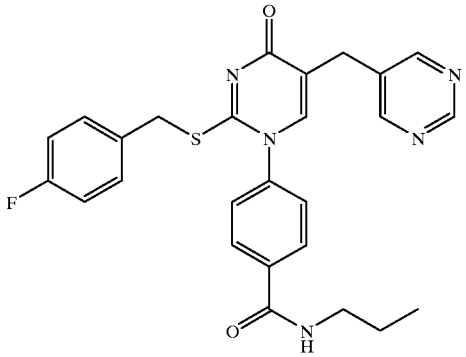

Prepared from Example 292 by general method E. $^1$H NMR (CDCl$_3$) δ: 1.00 (t, 3H), 1.65 (m, 2H), 3.44 (q, 2H), 3.81 (s, 2H), 4.35 (s, 2H), 6.15 (t, 1H), 6.95 (t, 2H), 7.20 (s, 1H), 7.25 (m, 2H), 7.41 (d, 2H), 7.89 (d, 2H), 8.95 (s, 2H), 9.20 (s, 1H). MS (APCI+) Found (M+1)=490; $C_{26}H_{24}FN_5O_2S$ requires 489.

Example 392

1-(4-(But-1-ylaminocarbonyl)phenyl)-2-(8-(4-chlorophenyl)-8-oxooct-1-yl)thio-5-(pyrimid-5-ylmethyl)pyrimidin-4-one

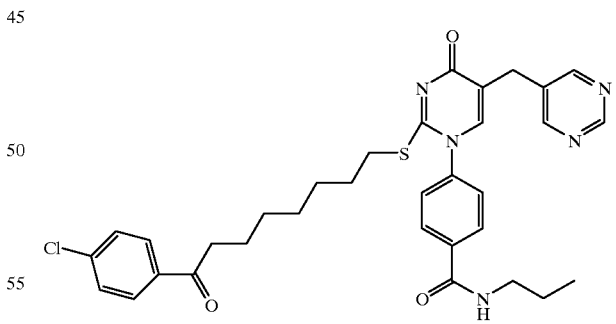

Prepared from Example 293 by general method E. $^1$H NMR (CDCl$_3$) δ: 1.01 (t, 3H), 1.21 (m, 2H), 1.3 (m, 6H), 1.7 (m, 4H), 2.91 (t, 2H), 3.15 (t, 2H), 3.46 (m, 2H), 3.73 (s, 2H), 6.29 (t, 1H), 7.03 (s, 1H), 7.4 (m, 4H), 7.95 (m, 4H), 8.71 (s, 2H), 9.08 (s, 1H). MS (APCI+) Found (M+1)=618/620; $C_{33}H_{36}ClN_5O_3S$ requires 618.

Example 393

1-(4-(Hex-1-yloxycarbonyl)phenyl)-2-(4-fluorobenzyl)thio-5-(pyrimid-5-ylmethyl)pyrimidin-4-one

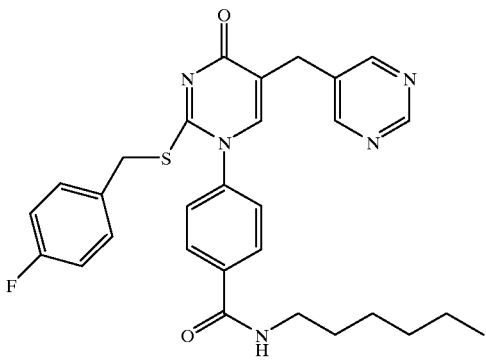

Prepared from Example 292 by general method E as a white solid, m.p. 121–123. $^1$H NMR (CDCl$_3$) δ: 0.89 (t, 3H), 1.35 (m, 4H), 1.65 (m, 4H), 3.46 (q, 2H), 3.74 (s, 2H), 4.36 (s, 2H), 6.11 (t, 1H), 6.95 (t, 2H), 7.04 (s, 1H), 7.30 (m, 2H), 7.39 (d, 2H), 7.90 (d, 2H), 8.72 (s, 2H), 9.10 (s, 1H). MS (APCI+) Found (M+1)=532; C$_{29}$H$_{30}$FN$_5$O$_2$S requires 531.

Example 394

1-(4-Methylaminocarbonylbenzyl)-2-(4-fluorobenzyl)thio-5-(pyrimid-5-ylmethyl)pyrimidin-4-one

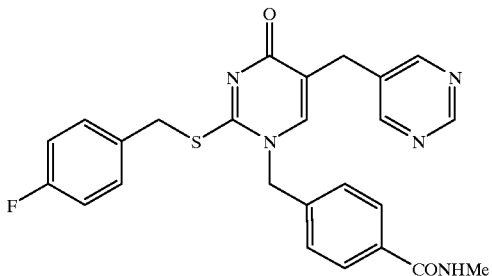

Carbonyl diimidazole (105 mg, 0.65 mmol) was added to a suspension of Example 284 (150 mg, 0.32 mmol) in dichloromethane (10 ml) under an atmosphere of argon and the reaction stirred for 1 h. Methylamine (1.62 ml, 2M solution in THF) was added and stirring continued for 2 h. The solvent was removed under reduced pressure and the residue partitioned between ethyl acetate and water. The aqueous phase was extracted with ethyl acetate and the combined organic phase dried (MgSO$_4$) and the the solvent removed under reduced pressure. The residue was purified by flash chromatography (10% methanol/ethyl acetate) to afford the desired compound as an off white solid (77 mg, 50%).

$^1$H-NMR (CDCl$_3$) 8.90 (s, 1H), 8.47 (s, 2H), 7.60 (m, 2H), 7.25–6.65 (m, 6H), 6.28 (s, 1H), 4.85 (s, 2H), 4.27 (s, 2H), 3.51 (s, 2H), 2.85 (s, 3H). MS (AP+) 476 (M+H$^+$, 100%).

Example 395

1-(3-Methylaminocarbonyl-4-(hept-1-yloxy)benzyl)-2-(4-fluorobenzyl)thio-5-(pyrimid-5-ylmethyl)pyrimidin-4-one

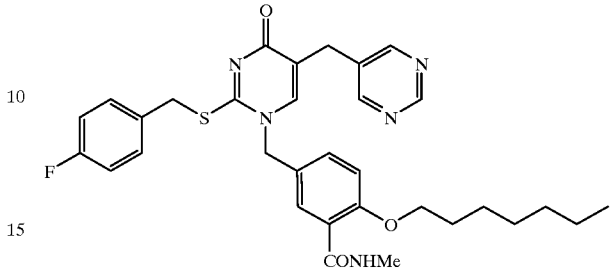

Prepared analogously to Example 394, from Example 298, as an off white solid. 1H-NMR (CDCl$_3$) 8.98 (s, 1H), 8.67 (s. 2H), 8.58 (s, 1H), 8.06 (m, 1H), 7.28 (m, 2H), 7.06 (m, 2H), 6.89 (m, 2H), 4.87 (s, 2H), 4.38 (s, 2H), 4.05 (t, 2H), 3.58 (s, 2H), 2.93 (s, 3H), 1.81 (m, 2H), 1.45–1.15 (m, 8H), 0.82 (m, 3H). MS (AP+) 590 (M+H$^+$, 100%).

Example 396

1-(2-(t-Butoxycarbonylamino)ethyl)-2-(4-fluorobenzyl)thio-5-(pyrimid-5-ylmethyl)pyrimidin-4-one Prepared from intermediate B138 by general method A2. $^1$H-NMR (CDCl$_3$) δ 1.41 (9H, s), 3.43 (2H, q, J 6.0 Hz), 3.67 (2H, s), 3.97 (2H, s), 4.46 (2H, s), 4.88 (1H, s), 6.99 (2H, m), 7.07 (1H, s), 7.36 (2H, m), 8.70 (2H, s) and 9.09 (1H, s). (APCI$^+$) Found (M+1)=472. C$_{23}$H$_{26}$FN$_5$O$_3$S requires 471.

Example 397

1-(2-(Trifluoroacetylamino)ethyl)-2-(4-fluorobenzyl)thio-5-(pyrimid-5-ylmethyl)pyrimidin-4-one The compound of Example 396 (200 mg) was dissolved in neat TFA (1 ml) at room temperature. After 5 min. the solution was concentrated to a brown gum and re-evaporated from ethyl acetate. The crude amine salt in ethyl acetate (5 ml) was treated with diisopropylethylamine (81 mg) and acetyl chloride (50 mg) for 24 h. The crude reaction mixture was purified by silica gel chromatography to give the title compound as a colourless solid, (72 mg, 37%), $^1$H-NMR (CDCl$_3$) δ 3.58 (2H, s), 3.77 (2H, m), 4.11 (2H, t, J 4.7 Hz), 4.37 (2H, s), 6.92–7.02 (3H, m), 7.24–7.31 (2H, m), 8.63 (2H, s), 9.04 (1H, s) and 9.13 (1H, t, J 5.5 Hz). (APCI–) Found (M–1)=466. C$_{20}$H$_{17}$F$_4$N$_5$O$_2$S requires 467.

Example 398

1-(2-(Benzoylamino)ethyl)-2-(4-fluorobenzyl)thio-5-(pyrimid-5-ylmethyl)pyrimidin-4-one

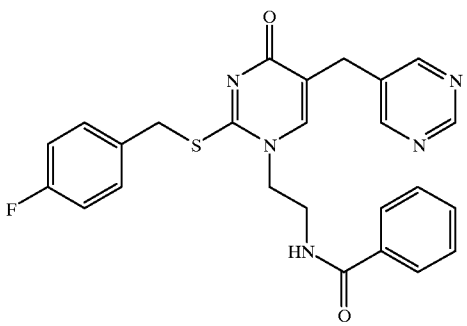

The compound of Example 396 was treated with trifluoroacetic acid as described in the previous example. A solution of the salt in ethyl acetate was treated with excess 1M hydrochloric acid in ether. The corresponding dihydrochloride salt was precipitated, filtered, washed with ether and dried in vacuo to give the crude salt as a white solid. 1-(3-Dimethylaminopropyl)-3-ethylcarbodiimide hydrochloride (72 mg), 1-hydroxy-benzotriazole hydrate (52 mg) and benzoic acid (42 mg) in dichloromethane (5 ml) at room temperature was treated with the above dihydrochloride (150 mg). Diisopropylethylamine (88 mg) in DMF (1 ml) was added and the solution stirred for 48 h. The reaction mixture was diluted with dichloromethane washed with water, brine, dried over anhydrous magnesium sulfate and concentrated. The crude product was purified by silica gel chromatography to give the title compound as a white solid, (84 mg, 52%), $^1$H-NMR (CDCl$_3$) 3.52 (2H, s), 3.60 (2H, m), 4.04 (2H, t, J 5.5 Hz), 4.36 (2H, s), 7.09 (2H, m), 7.35–7.53 (5H, m), 7.71–7.75 (3H, m), 8.63 (3H, m and s) and 9.02 (1H, s). (APCI$^+$) Found (M+1)=476. C$_{25}$H$_{22}$FN$_5$O$_2$S requires 475.

Example 399

1-(2-(Hex-1-ylcarbonylamino)ethyl)-2-(4-fluorobenzyl)thio-5-(pyrimid-5-ylmethyl)pyrimidin-4-one

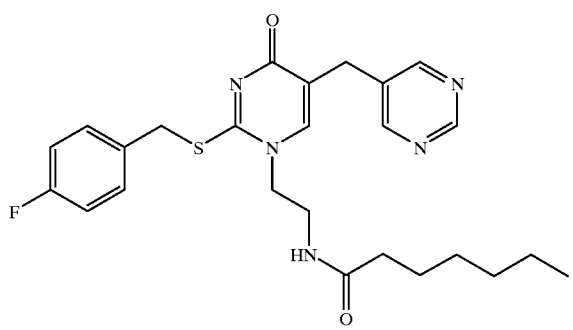

Prepared analogously to Example 398, using heptanoic acid. 1H-NMR (CDCl$_3$) δ 0.87 (3H, t, J 6.8 Hz), 1.26 (6H, br.s), 1.56 (2H, m), 2.14 (2H, t, J 7.9 Hz), 3.54 (2H, dd, J 5.8, 5.9 Hz), 3.66 (2H, s), 4.00 (2H, t, J 5.9 Hz), 4.43 (2H, s), 6.19 (1H, t, J 5.8 Hz) 7.02 (2H, m), 7.06 (1H, s), 8.70 (2H, s) and 9.08 (1H, s). (APCI$^+$) Found (M+1)=484. C$_{25}$H$_{30}$FN$_5$O$_2$S requires 483.

Example 400

1-(2-(5-Phenylpent-1-ylcarbonylamino)ethyl)-2-(4-fluorobenzyl)thio-5-(pyrimid-5-ylmethyl)pyrimidin-4-one

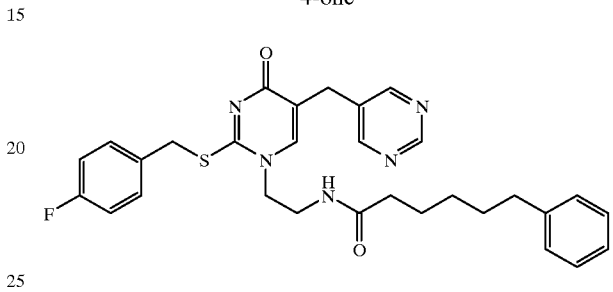

a) Prepared analogously to Example 398, using 6-phenylhexanoic acid. 1H-NMR (CDCl$_3$) δ 1.33 (2H, m), 1.61 (4H, m), 2.13 (2H, t, J 7.7 Hz), 2.59 (2H, t, J 7.7 Hz), 3.52 (2H, m), 3.60 (2H, s), 3.97 (2H, t, J 5.8 Hz), 4.40 (2H, s), 6.44 (1H, t, J 5.2 Hz), 6.99 (2H, t, J 8.6 Hz), 7.04 (1H, s), 7.12–8.57 (7H, m), 8.67 (2H, s) and 9.05 (1H, s). (APCI$^+$) Found (M+1)=546. C$_{30}$H$_{32}$FN$_5$O$_2$S requires 545.

b) Also prepared by reaction of the amine dihydrochloride with 6-phenylhexanoyl chloride in the presence of diisopropylamine. After work up and purification by silica gel chromatography, the title compound was obtained as a colourless solid in 49% yield.

Example 401

1-(2-(Hept-1-ylcarbonylamino)ethyl)-2-(4-fluorobenzyl)thio-5-(pyrimid-5-ylmethyl)pyrimidin-4-one

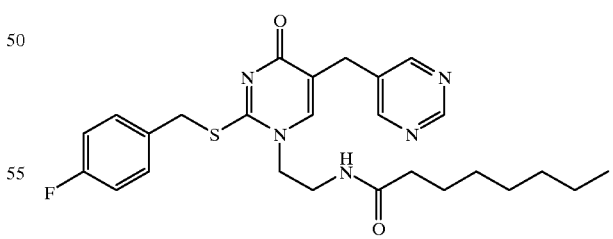

Prepared analogously to Example 398, using octanoic acid. 1H-NMR (CDCl$_3$) δ 0.86 (3H, t, J 6.8 Hz), 1.25 (8H, br.s), 1.58 (2H, m), 2.16 (2H, t, J 7.8 Hz), 3.55 (2H, m), 3.63 (2H, s), 4.01 (2H, t, J 5.7 Hz), 4.40 (2H, s), 6.69 (1H, br.t, J 5.4 Hz), 6.98 (2H, t, J 8.5 Hz), 7.09 (1H, s), 7.31 (2H, m), 8.69 (2H, s) and 9.07 (1H, s). (APCI$^+$) Found (M+1)=498. C$_{26}$H$_{32}$FN$_5$O$_2$S requires 497.

Example 402

1-(2-Acetylaminoethyl)-2-(8-(4-chlorophenyl)-8-oxooct-1-yl)thio-5-pyrimid-5-ylmethylpyrimidin-4-one

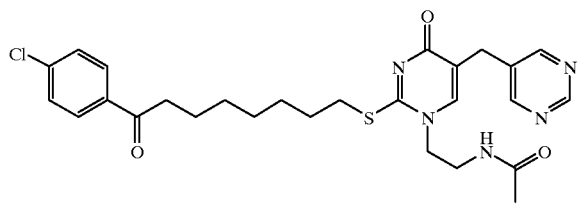

Prepared from intermediate B76 by general method A4. $^1$H-NMR (CDCl$_3$) δ 1.2–1.9(10H, m), 2.02(3H, s), 2.92(2H, t), 3.20(2H, t), 3.5–3.8(4H, m), 4.04(2H, m), 7.04(1H, s), 7.43(2H, m), 7.88(2H, m), 8.71(2H, s) and 9.06(1H, s); MS (APCI+) found (M+1)=542; C$_{27}$H$_{32}$ClN$_5$O$_3$S requires 541.

Example 403

1-(4-(tert-Butoxycarbonylamino)but-1-yl)-2-(4-fluorobenzyl)thio-5-(pyrimid-5-ylmethyl)pyrimidin-4-one

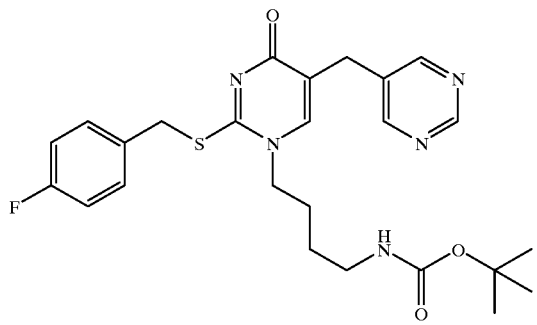

Prepared from intermediate B122 by general method A2. $^1$H NMR (CDCl$_3$) δ: 1.43 (s, 9H), 1.5 (m, 2H), 1.75 (m, 2H), 3.15 (m, 2H), 3.70 (s, 2H), 3.83 (t, 2H), 4.46 (s, 2H), 4.65 (br s, 1H), 7.00 (t, 2H), 7.20 (s, 1H), 7.37 (m, 2H), 8.70 (s, 2H), 9.08 (s, 1H). MS (APCI+) Found (M+1)=500; C$_{25}$H$_{30}$FN$_5$O$_3$S requires 499.

Example 404

1-(3-(Ethoxycarbonylamino)prop-1-yl)-2-(4-fluorobenzyl)thio-5-(pyrimid-5-ylmethyl)pyrimidin-4-one

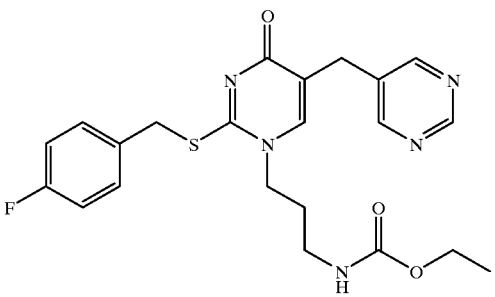

Prepared from intermediate B123 by general method A2. $^1$H NMR (CDCl$_3$) δ: 1.23 (t, 3H), 1.93 (m, 2H), 3.20 (q, 2H), 3.71 (s, 2H), 3.86 (t, 2H), 4.10 (m, 2H), 4.46 (s, 2H), 5.25 (br s, 1H), 7.00 (t, 2H), 7.30 (s, 1H), 7.40 (m, 2H), 8.72 (s, 2H), 9.06 (s, 1H). MS (APCI+) Found (M+1)=458; C$_{22}$H$_{24}$FN$_5$O$_3$S requires 457.

Example 405

1-(2-(Benzylaminocarbonylamino)ethyl)-2-(4-fluorobenzyl)thio-5-pyrimid-5-ylmethyl)pyrimidin-4-one

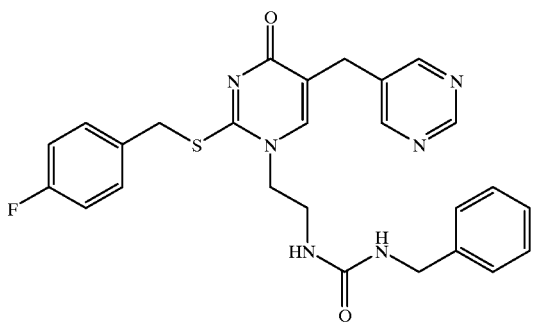

Prepared from Example 396 by general method F. 1H-NMR (CDCl$_3$) δ 3.39 (2H, s), 3.58 (2H, m), 4.03 (2H, t, J 5.7 Hz), 4.31 (2H, s), 4.30 (2H, d, J 5.0 Hz), 5.97 (1H, t, J 5.9 Hz), 6.26 (1H, t, J 5.6 Hz), 6.91–6.99 (3H, m), 7.20–8.58 (7H, m), 8.58 (2H, s) and 9,05 (1H, s). (APCI$^+$) Found (M+1)=505. C$_{26}$H$_{25}$FN$_6$O$_2$S requires 504.

Example 406

1-(2-(Dodec-1-ylaminocarbonylamino)ethyl)-2-(4-fluorobenzyl)thio-5-(pyrimid-5-ylmethyl)pyrimidin-4-one

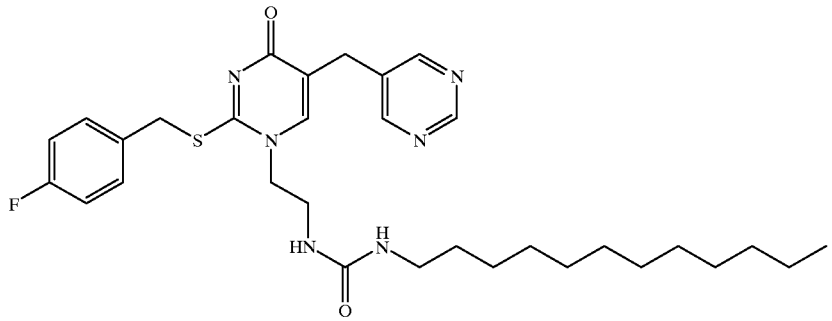

Prepared from Example 396 by general method F.
1H-NMR (CDCl$_3$) δ 0.87 (3H, t, J 6.8 Hz), 1.27 (18H, v.br s), 1.48 (2H, m), 3.17 (2H, dd, J 6.5, 13.0 Hz), 3.52 (2H, m), 3.58 (2H, s), 4.03 (2H, t, J 5.0 Hz), 4.40 (2H, s), 5.21 (1H, m), 5.70 (1H, m), 6.95 (2H, m), 7.10 (1H, s), 7.30 (2H, m), 8.66 (2H, s) and 9.08 (1H, s). (APCI$^+$) Found (M+1)=583. C$_{31}$H$_{43}$FN$_6$O$_2$S requires 582.

Example 407

1-(2-(Hept-1-ylaminocarbonylamino)ethyl)-2-(4-fluorobenzyl)thio-5-(pyrimid-5-ylmethyl)pyrimidin-4-one

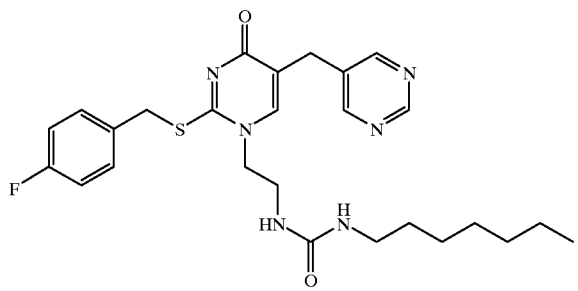

Prepared from Example 396 by general method F.
1H-NMR (CDCl$_3$) δ 0.85 (3H, m), 1.26 (8H, m), 1.49 (2H, m), 3.16 (2H, m), 3.51–3.60 (4H, s and m), 4.04 (2H, t, J 5.8 Hz), 4.39 (2H, s), 5.30 (1H, m), 5.83 (1H, m), 6.94–7.02 (2H, m), 7.07 (1H, s), 7.28–8.60 (2H, m), 8.67 (2H, s) and 9.08 (1H, s). (APCI$^+$) Found (M+1)=513. C$_{26}$H$_{33}$FN$_6$O$_2$S requires 512.

Example 408

1-(2-(Oct-1-ylaminocarbonylamino)ethyl)-2-(4-fluorobenzyl)thio-5-(pyrimid-5-ylmethyl)pyrimidin-4-one

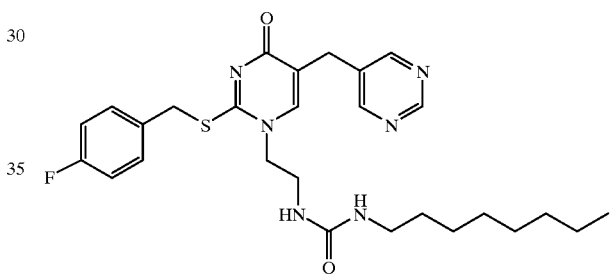

Prepared from Example 396 by general method F.
1H-NMR (CDCl$_3$) δ 0.86 (3H, m), 1.24 (10H, m), 1.50 (2H, m), 3.17 (2H, dd, J 6.8, 13.0 Hz), 3.52 (2H, m), 3.57 (2H, s), 4.04 (2H, t, J 5.5 Hz), 4.39 (2H, s), 5.31 (1H, m), 5.85 (1H, m), 7.01 (2H, m), 7.07 (1H, s), 7.30 (2H, m), 7.68 (2H, s) and 9.08 (1H, s). (APCI$^+$) Found (M+1)527. C$_{27}$H$_{35}$FN$_6$O$_2$S requires 526.

Example 409

1-(2-(2-Thien-2-ylethylaminocarbonylamino)ethyl)-2-(4-fluorobenzyl)thio-5-(pyrimid-5-ylmethyl)pyrimidin-4-one

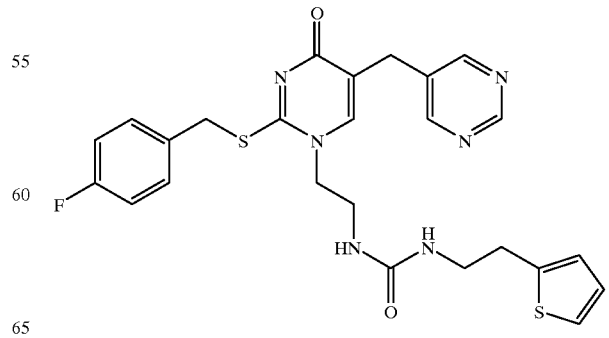

Prepared from Example 396 by general method F. 1H-NMR (CDCl₃) δ 3.06 (2H, t, J 6.8 Hz), 3.52 (6H, m), 4.01 (2H, t, J 5.6 Hz), 4.37 (2H, s), 5.47 (1H, t, J 5.7 Hz), 5.97 (1H, t, J 5.3 Hz), 6.85–7.31 (8H, m), 8.65 (2H, s) and 9.07 (1H, s). (APCI⁺) Found (M+1)=525. $C_{25}H_{25}FN_6O_2S_2$ requires 524.

Example 410

1-(2-(1,1,3,3-Tetramethylbut-1-ylaminocarbonylamino)ethyl)-2-(4-fluorobenzyl)thio-5-(pyrimid-5-ylmethyl)pyrimidin-4-one

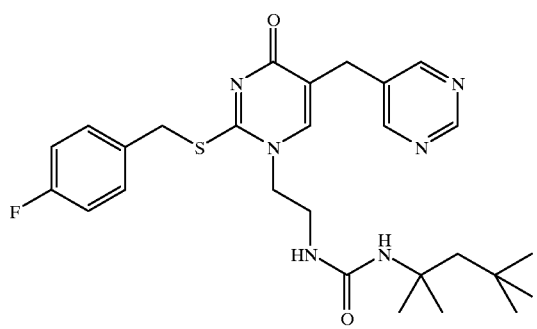

Prepared from Example 396 by general method F. 1H-NMR (CDCl₃) δ 1.01 (9H, s), 1.39 (6H, s), 1.75 (2H, s), 3.51 (2H, m), 3.59 (2H, s), 4.02 (2H, t, J 5.5 Hz), 4.39 (2H, s), 5.25 (1H, s), 5.78 (1H, t, J 5.6 Hz), 6.98 (2H, m), 7.13 (1H, s), 7.31 (2H, m), 8.67 (2H, s) and 9.08 (1H, s). (APCI⁺) Found (M+1)=527. $C_{27}H_{35}FN_6O_2S$ requires 526.

Example 411

1-(2-(4-(Butoxycarbonyl)phenylaminocarbonylamino)ethyl)-2-(4-fluorobenzyl)thio-5-(pyrimid-5-ylmethyl)pyrimidin-4-one

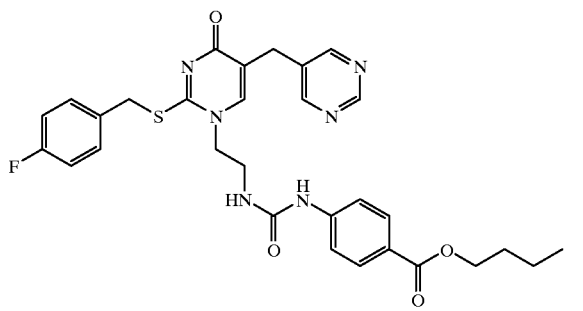

Prepared from Example 396 by general method F. 1H-NMR (CDCl₃) δ 0.97 (3H, t, J 7.4 Hz), 1.44 (2H, m), 1.73 (2H, m), 3.54 (2H, s), 3.67 (2H, m), 4.13 (2H, m), 4.28 (4H, m), 6.92 (3H, m), 7.18 (2H, m), 7.55 (2H, d, J 8.8 Hz), 7.93 (2H, d, J 8.8 Hz), 8.62 (2H, s), 8.82 (1H, s) and 9.10 (1H, s). (APCI⁺) Found (M+1)=591. $C_{30}H_{31}FN_6O_4S$ requires 590.

Example 412

1-(2-(4-(1-Methylethyl)phenylaminocarbonylamino)ethyl)-2-(4-fluorobenzyl)thio-5-(pyrimid-5-ylmethyl)pyrimidin-4-one

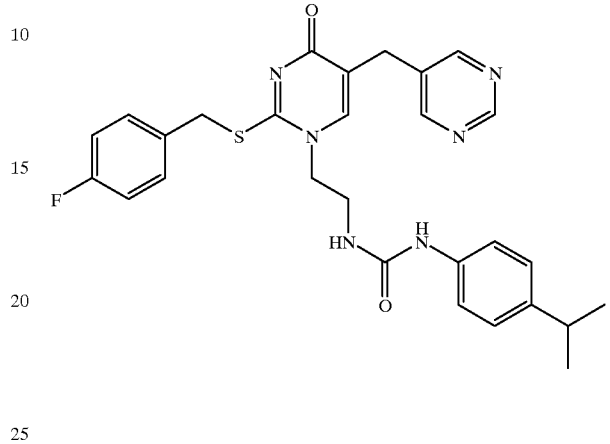

Prepared from Example 396 by general method F. 1H-NMR (CDCl₃) δ 1.20 (6H, d, J 6.9 Hz), 2.84 (1H, m), 3.55 (2H, s), 3.60 (2H, m), 4.12 (2H, t, J 4.8 Hz), 4.33 (2H, s), 6.48 (1H, m), 6.92 (2H, m), 7.11–7.34 (7H, m), 8.00 (1H, s), 8.63 (2H, s) and 9.10 (1H, s). (APCI⁺) Found (M+1)=533. $C_{28}H_{29}FN_6O_2S$ requires 532.

Example 413

1-(2-(4-Methylphenylaminocarbonylamino)ethyl)-2-(4-fluorobenzyl)thio-5-(pyrimid-5-ylmethyl)pyrimidin-4-one

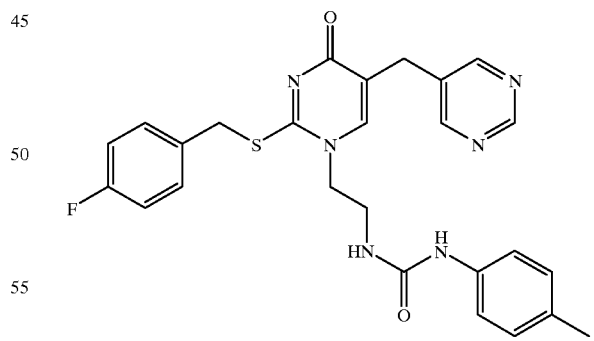

Prepared from Example 396 by general method F. 1H-NMR (CDCl₃) δ 2.29 (3H, s), 3.54 (2H, s), 3.60 (2H, m), 4.11 (2H, t J 5.5 Hz), 4.32 (2H, s), 6.50 (1H, m), 6.90–7.08 (4H, m), 7.18–7.30 (5H, m), 8.03 (1H, br.s), 8.64 (2H, s) and 9.09 (1H, s). (APCI⁺) Found (M+1)=5.05. $C_{26}H_{25}FN_6O_2S$ requires 504.

Example 414

1-(2-(4-Ethoxyphenylaminocarbonylamino)ethyl)-2-(4-fluorobenzyl)thio-5-(pyrimid-5-ylmethyl)pyrimidin-4-one

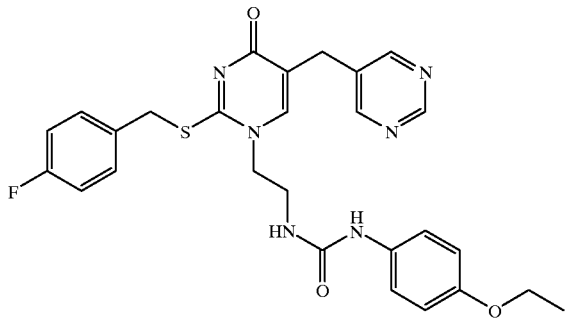

Prepared from Example 396 by general method F.
1H-NMR (CDCl$_3$) δ 1.40 (3H, t, J 4.2 Hz), 3.57 (4H, v.br.s), 3.97 (2H, q, J 4.2 Hz), 4.08 (2H, t, J 5.4 Hz), 4.34 (2H, s), 6.13 (1H, br.s), 6.79–6.98 (4H, m), 7.17 (1H, s), 7.23 (4H, m), 7.63 (1H, br.s), 8.66 (2H, s) and 9.09 (1H, s). (APCI$^+$) Found (M+1)=535. $C_{27}H_{27}FN_6O_3S$ requires 534.

Example 415

1-(2-(4-Phenoxyphenylaminocarbonylamino)ethyl)-2-(4-fluorobenzyl)thio-5-(pyrimid-5-ylmethyl)pyrimidin-4-one

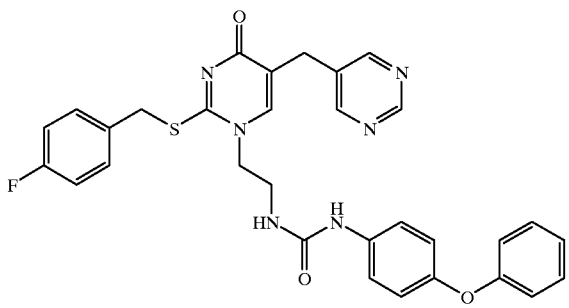

Prepared from Example 396 by general method F.
$^1$H-NMR (CDCl3) δ 3.56 (2H, s), 3.63 (2H, m), 4.13 (2H, m), 6.57 (1H, m), 6.57–8.22 (14H, m), 8.23 (1H, s), 8.65 (2H, s) and 9.05 (1H, s). (APCI$^+$) Found (M+1)=583. $C_{31}H_{27}FN_6O_3S$ requires 582.

REFERENCES

1. EP 645370 (1995)
2. Eur J Med Chem 1989, 24 (1), 65
3. Eur J Med Chem 1990, 25 (3), 217
4. Eur J Med Chem 1993, 28 (7–8), 601
5. J Labelled Comp Radiopharn 1987, 24 (4), 431
6. J Med Chem 1995, 38, 3850
7. EP 117345 (1984)
8. EP 68833 (1982)
9. Liebigs Ann Chem 1994, 1849
10. J Amer Chem Soc 1950, 72, 3539
11. GB 1 582 527
12. Bull. Soc. Chi. Fr. 1263 (1956); ibid. 1466 (1957)
13. DE 84-3414752 A11984
14. Tet Lett 1983, 24(48), 5309–5312
15. J. Chem. Soc. 1957, 3314.

Biological Data

1. Screen for Lp-PLA$_2$ inhibition.

Enzyme activity was determined by measuring the rate of turnover of the artificial substrate (A) at 37 C. in 50 mM HEPES (N-2-hydroxyethylpiperazine-N'-2-ethanesulphonic acid) buffer containing 150 mM NaCl, pH 7.4.

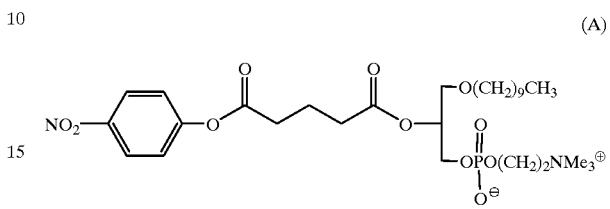

(A)

Assays were performed in 96 well titre plates. Recombinant LpPLA$_2$ was purified to homogeneity from baculovirus infected Sf9 cells, using a zinc chelating column, blue sepharose affinity chromatography and an anion exchange column. Following purification and ultrafiltration, the enzyme was stored at 6 mg/ml at 4° C. Assay plates of compound or vehicle plus buffer were set up using automated robotics to a volume of 170 μl. The reaction was initiated by the addition of 20 μl of 10× substrate (A) to give a final substrate concentration of 20 μM and 10 μl of diluted enzyme to a final 0.2 nM LpPLA$_2$.

The reaction was followed at 405 nm and 37 ° C. for 20 minutes using a plate reader with automatic mixing. The rate of reaction was measured as the rate of change of absorbance.

Results

The compounds described in the above Examples were tested as hereinbefore described and were found to have IC$_{50}$ values in the range 0.0001 to 60 uM.

What is claimed is:

1. A compounds of formula (I):

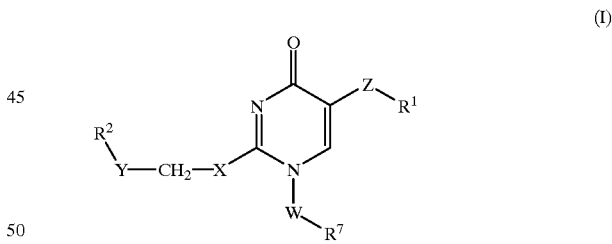

(I)

in which:
Z is CR$^3$R$^4$, where R$^3$ and R$^4$ are each hydrogen or C$_{(1-4)}$alkyl, or R$^3$ and R$^4$ together with the intervening carbon atom form a C$_{(3-6)}$cycloalkyl ring; and
R$^1$ is an aryl or heteroaryl group, substituted or substituted by 1, 2, 3 or 4 substituents selected from the group consisting of C$_{(1-18)}$alkyl, C$_{(1-18)}$alkoxy, C$_{(1-18)}$alkylthio, arylC$_{(1-18)}$alkoxy, oxo, hydroxy, halogen, CN, COR$^5$, COOR$^5$, CONR$^5$R$^6$, NR$^5$COR$^6$, SO$_2$NR$^5$R$^6$, NR$^5$SO$_2$R$^6$, NR$^5$R$^6$, mono to perfluoro-C$_{(1-4)}$alkyl and mono to perfluoro-C$_{(1-4)}$alkoxy;
X is O or S;
Y is —A$^1$—A$^2$—A$^3$— in which A$^1$ and A$^3$ each represent a bond or a straight chain or branched C$_{(1-10)}$alkylene group and $A^2$ represents a bond or O, S, SO, $SO_2$, CO, C=$CH_2$, CH=CH , C•C, CONH, NHCO, or $CR^5R^6$, providing that when $A^2$ is O, S, SO, $SO_2$ or CONH, $A^3$ contains at least two carbon atoms linking the $A^2$ group and the $CH_2$ group in formula (I);

$R^2$ is an aryl or heteroaryl group, unsubstituted or substituted by 1, 2, 3 or 4 substituents selected from the substituents hereinbefore defined for $R^1$, as well as aryl and aryl$C_{(1-4)}$alkyl;

W is $SO_2$ or a bond; and $R^7$ is $R^1$ or a hydrocarbyl group which hydrocarbyl group may be optionally interrupted within the carbon chain by a group selected from the group consisting of O, COO, OCO, CO, CONR$^8$, NR$^8$CO, NR$^8$CONR$^9$, NR$^8$COO, OCONR$^8$, and NR$^8$, and which hydrocarbyl group may also be optionally substituted by 1 or 2 substituents selected from the group consisting of mono to perfluoro-$C_{(1-4)}$alkyl, OR$^8$, COOR$^8$, CONR$^8$R$^9$, NR$^8$COR$^9$, NR$^8$CONR$^9$R$^{10}$, NR$^8$COOR$^9$, OCONR$^8$R$^9$, NR$^{11}$R$^{12}$ and $R^1$;

$R^5$ and $R^6$ are independently hydrogen or $C_{(1-20)}$alkyl; for instance $C_{(1-4)}$alkyl (e.g. methyl or ethyl);

$R^8$, $R^9$ and $R^{10}$ are independently selected from the group consisting of hydrogen, $C_{(1-20)}$alkyl which may be fluorinated, including up to perfluorinated on the terminal 1 to 3 carbon atoms), $C_{(1-20)}$alkenyl (preferably $C_{(12-18)}$alkenyl, aryl, aryl$C_{(1-10)}$alkyl, $C_{(1-10)}$alkoxy$C_{(1-10)}$alkyl, or aryloxy$C_{(1-10)}$alkyl and in which an aryl group may have one or two substituents selected from the group consisting of halogen, $C_{(1-20)}$alkyl, $C_{(1-20)}$alkoxy, aryloxy and COO$C_{(1-20)}$alkyl; and $R^{11}$ and $R^{12}$ are independently selected from one of the values hereinbefore defined for $R^8$ and $R^9$ or $R^{11}$ and $R^{12}$ together with the nitrogen atom to which they are attached form a 5- to 7 membered ring optionally containing one or two further heteroatoms selected from the group consisting of oxygen, nitrogen and sulphur, and optionally substituted by one or two substituents which is hydroxy, oxo, $C_{(1-4)}$alkyl, phenyl, or benzyl.

2. A compound as claimed in claim 1, in which Z is $CH_2$.

3. A compound as claimed in claim 1 in which $R^1$ is an aryl group selected from the group consisting of phenyl, naphthyl, and a 5- or 6- membered, monocyclic heteroaryl group containing 1 or 2 nitrogen heteroatoms.

4. A compound as claimed in claim 3 in which $R^1$ is selected from the group consisting of pyridyl, pyrimidyl and pyrazolyl.

5. A compound as claimed in claim 1 in which X is S.

6. A compound as claimed in claim 1 in which $A^1$, $A^2$ and $A^3$ each represent a bond or $A^1$ and $A^3$ are straight chain $C_{(1-10)}$alkylene groups and $A^2$ is CO, C=$CH_2$ or O.

7. A compound as claimed in claim 1 in which $R^2$ is phenyl optionally substituted by 1, 2 or 3 substituents selected from the group consisting of halogen, $C_{(1-4)}$alkyl, $C_{(1-4)}$alkoxy, phenyl and benzyl.

8. A compound as claimed in claim 1 in which $R^2YCH_2X$ is a 4-fluorobenzylthio group.

9. A compound according to claim 1 in which W is a bond.

10. A compound according to claim 1 in which $R^7$, when a hydrocarbyl group, is $C_{(1-20)}$alkyl, $C_{(2-20)}$alkenyl, $C_{(2-20)}$alkynyl, $C_{(3-6)}$cycloalkyl, $C_{(3-6)}$cycloalkyl$C_{(1-5)}$alkyl, or $C_{(1-15)}$alkoxy$C_{(1-10)}$alkyl each of which may be optionally substituted by 1 or 2 substituents selected from the group consisting of mono to perfluoro-$C_{(1-4)}$alkyl, OR$^8$, COOR$^8$, CONR$^8$R$^9$, NR$^8$COR$^9$, NR$^8$CONR$^9$R$^{10}$, NR$^8$COOR$^9$, OCONR$^8$R$^9$, NR$^{11}$ R$^{12}$ and $R^1$.

11. A compound according to claim 1 in which W is a bond and $R^7$ is:

(a) $C_{(1-10)}$alkyl which is substituted by one or two substituents selected from the group consisting of hydroxy, $C_{(1-10)}$alkoxy, COO$C_{(1-10)}$alkyl, CONR$^8$R$^9$, NR$^8$CONR$^9$R$^{10}$, NHCOR$^8$ in which $R^8$, $R^9$ and $R^{10}$ is each independently $C_{(1-20)}$alkyl), NR$^{11}$R$^{12}$, phenyl which may be optionally substituted by COO$C_{(1-16)}$alkyl and heteroaryl; or (b) $R^7$ is a phenyl or a phenyl$C_{(1-8)}$alkyl group substituted on the phenyl ring by 1 or 2 substituents selected from the group consisting of $C_{(6-12)}$alkyl, $C_{(6-12)}$alkoxy, COOH, COO$C_{(6-12)}$alkyl and CONH$C_{(6-12)}$alkyl; or (c) $R^7$ is heteroaryl$C_{(1-8)}$alkyl in which the heteroaryl ring is monocyclic with 5 to 6 members and one or two heteroatoms selected from the group consisting of nitrogen, oxygen and sulphur.

12. A compound according at claim 1 in which W is a bond and $R^7$ is a $(CH_2)_nBR^{13}$ where n is an integer from 1 to 6, B is NR$^{14}$CO, CONR$^{14}$, NR$^{14}$CONR$^{15}$, NR$^{15}$COO in which $R^{14}$ and $R^{15}$ are independently hydrogen or $C_{(1-6)}$alkyl; and $R^{13}$ is $C_{(8-18)}$alkyl which is optionally substituted by fluorine, including up to perfluorinated on the terminal 1 to 3 carbon atoms, $C_{(8-18)}$alkenyl, phenyl $C_{(1-6)}$alkyl and phenyl$C_{(1-8)}$alkoxy$C_{(1-6)}$alkyl in which phenyl may be unsubstituted or substituted by halogen or $C_{(1-6)}$alkyl.

13. A compound of formula (I) as defined in claim 1 selected from the group consisting of:

1-(4-hydroxycyclohexyl)-2-(8-(4-chlorophenyl)-8-oxooct-1-yl)thio-5-(pyrimid-5-yl-methyl)pyrimidin-4-one;

1-(2-methoxyethyl)-2-(8-(4-chlorophenyl)-8-oxooct-1-yl)thio-5-(pyrimid-5-ylmethyl)pyrimidin-4-one;

1-(3-(1-imidazolyl)prop-1-yl)-2-(8-(4-chlorophenyl)-8-oxooct-1-yl)thio-5-(pyrimid-5-ylmethyl)pyrimidin-4-one;

1-(3-(1-morpholino)prop-1-yl)-2-(8-(4-chlorophenyl)-8-oxooct-1-yl)thio-5-(pyrimid-5-ylmethyl)pyrimidin-4-one;

1-(3-(2-oxo-1-pyrrolidino)prop-1-yl)-2-(8-(4-chlorophenyl)-8-oxooct-1-yl)thio-(pyrimidin-5-ylmethyl)pyrimidin-4-one;

1-(3-dimethylaminoprop-1-yl)-2-(8-(4-chlorophenyl)-8-oxooct-1-yl)thio-5-(pyrimid-5-ylmethyl)pyrimidin-4-one;

1-(3-hydroxyprop-1-yl)-2-(8-(4-chlorophenyl)-8-oxooct-1-yl)thio-5-(pyrimid-5-ylmethyl)pyrimidin-4-one;

1-(3-hydroxyprop-1-yl)-2-(8-(4-chlorophenyl)oct-1-yl)thio-5-benzylpyrimidin-4-one;

1-(3-methoxyprop-1-yl)-2-(8-(4-chlorophenyl)-8-oxooct-1-yl)thio-5-(pyrimid-5-ylmethyl)pyrimidin-4-one;

1-(3-phenylprop-1-yl)-2-(8-(4-chlorophenyl)-8-oxooct-1-yl)thio-5-(pyrimid-5-ylmethyl)pyrimidin-4-one;

1-(5-hydroxypent-1-yl)-2-(8-(4-chlorophenyl)-8-oxooct-1-yl)thio-5-(pyrimid-5-ylmethyl)pyrimidin-4-one;

1-(pyrid-2-ylmethyl)-2-(8-(4-chlorophenyl)-8-oxooct-1-yl)thio-5-(pyrimid-5-ylmethyl)pyrimidin-4-one;

1-(pyrid-2-ylmethyl)-2-(8-(4-chlorophenyl)oct-1-yl)thio-5-benzylpyrimidin-4-one;

1-(pyrid-3-ylmethyl)-2-(8-(4-chlorophenyl)-8-oxooct-1-yl)thio-5-((1-methyl-2-oxo-pyrid-4-yl)methyl)pyrimidin-4-one;

1-(pyrid-3-ylmethyl)-2-(8-(4-chlorophenyl)-8-oxooct-1-yl)thio-5-(pyrimid-5-ylmethyl)pyrimidin-4-one;

1-(pyrid-3-ylmethyl)-2-(8-(4-chlorophenyl)oct-1-yl)thio-5-benzylpyrimidin-4-one;

1-(pyrid-4-ylmethyl)-2-(8-(4-chlorophenyl)oct-1-yl)thio-5-((1-methyl-2-oxo-pyrid-4-yl)methyl)pyrimidin-4-one;

1-(pyrid-4-ylmethyl)-2-(8-(4-chlorophenyl)-8-oxooct-1-yl)thio-5-((1-methyl-2-oxo-pyrid-4-yl)methyl)pyrimidin-4-one;

1-(pyrid-4-ylmethyl)-2-(8-(4-chlorophenyl)-8-oxooct-1-yl)thio-5-(pyrimid-5-ylmethyl)pyrimidin-4-one;

1-(pyrid-4-ylmethyl)-2-(8-(4-chlorophenyl)oct-1-yl)thio-5-benzylpyrimidin-4-one;

1-(pyrid-4-ylmethyl)-2-(8-(4-chlorophenyl)oct-1-yl)thiopyrimidin-4-one;

1-(2-(pyrid-2-yl)ethyl)-2-(8-(4-chlorophenyl)-8-oxooct-1-yl)thio-5-(pyrimid-5-ylmethyl)pyrimidin-4-one;

1-(2-(pyrid-3-yl)ethyl)-2-(8-(4-chlorophenyl)-8-oxooct-1-yl)thio-5-((1-methyl-2-oxo-pyrid-4-yl)methyl)pyrimidin-4-one;

1-(2-(pyrid-3-yl)ethyl)-2-(8-(4-chlorophenyl)-8-oxooct-1-yl)thio-5-(pyrimid-5-ylmethyl)pyrimidin-4-one; and 1-(2-(pyrid-4-yl)ethyl)-2-(8-(4-chlorophenyl)-8-oxooct-1-yl)thio-5-((1-methyl-2-oxo-pyrid-4-yl)methyl)pyrimidin-4-one.

14. A compound selected from the group consisting of:
2-(4-fluorobenzylthio)-5-((pyrimid-5-yl)methyl)pyrimidin-4-one;

1-methyl-2-(4-fluorobenzyl)thio-5-(pyrimid-5-ylmethyl)pyrimidin-4-one;

1-(tetradec-1-ylaminocarbonylmethyl)-2-(4-fluorobenzyl)thio-5-(pyrimid-5-ylmethyl)pyrimidin-4-one;

1-(N-(dodec-1-yl)-N-methylaminocarbonylmethyl)-2-(4-fluorobenzyl)thio-5-(pyrimid-5-ylmethyl)pyrimidin-4-one; and 1-(N-methyl-N-(dodec-1-yl)aminocarbonylmethyl)-2-(4-fluorobenzyl)thio-5-(2-methoxypyrimid-5-ylmethyl)pyrimidin-4-one.

15. A pharmaceutical composition comprising a compound of formula (I) as claimed in claim 1 and a pharmaceutically acceptable carrier.

16. A method of treating atherosclerosis which method involves treating a patient in need thereof with a therapeutically effective amount of a compound of formula (I) as claimed in claim 1.

17. A process for preparing a compound of formula (I)

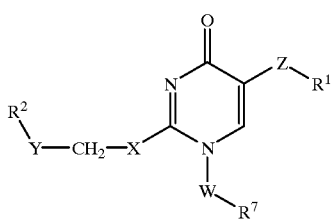

(I)

in which:
Z is a bond and $R^1$ is halogen; or
Z is $CR^3R^4$, where $R^3$ and $R^4$ are each hydrogen or $C_{(1-4)}$ alkyl, or $R^3$ and $R^4$ together with the intervening carbon atom form a $C_{(3-6)}$cycloalkyl ring; and
$R^1$ is an aryl or heteroaryl group, unsubstituted or substituted by 1, 2, 3 or 4 substituents selected from the group consisting of $C_{(1-18)}$alkyl, $C_{(1-18)}$alkoxy, $C_{(1-18)}$alkylthio, aryl$C_{(1-18)}$alkoxy, oxo, hydroxy, halogen, CN, $COR^5$, $COOR^5$, $CONR^5R^6$, $NR^5COR^6$, $SO_2NR^5R^6$, $NR^5SO_2R^6$, $NR^5R^6$, mono to perfluoro-$C_{(1-4)}$alkyl and mono to perfluoro-$C_{(1-4)}$alkoxy;

X is O or S;
Y is —$A^1$—$A^2$—$A^3$— in which $A^1$ and $A^3$ each represent a bond or a straight chain or branched $C_{(1-10)}$alkylene group and $A^2$ represents a bond or O, S, SO, $SO_2$, CO, C=$CH_2$, CH=CH, C•C, CONH, NHCO, or $CR^5R^6$, providing that when $A^2$ is O, S, SO, $SO_2$ or CONH, $A^3$ contains at least two carbon atoms linking the $A^2$ group and the $CH_2$ group in formula (I);

$R^2$ is an aryl or heteroaryl group, unsubstituted or substituted by 1, 2, 3 or 4 substituents selected from the substituents hereinbefore defined for $R^1$, as well as aryl and aryl$C_{(1-4)}$alkyl;

W is a bond and $R^7$ is hydrogen; or
W is $SO_2$ or a bond; and
$R^7$ is $R^1$ or a hydrocarbyl group which hydrocarbyl group may be optionally interrupted within the carbon chain by a group selected from the group consisting of O, COO, OCO, CO, $CONR^8$, $NR^8CO$, $NR^8CONR^9$, $NR^8COO$, $OCONR^8$, and $NR^8$, and which hydrocarbyl group may also be optionally substituted by 1 or 2 substituents selected from the group consisting of mono to perfluoro-$C_{(1-4)}$alkyl, $OR^8$, $COOR^8$, $CONR^8R^9$, $NR^8COR^9$, $NR^8CONR^9R^{10}$, $NR^8COOR^9$, $OCONR^8R^9$, $NR^{11}R^{12}$ and $R^1$;

$R^5$ and $R^6$ are independently hydrogen or $C_{(1-20)}$alkyl, for instance $C_{(1-4)}$alkyl (e.g. methyl or ethyl);

$R^8$, $R^9$ and $R^{10}$ are independently selected from the group consisting of hydrogen, $C_{(1-20)}$alkyl which may be fluorinated, including up to perfluorinated on the terminal 1 to 3 carbon atoms), $C_{(1-20)}$alkenyl (preferably $C_{(12-18)}$alkenyl), aryl, aryl$C_{(1-10)}$alkyl, $C_{(1-10)}$alkoxy$C_{(1-10)}$alkyl, or aryloxy$C_{(1-10)}$alkyl and in which an aryl group may have one or two substituents selected from the group consisting of halogen, $C_{(1-20)}$alkyl, $C_{(1-20)}$alkoxy, aryloxy and $COOC_{(1-20)}$alkyl; and $R^{11}$ and $R^{12}$ are independently selected from one of the values hereinbefore defined for $R^8$ and $R^9$ or $R^{11}$ and $R^{12}$ together with the nitrogen atom to which they are attached form a 5- to 7 membered ring optionally containing one or two further heteroatoms selected from the group consisting of oxygen, nitrogen and sulphur, and optionally substituted by one or two substituents which is hydroxy, oxo, $C_{(1-4)}$alkyl, phenyl, or benzyl;

which process comprises:
(a) treating a compound of formula (IIA):

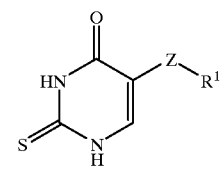

(IIA)

in which
Z and $R^1$ are the same as in Formula (I) with a compound of formula (III):

$R^2YCH_2L^1$ (III)

in which
$R^2$ and Y are the same as in Formula (I); and
$L^1$ is a leaving group; to give a compound of formula (IA):

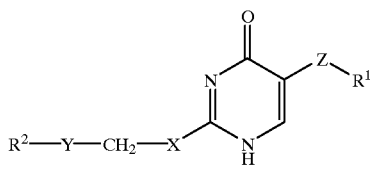
(IA)

in which Z, Y, R¹ and R² are the same as in formula (I) and X is S; or (b) treating a compound of formula (IV):

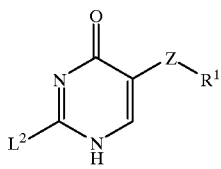
(IV)

in which Z and R¹ are the same as in formula (I) and $L^2$ is a leaving group which is halogen, alkylthio, or —$NHNO_2$, with a compound of formula (V):

$R^2YCH_2XH$          (V)

in which X, Y and R² are the same as in formula (I) in a solvent such as pyridine, to give a compound of formula (IA); and thereafter;

treating a compound of formula (IA) form (a) or (b) above with a compound of formula (VI):

$R^7WL^1$          (VI)

in which $L^1$, W and R⁷ are the same as in formula (I); to give a compound of formula (IB):

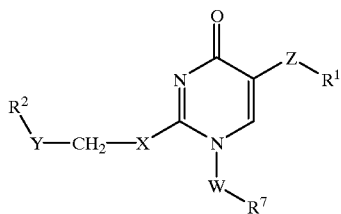
(IB)

in which X, Y, Z, R¹ and R² are the same as in formula (I), and WR⁷ is the same as in formula (I) other than -H;

(c) treating a compound of formula (IIB):

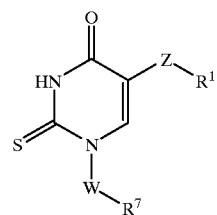
(IIB)

in which W is a bond, Z and R¹ and R⁷ are are the same as defined in formula (I), except the R⁷ is not H; with a compound of formula (III) as hereinbefore defined, to obtain a compound of formula (IB); and, thereafter; treating a compound of formula (IA) or (IB) in which X is S with a compound of formula (V):

$R^2YCH_2OH$          (VII)

in which Y and R² are the same as in formula (I); to give a corresponding compound of formula (I) in which X is O; or (d) for a compound of formula (I) in which Z is a bond and R¹ is halogen, treating a compound of formula (VIII):

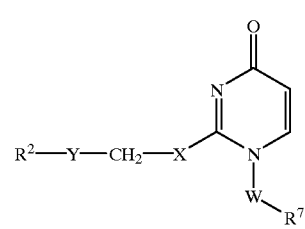
(VIII)

in which W, Y, R², and R⁷ are the same as in formula (I) with a halogenating agent to form a compound of formula (I) in which Z is a bond and R¹ is bromine.

* * * * *